(12) United States Patent
Palchaudhuri et al.

(10) Patent No.: US 12,291,576 B2
(45) Date of Patent: May 6, 2025

(54) ANTI-CD45 ANTIBODIES AND CONJUGATES THEREOF

(71) Applicant: Vor Biopharma Inc., Cambridge, MA (US)

(72) Inventors: Rahul Palchaudhuri, Somerville, MA (US); Bradley R. Pearse, Watertown, MA (US); Hillary Adams, Medford, MA (US); Sean McDonough, Littleton, MA (US); Michael Cooke, Boston, MA (US); Anthony Boitano, Newton, MA (US)

(73) Assignee: Vor Biopharma Inc., Cambridge, MA (US)

( * ) Notice: Subject to any disclaimer, the term of this patent is extended or adjusted under 35 U.S.C. 154(b) by 865 days.

(21) Appl. No.: 17/244,856

(22) Filed: Apr. 29, 2021

(65) Prior Publication Data

US 2021/0371524 A1 Dec. 2, 2021

Related U.S. Application Data

(63) Continuation of application No. PCT/US2019/058971, filed on Oct. 30, 2019.

(60) Provisional application No. 62/807,582, filed on Feb. 19, 2019, provisional application No. 62/774,006, filed on Nov. 30, 2018, provisional application No. 62/753,002, filed on Oct. 30, 2018.

(51) Int. Cl.
| | |
|---|---|
| *C07K 16/28* | (2006.01) |
| *A61K 38/12* | (2006.01) |
| *A61K 39/00* | (2006.01) |
| *A61K 47/68* | (2017.01) |
| *A61P 35/02* | (2006.01) |

(52) U.S. Cl.
CPC ........... *C07K 16/289* (2013.01); *A61K 38/12* (2013.01); *A61K 47/6831* (2017.08); *A61K 47/6849* (2017.08); *A61P 35/02* (2018.01); *A61K 2039/505* (2013.01)

(58) Field of Classification Search
None
See application file for complete search history.

(56) References Cited

U.S. PATENT DOCUMENTS

| | | |
|---|---|---|
| 2009/0175881 A1 | 7/2009 | Presta et al. |
| 2016/0311903 A1 | 10/2016 | West et al. |
| 2018/0237521 A1 | 8/2018 | Finney et al. |
| 2018/0251532 A1 | 9/2018 | Gavathiotis et al. |

FOREIGN PATENT DOCUMENTS

| | | |
|---|---|---|
| WO | WO-2014177460 A1 | 11/2014 |
| WO | WO-2015200073 A1 | 12/2015 |
| WO | WO-2017155937 A1 | 9/2017 |
| WO | WO-2017219025 A1 | 12/2017 |
| WO | WO-2020086776 A1 | 4/2020 |
| WO | WO-2021087368 A2 | 5/2021 |

OTHER PUBLICATIONS

Janeway CA Jr, Travers P, Walport M, et al. Immunobiology: The Immune System in Health and Disease. 5th edition. New York: Garland Science; 2001 (Year: 2001).*
Scott et al. Antibody therapy of cancer. Nature Reviews. 2012. 12: 278-287. (Year: 2012).*
Chan and Carter. Therapeutic antibodies for autoimmunity and inflammation. Nature Reviews. 2010. 10: 301-316. (Year: 2010).*
Huss et al. Anti-CD25 monoclonal antibody Fc variants differentially impact regulatory T cells and immune homeostasis. Immunology. 2016. 148: 276-286 (Year: 2016).*
Rabia et al. Understanding and overcoming trade-offs between antibody affinity, specificity, stability and solubility. Biochem Eng J 2018. 137: 365-374. (Year: 2018).*
Atlas Antibodies •AMAb90518 Dec. 2012 [online], [Retrieved on Mar. 2, 2020]. Retrieved from the internet <URL:https://www.atlasantibodies.com/api/print_datasheet/AMAb90518.pdf> p. 1, Antigen Sequence.
Brenner et al., "Complement-Fixing CD45 Monoclonal Antibodies to Facilitate Stem Cell Transplantation in Mouse and Man", Annals of the New York Academy of Sciences, 2003, pp. 80-88, vol. 996, No. 1.
EPO, "Supplementary European Search Report" dated Jun. 24, 2022, for EP App. No. 19878736.8.
Glatting et al., "Anti-CD45, Monoclonal Antibody YAML568: A Promising Radioimmunoconjugate for Targeted Therapy of Acute Leukemia", The Journal of nuclear medicine, 2006, pp. 1335-1341, XP55865905, United States.
Jager et al., "A Depleting Anti-CD45 Monoclonal Antibody as Isolated Conditioning for Bone Marrow Transplantation in the Rat", Plos One, May 3, 2016, vol. 11, No. 5, p. 1-17, XP55595236, DOI: 10.1371/journal.pone.0154682.
Pagel et al., "1311-anti-CD45 antibody plus busulfan and cyclophosphamide before allogeneic hematopoietic cell transplantation for treatment of acute myeloid leukemia in first remission", Blood, Mar. 1, 2006, pp. 2184-2191, vol. 107, No. 5, XP55521263, US ISSN: 0006-4971, DOT:10.1182/blood--2005-06-2317.
Palchaudhuri et al., "Non-genotoxic conditioning for hematopoietic stem cell transplantation using a hematopoietic-cell-specific internalizing immunotoxin", Nature Biotechnology, vol. 34, No. 7, Jun. 6, 2016 (Jun. 6, 2016), pp. 738-745, XP55322275, New York ISSN: 1087-0156, DOI: 10.1038/nbt.3584.

(Continued)

*Primary Examiner* — Daniel E Kolker
*Assistant Examiner* — Maureen Varina Driscoll
(74) *Attorney, Agent, or Firm* — Womble Bond Dickinson (US) LLP; Cristin Howley Cowles; Rachel E. Yunck

(57) ABSTRACT

Disclosed are anti-CD45 antibodies and antibody drug conjugates (ADCs) useful in therapeutic methods, including targeting CD45 expressing hematopoietic stem cells (HSCs) or immune cells prior to transplantation.

26 Claims, 23 Drawing Sheets
Specification includes a Sequence Listing.

(56) References Cited

OTHER PUBLICATIONS

WIPO, "International Preliminary Report on Patentability" dated Apr. 27, 2021, for International App. No. PCT/US2019/058971.
Wulf et al., "CD45 monoclonal antibody-mediated cytolysis of human NK and T lymphoma cells", Haematologica/The Hematology Journal, 2006, pp. 886-894, vol. 91, No. 7.

* cited by examiner

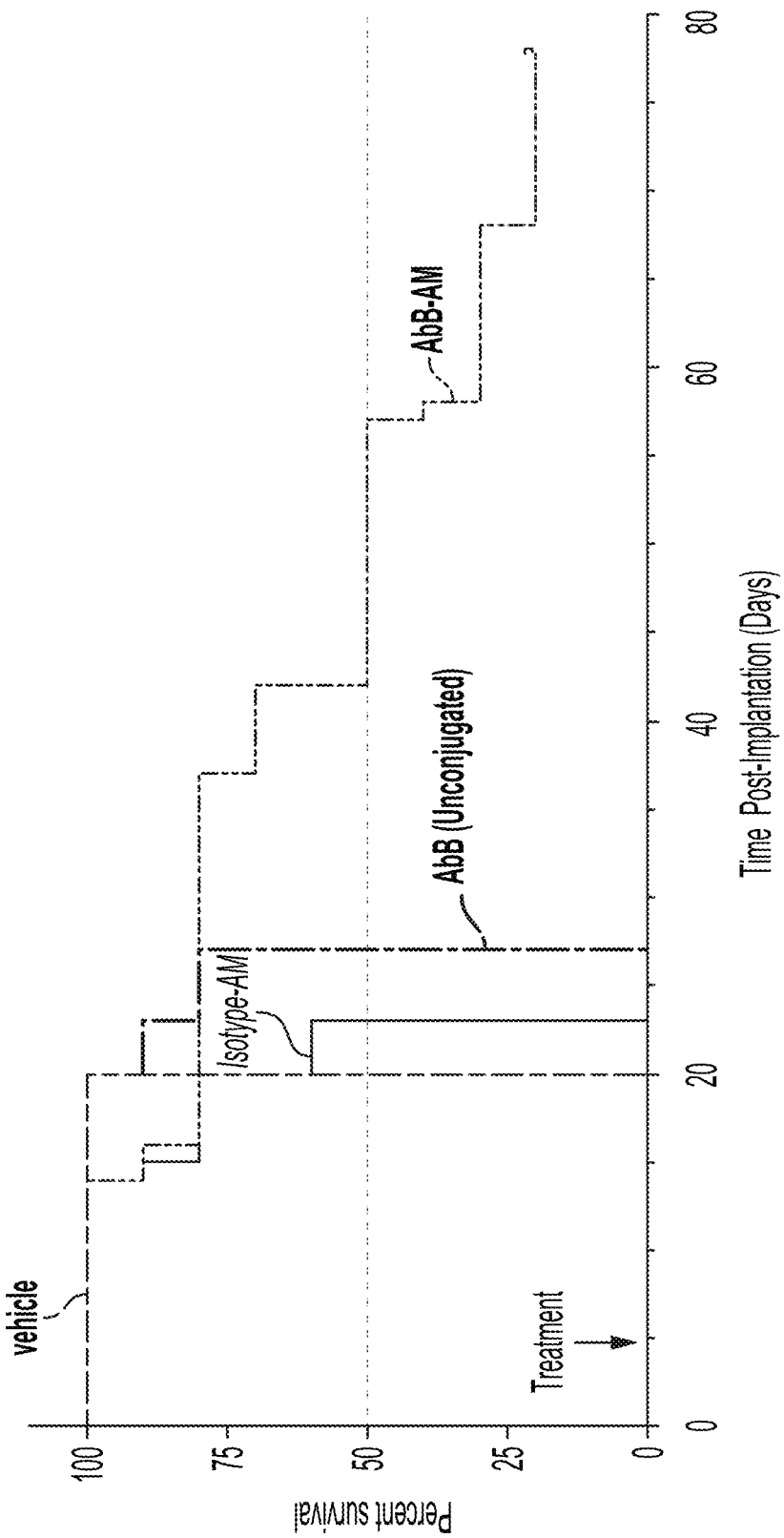

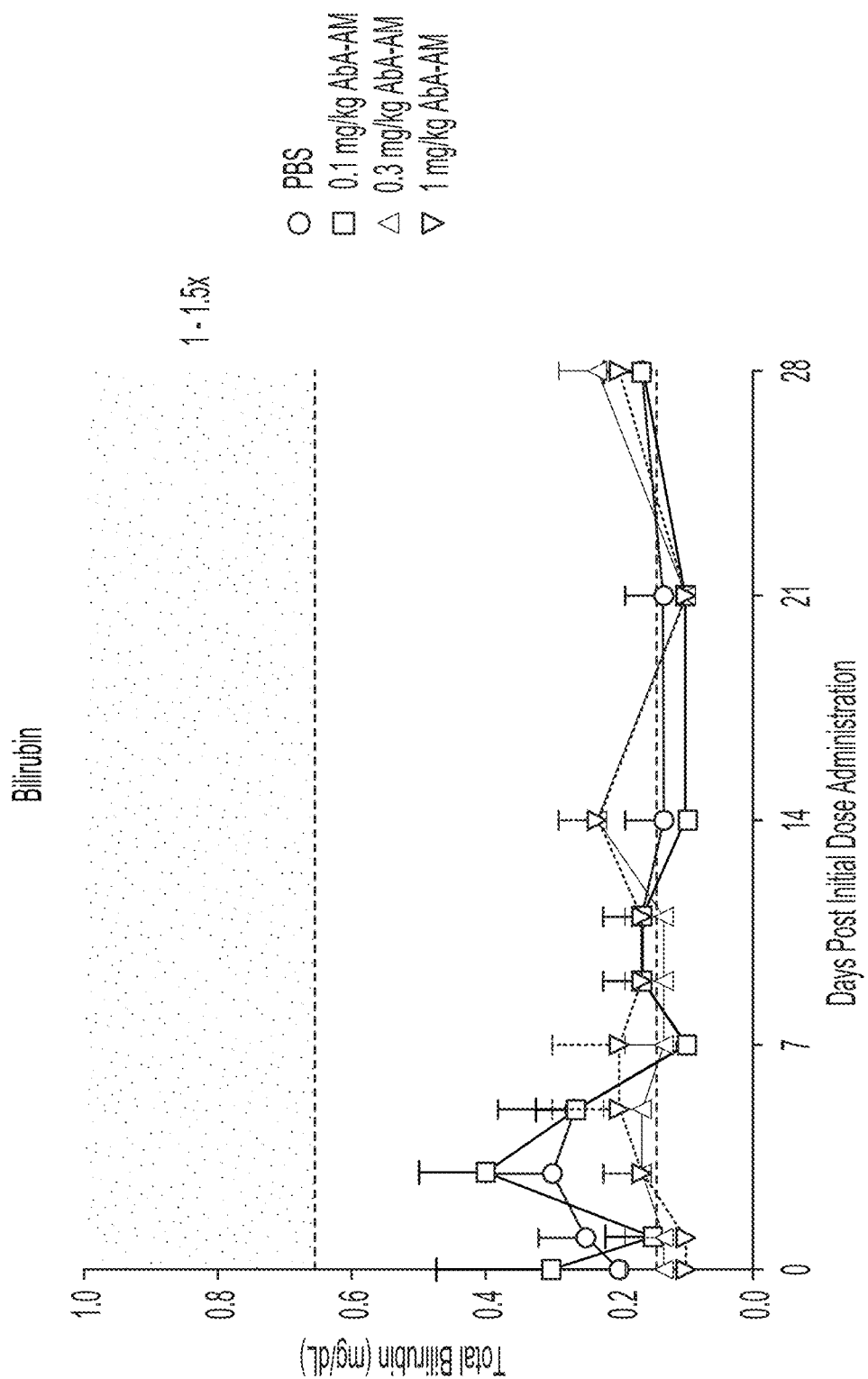

SEQ ID NO: 40  human
SEQ ID NO: 41  cyno human   QSFTPSPTAYLNASETTLPSGSAVISTTIATTPSKTCDEKYANITVDYLYNKETK
cyno    ------------NASETTTPSPSGSTVISTPTIGDVT--LSHTEKYATIPVDYLYNNKTK
        ****:    :    :    .  ******:;:

human   LFTAKLNVNENVECGNN-----TCTNNEVHNLTECKNASVSISHNSCTAPDKTLILDVPP
cyno    LFTAKLNVNENVECTNNMHTHNICTNNEVINLPECKEMNVVSHNSCTDRHKRLKLDVPP
        **********       ***: ****:..*.*****:: ::

human   GVEKFQLHDCTQVEKADTTICLKWKNIETFTCDTQNITRFQCGNMIFDNKEIKLENLEP
cyno    EVEKFQLDDCTPDVEANTTICLKWKIIETFACDKSKITYRFQCGNKIYMKEGIYLENLEP
        .****:*.:*:***::.:::****:*:::::*** human   EHEYKCDSEILYNNHKFTNASKIIKTEFGSPGEPQIIFCRSEAAHQGVITWNPPQRSFHN
cyno    EVEYKCDSEILYNNHKYINITKLIKTEFGIPGQPQNVCREDAHQGVITWNPPQRSFHN
        * **************: *:::***** :** :*.*:.*************** human   FTLCVIKEFEKDCINLDKNLIKYDLQNIKPYTKVLSLHAYIIAKVQRNGSAAMCHFTTK
cyno    FTLCVSKTAKKCLSLDKHLTEYHLQMLKPYTNVSLSLHAYIIAKVQRNGTAATCNFTTE
        *****.:.  *.:*.** * *: :**:* **************: *:***:

human   SAPSQVRNMTVSMTSDNSMHVCRPPPPDRNGPHERYHLEVEAGNTLVRNESHKNCDFRV
cyno    SAPSQVQRMIVS--TSDNSMRVCEGPRDVNGPTGLYHLEVEAGNTLVRNLSQSKCDFSV
        ******:.*:  :* ..:*.:.  :***********. ::*.*** * human   KDLQYSTDYTFKAYFHNGDYPGEPFILHHSTYNSKALIAFLAFLIIVTSIALLVLYKI
cyno    NNLQSTYYNLKAYYHNGKVSGEPVILRESTYNSKALIAFLAFLIIVTSIALIV-----
        ::**.* *: * *. .* *: ********************:* human   YDLHKKRSCNLDEQQELVERDEKQLMNVEPIHADILLETYKRKIADEGRL
cyno    ---------------PIHADILLETYKRKIADEGRL
                       **********************

FIG. 10

SEQUENCE LISTING

```
<160> NUMBER OF SEQ ID NOS: 41

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Asp Arg Val Gln Pro Gly Arg
1               5                   10                  15

Ser Leu Thr Leu Ser Cys Val Thr Ser Gly Phe Thr Phe Asn Asn Tyr
            20                  25                  30

Trp Met Thr Trp Ile Arg Gln Val Pro Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Thr Tyr Tyr Cys
                85                  90                  95

Ala Arg Asp Glu Arg Trp Ala Gly Ala Met Asp Ala Trp Gly Gln Gly
            100                 105                 110

Thr Ser Val Thr Val Ser Ser
        115

<210> SEQ ID NO 2
```

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Thr Phe Asn Asn Tyr Trp Met Thr
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ile Ser Ser Ser Gly Gly Ser Ile Tyr Tyr Pro Asp Ser Val Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Arg Asp Glu Arg Trp Ala Gly Ala Met Asp Ala
1               5                   10

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Ile
        35                  40                  45

Tyr Glu Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln His Asn Ser Arg Phe Thr
                85                  90                  95

Phe Gly Ser Gly Thr Lys Leu Glu Ile Lys
            100                 105

<210> SEQ ID NO 6
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Lys Ala Ser Gln Asn Ile Asn Lys Asn Leu Asp
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Thr Asn Asn Leu Gln Thr
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Gln His Asn Ser Arg Phe Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Asp Leu Val Gln Pro Gly Arg
1               5                   10                  15

Ser Leu Lys Leu Ser Cys Ile Ala Ser Gly Phe Thr Phe Thr Asn Phe
            20                  25                  30

Trp Met Thr Trp Ile Arg Gln Val Ser Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Asp Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Thr Tyr Tyr Cys
                85                  90                  95

Val Lys Leu His Tyr Tyr Ser Gly Gly Gly Asp Ala Trp Gly Gln Gly
            100                 105                 110

Thr Ser Val Thr Val Ser Ser
        115

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 10

Phe Thr Phe Thr Asn Phe Trp Met Thr
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ile Ser Ser Ser Gly Gly Ser Ile Tyr Tyr Pro Asp Ser Val Lys
1               5                   10                  15

Asp

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Lys Leu His Tyr Tyr Ser Gly Gly Gly Asp Ala
1               5                   10

<210> SEQ ID NO 13
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
                20                  25                  30

Leu Asp Trp Tyr Gln Gln Lys His Gly Glu Ala Pro Lys Leu Leu Ile
            35                  40                  45

His Tyr Thr Asn Asn Leu His Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln His Ser Ser Arg Trp Thr
                85                  90                  95

Phe Gly Gly Gly Thr Lys Leu Glu Leu Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Ala Ser Gln Asn Ile Asn Lys Tyr Leu Asp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Thr Asn Asn Leu His Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gln His Ser Ser Arg Trp Thr
1               5

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Asp Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Val Pro Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Asp Arg Phe Thr Ile Ser Arg Asp Asn Ala Lys Asn Thr Leu Phe
65                  70                  75                  80

Leu Gln Met Asn Ser Leu Arg Ser Glu Asp Thr Ala Thr Tyr Tyr Cys
                85                  90                  95

Ala Arg Leu Tyr Tyr Tyr Ser Gly Gly Gly Asp Ala Trp Gly Gln Gly
            100                 105                 110

Thr Ser Val Thr Val Ser Ser
        115

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Thr Phe Asn Asn Tyr Trp Met Thr

```
<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ile Ser Ser Ser Gly Gly Ser Ile Tyr Tyr Pro Asp Ser Val Lys
1               5                   10                  15

Asp

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Leu Tyr Tyr Tyr Ser Gly Gly Gly Asp Ala
1               5                   10

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Phe Leu Ser Ala Ser Val Gly
1               5                   10                  15

Asp Arg Val Thr Ile Ile Cys Lys Ala Ser Gln Asp Ile Asn Lys Tyr
            20                  25                  30

Leu Asp Trp Tyr Gln Gln Lys Leu Gly Glu Ala Pro Lys Leu Leu Ile
        35                  40                  45

Tyr Asn Thr Asn Asn Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln His Ile Ser Arg Trp Thr
                85                  90                  95

Phe Gly Gly Gly Thr Lys Leu Glu Leu Lys
            100                 105

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Ser Gln Asp Ile Asn Lys Tyr Leu Asp
1               5                   10
```

```
<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Thr Asn Asn Leu His Thr
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Gln His Ile Ser Arg Trp Thr
1               5

<210> SEQ ID NO 25
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gacatccaga tgacccagtc tccacctgtg ctgtctgcat ctgtaggaga cagagtcacc      60
ctttcatgca aggcaagtca gaatattaac aaaaatttag actggtatca gcagaaacat    120
ggggaagccc ctaagctcct gatctatgag acaaataatt tgcaaacggg gatcccatca    180
aggttcagtg gcagtggatc tgggacagat tacactctca ccatcagcag tctgcaacct    240
gaagatgtgg caacttacta ctgttaccag cacaactcca gattcacttt tggctcaggg    300
accaagctgg agatcaaa                                                  318

<210> SEQ ID NO 26
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gaagtgcagc tggtggagtc tgggggagac agggtacagc ctggcaggtc cctgacactc      60
tcctgtgtaa catctggatt caccttaac aactattgga tgacctggat ccggcaagta    120
ccagggaagg gcctggagtg ggtcgcttct attagttcca gtggcggtag catatattat    180
cccgactctg tgaagggccg attcaccatc tccagagaca cgccaagaa caccctgtat    240 ctgcaaatga acagtctgag atccgaggac acggcgacct actactgcgc aagagacgaa    300
agatgggctg cgctatgga cgcctggggg caagggacct ccgtcaccgt ctcctca       357

<210> SEQ ID NO 27
<211> LENGTH: 318
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 27
gacatccaga tgacccagtc tccatccttc ctgtctgcat ctgtaggaga cagagtcacc    60
atcaactgca aggcgagtca gaacattaat aaatatttag attggtatca gcagaaacat   120
ggggaggccc ctaagctcct gatccattac accaataatt tgcacacagg gataccatca   180
aggttcagtg gaagtggatc tgggacagat tacactttga ccatcagcag cctgcagcct   240
gaagatgttg caacatattt ctgtctgcaa cattccagca ggtggacctt cggcggaggg   300
accaagcttg agctgaaa                                                 318

<210> SEQ ID NO 28
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gggaagggcc tggagtgggt cgctagcatt agttctagtg gaggtagcat atattatccc    60
gactctgtga aggaccgatt caccatctcc agagacaacg ccaagaacac actgtatctg   120
caaatgaaca gtctgagatc cgaggacacg gcgacatact actgcgttaa gcttcactac   180
tattccggag ggggtgatgc ttggggccaa ggaacctccg tcaccgtctc ctca         234

<210> SEQ ID NO 29
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gacatccaga tgacccagtc tccatccttc ctgtctgcat ctgtaggaga cagagtcacc    60
atcatctgca aggcgagtca ggacattaac aagtatttag actggtatca gcagaaattg   120
ggggaagccc ctaagctcct gatctacaat acaaataatt tgcacacagg gataccatca   180
aggttcagtg gaagtggatc tgggacagat tacactttga ccatcagcag cctgcagcct   240
gaagatgtcg caacatattt ttgtctgcag cacattagca gatggacctt cggcggaggg   300
accaagctgg agctgaaa                                                 318

<210> SEQ ID NO 30
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gaagtgcagc tggtggagtc tgggggagat ttggtacagc ctggcaggtc cctgaaactc    60
tcctgtgttg cctctggatt cacctttaat aactattgga tgacatggat tcggcaagtt   120
ccagggaagg gcctggagtg ggtcgcttcc attagtagta gtggtggtag catatattat   180
cccgactctg tgaaggatcg attcaccatc tccagagaca cgccaagaa cacactgttt   240 ctgcaaatga acagtctgag atctgaggac acggcgacat actactgcgc gagactgtat   300
```

-continued

```
tactattctg gtggtggcga tgcgtggggc caaggaacct ccgtcaccgt ctcctca        357
```

<210> SEQ ID NO 31
<211> LENGTH: 1211
<212> TYPE: PRT
<213> ORGANISM: Homo sapiens

<400> SEQUENCE: 31

| | | | | | | | | | | | | | | |
|---|---|---|---|---|---|---|---|---|---|---|---|---|---|---|
| Met | Thr | Met | Tyr | Leu | Trp | Leu | Lys | Leu | Leu | Ala | Phe | Gly | Phe | Ala | Phe |
| 1 | | | | 5 | | | | | 10 | | | | | 15 | |
| Leu | Asp | Thr | Glu | Val | Phe | Val | Thr | Gly | Gln | Ser | Pro | Thr | Pro | Ser | Pro |
| | | | 20 | | | | | 25 | | | | | 30 | | |
| Thr | Gly | Leu | Thr | Thr | Ala | Lys | Met | Pro | Ser | Val | Pro | Leu | Ser | Ser | Asp |
| | | | 35 | | | | | 40 | | | | | 45 | | |
| Pro | Leu | Pro | Thr | His | Thr | Thr | Ala | Phe | Ser | Pro | Ala | Ser | Thr | Phe | Glu |
| | 50 | | | | | 55 | | | | | 60 | | | | |
| Arg | Glu | Asn | Asp | Phe | Ser | Glu | Thr | Thr | Thr | Ser | Leu | Ser | Pro | Asp | Asn |
| 65 | | | | | 70 | | | | | 75 | | | | | 80 |
| Thr | Ser | Thr | Gln | Val | Ser | Pro | Asp | Ser | Leu | Asp | Asn | Ala | Ser | Ala | Phe |
| | | | | 85 | | | | | 90 | | | | | 95 | |
| Asn | Thr | Thr | Asp | Ala | Tyr | Leu | Asn | Ala | Ser | Glu | Thr | Thr | Thr | Leu | Ser |
| | | | 100 | | | | | 105 | | | | | 110 | | |
| Pro | Ser | Gly | Ser | Ala | Val | Ile | Ser | Thr | Thr | Thr | Ile | Ala | Thr | Thr | Pro |
| | | | 115 | | | | | 120 | | | | | 125 | | |
| Ser | Lys | Pro | Thr | Cys | Asp | Glu | Lys | Tyr | Ala | Asn | Ile | Thr | Val | Asp | Tyr |
| | 130 | | | | | 135 | | | | | 140 | | | | |
| Leu | Tyr | Asn | Lys | Glu | Thr | Lys | Leu | Phe | Thr | Ala | Lys | Leu | Asn | Val | Asn |
| 145 | | | | | 150 | | | | | 155 | | | | | 160 |
| Glu | Asn | Val | Glu | Cys | Gly | Asn | Asn | Thr | Cys | Thr | Asn | Asn | Glu | Val | His |
| | | | | 165 | | | | | 170 | | | | | 175 | |
| Asn | Leu | Thr | Glu | Cys | Lys | Asn | Ala | Ser | Val | Ser | Ile | Ser | His | Asn | Ser |
| | | | 180 | | | | | 185 | | | | | 190 | | |
| Cys | Thr | Ala | Pro | Asp | Lys | Thr | Leu | Ile | Leu | Asp | Val | Pro | Pro | Gly | Val |
| | | | 195 | | | | | 200 | | | | | 205 | | |
| Glu | Lys | Phe | Gln | Leu | His | Asp | Cys | Thr | Gln | Val | Glu | Lys | Ala | Asp | Thr |
| | 210 | | | | | 215 | | | | | 220 | | | | |
| Thr | Ile | Cys | Leu | Lys | Trp | Lys | Asn | Ile | Glu | Thr | Phe | Thr | Cys | Asp | Thr |
| 225 | | | | | 230 | | | | | 235 | | | | | 240 |
| Gln | Asn | Ile | Thr | Tyr | Arg | Phe | Gln | Cys | Gly | Asn | Met | Ile | Phe | Asp | Asn |
| | | | | 245 | | | | | 250 | | | | | 255 | |
| Lys | Glu | Ile | Lys | Leu | Glu | Asn | Leu | Glu | Pro | Glu | His | Glu | Tyr | Lys | Cys |
| | | | 260 | | | | | 265 | | | | | 270 | | |
| Asp | Ser | Glu | Ile | Leu | Tyr | Asn | Asn | His | Lys | Phe | Thr | Asn | Ala | Ser | Lys |
| | | | | 275 | | | | | 280 | | | | | 285 | |
| Ile | Ile | Lys | Thr | Asp | Phe | Gly | Ser | Pro | Gly | Glu | Pro | Gln | Ile | Ile | Phe |
| | | | 290 | | | | | 295 | | | | | 300 | | |
| Cys | Arg | Ser | Glu | Ala | Ala | His | Gln | Gly | Val | Ile | Thr | Trp | Asn | Pro | Pro |
| 305 | | | | | 310 | | | | | 315 | | | | | 320 |
| Gln | Arg | Ser | Phe | His | Asn | Phe | Thr | Leu | Cys | Tyr | Ile | Lys | Glu | Thr | Glu |
| | | | | 325 | | | | | 330 | | | | | 335 | |
| Lys | Asp | Cys | Leu | Asn | Leu | Asp | Lys | Asn | Leu | Ile | Lys | Tyr | Asp | Leu | Gln |
| | | | 340 | | | | | 345 | | | | | 350 | | |
| Asn | Leu | Lys | Pro | Tyr | Thr | Lys | Tyr | Val | Leu | Ser | Leu | His | Ala | Tyr | Ile |
| | | | | 355 | | | | | 360 | | | | | 365 | |

```
Ile Ala Lys Val Gln Arg Asn Gly Ser Ala Ala Met Cys His Phe Thr
    370             375             380

Thr Lys Ser Ala Pro Pro Ser Gln Val Trp Asn Met Thr Val Ser Met
385             390             395             400

Thr Ser Asp Asn Ser Met His Val Lys Cys Arg Pro Pro Arg Asp Arg
            405             410             415

Asn Gly Pro His Glu Arg Tyr His Leu Glu Val Glu Ala Gly Asn Thr
            420             425             430

Leu Val Arg Asn Glu Ser His Lys Asn Cys Asp Phe Arg Val Lys Asp
            435             440             445

Leu Gln Tyr Ser Thr Asp Tyr Thr Phe Lys Ala Tyr Phe His Asn Gly
    450             455             460

Asp Tyr Pro Gly Glu Pro Phe Ile Leu His His Ser Thr Ser Tyr Asn
465             470             475             480

Ser Lys Ala Leu Ile Ala Phe Leu Ala Phe Leu Ile Ile Val Thr Ser
            485             490             495

Ile Ala Leu Leu Val Val Leu Tyr Lys Ile Tyr Asp Leu His Lys Lys
            500             505             510

Arg Ser Cys Asn Leu Asp Glu Gln Gln Glu Leu Val Glu Arg Asp Asp
            515             520             525

Glu Lys Gln Leu Met Asn Val Glu Pro Ile His Ala Asp Ile Leu Leu
    530             535             540

Glu Thr Tyr Lys Arg Lys Ile Ala Asp Glu Gly Arg Leu Phe Leu Ala
545             550             555             560

Glu Phe Gln Ser Ile Pro Arg Val Phe Ser Lys Phe Pro Ile Lys Glu
            565             570             575

Ala Arg Lys Pro Phe Asn Gln Asn Lys Asn Arg Tyr Val Asp Ile Leu
            580             585             590

Pro Tyr Asp Tyr Asn Arg Val Glu Leu Ser Glu Ile Asn Gly Asp Ala
    595             600             605

Gly Ser Asn Tyr Ile Asn Ala Ser Tyr Ile Asp Gly Phe Lys Glu Pro
    610             615             620

Arg Lys Tyr Ile Ala Ala Gln Gly Pro Arg Asp Glu Thr Val Asp Asp
625             630             635             640

Phe Trp Arg Met Ile Trp Glu Gln Lys Ala Thr Val Ile Val Met Val
            645             650             655

Thr Arg Cys Glu Glu Gly Asn Arg Asn Lys Cys Ala Glu Tyr Trp Pro
            660             665             670

Ser Met Glu Glu Gly Thr Arg Ala Phe Gly Asp Val Val Val Lys Ile
    675             680             685

Asn Gln His Lys Arg Cys Pro Asp Tyr Ile Ile Gln Lys Leu Asn Ile
    690             695             700

Val Asn Lys Lys Glu Lys Ala Thr Gly Arg Glu Val Thr His Ile Gln
705             710             715             720

Phe Thr Ser Trp Pro Asp His Gly Val Pro Glu Asp Pro His Leu Leu
            725             730             735

Leu Lys Leu Arg Arg Arg Val Asn Ala Phe Ser Asn Phe Phe Ser Gly
            740             745             750

Pro Ile Val Val His Cys Ser Ala Gly Val Gly Arg Thr Gly Thr Tyr
            755             760             765

Ile Gly Ile Asp Ala Met Leu Glu Gly Leu Glu Ala Glu Asn Lys Val
    770             775             780
```

```
Asp Val Tyr Gly Tyr Val Lys Leu Arg Arg Gln Arg Cys Leu Met
785                 790                 795                 800

Val Gln Val Glu Ala Gln Tyr Ile Leu Ile His Gln Ala Leu Val Glu
            805                 810                 815

Tyr Asn Gln Phe Gly Glu Thr Glu Val Asn Leu Ser Glu Leu His Pro
            820                 825                 830

Tyr Leu His Asn Met Lys Lys Arg Asp Pro Pro Ser Glu Pro Ser Pro
            835                 840                 845

Leu Glu Ala Glu Phe Gln Arg Leu Pro Ser Tyr Arg Ser Trp Arg Thr
850                 855                 860

Gln His Ile Gly Asn Gln Glu Glu Asn Lys Ser Lys Asn Arg Asn Ser
865                 870                 875                 880

Asn Val Ile Pro Tyr Asp Tyr Asn Arg Val Pro Leu Lys His Glu Leu
            885                 890                 895

Glu Met Ser Lys Glu Ser Glu His Asp Ser Asp Glu Ser Ser Asp Asp
            900                 905                 910

Asp Ser Asp Ser Glu Glu Pro Ser Lys Tyr Ile Asn Ala Ser Phe Ile
            915                 920                 925

Met Ser Tyr Trp Lys Pro Glu Val Met Ile Ala Ala Gln Gly Pro Leu
930                 935                 940

Lys Glu Thr Ile Gly Asp Phe Trp Gln Met Ile Phe Gln Arg Lys Val
945                 950                 955                 960

Lys Val Ile Val Met Leu Thr Glu Leu Lys His Gly Asp Gln Glu Ile
            965                 970                 975

Cys Ala Gln Tyr Trp Gly Glu Gly Lys Gln Thr Tyr Gly Asp Ile Glu
            980                 985                 990

Val Asp Leu Lys Asp Thr Asp Lys Ser Ser Thr Tyr Thr Leu Arg Val
            995                 1000                1005

Phe Glu Leu Arg His Ser Lys Arg Lys Asp Ser Arg Thr Val Tyr
    1010            1015            1020

Gln Tyr Gln Tyr Thr Asn Trp Ser Val Glu Gln Leu Pro Ala Glu
    1025            1030            1035

Pro Lys Glu Leu Ile Ser Met Ile Gln Val Val Lys Gln Lys Leu
    1040            1045            1050

Pro Gln Lys Asn Ser Ser Glu Gly Asn Lys His His Lys Ser Thr
    1055            1060            1065

Pro Leu Leu Ile His Cys Arg Asp Gly Ser Gln Gln Thr Gly Ile
    1070            1075            1080

Phe Cys Ala Leu Leu Asn Leu Leu Glu Ser Ala Glu Thr Glu Glu
    1085            1090            1095

Val Val Asp Ile Phe Gln Val Val Lys Ala Leu Arg Lys Ala Arg
    1100            1105            1110

Pro Gly Met Val Ser Thr Phe Glu Gln Tyr Gln Phe Leu Tyr Asp
    1115            1120            1125

Val Ile Ala Ser Thr Tyr Pro Ala Gln Asn Gly Gln Val Lys Lys
    1130            1135            1140

Asn Asn His Gln Glu Asp Lys Ile Glu Phe Asp Asn Glu Val Asp
    1145            1150            1155

Lys Val Lys Gln Asp Ala Asn Cys Val Asn Pro Leu Gly Ala Pro
    1160            1165            1170

Glu Lys Leu Pro Glu Ala Lys Glu Gln Ala Glu Gly Ser Glu Pro
    1175            1180            1185

Thr Ser Gly Thr Glu Gly Pro Glu His Ser Val Asn Gly Pro Ala
```

-continued

```
                    1190                1195                1200

Ser  Pro  Ala  Leu  Asn  Gln  Gly  Ser
     1205                1210

<210> SEQ ID NO 32
<211> LENGTH: 1145
<212> TYPE: PRT
<213> ORGANISM: Homo sapiens

<400> SEQUENCE: 32

Met  Thr  Met  Tyr  Leu  Trp  Leu  Lys  Leu  Leu  Ala  Phe  Gly  Phe  Ala  Phe
1                   5                       10                      15

Leu  Asp  Thr  Glu  Val  Phe  Val  Thr  Gly  Gln  Ser  Pro  Thr  Pro  Ser  Pro
                20                      25                      30

Thr  Asp  Ala  Tyr  Leu  Asn  Ala  Ser  Glu  Thr  Thr  Thr  Leu  Ser  Pro  Ser
                35                      40                      45

Gly  Ser  Ala  Val  Ile  Ser  Thr  Thr  Thr  Ile  Ala  Thr  Thr  Pro  Ser  Lys
        50                      55                      60

Pro  Thr  Cys  Asp  Glu  Lys  Tyr  Ala  Asn  Ile  Thr  Val  Asp  Tyr  Leu  Tyr
65                      70                      75                      80

Asn  Lys  Glu  Thr  Lys  Leu  Phe  Thr  Ala  Lys  Leu  Asn  Val  Asn  Glu  Asn
                85                      90                      95

Val  Glu  Cys  Gly  Asn  Asn  Thr  Cys  Thr  Asn  Asn  Glu  Val  His  Asn  Leu
                100                     105                     110

Thr  Glu  Cys  Lys  Asn  Ala  Ser  Val  Ser  Ile  Ser  His  Asn  Ser  Cys  Thr
            115                     120                     125

Ala  Pro  Asp  Lys  Thr  Leu  Ile  Leu  Asp  Val  Pro  Pro  Gly  Val  Glu  Lys
        130                     135                     140

Phe  Gln  Leu  His  Asp  Cys  Thr  Gln  Val  Glu  Lys  Ala  Asp  Thr  Thr  Ile
145                     150                     155                     160

Cys  Leu  Lys  Trp  Lys  Asn  Ile  Glu  Thr  Phe  Thr  Cys  Asp  Thr  Gln  Asn
                165                     170                     175

Ile  Thr  Tyr  Arg  Phe  Gln  Cys  Gly  Asn  Met  Ile  Phe  Asp  Asn  Lys  Glu
                180                     185                     190

Ile  Lys  Leu  Glu  Asn  Leu  Glu  Pro  Glu  His  Glu  Tyr  Lys  Cys  Asp  Ser
            195                     200                     205

Glu  Ile  Leu  Tyr  Asn  Asn  His  Lys  Phe  Thr  Asn  Ala  Ser  Lys  Ile  Ile
        210                     215                     220

Lys  Thr  Asp  Phe  Gly  Ser  Pro  Gly  Glu  Pro  Gln  Ile  Ile  Phe  Cys  Arg
225                     230                     235                     240

Ser  Glu  Ala  Ala  His  Gln  Gly  Val  Ile  Thr  Trp  Asn  Pro  Pro  Gln  Arg
                245                     250                     255

Ser  Phe  His  Asn  Phe  Thr  Leu  Cys  Tyr  Ile  Lys  Glu  Thr  Glu  Lys  Asp
                260                     265                     270

Cys  Leu  Asn  Leu  Asp  Lys  Asn  Leu  Ile  Lys  Tyr  Asp  Leu  Gln  Asn  Leu
            275                     280                     285

Lys  Pro  Tyr  Thr  Lys  Tyr  Val  Leu  Ser  Leu  His  Ala  Tyr  Ile  Ile  Ala
        290                     295                     300

Lys  Val  Gln  Arg  Asn  Gly  Ser  Ala  Ala  Met  Cys  His  Phe  Thr  Thr  Lys
305                     310                     315                     320

Ser  Ala  Pro  Pro  Ser  Gln  Val  Trp  Asn  Met  Thr  Val  Ser  Met  Thr  Ser
                325                     330                     335

Asp  Asn  Ser  Met  His  Val  Lys  Cys  Arg  Pro  Pro  Arg  Asp  Arg  Asn  Gly
                340                     345                     350
```

-continued

```
Pro His Glu Arg Tyr His Leu Glu Val Glu Ala Gly Asn Thr Leu Val
        355                 360                 365
Arg Asn Glu Ser His Lys Asn Cys Asp Phe Arg Val Lys Asp Leu Gln
    370                 375                 380
Tyr Ser Thr Asp Tyr Thr Phe Lys Ala Tyr Phe His Asn Gly Asp Tyr
385                 390                 395                 400
Pro Gly Glu Pro Phe Ile Leu His His Ser Thr Ser Tyr Asn Ser Lys
                405                 410                 415
Ala Leu Ile Ala Phe Leu Ala Phe Leu Ile Ile Val Thr Ser Ile Ala
                420                 425                 430
Leu Leu Val Val Leu Tyr Lys Ile Tyr Asp Leu His Lys Lys Arg Ser
            435                 440                 445
Cys Asn Leu Asp Glu Gln Gln Glu Leu Val Glu Arg Asp Asp Glu Lys
        450                 455                 460
Gln Leu Met Asn Val Glu Pro Ile His Ala Asp Ile Leu Leu Glu Thr
465                 470                 475                 480
Tyr Lys Arg Lys Ile Ala Asp Glu Gly Arg Leu Phe Leu Ala Glu Phe
                485                 490                 495
Gln Ser Ile Pro Arg Val Phe Ser Lys Phe Pro Ile Lys Glu Ala Arg
            500                 505                 510
Lys Pro Phe Asn Gln Asn Lys Asn Arg Tyr Val Asp Ile Leu Pro Tyr
        515                 520                 525
Asp Tyr Asn Arg Val Glu Leu Ser Glu Ile Asn Gly Asp Ala Gly Ser
        530                 535                 540
Asn Tyr Ile Asn Ala Ser Tyr Ile Asp Gly Phe Lys Glu Pro Arg Lys
545                 550                 555                 560
Tyr Ile Ala Ala Gln Gly Pro Arg Asp Glu Thr Val Asp Asp Phe Trp
                565                 570                 575
Arg Met Ile Trp Glu Gln Lys Ala Thr Val Ile Val Met Val Thr Arg
            580                 585                 590
Cys Glu Glu Gly Asn Arg Asn Lys Cys Ala Glu Tyr Trp Pro Ser Met
        595                 600                 605
Glu Glu Gly Thr Arg Ala Phe Gly Asp Val Val Val Lys Ile Asn Gln
    610                 615                 620
His Lys Arg Cys Pro Asp Tyr Ile Ile Gln Lys Leu Asn Ile Val Asn
625                 630                 635                 640
Lys Lys Glu Lys Ala Thr Gly Arg Glu Val Thr His Ile Gln Phe Thr
                645                 650                 655
Ser Trp Pro Asp His Gly Val Pro Glu Asp Pro His Leu Leu Leu Lys
            660                 665                 670
Leu Arg Arg Arg Val Asn Ala Phe Ser Asn Phe Phe Ser Gly Pro Ile
        675                 680                 685
Val Val His Cys Ser Ala Gly Val Gly Arg Thr Gly Thr Tyr Ile Gly
        690                 695                 700
Ile Asp Ala Met Leu Glu Gly Leu Glu Ala Glu Asn Lys Val Asp Val
705                 710                 715                 720
Tyr Gly Tyr Val Val Lys Leu Arg Arg Gln Arg Cys Leu Met Val Gln
                725                 730                 735
Val Glu Ala Gln Tyr Ile Leu Ile His Gln Ala Leu Val Glu Tyr Asn
            740                 745                 750
Gln Phe Gly Glu Thr Glu Val Asn Leu Ser Glu Leu His Pro Tyr Leu
        755                 760                 765
His Asn Met Lys Lys Arg Asp Pro Pro Ser Glu Pro Ser Pro Leu Glu
```

```
                770               775               780
Ala Glu Phe Gln Arg Leu Pro Ser Tyr Arg Ser Trp Arg Thr Gln His
785                 790               795                 800

Ile Gly Asn Gln Glu Glu Asn Lys Ser Lys Asn Arg Asn Ser Asn Val
                805                810                 815

Ile Pro Tyr Asp Tyr Asn Arg Val Pro Leu Lys His Glu Leu Glu Met
            820                 825                830

Ser Lys Glu Ser Glu His Asp Ser Asp Glu Ser Ser Asp Asp Asp Ser
                835                 840                845

Asp Ser Glu Glu Pro Ser Lys Tyr Ile Asn Ala Ser Phe Ile Met Ser
850                 855                 860

Tyr Trp Lys Pro Glu Val Met Ile Ala Ala Gln Gly Pro Leu Lys Glu
865                 870                875                  880

Thr Ile Gly Asp Phe Trp Gln Met Ile Phe Gln Arg Lys Val Lys Val
                885                 890                895

Ile Val Met Leu Thr Glu Leu Lys His Gly Asp Gln Glu Ile Cys Ala
            900                 905                910

Gln Tyr Trp Gly Glu Gly Lys Gln Thr Tyr Gly Asp Ile Glu Val Asp
        915                 920                925

Leu Lys Asp Thr Asp Lys Ser Ser Thr Tyr Thr Leu Arg Val Phe Glu
930                 935                940

Leu Arg His Ser Lys Arg Lys Asp Ser Arg Thr Val Tyr Gln Tyr Gln
945                 950                 955                960

Tyr Thr Asn Trp Ser Val Glu Gln Leu Pro Ala Glu Pro Lys Glu Leu
                965                970                975

Ile Ser Met Ile Gln Val Val Lys Gln Lys Leu Pro Gln Lys Asn Ser
            980                 985                990

Ser Glu Gly Asn Lys His His Lys Ser Thr Pro Leu Leu Ile His Cys
                995                1000              1005

Arg Asp Gly Ser Gln Gln Thr Gly Ile Phe Cys Ala Leu Leu Asn
    1010              1015              1020

Leu Leu Glu Ser Ala Glu Thr Glu Glu Val Val Asp Ile Phe Gln
    1025              1030              1035

Val Val Lys Ala Leu Arg Lys Ala Arg Pro Gly Met Val Ser Thr
    1040              1045              1050

Phe Glu Gln Tyr Gln Phe Leu Tyr Asp Val Ile Ala Ser Thr Tyr
    1055              1060              1065

Pro Ala Gln Asn Gly Gln Val Lys Lys Asn Asn His Gln Glu Asp
    1070              1075              1080

Lys Ile Glu Phe Asp Asn Glu Val Asp Lys Val Lys Gln Asp Ala
    1085              1090              1095

Asn Cys Val Asn Pro Leu Gly Ala Pro Glu Lys Leu Pro Glu Ala
    1100              1105              1110

Lys Glu Gln Ala Glu Gly Ser Glu Pro Thr Ser Gly Thr Glu Gly
    1115              1120              1125

Pro Glu His Ser Val Asn Gly Pro Ala Ser Pro Ala Leu Asn Gln
    1130              1135              1140

Gly Ser
    1145

<210> SEQ ID NO 33
<211> LENGTH: 1192
<212> TYPE: PRT
<213> ORGANISM: Homo sapiens
```

<400> SEQUENCE: 33

| | | | | | | | | | | | | | | |
|---|---|---|---|---|---|---|---|---|---|---|---|---|---|---|
| Met | Thr | Met | Tyr | Leu | Trp | Leu | Lys | Leu | Leu | Ala | Phe | Gly | Phe | Ala | Phe |
| 1 | | | | 5 | | | | | 10 | | | | | 15 | |
| Leu | Asp | Thr | Glu | Val | Phe | Val | Thr | Gly | Gln | Ser | Pro | Thr | Pro | Ser | Pro |
| | | | 20 | | | | | 25 | | | | | 30 | | |
| Thr | Gly | Val | Ser | Ser | Val | Gln | Thr | Pro | His | Leu | Pro | Thr | His | Ala | Asp |
| | | | | 35 | | | | | 40 | | | | | 45 | |
| Ser | Gln | Thr | Pro | Ser | Ala | Gly | Thr | Asp | Thr | Gln | Thr | Phe | Ser | Gly | Ser |
| | 50 | | | | | 55 | | | | | 60 | | | | |
| Ala | Ala | Asn | Ala | Lys | Leu | Asn | Pro | Thr | Pro | Gly | Ser | Asn | Ala | Ile | Ser |
| 65 | | | | | 70 | | | | | 75 | | | | | 80 |
| Asp | Ala | Tyr | Leu | Asn | Ala | Ser | Glu | Thr | Thr | Leu | Ser | Pro | Ser | Gly |
| | | | | 85 | | | | | 90 | | | | | 95 |
| Ser | Ala | Val | Ile | Ser | Thr | Thr | Thr | Ile | Ala | Thr | Thr | Pro | Ser | Lys | Pro |
| | | | | 100 | | | | | 105 | | | | | 110 | |
| Thr | Cys | Asp | Glu | Lys | Tyr | Ala | Asn | Ile | Thr | Val | Asp | Tyr | Leu | Tyr | Asn |
| | | | 115 | | | | | 120 | | | | | 125 | | |
| Lys | Glu | Thr | Lys | Leu | Phe | Thr | Ala | Lys | Leu | Asn | Val | Asn | Glu | Asn | Val |
| | 130 | | | | | 135 | | | | | 140 | | | | |
| Glu | Cys | Gly | Asn | Asn | Thr | Cys | Thr | Asn | Asn | Glu | Val | His | Asn | Leu | Thr |
| 145 | | | | | 150 | | | | | 155 | | | | | 160 |
| Glu | Cys | Lys | Asn | Ala | Ser | Val | Ser | Ile | Ser | His | Asn | Ser | Cys | Thr | Ala |
| | | | | 165 | | | | | 170 | | | | | 175 | |
| Pro | Asp | Lys | Thr | Leu | Ile | Leu | Asp | Val | Pro | Pro | Gly | Val | Glu | Lys | Phe |
| | | | 180 | | | | | 185 | | | | | 190 | | |
| Gln | Leu | His | Asp | Cys | Thr | Gln | Val | Glu | Lys | Ala | Asp | Thr | Thr | Ile | Cys |
| | | 195 | | | | | 200 | | | | | 205 | | | |
| Leu | Lys | Trp | Lys | Asn | Ile | Glu | Thr | Phe | Thr | Cys | Asp | Thr | Gln | Asn | Ile |
| | 210 | | | | | 215 | | | | | 220 | | | | |
| Thr | Tyr | Arg | Phe | Gln | Cys | Gly | Asn | Met | Ile | Phe | Asp | Asn | Lys | Glu | Ile |
| 225 | | | | | 230 | | | | | 235 | | | | | 240 |
| Lys | Leu | Glu | Asn | Leu | Glu | Pro | Glu | His | Glu | Tyr | Lys | Cys | Asp | Ser | Glu |
| | | | | 245 | | | | | 250 | | | | | 255 | |
| Ile | Leu | Tyr | Asn | Asn | His | Lys | Phe | Thr | Asn | Ala | Ser | Lys | Ile | Ile | Lys |
| | | | 260 | | | | | 265 | | | | | 270 | | |
| Thr | Asp | Phe | Gly | Ser | Pro | Gly | Glu | Pro | Gln | Ile | Ile | Phe | Cys | Arg | Ser |
| | | 275 | | | | | 280 | | | | | 285 | | | |
| Glu | Ala | Ala | His | Gln | Gly | Val | Ile | Thr | Trp | Asn | Pro | Pro | Gln | Arg | Ser |
| | 290 | | | | | 295 | | | | | 300 | | | | |
| Phe | His | Asn | Phe | Thr | Leu | Cys | Tyr | Ile | Lys | Glu | Thr | Glu | Lys | Asp | Cys |
| 305 | | | | | 310 | | | | | 315 | | | | | 320 |
| Leu | Asn | Leu | Asp | Lys | Asn | Leu | Ile | Lys | Tyr | Asp | Leu | Gln | Asn | Leu | Lys |
| | | | | 325 | | | | | 330 | | | | | 335 | |
| Pro | Tyr | Thr | Lys | Tyr | Val | Leu | Ser | Leu | His | Ala | Tyr | Ile | Ile | Ala | Lys |
| | | | 340 | | | | | 345 | | | | | 350 | | |
| Val | Gln | Arg | Asn | Gly | Ser | Ala | Ala | Met | Cys | His | Phe | Thr | Thr | Lys | Ser |
| | | 355 | | | | | 360 | | | | | 365 | | | |
| Ala | Pro | Pro | Ser | Gln | Val | Trp | Asn | Met | Thr | Val | Ser | Met | Thr | Ser | Asp |
| | 370 | | | | | 375 | | | | | 380 | | | | |
| Asn | Ser | Met | His | Val | Lys | Cys | Arg | Pro | Pro | Arg | Asp | Arg | Asn | Gly | Pro |
| 385 | | | | | 390 | | | | | 395 | | | | | 400 |
| His | Glu | Arg | Tyr | His | Leu | Glu | Val | Glu | Ala | Gly | Asn | Thr | Leu | Val | Arg |

-continued

```
                405                 410                 415
Asn Glu Ser His Lys Asn Cys Asp Phe Arg Val Lys Asp Leu Gln Tyr
            420                 425                 430

Ser Thr Asp Tyr Thr Phe Lys Ala Tyr Phe His Asn Gly Asp Tyr Pro
        435                 440                 445

Gly Glu Pro Phe Ile Leu His Ser Thr Ser Tyr Asn Ser Lys Ala
    450                 455                 460

Leu Ile Ala Phe Leu Ala Phe Leu Ile Val Thr Ser Ile Ala Leu
465                 470                 475                 480

Leu Val Val Leu Tyr Lys Ile Tyr Asp Leu His Lys Lys Arg Ser Cys
            485                 490                 495

Asn Leu Asp Glu Gln Gln Glu Leu Val Glu Arg Asp Asp Glu Lys Gln
        500                 505                 510

Leu Met Asn Val Glu Pro Ile His Ala Asp Ile Leu Leu Glu Thr Tyr
            515                 520                 525

Lys Arg Lys Ile Ala Asp Glu Gly Arg Leu Phe Leu Ala Glu Phe Gln
        530                 535                 540

Ser Ile Pro Arg Val Phe Ser Lys Phe Pro Ile Lys Glu Ala Arg Lys
545                 550                 555                 560

Pro Phe Asn Gln Asn Lys Asn Arg Tyr Val Asp Ile Leu Pro Tyr Asp
            565                 570                 575

Tyr Asn Arg Val Glu Leu Ser Glu Ile Asn Gly Asp Ala Gly Ser Asn
            580                 585                 590

Tyr Ile Asn Ala Ser Tyr Ile Asp Gly Phe Lys Glu Pro Arg Lys Tyr
        595                 600                 605

Ile Ala Ala Gln Gly Pro Arg Asp Glu Thr Val Asp Asp Phe Trp Arg
    610                 615                 620

Met Ile Trp Glu Gln Lys Ala Thr Val Ile Val Met Val Thr Arg Cys
625                 630                 635                 640

Glu Glu Gly Asn Arg Asn Lys Cys Ala Glu Tyr Trp Pro Ser Met Glu
            645                 650                 655

Glu Gly Thr Arg Ala Phe Gly Asp Val Val Lys Ile Asn Gln His
        660                 665                 670

Lys Arg Cys Pro Asp Tyr Ile Ile Gln Lys Leu Asn Ile Val Asn Lys
        675                 680                 685

Lys Glu Lys Ala Thr Gly Arg Glu Val Thr His Ile Gln Phe Thr Ser
        690                 695                 700

Trp Pro Asp His Gly Val Pro Glu Asp Pro His Leu Leu Lys Leu
705                 710                 715                 720

Arg Arg Arg Val Asn Ala Phe Ser Asn Phe Phe Ser Gly Pro Ile Val
                725                 730                 735

Val His Cys Ser Ala Gly Val Gly Arg Thr Gly Thr Tyr Ile Gly Ile
            740                 745                 750

Asp Ala Met Leu Glu Gly Leu Glu Ala Glu Asn Lys Val Asp Val Tyr
        755                 760                 765

Gly Tyr Val Val Lys Leu Arg Arg Gln Arg Cys Leu Met Val Gln Val
    770                 775                 780

Glu Ala Gln Tyr Ile Leu Ile His Gln Ala Leu Val Glu Tyr Asn Gln
785                 790                 795                 800

Phe Gly Glu Thr Glu Val Asn Leu Ser Glu Leu His Pro Tyr Leu His
            805                 810                 815

Asn Met Lys Lys Arg Asp Pro Pro Ser Glu Pro Ser Pro Leu Glu Ala
        820                 825                 830
```

-continued

Glu Phe Gln Arg Leu Pro Ser Tyr Arg Ser Trp Arg Thr Gln His Ile
                835                 840                 845

Gly Asn Gln Glu Glu Asn Lys Ser Lys Asn Arg Asn Ser Asn Val Ile
    850                 855                 860

Pro Tyr Asp Tyr Asn Arg Val Pro Leu Lys His Glu Leu Glu Met Ser
865                 870                 875                 880

Lys Glu Ser Glu His Asp Ser Asp Ser Ser Asp Asp Ser Asp
                885                 890                 895

Ser Glu Glu Pro Ser Lys Tyr Ile Asn Ala Ser Phe Ile Met Ser Tyr
            900                 905                 910

Trp Lys Pro Glu Val Met Ile Ala Ala Gln Gly Pro Leu Lys Glu Thr
            915                 920                 925

Ile Gly Asp Phe Trp Gln Met Ile Phe Gln Arg Lys Val Lys Val Ile
    930                 935                 940

Val Met Leu Thr Glu Leu Lys His Gly Asp Gln Glu Ile Cys Ala Gln
945                 950                 955                 960

Tyr Trp Gly Glu Gly Lys Gln Thr Tyr Gly Asp Ile Glu Val Asp Leu
                965                 970                 975

Lys Asp Thr Asp Lys Ser Ser Thr Tyr Thr Leu Arg Val Phe Glu Leu
            980                 985                 990

Arg His Ser Lys Arg Lys Asp Ser Arg Thr Val Tyr Gln Tyr Gln Tyr
            995                 1000                1005

Thr Asn Trp Ser Val Glu Gln Leu Pro Ala Glu Pro Lys Glu Leu
    1010                1015                1020

Ile Ser Met Ile Gln Val Val Lys Gln Lys Leu Pro Gln Lys Asn
    1025                1030                1035

Ser Ser Glu Gly Asn Lys His His Lys Ser Thr Pro Leu Leu Ile
    1040                1045                1050

His Cys Arg Asp Gly Ser Gln Gln Thr Gly Ile Phe Cys Ala Leu
    1055                1060                1065

Leu Asn Leu Leu Glu Ser Ala Glu Thr Glu Glu Val Val Asp Ile
    1070                1075                1080

Phe Gln Val Val Lys Ala Leu Arg Lys Ala Arg Pro Gly Met Val
    1085                1090                1095

Ser Thr Phe Glu Gln Tyr Gln Phe Leu Tyr Asp Val Ile Ala Ser
    1100                1105                1110

Thr Tyr Pro Ala Gln Asn Gly Gln Val Lys Lys Asn Asn His Gln
    1115                1120                1125

Glu Asp Lys Ile Glu Phe Asp Asn Glu Val Asp Lys Val Lys Gln
    1130                1135                1140

Asp Ala Asn Cys Val Asn Pro Leu Gly Ala Pro Glu Lys Leu Pro
    1145                1150                1155

Glu Ala Lys Glu Gln Ala Glu Gly Ser Glu Pro Thr Ser Gly Thr
    1160                1165                1170

Glu Gly Pro Glu His Ser Val Asn Gly Pro Ala Ser Pro Ala Leu
    1175                1180                1185

Asn Gln Gly Ser
    1190

<210> SEQ ID NO 34
<211> LENGTH: 1258
<212> TYPE: PRT
<213> ORGANISM: Homo sapiens

<400> SEQUENCE: 34

```
Met Thr Met Tyr Leu Trp Leu Lys Leu Leu Ala Phe Gly Phe Ala Phe
1               5                   10                  15
Leu Asp Thr Glu Val Phe Val Thr Gly Gln Ser Pro Thr Pro Ser Pro
            20                  25                  30
Thr Gly Leu Thr Thr Ala Lys Met Pro Ser Val Pro Leu Ser Ser Asp
        35                  40                  45
Pro Leu Pro Thr His Thr Thr Ala Phe Ser Pro Ala Ser Thr Phe Glu
    50                  55                  60
Arg Glu Asn Asp Phe Ser Glu Thr Thr Thr Ser Leu Ser Pro Asp Asn
65                  70                  75                  80
Thr Ser Thr Gln Val Ser Pro Asp Ser Leu Asp Asn Ala Ser Ala Phe
            85                  90                  95
Asn Thr Thr Gly Val Ser Ser Val Gln Thr Pro His Leu Pro Thr His
            100                 105                 110
Ala Asp Ser Gln Thr Pro Ser Ala Gly Thr Asp Thr Gln Thr Phe Ser
            115                 120                 125
Gly Ser Ala Ala Asn Ala Lys Leu Asn Pro Thr Pro Gly Ser Asn Ala
130                 135                 140
Ile Ser Asp Ala Tyr Leu Asn Ala Ser Glu Thr Thr Thr Leu Ser Pro
145                 150                 155                 160
Ser Gly Ser Ala Val Ile Ser Thr Thr Thr Ile Ala Thr Thr Pro Ser
            165                 170                 175
Lys Pro Thr Cys Asp Glu Lys Tyr Ala Asn Ile Thr Val Asp Tyr Leu
            180                 185                 190
Tyr Asn Lys Glu Thr Lys Leu Phe Thr Ala Lys Leu Asn Val Asn Glu
            195                 200                 205
Asn Val Glu Cys Gly Asn Asn Thr Cys Thr Asn Asn Glu Val His Asn
            210                 215                 220
Leu Thr Glu Cys Lys Asn Ala Ser Val Ser Ile Ser His Asn Ser Cys
225                 230                 235                 240
Thr Ala Pro Asp Lys Thr Leu Ile Leu Asp Val Pro Pro Gly Val Glu
            245                 250                 255
Lys Phe Gln Leu His Asp Cys Thr Gln Val Glu Lys Ala Asp Thr Thr
            260                 265                 270
Ile Cys Leu Lys Trp Lys Asn Ile Glu Thr Phe Thr Cys Asp Thr Gln
            275                 280                 285
Asn Ile Thr Tyr Arg Phe Gln Cys Gly Asn Met Ile Phe Asp Asn Lys
            290                 295                 300
Glu Ile Lys Leu Glu Asn Leu Glu Pro Glu His Glu Tyr Lys Cys Asp
305                 310                 315                 320
Ser Glu Ile Leu Tyr Asn Asn His Lys Phe Thr Asn Ala Ser Lys Ile
            325                 330                 335
Ile Lys Thr Asp Phe Gly Ser Pro Gly Glu Pro Gln Ile Ile Phe Cys
            340                 345                 350
Arg Ser Glu Ala Ala His Gln Gly Val Ile Thr Trp Asn Pro Pro Gln
            355                 360                 365
Arg Ser Phe His Asn Phe Thr Leu Cys Tyr Ile Lys Glu Thr Glu Lys
            370                 375                 380
Asp Cys Leu Asn Leu Asp Lys Asn Leu Ile Lys Tyr Asp Leu Gln Asn
385                 390                 395                 400
Leu Lys Pro Tyr Thr Lys Tyr Val Leu Ser Leu His Ala Tyr Ile Ile
            405                 410                 415
```

-continued

Ala Lys Val Gln Arg Asn Gly Ser Ala Ala Met Cys His Phe Thr Thr
            420                 425                 430

Lys Ser Ala Pro Pro Ser Gln Val Trp Asn Met Thr Val Ser Met Thr
            435                 440                 445

Ser Asp Asn Ser Met His Val Lys Cys Arg Pro Pro Arg Asp Arg Asn
            450                 455                 460

Gly Pro His Glu Arg Tyr His Leu Glu Val Glu Ala Gly Asn Thr Leu
465                 470                 475                 480

Val Arg Asn Glu Ser His Lys Asn Cys Asp Phe Arg Val Lys Asp Leu
            485                 490                 495

Gln Tyr Ser Thr Asp Tyr Thr Phe Lys Ala Tyr Phe His Asn Gly Asp
            500                 505                 510

Tyr Pro Gly Glu Pro Phe Ile Leu His His Ser Thr Ser Tyr Asn Ser
            515                 520                 525

Lys Ala Leu Ile Ala Phe Leu Ala Phe Leu Ile Ile Val Thr Ser Ile
            530                 535                 540

Ala Leu Leu Val Val Leu Tyr Lys Ile Tyr Asp Leu His Lys Lys Arg
545                 550                 555                 560

Ser Cys Asn Leu Asp Glu Gln Gln Glu Leu Val Glu Arg Asp Asp Glu
            565                 570                 575

Lys Gln Leu Met Asn Val Glu Pro Ile His Ala Asp Ile Leu Leu Glu
            580                 585                 590

Thr Tyr Lys Arg Lys Ile Ala Asp Glu Gly Arg Leu Phe Leu Ala Glu
            595                 600                 605

Phe Gln Ser Ile Pro Arg Val Phe Ser Lys Phe Pro Ile Lys Glu Ala
            610                 615                 620

Arg Lys Pro Phe Asn Gln Asn Lys Asn Arg Tyr Val Asp Ile Leu Pro
625                 630                 635                 640

Tyr Asp Tyr Asn Arg Val Glu Leu Ser Glu Ile Asn Gly Asp Ala Gly
            645                 650                 655

Ser Asn Tyr Ile Asn Ala Ser Tyr Ile Asp Gly Phe Lys Glu Pro Arg
            660                 665                 670

Lys Tyr Ile Ala Ala Gln Gly Pro Arg Asp Glu Thr Val Asp Asp Phe
            675                 680                 685

Trp Arg Met Ile Trp Glu Gln Lys Ala Thr Val Ile Val Met Val Thr
            690                 695                 700

Arg Cys Glu Glu Gly Asn Arg Asn Lys Cys Ala Glu Tyr Trp Pro Ser
705                 710                 715                 720

Met Glu Glu Gly Thr Arg Ala Phe Gly Asp Val Val Lys Ile Asn
            725                 730                 735

Gln His Lys Arg Cys Pro Asp Tyr Ile Ile Gln Lys Leu Asn Ile Val
            740                 745                 750

Asn Lys Lys Glu Lys Ala Thr Gly Arg Glu Val Thr His Ile Gln Phe
            755                 760                 765

Thr Ser Trp Pro Asp His Gly Val Pro Glu Asp Pro His Leu Leu Leu
            770                 775                 780

Lys Leu Arg Arg Arg Val Asn Ala Phe Ser Asn Phe Phe Ser Gly Pro
785                 790                 795                 800

Ile Val Val His Cys Ser Ala Gly Val Gly Arg Thr Gly Thr Tyr Ile
            805                 810                 815

Gly Ile Asp Ala Met Leu Glu Gly Leu Glu Ala Glu Asn Lys Val Asp
            820                 825                 830

```
Val Tyr Gly Tyr Val Lys Leu Arg Arg Gln Arg Cys Leu Met Val
                835                 840                 845

Gln Val Glu Ala Gln Tyr Ile Leu Ile His Gln Ala Leu Val Glu Tyr
        850                 855                 860

Asn Gln Phe Gly Glu Thr Glu Val Asn Leu Ser Glu Leu His Pro Tyr
865                 870                 875                 880

Leu His Asn Met Lys Lys Arg Asp Pro Pro Ser Glu Pro Ser Pro Leu
                885                 890                 895

Glu Ala Glu Phe Gln Arg Leu Pro Ser Tyr Arg Ser Trp Arg Thr Gln
                900                 905                 910

His Ile Gly Asn Gln Glu Glu Asn Lys Ser Lys Asn Arg Asn Ser Asn
                915                 920                 925

Val Ile Pro Tyr Asp Tyr Asn Arg Val Pro Leu Lys His Glu Leu Glu
                930                 935                 940

Met Ser Lys Glu Ser Glu His Asp Ser Asp Glu Ser Ser Asp Asp Asp
945                 950                 955                 960

Ser Asp Ser Glu Glu Pro Ser Lys Tyr Ile Asn Ala Ser Phe Ile Met
                965                 970                 975

Ser Tyr Trp Lys Pro Glu Val Met Ile Ala Ala Gln Gly Pro Leu Lys
            980                 985                 990

Glu Thr Ile Gly Asp Phe Trp Gln Met Ile Phe Gln Arg Lys Val Lys
            995                 1000                1005

Val Ile Val Met Leu Thr Glu Leu Lys His Gly Asp Gln Glu Ile
        1010                1015                1020

Cys Ala Gln Tyr Trp Gly Glu Gly Lys Gln Thr Tyr Gly Asp Ile
        1025                1030                1035

Glu Val Asp Leu Lys Asp Thr Asp Lys Ser Ser Thr Tyr Thr Leu
        1040                1045                1050

Arg Val Phe Glu Leu Arg His Ser Lys Arg Lys Asp Ser Arg Thr
        1055                1060                1065

Val Tyr Gln Tyr Gln Tyr Thr Asn Trp Ser Val Glu Gln Leu Pro
        1070                1075                1080

Ala Glu Pro Lys Glu Leu Ile Ser Met Ile Gln Val Val Lys Gln
        1085                1090                1095

Lys Leu Pro Gln Lys Asn Ser Ser Glu Gly Asn Lys His His Lys
        1100                1105                1110

Ser Thr Pro Leu Leu Ile His Cys Arg Asp Gly Ser Gln Gln Thr
        1115                1120                1125

Gly Ile Phe Cys Ala Leu Leu Asn Leu Leu Glu Ser Ala Glu Thr
        1130                1135                1140

Glu Glu Val Val Asp Ile Phe Gln Val Val Lys Ala Leu Arg Lys
        1145                1150                1155

Ala Arg Pro Gly Met Val Ser Thr Phe Glu Gln Tyr Gln Phe Leu
        1160                1165                1170

Tyr Asp Val Ile Ala Ser Thr Tyr Pro Ala Gln Asn Gly Gln Val
        1175                1180                1185

Lys Lys Asn Asn His Gln Glu Asp Lys Ile Glu Phe Asp Asn Glu
        1190                1195                1200

Val Asp Lys Val Lys Gln Asp Ala Asn Cys Val Asn Pro Leu Gly
        1205                1210                1215

Ala Pro Glu Lys Leu Pro Glu Ala Lys Glu Gln Ala Glu Gly Ser
        1220                1225                1230

Glu Pro Thr Ser Gly Thr Glu Gly Pro Glu His Ser Val Asn Gly
```

```
                1235                1240                1245
Pro Ala  Ser Pro Ala Leu Asn  Gln Gly Ser
        1250                1255

<210> SEQ ID NO 35
<211> LENGTH: 1240
<212> TYPE: PRT
<213> ORGANISM: Homo sapiens

<400> SEQUENCE: 35

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Val Ser Ser Val Gln Thr Pro His Leu Pro Thr His Ala Asp
        35                  40                  45

Ser Gln Thr Pro Ser Ala Gly Thr Asp Thr Gln Thr Phe Ser Gly Ser
    50                  55                  60

Ala Ala Asn Ala Lys Leu Asn Pro Thr Pro Gly Ser Asn Ala Ile Ser
65                  70                  75                  80

Asp Val Pro Gly Glu Arg Ser Thr Ala Ser Thr Phe Pro Thr Asp Pro
                85                  90                  95

Val Ser Pro Leu Thr Thr Thr Leu Ser Leu Ala His His Ser Ser Ala
            100                 105                 110

Ala Leu Pro Ala Arg Thr Ser Asn Thr Thr Ile Thr Ala Asn Thr Ser
        115                 120                 125

Asp Ala Tyr Leu Asn Ala Ser Glu Thr Thr Thr Leu Ser Pro Ser Gly
    130                 135                 140

Ser Ala Val Ile Ser Thr Thr Thr Ile Ala Thr Thr Pro Ser Lys Pro
145                 150                 155                 160

Thr Cys Asp Glu Lys Tyr Ala Asn Ile Thr Val Asp Tyr Leu Tyr Asn
                165                 170                 175

Lys Glu Thr Lys Leu Phe Thr Ala Lys Leu Asn Val Asn Glu Asn Val
            180                 185                 190

Glu Cys Gly Asn Asn Thr Cys Thr Asn Asn Glu Val His Asn Leu Thr
        195                 200                 205

Glu Cys Lys Asn Ala Ser Val Ser Ile Ser His Asn Ser Cys Thr Ala
    210                 215                 220

Pro Asp Lys Thr Leu Ile Leu Asp Val Pro Pro Gly Val Glu Lys Phe
225                 230                 235                 240

Gln Leu His Asp Cys Thr Gln Val Glu Lys Ala Asp Thr Thr Ile Cys
                245                 250                 255

Leu Lys Trp Lys Asn Ile Glu Thr Phe Thr Cys Asp Thr Gln Asn Ile
            260                 265                 270

Thr Tyr Arg Phe Gln Cys Gly Asn Met Ile Phe Asp Asn Lys Glu Ile
        275                 280                 285

Lys Leu Glu Asn Leu Glu Pro Glu His Glu Tyr Lys Cys Asp Ser Glu
    290                 295                 300

Ile Leu Tyr Asn Asn His Lys Phe Thr Asn Ala Ser Lys Ile Ile Lys
305                 310                 315                 320

Thr Asp Phe Gly Ser Pro Gly Glu Pro Gln Ile Ile Phe Cys Arg Ser
                325                 330                 335

Glu Ala Ala His Gln Gly Val Ile Thr Trp Asn Pro Pro Gln Arg Ser
            340                 345                 350
```

```
Phe His Asn Phe Thr Leu Cys Tyr Ile Lys Glu Thr Glu Lys Asp Cys
            355                 360                 365

Leu Asn Leu Asp Lys Asn Leu Ile Lys Tyr Asp Leu Gln Asn Leu Lys
        370                 375                 380

Pro Tyr Thr Lys Tyr Val Leu Ser Leu His Ala Tyr Ile Ile Ala Lys
385                 390                 395                 400

Val Gln Arg Asn Gly Ser Ala Ala Met Cys His Phe Thr Thr Lys Ser
                405                 410                 415

Ala Pro Pro Ser Gln Val Trp Asn Met Thr Val Ser Met Thr Ser Asp
            420                 425                 430

Asn Ser Met His Val Lys Cys Arg Pro Pro Arg Asp Arg Asn Gly Pro
        435                 440                 445

His Glu Arg Tyr His Leu Glu Val Glu Ala Gly Asn Thr Leu Val Arg
    450                 455                 460

Asn Glu Ser His Lys Asn Cys Asp Phe Arg Val Lys Asp Leu Gln Tyr
465                 470                 475                 480

Ser Thr Asp Tyr Thr Phe Lys Ala Tyr Phe His Asn Gly Asp Tyr Pro
                485                 490                 495

Gly Glu Pro Phe Ile Leu His His Ser Thr Ser Tyr Asn Ser Lys Ala
            500                 505                 510

Leu Ile Ala Phe Leu Ala Phe Leu Ile Ile Val Thr Ser Ile Ala Leu
        515                 520                 525

Leu Val Val Leu Tyr Lys Ile Tyr Asp Leu His Lys Lys Arg Ser Cys
    530                 535                 540

Asn Leu Asp Glu Gln Gln Glu Leu Val Glu Arg Asp Asp Glu Lys Gln
545                 550                 555                 560

Leu Met Asn Val Glu Pro Ile His Ala Asp Ile Leu Leu Glu Thr Tyr
                565                 570                 575

Lys Arg Lys Ile Ala Asp Glu Gly Arg Leu Phe Leu Ala Glu Phe Gln
            580                 585                 590

Ser Ile Pro Arg Val Phe Ser Lys Phe Pro Ile Lys Glu Ala Arg Lys
        595                 600                 605

Pro Phe Asn Gln Asn Lys Asn Arg Tyr Val Asp Ile Leu Pro Tyr Asp
    610                 615                 620

Tyr Asn Arg Val Glu Leu Ser Glu Ile Asn Gly Asp Ala Gly Ser Asn
625                 630                 635                 640

Tyr Ile Asn Ala Ser Tyr Ile Asp Gly Phe Lys Glu Pro Arg Lys Tyr
                645                 650                 655

Ile Ala Ala Gln Gly Pro Arg Asp Glu Thr Val Asp Asp Phe Trp Arg
            660                 665                 670

Met Ile Trp Glu Gln Lys Ala Thr Val Ile Val Met Val Thr Arg Cys
        675                 680                 685

Glu Glu Gly Asn Arg Asn Lys Cys Ala Glu Tyr Trp Pro Ser Met Glu
    690                 695                 700

Glu Gly Thr Arg Ala Phe Gly Asp Val Val Lys Ile Asn Gln His
705                 710                 715                 720

Lys Arg Cys Pro Asp Tyr Ile Ile Gln Lys Leu Asn Ile Val Asn Lys
                725                 730                 735

Lys Glu Lys Ala Thr Gly Arg Glu Val Thr His Ile Gln Phe Thr Ser
            740                 745                 750

Trp Pro Asp His Gly Val Pro Glu Asp Pro His Leu Leu Leu Lys Leu
        755                 760                 765

Arg Arg Arg Val Asn Ala Phe Ser Asn Phe Phe Ser Gly Pro Ile Val
```

```
                770              775              780
Val His Cys Ser Ala Gly Val Gly Arg Thr Gly Thr Tyr Ile Gly Ile
785              790              795              800

Asp Ala Met Leu Glu Gly Leu Glu Ala Glu Asn Lys Val Asp Val Tyr
             805              810              815

Gly Tyr Val Val Lys Leu Arg Arg Gln Arg Cys Leu Met Val Gln Val
             820              825              830

Glu Ala Gln Tyr Ile Leu Ile His Gln Ala Leu Val Glu Tyr Asn Gln
             835              840              845

Phe Gly Glu Thr Glu Val Asn Leu Ser Glu Leu His Pro Tyr Leu His
850              855              860

Asn Met Lys Lys Arg Asp Pro Pro Ser Glu Pro Ser Pro Leu Glu Ala
865              870              875              880

Glu Phe Gln Arg Leu Pro Ser Tyr Arg Ser Trp Arg Thr Gln His Ile
             885              890              895

Gly Asn Gln Glu Glu Asn Lys Ser Lys Asn Arg Asn Ser Asn Val Ile
             900              905              910

Pro Tyr Asp Tyr Asn Arg Val Pro Leu Lys His Glu Leu Glu Met Ser
             915              920              925

Lys Glu Ser Glu His Asp Ser Asp Glu Ser Ser Asp Asp Ser Asp
930              935              940

Ser Glu Glu Pro Ser Lys Tyr Ile Asn Ala Ser Phe Ile Met Ser Tyr
945              950              955              960

Trp Lys Pro Glu Val Met Ile Ala Ala Gln Gly Pro Leu Lys Glu Thr
             965              970              975

Ile Gly Asp Phe Trp Gln Met Ile Phe Gln Arg Lys Val Lys Val Ile
             980              985              990

Val Met Leu Thr Glu Leu Lys His Gly Asp Gln Glu Ile Cys Ala Gln
             995             1000             1005

Tyr Trp Gly Glu Gly Lys Gln Thr Tyr Gly Asp Ile Glu Val Asp
            1010             1015             1020

Leu Lys Asp Thr Asp Lys Ser Ser Thr Tyr Thr Leu Arg Val Phe
            1025             1030             1035

Glu Leu Arg His Ser Lys Arg Lys Asp Ser Arg Thr Val Tyr Gln
            1040             1045             1050

Tyr Gln Tyr Thr Asn Trp Ser Val Glu Gln Leu Pro Ala Glu Pro
            1055             1060             1065

Lys Glu Leu Ile Ser Met Ile Gln Val Val Lys Gln Lys Leu Pro
            1070             1075             1080

Gln Lys Asn Ser Ser Glu Gly Asn Lys His His Lys Ser Thr Pro
            1085             1090             1095

Leu Leu Ile His Cys Arg Asp Gly Ser Gln Gln Thr Gly Ile Phe
            1100             1105             1110

Cys Ala Leu Leu Asn Leu Leu Glu Ser Ala Glu Thr Glu Glu Val
            1115             1120             1125

Val Asp Ile Phe Gln Val Val Lys Ala Leu Arg Lys Ala Arg Pro
            1130             1135             1140

Gly Met Val Ser Thr Phe Glu Gln Tyr Gln Phe Leu Tyr Asp Val
            1145             1150             1155

Ile Ala Ser Thr Tyr Pro Ala Gln Asn Gly Gln Val Lys Lys Asn
            1160             1165             1170

Asn His Gln Glu Asp Lys Ile Glu Phe Asp Asn Glu Val Asp Lys
            1175             1180             1185
```

-continued

```
Val Lys Gln Asp Ala Asn Cys Val Asn Pro Leu Gly Ala Pro Glu
    1190                1195                1200

Lys Leu Pro Glu Ala Lys Glu Gln Ala Glu Gly Ser Glu Pro Thr
    1205                1210                1215

Ser Gly Thr Glu Gly Pro Glu His Ser Val Asn Gly Pro Ala Ser
    1220                1225                1230

Pro Ala Leu Asn Gln Gly Ser
    1235                1240

<210> SEQ ID NO 36
<211> LENGTH: 1306
<212> TYPE: PRT
<213> ORGANISM: Homo sapiens

<400> SEQUENCE: 36

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125

Gly Ser Ala Ala Asn Ala Lys Leu Asn Pro Thr Pro Gly Ser Asn Ala
130                 135                 140

Ile Ser Asp Val Pro Gly Glu Arg Ser Thr Ala Ser Thr Phe Pro Thr
145                 150                 155                 160

Asp Pro Val Ser Pro Leu Thr Thr Thr Leu Ser Leu Ala His His Ser
                165                 170                 175

Ser Ala Ala Leu Pro Ala Arg Thr Ser Asn Thr Thr Ile Thr Ala Asn
            180                 185                 190

Thr Ser Asp Ala Tyr Leu Asn Ala Ser Glu Thr Thr Thr Leu Ser Pro
        195                 200                 205

Ser Gly Ser Ala Val Ile Ser Thr Thr Thr Ile Ala Thr Thr Pro Ser
    210                 215                 220

Lys Pro Thr Cys Asp Glu Lys Tyr Ala Asn Ile Thr Val Asp Tyr Leu
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
            260                 265                 270

Leu Thr Glu Cys Lys Asn Ala Ser Val Ser Ile Ser His Asn Ser Cys
        275                 280                 285

Thr Ala Pro Asp Lys Thr Leu Ile Leu Asp Val Pro Pro Gly Val Glu
    290                 295                 300

Lys Phe Gln Leu His Asp Cys Thr Gln Val Glu Lys Ala Asp Thr Thr
```

```
                305              310              315              320
Ile Cys Leu Lys Trp Lys Asn Ile Glu Thr Phe Thr Cys Asp Thr Gln
                325              330              335
Asn Ile Thr Tyr Arg Phe Gln Cys Gly Asn Met Ile Phe Asp Asn Lys
                340              345              350
Glu Ile Lys Leu Glu Asn Leu Glu Pro Glu His Glu Tyr Lys Cys Asp
                355              360              365
Ser Glu Ile Leu Tyr Asn Asn His Lys Phe Thr Asn Ala Ser Lys Ile
                370              375              380
Ile Lys Thr Asp Phe Gly Ser Pro Gly Glu Pro Gln Ile Ile Phe Cys
385              390              395              400
Arg Ser Glu Ala Ala His Gln Gly Val Ile Thr Trp Asn Pro Pro Gln
                405              410              415
Arg Ser Phe His Asn Phe Thr Leu Cys Tyr Ile Lys Glu Thr Glu Lys
                420              425              430
Asp Cys Leu Asn Leu Asp Lys Asn Leu Ile Lys Tyr Asp Leu Gln Asn
                435              440              445
Leu Lys Pro Tyr Thr Lys Tyr Val Leu Ser Leu His Ala Tyr Ile Ile
                450              455              460
Ala Lys Val Gln Arg Asn Gly Ser Ala Ala Met Cys His Phe Thr Thr
465              470              475              480
Lys Ser Ala Pro Pro Ser Gln Val Trp Asn Met Thr Val Ser Met Thr
                485              490              495
Ser Asp Asn Ser Met His Val Lys Cys Arg Pro Pro Arg Asp Arg Asn
                500              505              510
Gly Pro His Glu Arg Tyr His Leu Glu Val Glu Ala Gly Asn Thr Leu
                515              520              525
Val Arg Asn Glu Ser His Lys Asn Cys Asp Phe Arg Val Lys Asp Leu
                530              535              540
Gln Tyr Ser Thr Asp Tyr Thr Phe Lys Ala Tyr Phe His Asn Gly Asp
545              550              555              560
Tyr Pro Gly Glu Pro Phe Ile Leu His His Ser Thr Ser Tyr Asn Ser
                565              570              575
Lys Ala Leu Ile Ala Phe Leu Ala Phe Leu Ile Ile Val Thr Ser Ile
                580              585              590
Ala Leu Leu Val Val Leu Tyr Lys Ile Tyr Asp Leu His Lys Lys Arg
                595              600              605
Ser Cys Asn Leu Asp Glu Gln Gln Glu Leu Val Glu Arg Asp Asp Glu
                610              615              620
Lys Gln Leu Met Asn Val Glu Pro Ile His Ala Asp Ile Leu Leu Glu
625              630              635              640
Thr Tyr Lys Arg Lys Ile Ala Asp Glu Gly Arg Leu Phe Leu Ala Glu
                645              650              655
Phe Gln Ser Ile Pro Arg Val Phe Ser Lys Phe Pro Ile Lys Glu Ala
                660              665              670
Arg Lys Pro Phe Asn Gln Asn Lys Asn Arg Tyr Val Asp Ile Leu Pro
                675              680              685
Tyr Asp Tyr Asn Arg Val Glu Leu Ser Glu Ile Asn Gly Asp Ala Gly
                690              695              700
Ser Asn Tyr Ile Asn Ala Ser Tyr Ile Asp Gly Phe Lys Glu Pro Arg
705              710              715              720
Lys Tyr Ile Ala Ala Gln Gly Pro Arg Asp Glu Thr Val Asp Asp Phe
                725              730              735
```

-continued

Trp Arg Met Ile Trp Glu Gln Lys Ala Thr Val Ile Val Met Val Thr
        740                 745                 750

Arg Cys Glu Glu Gly Asn Arg Asn Lys Cys Ala Glu Tyr Trp Pro Ser
        755                 760                 765

Met Glu Glu Gly Thr Arg Ala Phe Gly Asp Val Val Lys Ile Asn
770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
            805                 810                 815

Thr Ser Trp Pro Asp His Gly Val Pro Glu Asp Pro His Leu Leu Leu
            820                 825                 830

Lys Leu Arg Arg Arg Val Asn Ala Phe Ser Asn Phe Phe Ser Gly Pro
            835                 840                 845

Ile Val Val His Cys Ser Ala Gly Val Gly Arg Thr Gly Thr Tyr Ile
850                 855                 860

Gly Ile Asp Ala Met Leu Glu Gly Leu Glu Ala Glu Asn Lys Val Asp
865                 870                 875                 880

Val Tyr Gly Tyr Val Val Lys Leu Arg Arg Gln Arg Cys Leu Met Val
                885                 890                 895

Gln Val Glu Ala Gln Tyr Ile Leu Ile His Gln Ala Leu Val Glu Tyr
        900                 905                 910

Asn Gln Phe Gly Glu Thr Glu Val Asn Leu Ser Glu Leu His Pro Tyr
        915                 920                 925

Leu His Asn Met Lys Lys Arg Asp Pro Pro Ser Glu Pro Ser Pro Leu
        930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
            965                 970                 975

Val Ile Pro Tyr Asp Tyr Asn Arg Val Pro Leu Lys His Glu Leu Glu
            980                 985                 990

Met Ser Lys Glu Ser Glu His Asp  Ser Asp Glu Ser  Asp Asp Asp
        995                 1000                1005

Ser Asp  Ser Glu Glu Pro Ser  Lys Tyr Ile Asn Ala  Ser Phe Ile
    1010                1015                1020

Met Ser  Tyr Trp Lys Pro Glu  Val Met Ile Ala Ala  Gln Gly Pro
    1025                1030                1035

Leu Lys  Glu Thr Ile Gly Asp  Phe Trp Gln Met Ile  Phe Gln Arg
    1040                1045                1050

Lys Val  Lys Val Ile Val Met  Leu Thr Glu Leu Lys  His Gly Asp
    1055                1060                1065

Gln Glu  Ile Cys Ala Gln Tyr  Trp Gly Glu Gly Lys  Gln Thr Tyr
    1070                1075                1080

Gly Asp  Ile Glu Val Asp Leu  Lys Asp Thr Asp Lys  Ser Ser Thr
    1085                1090                1095

Tyr Thr  Leu Arg Val Phe Glu  Leu Arg His Ser Lys  Arg Lys Asp
    1100                1105                1110

Ser Arg  Thr Val Tyr Gln Tyr  Gln Tyr Thr Asn Trp  Ser Val Glu
    1115                1120                1125

Gln Leu  Pro Ala Glu Pro Lys  Glu Leu Ile Ser Met  Ile Gln Val
    1130                1135                1140

```
Val Lys Gln Lys Leu Pro Gln Lys Asn Ser Ser Glu Gly Asn Lys
    1145                1150                1155

His His Lys Ser Thr Pro Leu Leu Ile His Cys Arg Asp Gly Ser
    1160                1165                1170

Gln Gln Thr Gly Ile Phe Cys Ala Leu Leu Asn Leu Leu Glu Ser
    1175                1180                1185

Ala Glu Thr Glu Glu Val Val Asp Ile Phe Gln Val Val Lys Ala
    1190                1195                1200

Leu Arg Lys Ala Arg Pro Gly Met Val Ser Thr Phe Glu Gln Tyr
    1205                1210                1215

Gln Phe Leu Tyr Asp Val Ile Ala Ser Thr Tyr Pro Ala Gln Asn
    1220                1225                1230

Gly Gln Val Lys Lys Asn Asn His Gln Glu Asp Lys Ile Glu Phe
    1235                1240                1245

Asp Asn Glu Val Asp Lys Val Lys Gln Asp Ala Asn Cys Val Asn
    1250                1255                1260

Pro Leu Gly Ala Pro Glu Lys Leu Pro Glu Ala Lys Glu Gln Ala
    1265                1270                1275

Glu Gly Ser Glu Pro Thr Ser Gly Thr Glu Gly Pro Glu His Ser
    1280                1285                1290

Val Asn Gly Pro Ala Ser Pro Ala Leu Asn Gln Gly Ser
    1295                1300                1305

<210> SEQ ID NO 37
<211> LENGTH: 552
<212> TYPE: PRT
<213> ORGANISM: Homo sapiens

<400> SEQUENCE: 37

Gln Ser Pro Thr Pro Ser Pro Thr Gly Leu Thr Thr Ala Lys Met Pro
1               5                   10                  15

Ser Val Pro Leu Ser Ser Asp Pro Leu Pro Thr His Thr Thr Ala Phe
            20                  25                  30

Ser Pro Ala Ser Thr Phe Glu Arg Glu Asn Asp Phe Ser Glu Thr Thr
        35                  40                  45

Thr Ser Leu Ser Pro Asp Asn Thr Ser Thr Gln Val Ser Pro Asp Ser
    50                  55                  60

Leu Asp Asn Ala Ser Ala Phe Asn Thr Thr Gly Val Ser Ser Val Gln
65                  70                  75                  80

Thr Pro His Leu Pro Thr His Ala Asp Ser Gln Thr Pro Ser Ala Gly
                85                  90                  95

Thr Asp Thr Gln Thr Phe Ser Gly Ser Ala Ala Asn Ala Lys Leu Asn
            100                 105                 110

Pro Thr Pro Gly Ser Asn Ala Ile Ser Asp Val Pro Gly Glu Arg Ser
        115                 120                 125

Thr Ala Ser Thr Phe Pro Thr Asp Pro Val Ser Pro Leu Thr Thr Thr
    130                 135                 140

Leu Ser Leu Ala His His Ser Ser Ala Ala Leu Pro Ala Arg Thr Ser
145                 150                 155                 160

Asn Thr Thr Ile Thr Ala Asn Thr Ser Asp Ala Tyr Leu Asn Ala Ser
                165                 170                 175

Glu Thr Thr Thr Leu Ser Pro Ser Gly Ser Ala Val Ile Ser Thr Thr
            180                 185                 190

Thr Ile Ala Thr Thr Pro Ser Lys Pro Thr Cys Asp Glu Lys Tyr Ala
        195                 200                 205
```

-continued

```
Asn Ile Thr Val Asp Tyr Leu Tyr Asn Lys Glu Thr Lys Leu Phe Thr
            210                 215                 220

Ala Lys Leu Asn Val Asn Glu Asn Val Glu Cys Gly Asn Asn Thr Cys
225                 230                 235                 240

Thr Asn Asn Glu Val His Asn Leu Thr Glu Cys Lys Asn Ala Ser Val
                245                 250                 255

Ser Ile Ser His Asn Ser Cys Thr Ala Pro Asp Lys Thr Leu Ile Leu
            260                 265                 270

Asp Val Pro Pro Gly Val Glu Lys Phe Gln Leu His Asp Cys Thr Gln
            275                 280                 285

Val Glu Lys Ala Asp Thr Ile Cys Leu Lys Trp Lys Asn Ile Glu
            290                 295                 300

Thr Phe Thr Cys Asp Thr Gln Asn Ile Thr Tyr Arg Phe Gln Cys Gly
305                 310                 315                 320

Asn Met Ile Phe Asp Asn Lys Glu Ile Lys Leu Glu Asn Leu Glu Pro
                325                 330                 335

Glu His Glu Tyr Lys Cys Asp Ser Glu Ile Leu Tyr Asn Asn His Lys
            340                 345                 350

Phe Thr Asn Ala Ser Lys Ile Ile Lys Thr Asp Phe Gly Ser Pro Gly
            355                 360                 365

Glu Pro Gln Ile Ile Phe Cys Arg Ser Glu Ala Ala His Gln Gly Val
370                 375                 380

Ile Thr Trp Asn Pro Pro Gln Arg Ser Phe His Asn Phe Thr Leu Cys
385                 390                 395                 400

Tyr Ile Lys Glu Thr Glu Lys Asp Cys Leu Asn Leu Asp Lys Asn Leu
                405                 410                 415

Ile Lys Tyr Asp Leu Gln Asn Leu Lys Pro Tyr Thr Lys Tyr Val Leu
            420                 425                 430

Ser Leu His Ala Tyr Ile Ile Ala Lys Val Gln Arg Asn Gly Ser Ala
            435                 440                 445

Ala Met Cys His Phe Thr Thr Lys Ser Ala Pro Pro Ser Gln Val Trp
450                 455                 460

Asn Met Thr Val Ser Met Thr Ser Asp Asn Ser Met His Val Lys Cys
465                 470                 475                 480

Arg Pro Pro Arg Asp Arg Asn Gly Pro His Glu Arg Tyr His Leu Glu
                485                 490                 495

Val Glu Ala Gly Asn Thr Leu Val Arg Asn Glu Ser His Lys Asn Cys
            500                 505                 510

Asp Phe Arg Val Lys Asp Leu Gln Tyr Ser Thr Asp Tyr Thr Phe Lys
            515                 520                 525

Ala Tyr Phe His Asn Gly Asp Tyr Pro Gly Glu Pro Phe Ile Leu His
530                 535                 540

His Ser Thr Ser Tyr Asn Ser Lys
545                 550
```

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
    polynucleotide

<400> SEQUENCE: 38

Arg Asn Gly Pro His Glu Arg Tyr His Leu Glu Val Glu Ala Gly Asn

```
1               5                   10                  15
Thr

<210> SEQ ID NO 39
<211> LENGTH: 31
<212> TYPE: PRT
<213> ORGANISM: Artificial Sequence
<220> FEATURE:
<223> OTHER INFORMATION: Description of Artificial Sequence: Synthetic
      polynucleotide

<400> SEQUENCE: 39

Cys Arg Pro Pro Arg Asp Arg Asn Gly Pro His Glu Arg Tyr His Leu
1               5                   10                  15

Glu Val Glu Ala Gly Asn Thr Leu Val Arg Asn Glu Ser His Lys
            20                  25                  30

<210> SEQ ID NO 40
<211> LENGTH: 466
<212> TYPE: PRT
<213> ORGANISM: Homo sapiens

<400> SEQUENCE: 40

Gln Ser Pro Thr Pro Ser Pro Thr Asp Ala Tyr Leu Asn Ala Ser Glu
1               5                   10                  15

Thr Thr Thr Leu Ser Pro Ser Gly Ser Ala Val Ile Ser Thr Thr Thr
            20                  25                  30

Ile Ala Thr Thr Pro Ser Lys Pro Thr Cys Asp Glu Lys Tyr Ala Asn
        35                  40                  45

Ile Thr Val Asp Tyr Leu Tyr Asn Lys Glu Thr Lys Leu Phe Thr Ala
    50                  55                  60

Lys Leu Asn Val Asn Glu Asn Val Glu Cys Gly Asn Asn Thr Cys Thr
65                  70                  75                  80

Asn Asn Glu Val His Asn Leu Thr Glu Cys Lys Asn Ala Ser Val Ser
                85                  90                  95

Ile Ser His Asn Ser Cys Thr Ala Pro Asp Lys Thr Leu Ile Leu Asp
            100                 105                 110

Val Pro Pro Gly Val Glu Lys Phe Gln Leu His Asp Cys Thr Gln Val
        115                 120                 125

Glu Lys Ala Asp Thr Thr Ile Cys Leu Lys Trp Lys Asn Ile Glu Thr
    130                 135                 140

Phe Thr Cys Asp Thr Gln Asn Ile Thr Tyr Arg Phe Gln Cys Gly Asn
145                 150                 155                 160

Met Ile Phe Asp Asn Lys Glu Ile Lys Leu Glu Asn Leu Glu Pro Glu
                165                 170                 175

His Glu Tyr Lys Cys Asp Ser Glu Ile Leu Tyr Asn Asn His Lys Phe
            180                 185                 190
```

Thr Asn Ala Ser Lys Ile Ile Lys Thr Asp Phe Gly Ser Pro Gly Glu
            195                 200                 205

Pro Gln Ile Ile Phe Cys Arg Ser Glu Ala Ala His Gln Gly Val Ile
    210                 215                 220

Thr Trp Asn Pro Pro Gln Arg Ser Phe His Asn Phe Thr Leu Cys Tyr
225                 230                 235                 240

Ile Lys Glu Thr Glu Lys Asp Cys Leu Asn Leu Asp Lys Asn Leu Ile
                245                 250                 255

Lys Tyr Asp Leu Gln Asn Leu Lys Pro Tyr Thr Lys Tyr Val Leu Ser
                260                 265                 270

Leu His Ala Tyr Ile Ile Ala Lys Val Gln Arg Asn Gly Ser Ala Ala
                275                 280                 285

Met Cys His Phe Thr Thr Lys Ser Ala Pro Ser Gln Val Trp Asn
    290                 295                 300

Met Thr Val Ser Met Thr Ser Asp Asn Ser Met His Val Lys Cys Arg
305                 310                 315                 320

Pro Pro Arg Asp Arg Asn Gly Pro His Glu Arg Tyr His Leu Glu Val
                325                 330                 335

Glu Ala Gly Asn Thr Leu Val Arg Asn Glu Ser His Lys Asn Cys Asp
                340                 345                 350

Phe Arg Val Lys Asp Leu Gln Tyr Ser Thr Asp Tyr Thr Phe Lys Ala
            355                 360                 365

Tyr Phe His Asn Gly Asp Tyr Pro Gly Glu Pro Phe Ile Leu His His
            370                 375                 380

Ser Thr Ser Tyr Asn Ser Lys Ala Leu Ile Ala Phe Leu Ala Phe Leu
385                 390                 395                 400

Ile Ile Val Thr Ser Ile Ala Leu Leu Val Val Leu Tyr Lys Ile Tyr
                405                 410                 415

Asp Leu His Lys Lys Arg Ser Cys Asn Leu Asp Glu Gln Gln Glu Leu
                420                 425                 430

Val Glu Arg Asp Asp Glu Lys Gln Leu Met Asn Val Glu Pro Ile His
            435                 440                 445

Ala Asp Ile Leu Leu Glu Thr Tyr Lys Arg Lys Ile Ala Asp Glu Gly
    450                 455                 460

Arg Leu
465

<210> SEQ ID NO 41
<211> LENGTH: 421
<212> TYPE: PRT
<213> ORGANISM: Macaca mulatta

<400> SEQUENCE: 41

Asn Ala Ser Glu Thr Thr Thr Pro Ser Pro Ser Gly Ser Thr Val Ile
1               5                   10                  15

Ser Thr Pro Thr Ile Gly Asp Val Thr Leu Ser His Thr Glu Lys Tyr
            20                  25                  30

Ala Thr Ile Pro Val Asp Tyr Leu Tyr Asn Asn Lys Thr Lys Leu Phe
        35                  40                  45

Thr Ala Lys Leu Asn Val Asn Glu Asn Val Glu Cys Thr Asn Asn Asn
    50                  55                  60

His Thr His Asn Ile Cys Thr Asn Asn Glu Val Leu Asn Leu Pro Glu
65                  70                  75                  80

Cys Lys Glu Met Asn Val Phe Val Ser His Asn Ser Cys Thr Asp Arg
                85                  90                  95

```
His Lys Glu Leu Lys Leu Asp Val Pro Pro Glu Val Glu Lys Phe Gln
            100                 105                 110

Leu Asp Asp Cys Thr Pro Asp Val Glu Ala Asn Thr Thr Ile Cys Leu
            115                 120                 125

Lys Trp Lys Ile Ile Glu Thr Phe Ala Cys Asp Lys Ser Lys Ile Thr
            130                 135                 140

Tyr Arg Phe Gln Cys Gly Asn Lys Thr Tyr Asn Lys Glu Gly Ile Tyr
145                     150                 155                 160

Leu Glu Asn Leu Glu Pro Glu Tyr Glu Tyr Lys Cys Asp Ser Glu Ile
                165                 170                 175

Leu Tyr Asn Asn His Lys Tyr Ile Asn Ile Thr Lys Leu Ile Lys Thr
                180                 185                 190

Asp Phe Gly Ile Pro Gly Gln Pro Gln Asn Val Val Cys Arg His Glu
                195                 200                 205

Asp Ala His Gln Gly Val Ile Thr Trp Asn Pro Pro Gln Arg Ser Phe
            210                 215                 220

His Asn Phe Thr Leu Cys Tyr Val Ser Lys Thr Ala Lys Lys Cys Leu
225                     230                 235                 240

Ser Leu Asp Lys His Leu Thr Thr Tyr His Leu Gln Asn Leu Lys Pro
                245                 250                 255

Tyr Thr Asn Tyr Ser Leu Ser Leu His Ala Tyr Ile Ile Ala Lys Val
                260                 265                 270

Gln Arg Asn Gly Thr Ala Ala Thr Cys Asn Phe Thr Thr Glu Ser Ala
            275                 280                 285

Pro Pro Ser Gln Val Gln Asn Met Ile Val Ser Thr Ser Asp Asn Ser
            290                 295                 300

Met Arg Val Lys Cys Glu Gly Pro Arg Asp Val Asn Gly Pro Thr Gly
305                     310                 315                 320

Leu Tyr His Leu Glu Val Glu Ala Gly Asn Thr Leu Val Arg Asn Leu
                325                 330                 335

Ser Gln Ser Lys Cys Asp Phe Ser Val Asn Asn Leu Gln Tyr Ser Thr
                340                 345                 350

Tyr Tyr Asn Leu Lys Ala Tyr Tyr His Asn Gly Lys Tyr Ser Gly Glu
            355                 360                 365

Pro Val Ile Leu Arg Glu Ser Thr Ser Tyr Asn Ser Lys Ala Leu Ile
            370                 375                 380

Ala Phe Leu Ala Phe Leu Ile Ile Val Thr Ser Ile Ala Leu Leu Val
385                     390                 395                 400

Pro Ile His Ala Asp Ile Leu Leu Glu Thr Tyr Lys Arg Lys Ile Ala
                405                 410                 415

Asp Glu Gly Arg Leu
                420
```

ANTI-CD45 ANTIBODIES AND CONJUGATES THEREOF

RELATED APPLICATIONS

This application is a continuation of PCT/US2019/058971, filed Oct. 30, 2019, which claims priority to U.S. Provisional Application No. 62/753,002, filed on Oct. 30, 2018; U.S. Provisional Application No. 62/774,006, filed on Nov. 30, 2018; and U.S. Provisional Application No. 62/807,582, filed on Feb. 19, 2019. The entire content of each of the priority applications is incorporated by reference herein.

SEQUENCE LISTING

The instant application contains a Sequence Listing which has been submitted electronically in ASCII format and is hereby incorporated by reference in its entirety. Said ASCII copy, created on Apr. 29, 2021, is named M103034_1472US_C1_Sequence_Listing.txt and is 91,746 bytes in size.

FIELD

The present invention relates to the field of anti-CD45 antibodies or antibody drug conjugates thereof. The invention further relates to the treatment of patients suffering from various pathologies, such as blood diseases, metabolic disorders, cancers, and autoimmune diseases, among others, by administration of an anti-CD45 antibody or antibody drug conjugate (ADC), wherein the antibody or ADC is capable of binding CD45 on either hematopoietic stem cells or immune cells.

BACKGROUND

CD45 is a member of the protein tyrosine phosphatase (PTP) family and is a 180-240 kD transmembrane glycoprotein. CD45 is a signaling molecule that regulates a number of cellular processes including cell growth and differentiation. CD45 is a type I transmembrane protein that is found in various isoforms on differentiated hematopoietic cells, and has been shown to play a key role in T-cell and B-cells receptor signal transduction. In general, cells of hematopoietic origin, with the exception of mature erythrocytes and platelets, express CD45.

Different isoforms of CD45 exist due to variable splicing of its exons. The various isoforms of human CD45 differ in their extracellular domains, and are differentially expressed on subpopulations of B- and T-cell lymphocytes. At least six different human isoforms of CD45 mRNAs have been isolated, which contain all three exons (ABC isoform), two of the three exons (AB and BC isoform), only one exon (A isoform and B isoform), or no exons (O isoform) (Hermiston et al. (2003) *Annu Rev Immunol.* 21, 107-137). The suffix RA, RB, or RO indicates the requirement of the amino acid residues corresponding to exon A (RA), exon B (RB), or a lack of amino acid residues corresponding to exon A, B and C (RO) for the CD45 antigen expression, respectively.

Despite advances in the medicinal arts, there remains a demand for treating pathologies of the hematopoietic system, such as diseases of a particular blood cell, metabolic disorders, cancers, and autoimmune conditions, among others. While hematopoietic stem cells (HSCs) have significant therapeutic potential, a limitation that has hindered their use in the clinic has been the difficulty associated with ensuring engraftment of HSC transplants. In a host. In particular, hematopoietic stem cell therapies involving antibodies that target cell surface antigens on endogenous HSCs can trigger unwanted immunostimulatory and effector functions that impede engraftment of an exogenous HSC transplant. There remains a need. In the art for targeted therapies that can impact both HSCs and immune cells to improve transplantation, including therapies targeting CD45 as a potential antigen conditioning patients for HSC transplantation.

SUMMARY

Described herein are anti-CD45 antibodies (anti-human CD45 9(hCD45) antibodies) and antibody drug conjugates (ADCs) that bind to hematopoietic stem cells (HSCs) and are useful, for example, as conditioning agents for transplantation. In particular, the anti-CD45 antibodies and ADCs described herein can be used to specifically deplete host HSCs, immune cells and disease-causing cells. Further, the anti-CD45 antibodies and ADCs described herein may be used to treat patients with leukemia or lymphoma, as well as for treatment of patients with autoimmune diseases such as multiple sclerosis and scleroderma. The anti-CD45 antibodies and ADCs described herein satisfy a need for compositions and methods for promoting the engraftment of exogenous hematopoietic stem cell grafts such that the multipotency and hematopoietic functionality of these cells is preserved following transplantation.

In one embodiment, an isolated anti-CD45 antibody, or antigen binding portion thereof, comprises a heavy chain comprising a variable region comprising a CDR1 having the amino acid sequence as set forth in SEQ ID NO: 2, a CDR2 having the amino acid sequence as set forth in SEQ ID NO: 3, a CDR3 having the amino acid sequence as set forth in SEQ ID NO: 4, and comprises a light chain comprising a variable region comprising a CDR1 having the amino acid sequence as set forth in SEQ ID NO: 6, a CDR2 having the amino acid sequence as set forth in SEQ ID NO: 7, a CDR3 having the amino acid sequence as set forth in SEQ ID NO: 8.

In one embodiment, an isolated anti-CD45 antibody, or antigen binding portion thereof, comprises a heavy chain variable region comprises the amino acid sequence as set forth in SEQ ID NO: 1 and/or a light chain variable region comprises the amino acid sequence as set forth in SEQ ID NO: 5.

In one embodiment, an isolated anti-CD45 antibody, or antigen binding portion thereof, comprises a heavy chain comprising a variable region comprising a CDR1 having the amino acid sequence as set forth in SEQ ID NO: 10, a CDR2 having the amino acid sequence as set forth in SEQ ID NO: 11, a CDR3 having the amino acid sequence as set forth in SEQ ID NO: 12, and comprising a light chain comprising a variable region comprising a CDR1 having the amino acid sequence as set forth in SEQ ID NO: 14, a CDR2 having the amino acid sequence as set forth in SEQ ID NO: 15, a CDR3 having the amino acid sequence as set forth in SEQ ID NO: 16.

In one embodiment, an isolated anti-CD45 antibody, or antigen binding portion thereof, comprises a heavy chain variable region comprises the amino acid sequence as set forth in SEQ ID NO: 9 and/or a light chain variable region comprises the amino acid sequence as set forth in SEQ ID NO: 13.

In one embodiment, an isolated anti-CD45 antibody, or antigen binding portion thereof, comprises a heavy chain comprising a variable region comprising a CDR1 having the amino acid sequence as set forth in SEQ ID NO: 18, a CDR2 having the amino acid sequence as set forth in SEQ ID NO: 19, a CDR3 having the amino acid sequence as set forth in SEQ ID NO: 20, and comprising a light chain comprising a variable region comprising a CDR1 having the amino acid sequence as set forth in SEQ ID NO: 22, a CDR2 having the amino acid sequence as set forth in SEQ ID NO: 23, a CDR3 having the amino acid sequence as set forth in SEQ ID NO: 24.

In one embodiment, an isolated anti-CD45 antibody, or antigen binding portion thereof, comprises a heavy chain variable region comprises the amino acid sequence as set forth in SEQ ID NO: 17 and/or a light chain variable region comprises the amino acid sequence as set forth in SEQ ID NO: 21.

In one embodiment, an isolated anti-CD45 antibody, or antigen binding portion thereof, binds to the same epitope as an isolated anti-CD45 antibody, or antigen binding portion thereof, that comprises a heavy chain comprising a variable region comprising a CDR1 having the amino acid sequence as set forth in SEQ ID NO: 2, a CDR2 having the amino acid sequence as set forth in SEQ ID NO: 3, a CDR3 having the amino acid sequence as set forth in SEQ ID NO: 4, and comprises a light chain comprising a variable region comprising a CDR1 having the amino acid sequence as set forth in SEQ ID NO: 6, a CDR2 having the amino acid sequence as set forth in SEQ ID NO: 7, a CDR3 having the amino acid sequence as set forth in SEQ ID NO: 8; an isolated anti-CD45 antibody, or antigen binding portion thereof, that comprises a heavy chain variable region comprises the amino acid sequence as set forth in SEQ ID NO: 1 and/or a light chain variable region comprises the amino acid sequence as set forth in SEQ ID NO: 5; an isolated anti-CD45 antibody, or antigen binding portion thereof, that comprises a heavy chain comprising a variable region comprising a CDR1 having the amino acid sequence as set forth in SEQ ID NO: 10, a CDR2 having the amino acid sequence as set forth in SEQ ID NO: 11, a CDR3 having the amino acid sequence as set forth in SEQ ID NO: 12, and comprising a light chain comprising a variable region comprising a CDR1 having the amino acid sequence as set forth in SEQ ID NO: 14, a CDR2 having the amino acid sequence as set forth in SEQ ID NO: 15, a CDR3 having the amino acid sequence as set forth in SEQ ID NO: 16; an isolated anti-CD45 antibody, or antigen binding portion thereof, that comprises a heavy chain variable region comprises the amino acid sequence as set forth in SEQ ID NO: 9 and/or a light chain variable region comprises the amino acid sequence as set forth in SEQ ID NO: 13; or an isolated anti-CD45 antibody, or antigen binding portion thereof, that comprises a heavy chain comprising a variable region comprising a CDR1 having the amino acid sequence as set forth in SEQ ID NO: 18, a CDR2 having the amino acid sequence as set forth. In SEQ ID NO: 19, a CDR3 having the amino acid sequence as set forth in SEQ ID NO: 20, and comprising a light chain comprising a variable region comprising a CDR1 having the amino acid sequence as set forth in SEQ ID NO: 22, a CDR2 having the amino acid sequence as set forth in SEQ ID NO: 23, a CDR3 having the amino acid sequence as set forth in SEQ ID NO: 24.

In one embodiment, an isolated anti-CD45 antibody, or an antigen binding portion thereof, specifically binds to an epitope of human CD45 comprising residues 486R, 493Y, and 502T of SEQ ID NO: 37, and binds to cynomolgous and rhesus CD45; or specifically binds to an epitope of human CD45 comprising the amino acid sequence RNGPHERYHLEVEAGNT (SEQ ID NO: 38), and binds to cynomolgous and rhesus CD45; or specifically binds to an epitope of human CD45 comprising the amino acid sequence CRPPRDRNGPHERYHLEVEAGNTLVRNESHK (SEQ ID NO: 39), and binds to cynomolgous and rhesus CD45.

In another embodiment, an isolated anti-CD45 antibody, or an antigen binding portion thereof, that specifically binds to an epitope of human CD45 comprising residues 488R, 493Y, and 502T of SEQ ID NO: 37; binds to at least one additional amino acid, at least two additional amino acids, at least three additional amino acids, at least four additional amino acids, or at least five additional amino acids in a peptide comprising RNGPHERYHLEVEAGNT (SEQ ID NO: 38), wherein the additional amino acid residues are not residues 488R, 493Y, and 502T of SEQ ID NO: 37; and/or binds to cynomolgous and rhesus CD45.

In another embodiment, provided herein is an anti-CD45 antibody, or an antigen binding portion thereof, specifically binds to an epitope of human CD45 comprising residues 488R, 493Y, and 502T of SEQ ID NO: 37, and binds to cynomolgous and rhesus CD45.

In yet another embodiment, provided herein is an anti-CD45 antibody, or an antigen binding portion thereof, that specifically binds to an epitope of human CD45 comprising the amino acid sequence RNGPHERYHLEVEAGNT (SEQ ID NO: 38), and binds to cynomolgous and rhesus CD45.

In a further embodiment, provided herein is an anti-CD45 antibody, or an antigen binding portion thereof, that specifically binds to an epitope of human CD45 comprising the amino acid sequence CRPPRDRNGPHERYHLEVEAGNTLVRNESHK (SEQ ID NO: 39), and binds to cynomolgous and rhesus CD45.

In one embodiment, the antibody competes with antibody AbA for binding to human CD45.

In one embodiment, an isolated anti-CD45 antibody, or antigen binding portion thereof, is a de-immunized antibody described herein.

In one embodiment, an isolated anti-CD45 antibody, or antigen binding portion thereof, is a chimeric antibody, e.g., chimeric AbA, AbB, or AbC.

In one embodiment, an isolated anti-CD45 antibody, or antigen binding portion thereof, is a humanized antibody, e.g., humanized AbA, AbB, or AbC.

In one embodiment, an isolated anti-CD45 antibody, or antigen binding portion thereof, is an intact antibody, e.g., an intact IgG antibody.

In another embodiment, an isolated anti-CD45 antibody, or antigen binding portion thereof, is an isolated de-immunized monoclonal anti-CD45 antibody, or antigen binding portion thereof, that specifically binds human CD45 and cyno CD45, wherein the anti-CD45 antibody, or antigen binding portion thereof, of any one of claims 1-15 is the parent antibody of the de-immunized anti-CD45 antibody, or antigen binding portion thereof.

In one embodiment, an isolated anti-CD45 antibody, or antigen binding portion thereof, comprises an Fc region comprising at least one amino acid substitution is H435 or I235/H310/H435 (EU numbering), e.g., H435A (EU numbering), I235A/H310A/H435A (EU numbering).

In one embodiment, an isolated anti-CD45 antibody, or antigen binding portion thereof, is an IgG, e.g., an IgG1 or an IgG4.

In one embodiment, the invention features is an antibody drug conjugate (ADC) comprising an anti-CD45 antibody disclosed herein conjugated to a cytotoxin via a linker.

In some embodiments, the cytotoxin is an amatoxin, pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer.

In some embodiments, the cytotoxin is a microtubule-binding agent or an RNA polymerase inhibitor. In one embodiment, the cytotoxin is an RNA polymerase inhibitor.

In one embodiment, the RNA polymerase inhibitor is an amatoxin.

In some embodiments, the amatoxin is α-amanitin, β-amanitin, γ-amanitin, ε-amanitin, amanin, amaninamide, amanullin, amanullinic acid, or proamanullin.

In one embodiment, the amatoxin is represented by formula (IV)

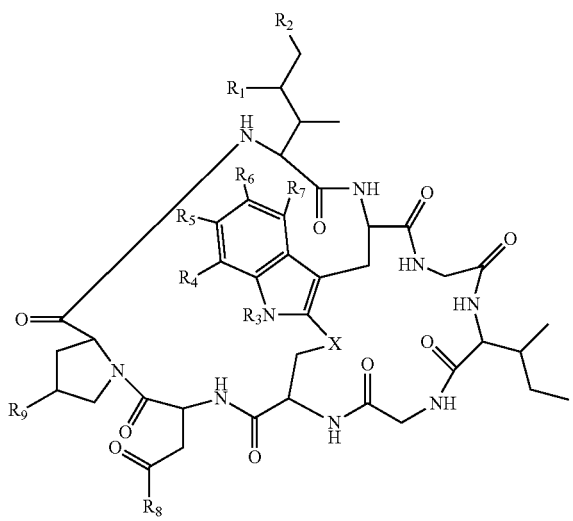

(IV)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a peptide, a dipeptide, —(C=O)—, or a combination thereof; and Z is a chemical moiety formed from a coupling reaction between a reactive substituent present on L and a reactive substituent present within the antibody or antigen-binding fragment thereof.

In one embodiment, the amatoxin-linker conjugate (Am-L-Z) is represented by formula (IA)

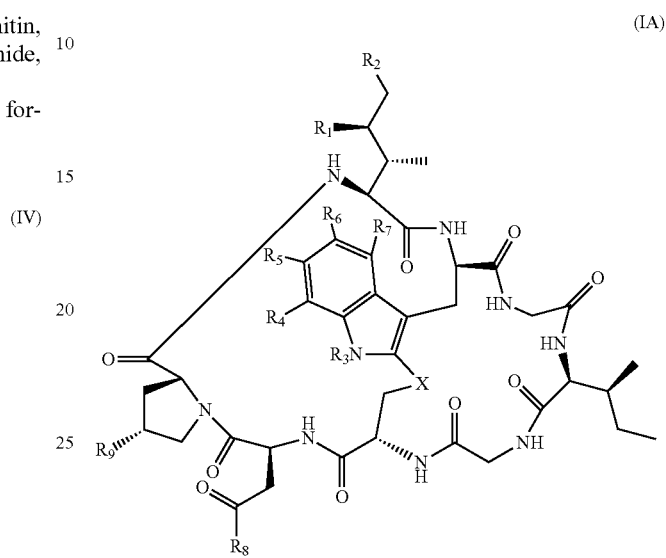

(IA)

wherein
$R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$ and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene a peptide, a dipeptide, —(C=O)—, or a combination thereof; and
Z is a chemical moiety formed from a coupling reaction between a reactive substituent Z' present on L, and a reactive substituent present within the antibody or antigen-binding fragment thereof,
wherein Am comprises exactly one $R_C$ substituent.

In some embodiments, L-Z is
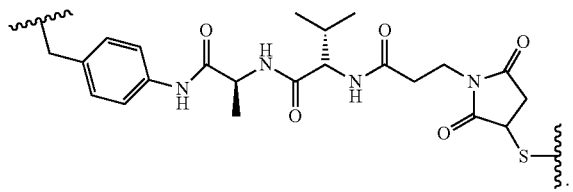
In one embodiment, the ADC has a formula Am-L-Z-Ab, represented by
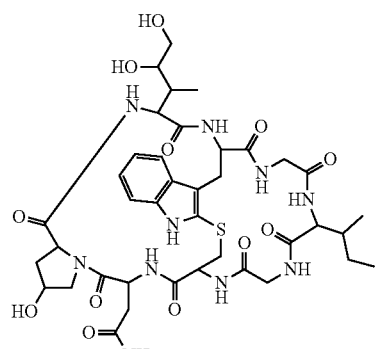
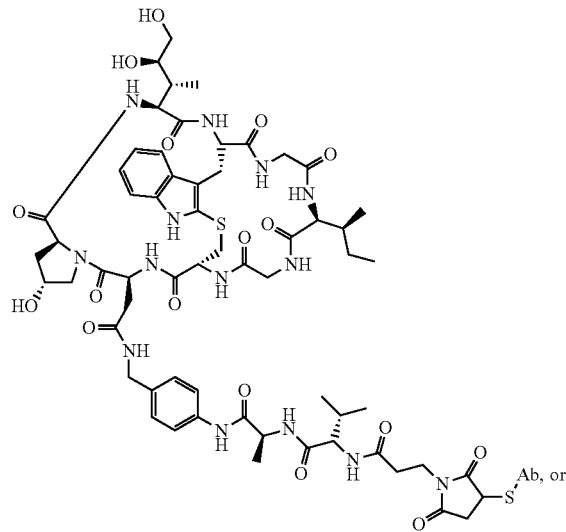
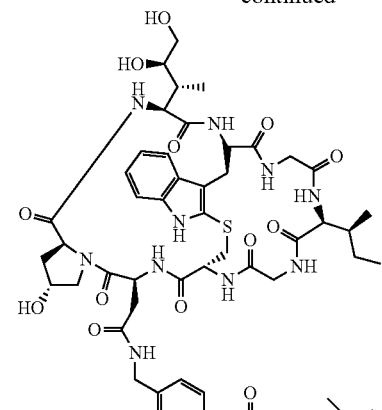
wherein Ab represents the point of attachment of the anti-CD45 antibody.
In some embodiments, the linker-chemical moiety L-Z is
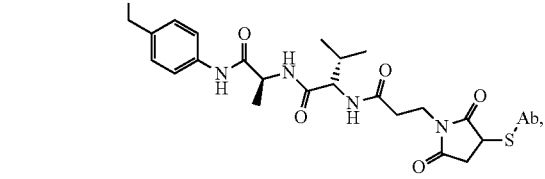
or
In some embodiments, L-Z is
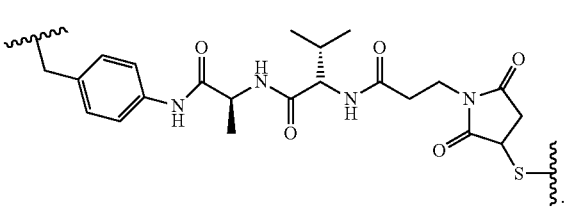
In one embodiment, the ADC has a formula Am-L-Z-Ab, represented by

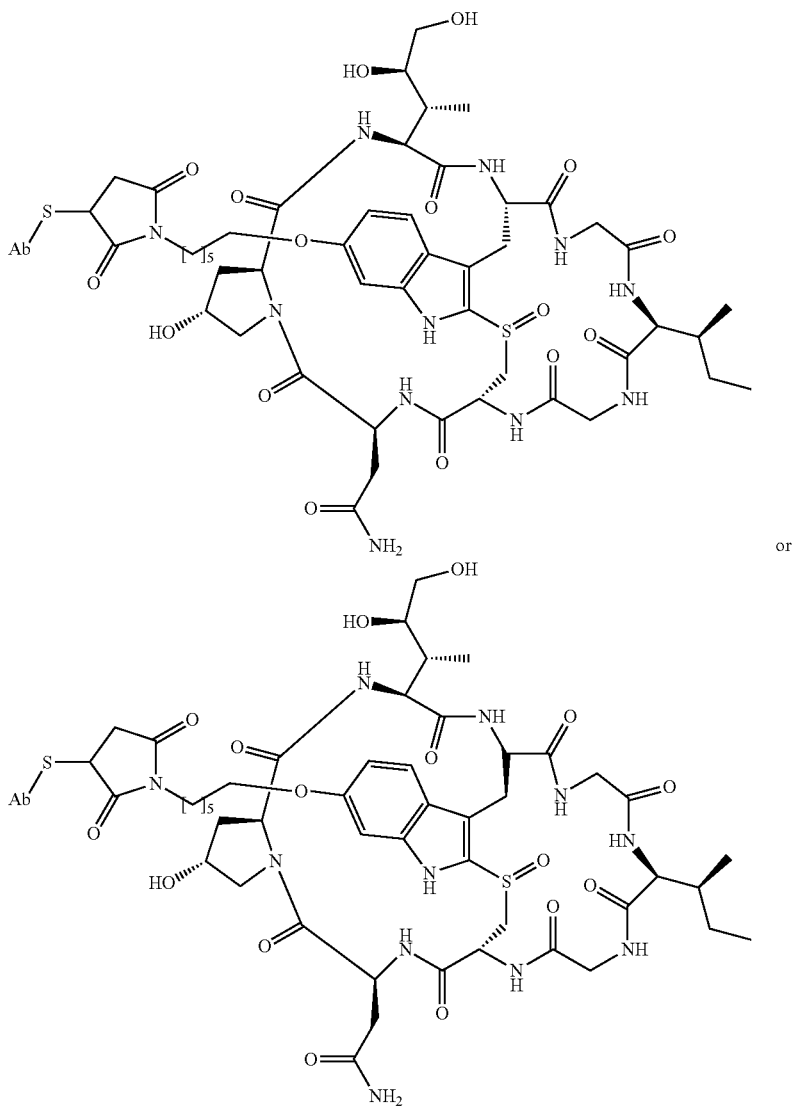

wherein Ab represents the point of attachment of the anti-CD45 antibody.

In one embodiment, the RNA polymerase inhibitor is an amanitin.

In one embodiment, the cytotoxin is selected from the group consisting of an pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or an indolinobenzodiazepine pseudodimer.

In some embodiments, the cytotoxin is a microtubule-binding agent or an auristatin. In some embodiments, the microtubule-binding agent is maytansine. In some embodiments, the microtubule-binding agent is a maytansinoid. In some embodiments, the maytansinoid is selected from the group consisting of DM1, DM3, and DM4, and maytansinol.

In one embodiment, the auristatin is MMAE or MMAF.

In some embodiments, the cytotoxin is an anthracycline selected from the group consisting of daunorubicin, doxorubicin, epirubicin, and idarubicin.

In one embodiment, the antibody is conjugated to the toxin by way of a cysteine residue in the Fc domain of the antibody.

In one embodiment, the cysteine residue is introduced by way of an amino acid substitution in the Fc domain of the antibody.

In one embodiment, the amino acid substitution is D265C and/or V205C (EU numbering).

In one embodiment, the ADC has a drug to antibody ratio (DAR) of 1, 2, 3, 4, 5, 6, 7, or 8.

Also provided is a pharmaceutical composition comprising an antibody or ADC described herein, and a pharmaceutically acceptable carrier.

Further provided is a method of depleting a population of hematopoietic stem cells (HSC) in a human patient, the method comprising administering to the patient an effective amount of an antibody or ADC described herein. In one embodiment, the method further comprises administering to the patient a transplant comprising hematopoietic stem cells.

In one embodiment, the transplant is allogeneic.

In one embodiment, the transplant is autologous.

Also provided is a method comprising administering to a human patient a transplant comprising hematopoietic stem cells, wherein the patient has been previously administered an antibody or ADC described herein in an amount sufficient to deplete a population of hematopoietic stem cells in the patient.

In one embodiment, the hematopoietic stem cell is a CD45+ cell.

In one embodiment, the patient has a blood disease, a metabolic disorder, cancer, or an autoimmune disease, or severe combined immunodeficiency disease (SCID).

Also disclosed is a method of treating leukemia in a human patient, said method comprising administering an antibody or ADC described herein to the human patient having leukemia.

Further provided is a method comprising administering to a human patient a transplant comprising hematopoietic stem cells, wherein the patient has been previously administered an antibody or an ADC described herein in an amount sufficient to deplete a population of immune cells in the patient.

In one embodiment, the immune cell is a CD137+, CD2+, or CD5+ cell.

In one embodiment, the immune cell is a T cell.

BRIEF DESCRIPTION OF THE FIGURES

In FIG. 2A, human PBMCs were cultured for four days in the presence of the indicated anti-CD45-amanitin conjugate (antibody AbB-amanitin; "CD45-AM") or control non-targeting isotype matched-ADCs ("Isotype-AM") and cell viability was measured in luminescence (RLU; y-axis) by Celltiter Glo as a function of antibody concentration (x-axis). In FIG. 2B, primary human CD34+ bone marrow cells were cultured for 5 days with CD45-AM or isotype-AM, and live CD34+ CD90+ HSC counts (y-axis) were determined by flow cytometry as a function of antibody concentration (x-axis).

FIGS. 3A and 3B graphically depict the results from an in vivo survival study using a xenograft murine model inoculated with human leukemia cells from immortalized cell lines that express CD45 (REH-Luc, a CD45 expressing ALL cell line tagged with luciferase ($5\times10^5$ cells/mouse)), showing that anti-CD45-AM (AbB conjugated to amanitin) doubles median survival to 40 days in the REH-Luc Xenograft Model. FIG. 3A shows that a single injection of 1 mg/kg anti-CD45-AM on day 5 after ALL inoculation resulted in longer survival by a median of 15 days compared to vehicle (PBS) treated controls or unconjugated anti-CD45 antibody (n=10 mice/group, p<0.0001). FIG. 3B shows representative bioluminescence signal pseudocolored images captured using the IVIS imaging system (Perkin Elmer) on day 19 post-implantation of the Anti-CD45-Am and isotype-AM treatment groups.

FIG. 4A shows results from a flow cytometry assay to evaluate CD45 cell surface expression on CD33+ splenocytes from diseased mice. FIGS. 4B-4G show survival curves of various PDX AML mice treated with a single intravenous dose of anti-CD45-AM, IgG1 isotype-AM, or vehicle (PBS), which were administered when 2-5% blasts were observed in the blood (4-5 mice/group/AML-PDX model). FIG. 4H shows CD45 cell surface expression on splenocytes from diseased mice evaluated by flow cytometry.

FIG. 5A is a schematic of an in vivo humanized NSG model. FIG. 5B shows the absolute number of human CD45+ cells in peripheral blood 14 days post-injection with anti-CD45-amanitin ("CD45-AM"), unconjugated anti-CD45 antibody ("CD45-naked"), or control non-targeting isotype matched-ADCs ("isotype-AM"). FIG. 5C shows the absolute number of human CD34+ cells in the bone marrow of humanized NSG mice 14 days post-administration. Similar results were obtained for CD34+CD90+ (data not shown). * p<0.05 when comparing CD45-AM against any control group.

FIG. 6A depicts a schematic of the in vivo cynomolgus model and study design (n=3/group except n=2 for 1 mg/kg. FIGS. 6B and 6C graphically depicts the pharmacokinetic of anti-CD45-amanitin ("CD45-AM") in cynomolgus monkeys, showing that CD45-AM exhibits non-linear PK indicative of target-mediated drug disposition (TMDD) PK with a short half-life suitable for transplant. "TAb" as used in FIG. 6B refers to total antibody using anti-hIgG1 detection, while ADC refers to anti-amanitin detection.

FIGS. 8A-8D graphically depict the results of assays detecting red blood cell count (FIG. 8A; in units of $10^6/\mu L$), the platelet count (FIG. 8B; in units of $10^3/\mu L$), plasma alanine aminotransaminase levels (FIG. 8C; in units of U/L) and plasma bilirubin levels (FIG. 8D; in U/mL) as a function of days post dose administration of varying doses of a fast half-life anti-CD45 amanitin antibody drug conjugate (CD45-Am) in comparison to a vehicle control (i.e., PBS).

FIG. 9A is a schematic of the AbA interaction site on CD45, with the amino acid sequence (SEQ ID NO: 39) of the region including the AbA epitope notated. Contact residues are highlighted as 486R, 493Y, and 502T (numbering referring to SEQ ID NO: 37) FIG. 9B shows the CD45 PDB structure (5FMV) with the epitope site indicated in black, corresponding to amino acid residues 486-502 (RNGPHERYHLEVEAGNT; SEQ ID NO: 38) of CD45. FIG. 9B includes a ribbon/surface representation of a front view (A); back view (B), side view 1 (C), side view 2 (D) and top view (E).

FIG. 10 depicts a sequence alignment of the fibronectin D1-D4 region of human CD45R0 (SEQ ID NO: 40) to the corresponding region in cynomolgus (cyno) CD45 (SEQ ID NO: 41). The epitope region of human CD45 bound by AbA and the corresponding region in cyno CD45 is indicated in bold.

DETAILED DESCRIPTION

Figure 1A:
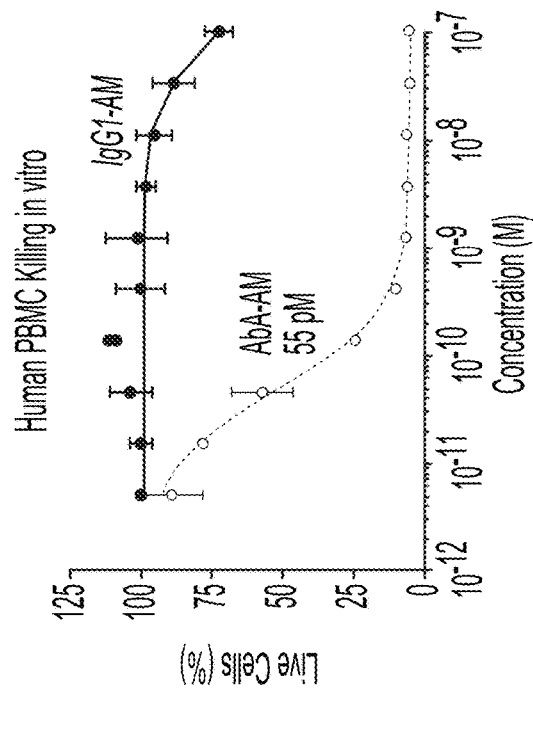
FIGS. 1A, 1B, 1C, 1D and 1E graphically depict results from experiments showing that anti-CD45 amanitin antibody drug conjugate (CD45-Am) enables in vitro and in vivo depletion of lymphocytes and hematopoietic stem cells (HSCs).

Disclosed herein are anti-CD45 antibodies, and conjugates thereof (antibody drug conjugates; ADC) that are useful as therapeutic agents, e.g., in treating leukemia or acting as a conditioning agent for transplantation. Accordingly, included herein are anti-hematopoietic cell antibodies (anti-CD45 antibodies) useful in hematopoietic stem cell therapies. For example, the antibodies or ADCs herein are useful in conditioning procedures, in which a patient is prepared for receipt of a transplant including hematopoietic stem cells. Such procedures promote the engraftment of a hematopoietic stem cell transplant. According to the methods described herein, a patient may be conditioned for hematopoietic stem cell transplant therapy by administration to the patient of an anti-CD45 ADC, antibody or antigen-binding fragment thereof capable of binding CD45 (e.g., CD45 expressed by hematopoietic cells (e.g., hematopoietic stem cells or mature immune cells (e.g., T cells)). As described herein, the anti-CD45 antibody may be covalently conjugated to a cytotoxin so as to form an antibody drug conjugate (ADC). Administration of an ADC capable of binding CD45 to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

The sections that follow provide a description of the anti-CD45 antibodies, or conjugates thereof, that can be administered to a patient, such as a patient suffering from a cancer or autoimmune disease, or a patient in need of hematopoietic stem cell transplant therapy in order to promote engraftment of hematopoietic stem cell grafts, as well as methods of administering such therapeutics to a patient (e.g., prior to hematopoietic stem cell transplantation).

Definitions

As used herein, the term "about" refers to a value that is within 5% above or below the value being described.

As used herein, the term "allogeneic", when used in the context of transplantation, is used to define cells (or tissue or an organ) that are transplanted from a genetically dissimilar donor to a recipient of the same species.

As used herein, the term "autologous" refers to cells or a graft where the donor and recipient are the same subject.

As used herein, the term "xenogeneic" refers to cells where the donor and recipient species are different.

As used herein, the term "immune cell" is intended to include, but is not limited to, a cell that is of hematopoietic origin and that plays a role in the immune response. Immune cells include, but are not limited to, T cells and natural killer (NK) cells. Natural killer cells are well known in the art. In one embodiment, natural killer cells include cell lines, such as NK-92 cells. Further examples of NK cell lines include NKG, YT, NK-YS, HANK-1, YTS cells, and NKL cells. An immune cell can be allogeneic or autologous.

As used herein, the term "antibody" refers to an immunoglobulin molecule that specifically binds to, or is immunologically reactive with, a particular antigen. An antibody includes, but is not limited to, monoclonal antibodies, polyclonal antibodies, multispecific antibodies (e.g., bispecific antibodies), genetically engineered antibodies, and otherwise modified forms of antibodies, including but not limited to de-immunized antibodies, chimeric antibodies, humanized antibodies, heteroconjugate antibodies (e.g., bi-tri- and quad-specific antibodies, diabodies, triabodies, and tetrabodies), and antibody fragments (i.e., antigen binding fragments of antibodies), including, for example, Fab', F(ab')$_2$, Fab, Fv, rIgG, and scFv fragments, so long as they exhibit the desired antigen-binding activity.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding fragment," as used herein, refers to one or more portions or an antibody that retain the ability to specifically bind to a target antigen. The antigen-binding function or an antibody can be performed by fragments of a full-length antibody. The antibody fragments can be, for example, a Fab, F(ab')$_2$, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL, and CH1 domains; (ii) a F(ab')$_2$ fragment, a bivalent fragment containing two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment that consists or a VH domain (see, e.g., Ward et al., Nature 341:544-546, 1989); (vii) a dAb which consists of a VH or a VL domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage or intact immunoglobulins, or, in certain cases, by chemical peptide synthesis procedures known in the art.

An "intact" or "full length" antibody, as used herein, refers to an antibody having two heavy (H) chain polypeptides and two light (L) chain polypeptides interconnected by disulfide bonds.

The term "specifically binds", as used herein, refers to the ability of an antibody (or ADC) to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. By way of example, an antibody "binds specifically" to a target if the antibody, when labeled, can be competed away from its target by the corresponding non-labeled antibody. In one embodiment, an antibody specifically binds to a target, e.g., an antigen expressed by hematopoietic stem cells, such as CD45; if the antibody has a $K_D$ for the target of at least about $10^{-4}$ M, about $10^{-5}$ M, about $10^{-6}$ M, about $10^{-7}$ M, about $10^{-8}$ M, about $10^{-9}$ M, about $10^{-10}$ M, about $10^{-11}$ M, about $10^{-12}$ M, or less (less meaning a number that is less than about $10^{-12}$, e.g. $10^{-13}$). In one embodiment, $K_D$ is determined according to standard bio-layer interferometry (BLI). It shall be understood, however, that the antibody may be capable of specifically binding to two or more antigens which are related in sequence. For example, in one embodiment, an antibody can specifically bind to both human and a non-human (e.g., mouse or non-human primate) orthologs of an antigen, e.g., CD45. Thus, as used herein, an antibody that "specifically binds to human CD45" is intended to refer to an antibody that binds to human CD45 (and possibly CD45 from one or more non-human species) but does not substantially bind to non-CD45 proteins. Preferably, the antibody binds to human CD45 with a $K_D$ or $1\times10^{-7}$ M or less, a $K_D$ or $5\times10^{-8}$ M or less, a $K_D$ of $3\times10^{-8}$ M or less, a $K_D$ of $1\times10^{-8}$ M or less, or a $K_D$ of $5\times10^{-8}$ M or less.

As used herein, the term "anti-CD45 antibody" or "an antibody that binds to CD45" refers to an antibody that is capable of binding CD45 with sufficient affinity such that the antibody is useful as a diagnostic and/or therapeutic agent in targeting CD45. In one embodiment, and anti-CD45 antibody (or fragment thereof) is an anti-human CD45 (hCD45) antibody (or fragment thereof).

The antibodies of the present disclosure are generally isolated or recombinant. "Isolated," when used herein refers to a polypeptide, e.g., an antibody, that has been separated and/or recovered from a cell or cell culture from which it was expressed. Ordinarily, an isolated antibody will be prepared by at least one purification step. Thus, an "isolated antibody," refers to an antibody which is substantially free of other antibodies having different antigenic specificities. For instance, an isolated antibody that specifically binds to CD45 is substantially free of antibodies that specifically bind antigens other than CD45.

The term "monoclonal antibody" as used herein refers to an antibody that is derived from a single clone, including any eukaryotic, prokaryotic, or phage clone, by any means available or known in the art, and is not limited to antibodies produced through hybridoma technology. Monoclonal antibodies useful with the present disclosure can be prepared using a wide variety of techniques known in the art including the use of hybridoma, recombinant, and phage display technologies, or a combination thereof.

As used herein, the term "diabody" refers to a bivalent antibody containing two polypeptide chains, in which each polypeptide chain includes VH and VL domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabody" refers to trivalent antibodies containing three peptide chains, each of which contains one VH domain and one VL domain joined by a linker that is exceedingly short (e.g., a linker composed of 1-2 amino acids) to permit intramolecular association of VH and VL domains within the same peptide chain. In order to fold into their native structures, peptides configured in this way typically trimerize so as to position the VH and VL domains of neighboring peptide chains spatially proximal to one another (see, for example, Holliger et al., Proc. Natl. Acad. Sci. USA 90:6444-48, 1993).

As used herein, the term "bispecific antibody" refers to an antibody, for example, a monoclonal, e.g., a de-immunized or humanized antibody, that is capable of binding two different epitopes that can be on the same or different antigens. For instance, one of the binding specificities can be directed towards an epitope on a hematopoietic stem cell surface antigen, such as CD45, and the other can specifically bind an epitope on a different hematopoietic stem cell surface antigen or another cell surface protein, such as a receptor or receptor subunit involved in a signal transduction pathway that potentiates cell growth, among others. In some embodiments, the binding specificities can be directed towards unique, non-overlapping epitopes on the same target antigen (i.e., a biparatopic antibody).

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each contain four framework regions that primarily adopt a β-sheet configuration, connected by three CDRs, which form loops that connect, and in some cases form part of, the β-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, MD., 1987). In certain embodiments, numbering of immunoglobulin amino acid residues is performed according to the immunoglobulin amino acid residue numbering system of Kabat et al., unless otherwise indicated (although any antibody numbering scheme, including, but not limited to IMGT and Chothia, can be utilized).

Also provided are "conservative sequence modifications" of the sequences set forth in SEQ ID NOs described herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs described herein by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CD45 antibody is preferably replaced with another amino acid residue from the same side chain family. Methods of identifying nucleotide and amino acid conservative substitutions that do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)).

The terms "Fc", "Fc region," "Fc domain," and "IgG Fc domain" as used herein refer to the portion of an immunoglobulin, e.g., an IgG molecule, that correlates to a crystallizable fragment obtained by papain digestion of an IgG molecule. The Fc region comprises the C-terminal half of two heavy chains of an IgG molecule that are linked by disulfide bonds, it has no antigen binding activity but contains the carbohydrate moiety and binding sites for complement and Fc receptors, including the FcRn receptor (see below). For example, an Fc domain contains the second constant domain CH2 (e.g., residues at EU positions 231-340 of human IgG1) and the third constant domain CH3 (e.g., residues at EU positions 341-447 of human IgG1). As used herein, the Fc domain includes the "lower hinge region" (e.g., residues at EU positions 233-239 of human IgG1).

Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known. In the art can exist. Thus, a "wild type IgG Fc domain" or "WT IgG Fc domain" refers to any naturally occurring IgG Fc region (i.e., any allele). The sequences of the heavy chains of human IgG1, IgG2, IgG3 and IgG4 can be found. In a number of sequence databases, for example, at the Uniprot database (www.uniprot.org) under accession numbers P01857 (IGHG1_HUMAN), P01859 (IGHG2_HUMAN), P01880 (IGHG3_HUMAN), and P01881 (IGHG1_HUMAN), respectively.

The terms "modified Fc region" or "variant Fc region" as used herein refers to an IgG Fc domain comprising one or more amino acid substitutions, deletions, insertions or modifications introduced at any position within the Fc domain. In certain aspects a variant IgG Fc domain comprises one or more amino acid substitutions resulting in decreased or ablated binding affinity for an Fc gamma R and/or C1q as compared to the wild type Fc domain not comprising the one or more amino acid substitutions. Further, Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a variant Fc domain (e.g., an antibody, fusion protein or conjugate) can exhibit altered binding affinity for at least one or more Fc ligands (e.g., Fc gamma Rs) relative to a corresponding antibody otherwise having the same amino acid sequence but not comprising the one or more amino acid substitution, deletion, insertion or modifications such as, for example, an unmodified Fc region containing naturally occurring amino acid residues at the corresponding position in the Fc region.

Variant Fc domains are defined according to the amino acid modifications that compose them. For all amino acid substitutions discussed herein in regard to the Fc region, numbering is always according to the EU index as in Kabat. Thus, for example, D265C is an Fc variant with the aspartic acid (D) at EU position 285 substituted with cysteine (C) relative to the parent Fc domain. It is noted that the order in which substitutions are provided is arbitrary. Likewise, e.g., D285C/L234A/L235A defines a variant Fc variant with substitutions at EU positions 285 (D to C), 234 (L to A), and 235 (L to A) relative to the parent Fc domain. A variant can also be designated according to its final amino acid composition in the mutated EU amino acid positions. For example, the L234A/L235A mutant can be referred to as "LALA". As a further example, the E233P.L234V.L235A.delG238 (deletion of 238) mutant can be referred to as "EPLVLAdelG". As yet another example, the I253A.H310A.H435A mutant can be referred to as "IHH". It is noted that the order in which substitutions are provided is arbitrary.

The terms "Fc gamma receptor" or "Fc gamma R" as used herein refer to any member of the family of proteins that bind the IgG antibody Fc region and are encoded by the Fc gamma R genes. In humans this family includes but is not limited to Fcg amma RI (CD64), including isoforms Fc gamma RIa, Fc gamma RIb, and Fc gamma RIc; Fc gamma RII (CD32), including isoforms Fc gamma RIIa (including allotypes H131 and R131), Fc gamma RIIb (including Fc gamma RIIb-1 and Fc gamma RIIb-2), and Fc gamma RIIc; and Fc gamma RIII (CD16), including isoforms Fc gamma RIIIa (including allotypes V158 and F158) and Fc gamma RIIIb (including allotypes Fc gamma RIIIb-NA1 and Fc gamma RIIIb-NA2), as well as any undiscovered human Fc gamma Rs or Fc gamma R isoforms or allotypes. An Fc gamma R can be from any organism, including but not limited to humans, mice, rats, rabbits, and monkeys. Mouse Fc gamma Rs include but are not limited to Fc gamma RI (CD64), Fc gamma RII (CD32), Fc gamma RIII (CD16), and Fc gamma RIII-2 (CD16-2), as well as any undiscovered mouse Fc gamma Rs or Fc gamma R isoforms or allotypes.

The term "effector function" as used herein refers to a biochemical event that results from the interaction of an Fc domain with an Fc receptor. Effector functions include but are not limited to ADCC, ADCP, and CDC. By "effector cell" as used herein is meant a cell of the immune system that expresses or one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and gamma delta T cells, and can be from any organism included but not limited to humans, mice, rats, rabbits, and monkeys.

The term "silent", "silenced", or "silencing" as used herein refers to an antibody having a modified Fc region described herein that has decreased binding to an Fc gamma receptor (FcγR) relative to binding of an identical antibody comprising an unmodified Fc region to the FcγR (e.g., a decrease in binding to a FcγR by at least 70%, at least 80%, at least 90%, at least 95%, at least 98%, at least 99%, or 100% relative to binding of the identical antibody comprising an unmodified Fc region to the FcγR as measured by, e.g., BLI). In some embodiments, the Fc silenced antibody has no detectable binding to an FcγR. Binding of an antibody having a modified Fc region to an FcγR can be determined using a variety of techniques known. In the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE™ analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more or the components being examined and/or employ a variety of detection methods including but not limited to chromogenic, fluorescent, luminescent, or isotopic labels. A detailed description of binding affinities and kinetics can be found. In Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

As used herein, the term "identical antibody comprising an unmodified Fc region" refers to an antibody that lacks the recited amino acid substitutions (e.g., D265C, H435A, L234A, and/or L235A), but otherwise has the same amino acid sequence as the Fc modified antibody to which it is being compared.

The terms "antibody-dependent cell-mediated cytotoxicity" or "ADCC" refer to a form of cytotoxicity in which a polypeptide comprising an Fc domain, e.g., an antibody, bound onto Fc receptors (FcRs) present on certain cytotoxic cells (e.g., primarily NK cells, neutrophils, and macrophages) and enables these cytotoxic effector cells to bind specifically to an antigen-bearing "target cell" and subsequently kill the target cell with cytotoxins. (Hogarth et al., Nature review Drug Discovery 2012, 11:313) It is contemplated that, in addition to antibodies and fragments thereof, other polypeptides comprising Fc domains, e.g., Fc fusion proteins and Fc conjugate proteins, having the capacity to bind specifically to an antigen-bearing target cell will be able to effect cell-mediated cytotoxicity.

For simplicity, the cell-mediated cytotoxicity resulting from the activity of a polypeptide comprising an Fc domain is also referred to herein as ADCC activity. The ability of any particular polypeptide of the present disclosure to mediate lysis of the target cell by ADCC can be assayed. To assess ADCC activity, a polypeptide of interest (e.g., an antibody) is added to target cells in combination with immune effector cells, resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Bruggemann et al., J. Exp. Med. 166:1351 (1987); Wilkinson et al., J. Immunol. Methods 258:183 (2001); Patel et al., J. Immunol. Methods 184:29 (1995). Alternatively, or additionally, ADCC activity of the antibody of interest can be assessed in vivo, e.g., in an animal model such as that disclosed in Clynes et al., Proc. Natl. Acad. Sci. USA 95:652 (1998).

As used herein, the terms "condition" and "conditioning" refer to processes by which a patient is prepared for receipt of a transplant, e.g., a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation). According to the methods described herein, a patient may be conditioned for hematopoietic stem cell transplant therapy by administration to the patient of an ADC, an antibody or an antigen-binding fragment thereof capable of binding CD45 expressed by hematopoietic stem cells. As described herein, the antibody may be covalently conjugated to a cytotoxin so as to form a drug-antibody conjugate (also referred to interchangeably herein as an antibody drug conjugate (ADC)). Administration of an ADC, or an antibody, or an antigen-binding fragment thereof, capable of binding one or more of the foregoing antigens to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

As used herein, the term "effective amount" or "therapeutically effective amount" refers to an amount of a therapeutic agent, e.g., an anti-CD45 ADC, that is sufficient to achieve the desired result or to have an effect on an autoimmune disease or cancer in a human patient.

As used herein, the term "half-life" refers to the time it takes for the plasma concentration of the antibody drug in the body to be reduced by one half or 50% in a subject, e.g., a human subject. This 50% reduction in serum concentration reflects the amount of drug circulating.

As used herein, the term "human antibody" is intended to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625,126; 5,633,425; 5,569,825; 5,661,016; 5,545,806; 5,814,318; 5,885,793; 5,916,771; and 5,939,598).

The term "chimeric antibody" is intended to refer to antibodies in which the variable region sequences are derived from one species and the constant region sequences are derived from another species, such as an antibody in which the variable region sequences are derived from a rat antibody and the constant region sequences are derived from a human antibody. Methods for producing chimeric antibodies are known in the art. See, e.g., Morrison, 1985, Science 229(4719):1202-7; Oi et al., 1986. BioTechniques 4:214-221; Gillies et al., 1985, J. Immunol. Methods 125:191-202; U.S. Pat. Nos. 5,807,715; 4,816,567; and 4,816,397.

The term "de-immunized" or "de-immunization", as used herein, relates to modification of an original wild type construct (or parent antibody) by rendering said wild type construct non-immunogenic or less immunogenic in humans. De-immunized antibodies contain part(s), e.g., a framework region(s) and/or a CDR(s), of non-human origin. As used herein, the term "deimmunized antibody" refers to an antibody that is de-immunized by mutation not to activate the immune system of a subject (for example, Nanus et al., J. Urology 170:S84-S89, 2003; WO98/52976; WO00/34317).

"Humanized" forms of non-human (e.g., murine or rat) antibodies are immunoglobulins that contain minimal sequences derived from non-human immunoglobulin. In general, a humanized antibody will comprise substantially all of at least one, and typically two, variable domains, in which all or substantially all of the CDR regions correspond to those or a non-human immunoglobulin and all or substantially all of the FR regions are those or a human immunoglobulin sequence. A humanized antibody can also comprise at least a portion of an immunoglobulin constant region (Fc), typically that or a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,585,332.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "hematopoietic stem cells" ("HSCs") refers to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B cells and T cells). Such cells may include $CD34^+$ cells. $CD34^+$ cells are immature cells that express the CD34 cell surface marker. In humans, $CD34^+$ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSCs are CD34−, SCA-1+, C-kit+, CD135−, Slamfl/CD150+, CD48−, and lin− (negative for mature lineage markers including Ter119, CD11b, Gr1, CD3, CD4, CD8, B220, IL7ra), whereas ST-HSCs are CD34+, SCA-1+, C-kit+, CD135−, Slamfl/CD150+, and lin− (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self renewal potential (i.e., they survive throughout adulthood, and can be serially transplanted through successive recipients), whereas ST-HSCs have limited self renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, T cells and B cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the terms "subject" and "patient" refer to an organism, such as a human, that receives treatment for a particular disease or condition as described herein. For instance, a patient, such as a human patient, may receive treatment prior to hematopoietic stem cell transplant therapy in order to promote the engraftment of exogenous hematopoietic stem cells.

As used herein, the term "donor" refers to a human or animal from which one or more cells are isolated prior to administration of the cells, or progeny thereof, into a recipient. The one or more cells may be, for example, a population or hematopoietic stem cells.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the phrase "substantially cleared from the blood" refers to a point. In time following administration of a therapeutic agent (such as an anti-CD45 antibody, or antigen-binding fragment thereof) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, antibody fragments, and protein ligands, such as ELISA-based detection assays known in the art or described herein. Additional assays that can be used to detect antibodies, or antibody fragments, include immunoprecipitation techniques and immunoblot assays, among others known in the art.

As used herein "to treat" or "treatment", refers to reducing the severity and/or frequency of disease symptoms, eliminating disease symptoms and/or the underlying cause or said symptoms, reducing the frequency or likelihood of disease symptoms and/or their underlying cause, and improving or remediating damage caused, directly or indirectly, by disease, any improvement of any consequence of disease, such as prolonged survival, less morbidity, and/or a lessening of side effects which are the byproducts of an alternative therapeutic modality; as is readily appreciated. In the art, full eradication of disease is a preferred but albeit not a requirement for a treatment act. Beneficial or desired clinical results include, but are not limited to, promoting the engraftment of exogenous hematopoietic cells in a patient following antibody conditioning therapy as described herein and subsequent hematopoietic stem cell transplant therapy Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell. T-lymphocyte, or B-lymphocyte, following conditioning therapy and subsequent hematopoietic stem cell transplant therapy. Additional beneficial results may include the reduction in quantity of a disease-causing cell population, such as a population of cancer cells (e.g., CD45+ leukemic cells) or autoimmune cells (e.g., CD45+ autoimmune lymphocytes, such as a CD45+ T-cell that expresses a T-cell receptor that cross-reacts with a self antigen). Insofar as the methods of the present disclosure are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present disclosure may occur prior to onset of a disease. The term does not imply that the disease state is completely avoided.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is. In need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolpidoses, metachromatic leukodystrophy, or any other diseases or disorders which may benefit from the treatments and therapies disclosed herein and including, without imitation, severe combined immunodeficiency, Wiscott-Aldrich syndrome, hyper immunoglobin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subjects target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Crohn's disease. Additional diseases that may be treated using the conditioning and/or transplantation methods described herein include a malignancy, such as a neuroblastoma or a hematologic cancer, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without imitation, severe combined immunodeficiency, Wiscott-Aldrich syndrome, hyper immunoglobin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "conjugate" or "antibody drug conjugate" or "ADC" refers to an antibody which is inked to a cytotoxin. An ADC is formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another, e.g., between an antibody and a cytotoxin. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

As used herein, "drug-to-antibody ratio" or "DAR" refers to the number of drugs, e.g., amatoxin, attached to the antibody of a conjugate. The DAR of an ADC can range from 1 to 8, although higher loads are also possible depending on the number of linkage sites on an antibody. In certain embodiments, the conjugate has a DAR of 1, 2, 3, 4, 5, 6, 7, or 8.

As used herein, the term "microtubule-binding agent" refers to a compound which acts by disrupting the microtubular network that is essential for mitotic and interphase cellular function in a cell. Examples of microtubule-binding agents include, but are not limited to, maytasine, maytansinoids, and derivatives thereof, such as those described herein or known in the art, vinca alkaloids, such as vinblastine, vinblastine sulfate, vincristine, vincristine sulfate, vindesine, and vinorelbine, taxanes, such as docetaxel and paclitaxel, macrolides, such as discodermolides, colchicine, and epothilones, and derivatives thereof, such as epothilone B or a derivative thereof.

As used herein, the term "amatoxin" refers to a member of the amatoxin family of peptides produced by *Amanita phalloides* mushrooms, or a variant or derivative thereof, such as a variant or derivative thereof capable of inhibiting RNA polymerase II activity. Amatoxins useful in conjunction with the compositions and methods described herein include compounds such, as but not limited to, compounds of Formulas (IV), (IVA), (IVB), and (IVC), or other amatoxins, e.g., α-amanitin, β-amanitin, γ-amanitin, ε-amanitin, amanin, amaninamide, amanullin, amanullinic acid, or proamanullin. As described herein, amatoxins may be conjugated to an antibody, or antigen-binding fragment thereof, for instance, by way of a linker moiety (L) (thus forming an ADC). Exemplary methods of amatoxin conjugation and linkers useful for such processes are described below. Exemplary inker-containing amatoxins useful for conjugation to an antibody, or antigen-binding fragment, in accordance with the compositions and methods are also described herein.

The term "acyl" as used herein refers to —C(=O)R, wherein R is hydrogen ("aldehyde"), $C_1$-$C_{12}$ alkyl, $C_2$-$C_{12}$ alkenyl, $C_2$-$C_{12}$ alkynyl, $C_3$-$C_7$ carbocyclyl, $C_6$-$C_{20}$ aryl, 5-10 membered heteroaryl, or 5-10 membered heterocyclyl, as defined herein. Non-limiting examples include formyl, acetyl, propanoyl, benzoyl, and acryloyl.

The term "$C_1$-$C_{12}$ alkyl" as used herein refers to a straight chain or branched, saturated hydrocarbon having from 1 to 12 carbon atoms. Representative $C_1$-$C_{12}$ alkyl groups include, but are not limited to, -methyl, -ethyl, -n-propyl, -n-butyl, -n-pentyl, and -n-hexyl; while branched $C_1$-$C_{12}$ alkyls include, but are not limited to, -isopropyl, -sec-butyl, -isobutyl, -tert-butyl, -isopentyl, and 2-methylbutyl. A $C_1$-$C_{12}$ alkyl group can be unsubstituted or substituted.

The term "alkenyl" as used herein refers to $C_2$-$C_{12}$ hydrocarbon containing normal, secondary, or tertiary carbon atoms with at least one site of unsaturation, i.e., a carbon-carbon, $sp^2$ double bond. Examples include, but are not limited to: ethylene or vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, and the like. An alkenyl group can be unsubstituted or substituted.

"Alkynyl" as used herein refers to a $C_2$-$C_{12}$ hydrocarbon containing normal, secondary, or tertiary carbon atoms with at least one site of unsaturation, i.e., a carbon-carbon, sp triple bond. Examples include, but are not limited to acetylenic and propargyl. An alkynyl group can be unsubstituted or substituted.

"Aryl" as used herein refers to a $C_6$-$C_{20}$ carbocyclic aromatic group. Examples of aryl groups include, but are not limited to, phenyl, naphthyl and anthracenyl. An aryl group can be unsubstituted or substituted.

"Arylalkyl" as used herein refers to an acyclic alkyl radical in which one of the hydrogen atoms bonded to a carbon atom, typically a terminal or sp carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms. An alkaryl group can be unsubstituted or substituted.

"Cycloalkyl" as used herein refers to a saturated carbocyclic radical, which may be mono- or bicyclic. Cycloalkyl groups include a ring having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted.

"Cycloalkenyl" as used herein refers to an unsaturated carbocyclic radical, which may be mono- or bicyclic. Cycloalkenyl groups include a ring having 3 to 6 carbon atoms as a monocycle or 7 to 12 carbon atoms as a bicycle. Examples of monocyclic cycloalkenyl groups include 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. A cycloalkenyl group can be unsubstituted or substituted.

"Heteroaralkyl" as used herein refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl radical comprises 2 to 20 carbon atoms and 1 to 3 heteroatoms selected from N, O, P, and S. A heteroaryl or heterocycloalkyl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl and heterocycloalkyl can be unsubstituted or substituted.

Heteroaryl and heterocycloalkyl groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heteroaryl groups include by way of example and not limitation pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolzinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl.

Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

By way of example and not limitation, carbon bonded heteroaryls and heterocycloalkyls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heteroaryls and heterocycloalkyls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline. Still more typically, nitrogen bonded heterocycles include 1-aziridyl, 1-azetedyl, 1-pyrrolyl, 1-imidazolyl, 1-pyrazolyl, and 1-piperidinyl.

"Substituted" as used herein and as applied to any of the above alkyl, alkenyl, alkynyl, aryl, arylalkyl, cycloalkyl, heteroaryl, heterocyclyl, and the like, means that one or more hydrogen atoms are each independently replaced with a substituent. Typical substituents include, but are not limited to, —X, —R, —OH, —OR, —SH, —SR, NH$_2$, —NHR, —N(R)$_2$, —N$^+$(R)$^3$, —CX$_3$, —CN, —OCN, —SCN, —NCO, —NCS, —NO, —NO$_2$, —N$_3$, —NC(=O)H, —NC(=O)R, —C(=O)H, —C(=O)R, —C(=O)NH$_2$, —C(=O)N(R)$_2$, —SO$_3$—, —SO$_3$H, —S(=O)$_2$R, —OS(=O)$_2$OR, —S(=O)$_2$NH$_2$, —S(=O)$_2$N(R)$_2$, —S(=O)R, —OP(=O)(OH)$_2$, —OP(=O)(OR)$_2$, —P(=O)(OR)$_2$, —PO$_3$, —PO$_3$H$_2$, —C(=O)X, —C(=S)R, —CO$_2$H, —CO$_2$R, —CO$_2$—, —C(=S)OR, —C(=O)SR, —C(=S)SR, —C(=O)NH$_2$, —C(=O)N(R)$_2$, —C(=S)NH$_2$, —C(=S)N(R)$_2$, —C(=NH)NH$_2$, and —C(=NR)N(R)$_2$; wherein each X is independently selected for each occasion from F, Cl, Br, and I; and each R is independently selected for each occasion from C$_1$-C$_{12}$ alkyl, C$_6$-C$_{20}$ aryl, C$_3$-C$_{14}$ heterocycloalkyl or heteroaryl, protecting group and prodrug moiety. Wherever a group is described as "optionally substituted," that group can be substituted with one or more of the above substituents, independently for each occasion.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene." "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated.

Anti-CD45 Antibodies

Disclosed herein are anti-CD45 antibodies that are capable of binding both human and cynomolgus CD45, and can be used as therapeutic agents alone or as antibody drug conjugates (ADCs) to, for example, (i) treat cancers and autoimmune diseases characterized by CD45+ cells and (ii) promote the engraftment of transplanted hematopoietic stem cells in a patient in need of transplant therapy. These therapeutic activities can be caused, for instance, by the binding of isolated anti-CD45 antibodies, antigen-binding fragments thereof, that bind to CD45 expressed on the surface of a cell, such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein.

CD45 is a hematopoietic cell-specific transmembrane protein tyrosine phosphatase essential for T and B cell antigen receptor-mediated signaling. CD45 includes a large extracellular domain, and a phosphatase containing cytosolic domain. CD45 may act as both a positive and negative regulator depending on the nature of the stimulus and the cell type involved. Although there are a large number of permutations possible in the CD45 gene, only six isoforms are traditionally identified in humans. The isoforms are RA (Uniprot Accession No: P08575-8; SEQ ID NO: 31), RO (NCBI Accession No: NP_583578.2; SEQ ID NO: 32), RB (NCBI Accession No: XP_006711537.1; SEQ ID NO: 33), RAB (NCBI Accession No: XP_006711535.1; SEQ ID NO: 34), RBC (NCBI Accession No: XP_006711538.1; SEQ ID NO: 35) and RABC (NCBI Accession No. NP_002829.3; SEQ ID NO: 36) (Hermiston et al. 2003 "CD45: a critical regulator of signaling thresholds in immune cells." *Annu Rev Immunol.* 2:107-137). CD45RA is expressed on naïve T cells, and CD45RO is expressed on activated and memory T cells, some B cell subsets, activated monocytes/macrophages, and granulocytes. CD45RB is expressed on peripheral B cells, naïve T cells, thymocytes, weakly on macrophages, and dendritic cells.

As described below, novel anti-human CD45 (hCD45) antibodies, and fragments thereof, were identified by immunizing rats with human CD45. The identified antibodies have diagnostic and therapeutic characteristics. Antibody A (AbA), Antibody B (AbB), and Antibody C (AbC) were identified in this screen. These antibodies cross react with human CD45 and rhesus CD45. Further, these antibodies disclosed herein are able to bind the extracellular domains of the various isoforms of human CD45. Accordingly, in certain embodiments, the antibody herein is a pan-specific anti-CD45 antibody (i.e., an antibody that binds all six human CD45 isoforms). Further, AbA, AbB, and AbC disclosed herein (or antibodies having the binding regions or specificity of these antibodies) can also bind to cynomolgus CD45. Identifying both cross-reactive cyno/human anti-CD45 antibodies, and antibodies pan-specific to the human isoforms of CD45 was a challenge met by the screen described below in Example 1.

The amino acid sequences for the various binding regions of anti-CD45 antibodies AbA, AbB, and AbC are described in Table 3. Included in the invention are humanized and chimeric anti-CD45 antibodies based on antibodies AbA, AbB, or AbC, e.g., that comprise the CDRs as set forth in Table 3.

In one embodiment, the disclosure provides an anti-CD45 antibody, or antigen-binding fragment thereof, comprising binding regions, e.g., CDRs, variable regions, corresponding to those of AbA. The heavy chain variable region (VH) amino acid sequence of Ab is set forth in SEQ ID NO: 1 (see Table 3). The VH CDR domain amino acid sequences of AbA are set forth in SEQ ID NO: 2 (VH CDR1); SEQ ID NO: 3 (VH CDR2), and SEQ ID NO: 4 (VH CDR3). The light chain variable region (VL) amino acid sequence of AbA is described in SEQ ID NO: 5 (see Table 3). The VL CDR domain amino acid sequences of AbA are set forth in SEQ ID NO: 6 (VL CDR1); SEQ ID NO: 7 (VL CDR2), and SEQ ID NO: 8 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 1, and a light chain variable region comprising the amino acid sequence as set forth in SEQ ID NO: 5. In one embodiment, the anti-CD45 antibody comprises a heavy chain comprising a CDR1, CDR2 and CDR3 comprising the amino acid sequences set forth in SEQ ID NOs: 2, 3, and 4, and a light chain variable region comprising a CDR1, CDR2 and CDR3 comprising the amino acid sequences set forth in SEQ ID NOs: 6, 7, and 8.

Anti-human CD45 antibodies, or fragments thereof, that bind to the epitope on human CD45 bound by any one of antibodies AbA, AbB, or AbC (or antibodies having the binding regions of AbA, AbB, or AbC), are also contemplated herein. Further contemplated are anti-human CD45 antibodies, or antigen binding fragments thereof, that compete with any one of antibodies AbA, AbB, or AbC (or antibodies having the binding regions of AbA, AbB, or AbC).

In some embodiments, an anti-CD45 antibody, or antigen-binding fragment thereof, specifically binds to human CD45 at a region comprising the amino acid sequence RNGPHERYHLEVEAGNT (SEQ ID NO: 38). For example, in certain embodiments, the anti-CD45 antibody, or antigen-binding fragment thereof, specifically binds to human CD45 at amino acid residues 486R, 493Y, and 502T of SEQ ID NO: 37 (fragment of CD45 isoform corresponding to NP_002829.3), or at residues corresponding thereto in a region comprising the sequence RNGPHERYHLEVEAGNT (SEQ ID NO: 38; bold residues indicate binding site) in other human CD45 isoforms. In some embodiments, the anti-CD45 antibody, or antigen-binding fragment thereof, specifically binds to a fibronectin domain (e.g., fibronectin d4 domain) of human CD45.

In one embodiment, an isolated anti-CD45 antibody, or an antigen binding portion thereof, specifically binds to an epitope of human CD45 comprising residues 488R, 493Y, and 502T of SEQ ID NO: 37, and also binds to cynomolgous and/or rhesus CD45.

In one embodiment, an isolated anti-CD45 antibody, or an antigen binding portion thereof, specifically binds to an epitope of human CD45 comprising the amino acid sequence RNGPHERYHLEVEAGNT (SEQ ID NO: 38), and also binds to cynomolgous and rhesus CD45.

In one embodiment, an isolated anti-CD45 antibody, or an antigen binding portion thereof, specifically binds to an epitope of human CD45 comprising the amino acid sequence CRPPRDRNGPHERYHLEVEAGNTLVRNESHK (SEQ ID NO: 39), and binds to cynomolgous and rhesus CD45.

In one embodiment, an isolated anti-CD45 antibody, or an antigen binding portion thereof, specifically binds to an epitope of human CD45 comprising residues 486R, 493Y, and 502T or SEQ ID NO: 37; binds to at least one additional amino acid, at least two additional amino acids, at least three additional amino acids, at least four additional amino acids, or at least five additional amino acids in a peptide comprising RNGPHERYHLEVEAGNT (SEQ ID NO: 38), wherein the additional amino acid residues are not residues 486R, 493Y, and 502T of SEQ ID NO: 37; and also binds to cynomolgous and rhesus CD45.

In one embodiment, the invention provides an anti-CD45 antibody, or antigen-binding fragment thereof, comprising binding regions, e.g., CDRs, variable regions, corresponding to those of AbB. The heavy chain variable region (VH) amino acid sequence of AbB is set forth in SEQ ID NO: 9 (see Table 3). The VH CDR domain amino acid sequences of AbB are set forth in SEQ ID NO: 10 (VH CDR1); SEQ ID NO: 11 (VH CDR2), and SEQ ID NO: 12 (VH CDR3). The light chain variable region (VL) amino acid sequence or AbB is described in SEQ ID NO: 13 (see Table 3). The VL CDR domain amino acid sequences of AbB are set forth in SEQ ID NO: 14 (VL CDR1); SEQ ID NO: 15 (VL CDR2), and SEQ ID NO: 16 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 9, and a light chain variable region comprising the amino acid sequence as set forth in SEQ ID NO:

13. In one embodiment, the anti-CD45 antibody comprises a heavy chain comprising a CDR1, CDR2 and CDR3 comprising the amino acid sequences set forth in SEQ ID NOs: 10, 11, and 12, and a light chain variable region comprising a CDR1, CDR2 and CDR3 comprising the amino acid sequences set forth in SEQ ID NOs: 14, 15, and 16.

In one embodiment, the invention provides an anti-CD45 antibody, or antigen-binding fragment thereof, comprising binding regions, e.g., CDRs, variable regions, corresponding to those of AbC. The heavy chain variable region (VH) amino acid sequence of AbC is set forth in SEQ ID NO: 17 (see Table 3). The VH CDR domain amino acid sequences of AbC are set forth in SEQ ID NO: 18 (VH CDR1); SEQ ID NO: 19 (VH CDR2), and SEQ ID NO: 20 (VH CDR3). The light chain variable region (VL) amino acid sequence of AbC is described in SEQ ID NO: 21 (see Table 3). The VL CDR domain amino acid sequences of AbC are set forth in SEQ ID NO: 22 (VL CDR1); SEQ ID NO: 23 (VL CDR2), and SEQ ID NO: 24 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 17, and a light chain variable region comprising the amino acid sequence as set forth in SEQ ID NO: 21. In one embodiment, the anti-CD45 antibody comprises a heavy chain comprising a CDR1, CDR2 and CDR3 comprising the amino acid sequences set forth in SEQ ID NOs: 18, 19, and 20, and a light chain variable region comprising a CDR1, CDR2 and CDR3 comprising the amino acid sequences set forth in SEQ ID NOs: 22, 23, and 24.

In certain embodiments, an antibody comprises a modified heavy chain (HC) variable region comprising an HC variable domain described in Table 3, or a variant of a HC variant region in Table 3, which variant (i) differs from a HC variable domain described in Table 3 in 1, 2, 3, 4 or 5 amino acids substitutions, additions or deletions; (ii) differs from a HC variable domain described in Table 3 in at most 5, 4, 3, 2, or 1 amino acids substitutions, additions or deletions; (iii) differs from a HC variable domain described in Table 3 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 1, wherein in any of (i)-(iv), an amino acid substitution may be a conservative amino acid substitution or a non-conservative amino acid substitution.

In certain embodiments, an antibody comprises a modified light chain (LC) variable region comprising a LC variable domain described in Table 3, or a variant thereof, which variant (i) differs from a LC variable domain described in Table 3 in 1, 2, 3, 4 or 5 amino acids substitutions, additions or deletions; (ii) differs from a LC variable domain described in Table 3 in at most 5, 4, 3, 2, or 1 amino acids substitutions, additions or deletions; (iii) differs from a LC variable domain described in Table 3 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to a LC variable domain described in Table 3, wherein in any of (i)-(iv), an amino acid substitution may be a conservative amino acid substitution or a non-conservative amino acid substitution.

In certain embodiments, an anti-CD45 antibody comprises the CDRs described herein in Table 3 wherein the CDR comprises a conservative amino acid substitution (or 2, 3, 4, or 5 amino acid substitutions) while retaining the CD45 specificity of the antibody (i.e., specificity similar to AbA, AbB, or AbC).

In certain embodiments, an anti-CD45 antibody is a de-immunized antibody based on AbA, AbB or AbC antibodies, or antigen binding portions thereof. A de-immunized antibody is one whose V regions have been chosen to lack T-cell epitopes or altered to remove T-cell epitopes, thereby minimizing or eliminating the potential for the antibody to be immunogenic. In certain embodiments, an anti-CD45 antibody is de-immunized by selecting or engineering framework domains to be without T-cell epitopes, which if present in the antibody sequence would enable the human subject to make a HAHA/HAMA response against the anti-CD45 antibody, resulting in an immune-mediated reaction that causes adverse events in human subjects or diminished treatment effectiveness. The antibodies disclosed herein (i.e., the AbA, AbB, and AbC variable and CDR sequences described in Table 3) can serve as a parent sequence from which a de-immunized antibody can be derived.

Humanized Anti-CD45 Antibodies

The present invention encompasses humanized anti-CD45 antibodies based on antibodies AbA, AbB, or AbC described herein. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J Immunol. 151:2296; Chothia et al. (1987) J Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Fc-Modified Antibodies

The present invention is based in part on the discovery that antibodies, or antigen-binding fragments thereof, having Fc modifications that allow Fc silencing capable of binding an antigen expressed by hematopoietic stem cells, such as CD45, can be used as therapeutic agents alone or as ADCs to (i) treat cancers and autoimmune diseases characterized by CD45+ hematopoietic stem cells; and (ii) promote the engraftment of transplanted hematopoietic stem cells in a patient in need of transplant therapy. These therapeutic activities can be caused, for instance, by the binding of an anti-CD45 antibody, or antigen-binding fragment thereof, that binds to expressed by a hematopoietic cell (e.g., hematopoietic stem cell or mature immune cell (e.g., T cell)), such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein. The Fc-modified antibodies and ADCs herein not only allow for selective depletion of endogenous hematopoietic stem cells but also have reduced cytotoxic effects on the exogenous hematopoietic stem cell transplant, thereby further promoting engraftment of the hematopoietic stem cell graft.

The antibodies or binding fragments described herein may also include modifications and/or mutations that alter the properties of the antibodies and/or fragments, such as those that increase half-life, or increase or decrease ADCC.

In one embodiment, antibodies comprising one or more radiolabeled amino acids are provided. A radiolabeled antibody may be used for both diagnostic and therapeutic purposes (conjugation to radiolabeled molecules is another possible feature). Non-limiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-886 (2d edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method.

In one embodiment, the anti-CD45 antibody, or binding fragment thereof, comprises a modified Fc region, wherein said modified Fc region comprises at least one amino acid modification relative to a wild-type Fc region, such that said molecule has an altered affinity for or binding to an FcgammaR (FcγR). Certain amino acid positions within the Fc region are known through crystallography studies to make a direct contact with FcγR. Specifically amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). In some embodiments, the antibodies described herein may comprise variant Fc regions comprising modification of at least one residue that makes a direct contact with an FcγR based on structural and crystallographic analysis. In one embodiment, the Fc region of the anti-CD45 antibody (or fragment thereof) comprises an amino acid substitution at amino acid 265 according to the EU index as in Kabat et al., Sequences of Proteins of Immunological Interest, 5th Ed. Public Health Service, NH1, MD (1991), expressly incorporated herein by reference. The "EU index as in Kabat" refers to the numbering of the human IgG1 EU antibody. In one embodiment, the Fc region comprises a D265A mutation. In one embodiment, the Fc region comprises a D265C mutation. In some embodiments, the Fc region of the antibody (or fragment thereof) comprises an amino acid substitution at amino acid 234 according to the EU index as in Kabat.

In one embodiment, the Fc region comprises a mutation at an amino acid position of D285, V205, H435, I253, and/or H310. For example, specific mutations at these positions include D265C, V205C, H435A, I253A, and/or H310A.

In one embodiment, the Fc region comprises a L234A mutation. In some embodiments, the Fc region of the anti-CD45 antibody (or fragment thereof) comprises an amino acid substitution at amino acid 235 according to the EU index as in Kabat. In one embodiment, the Fc region comprises a L235A mutation. In yet another embodiment, the Fc region comprises a L234A and L235A mutation. In a further embodiment, the Fc region comprises a D285C, L234A, and L235A mutation. In yet a further embodiment, the Fc region comprises a D285C, L234A, L235A, and H435A mutation. In a further embodiment, the Fc region comprises a D265C and H435A mutation.

In yet another embodiment, the Fc region comprises a L234A and L235A mutation (also referred to herein as "L234A.L235A" or as "LALA"). In another embodiment, the Fc region comprises a L234A and L235A mutation, wherein the Fc region does not include a P329G mutation. In a further embodiment, the Fc region comprises a D265C, L234A, and L235A mutation (also referred to herein as "D265C.L234A.L235A"). In another embodiment, the Fc region comprises a D265C, L234A, and L235A mutation, wherein the Fc region does not include a P329G mutation. In yet a further embodiment, the Fc region comprises a D265C, L234A, L235A, and H435A mutation (also referred to herein as "D285C.L234A.L235A.H435A"). In another embodiment, the Fc region comprises a D285C, L234A, L235A, and H435A mutation, wherein the Fc region does not include a P329G mutation. In a further embodiment, the Fc region comprises a D265C and H435A mutation (also referred to herein as "D265C.H435A"). In yet another embodiment, the Fc region comprises a D265A, S239C, L234A, and L235A mutation (also referred to herein as "D265A.S239C.L234A.L235A"). In yet another embodiment, the Fc region comprises a D285A, S239C, L234A, and L235A mutation, wherein the Fc region does not include a P329G mutation. In another embodiment, the Fc region comprises a D265C, N297G, and H435A mutation (also referred to herein as "D265C.N297G.H435A"). In another embodiment, the Fc region comprises a D265C, N297Q, and H435A mutation (also referred to herein as "D265C.N297Q.H435A"). In another embodiment, the Fc region comprises a E233P, L234V, L235A and delG238 (deletion of 238) mutation (also referred to herein as "E233P.L234V.L235A.delG236" or as "EPLVLAdelG"). In another embodiment, the Fc region comprises a E233P, L234V, L235A and delG238 (deletion of 238) mutation, wherein the Fc region does not include a P329G mutation. In another embodiment, the Fc region comprises a E233P, L234V, L235A, delG238 (deletion of 238) and H435A mutation (also referred to herein as "E233P.L234V.L235A.delG236.H435A" or as "EPLVLAdelG.H435A"). In another embodiment, the Fc region comprises a E233P, L234V, L235A, delG236 (deletion of 236) and H435A mutation, wherein the Fc region does not include a P329G mutation. In another embodiment, the Fc region comprises a L234A, L235A, S239C and D265A mutation. In another embodiment, the Fc region comprises a L234A, L235A, S239C and D265A mutation, wherein the Fc region does not include a P329G mutation. In another embodiment, the Fc region comprises a H435A, L234A, L235A, and D265C mutation. In another embodiment, the Fc region comprises a H435A, L234A, L235A, and D285C mutation, wherein the Fc region does not include a P329G mutation.

In some embodiments, the antibody has a modified Fc region such that, the antibody decreases an effector function in an in vitro effector function assay with a decrease in binding to an Fc receptor (Fc R) relative to binding of an identical antibody comprising an unmodified Fc region to the FcR. In some embodiments, the antibody has a modified Fc region such that, the antibody decreases an effector function in an in vitro effector function assay with a decrease in binding to an Fc gamma receptor (FcγR) relative to binding of an identical antibody comprising an unmodified Fc region to the FcγR. In some embodiments, the FcγR is FcγR1. In some embodiments, the FcγR is FcγR2A. In some embodiments, the FcγR is FcγR2B. In other embodiments, the FcγR is FcγR2C. In some embodiments, the FcγR is FcγR3A. In some embodiments, the FcγR is FcγR3B. In other embodiments, the decrease in binding is at least a 70% decrease, at least a 80% decrease, at least a 90% decrease, at least a 95% decrease, at least a 98% decrease, at least a 99% decrease, or a 100% decrease in antibody binding to a FcγR relative to binding of the identical antibody comprising an unmodified Fc region to the FcγR. In other embodiments, the decrease in binding is at least a 70% to a 100% decrease, at least a 80% to a 100% decrease, at least a 90% to a 100% decrease, at least a 95% to a 100% decrease, or at least a 98% to a 100% decrease, in antibody binding to a FcγR relative to binding of the identical antibody comprising an unmodified Fc region to the FcγR In some embodiments, the antibody has a modified Fc region such that, the antibody decreases cytokine release in an in vitro cytokine release assay with a decrease in cytokine release of at least 50% relative to cytokine release of an identical antibody comprising an unmodified Fc region. In some embodiments, the decrease in cytokine release is at least a 70% decrease, at least a 80% decrease, at least a 90% decrease, at least a 95% decrease, at least a 98% decrease, at least a 99% decrease, or a 100% decrease in cytokine release relative to cytokine release of the identical antibody comprising an unmodified Fc region. In some embodiments, the decrease in cytokine release is at least a 70% to a 100% decrease, at least an 80% to a 100% decrease, at least a 90% to a 100% decrease, at least a 95% to a 100% decrease in cytokine release relative to cytokine release of the identical antibody comprising an unmodified Fc region. In certain embodiments, cytokine release is by immune cells.

In some embodiments, the antibody has a modified Fc region such that, the antibody decreases mast cell degranulation in an in vitro mast cell degranulation assay with a decrease in mast cell degranulation of at least 50% relative to mast cell degranulation of an identical antibody comprising an unmodified Fc region. In some embodiments, the decrease in mast cell degranulation is at least a 70% decrease, at least a 80% decrease, at least a 90% decrease, at least a 95% decrease, at least a 98% decrease, at least a 99% decrease, or a 100% decrease in mast cell degranulation relative to mast cell degranulation of the identical antibody comprising an unmodified Fc region. In some embodiments, the decrease in mast cell degranulation is at least a 70% to a 100% decrease, at least a 80% to a 100% decrease, at least a 90% to a 100% decrease, or at least a 95% to a 100% decrease, in mast cell degranulation relative to mast cell degranulation of the identical antibody comprising an unmodified Fc region.

In some embodiments, the antibody has a modified Fc region such that, the antibody decreases or prevents antibody dependent cell phagocytosis (ADCP) in an in vitro antibody dependent cell phagocytosis assay, with a decrease in ADCP of at least 50% relative to ADCP of an identical antibody comprising an unmodified Fc region. In some embodiments, the decrease in ADCP is at least a 70% decrease, at least a 80% decrease, at least a 90% decrease, at least a 95% decrease, at least a 98% decrease, at least a 99% decrease, or a 100% decrease in cytokine release relative to cytokine release of the identical antibody comprising an unmodified Fc region.

In some embodiments, the anti-CD45 antibody described herein comprises an Fc region comprising one of the following modifications or combinations of modifications: D265A, D265C, D285C/H435A, D285C/LALA, D285C/LALA/H435A, D285A/S239C/L234A/L235A/H435A, D285A/S239C/L234A/L235A, D265C/N297G, D265C/N297G/H435A, D285C (EPLVLAdelG*), D285C (EPLVL-AdelG)/H435A, D265C/N297Q/H435A, D265C/N297Q, EPLVLAdelG/H435A, EPLVLAdelG/D285C, EPLVL-AdelG/D285A, N297A, N297G, or N297Q.

Binding or affinity between a modified Fc region and a Fc gamma receptor can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE® analysis or Octet® analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmune assay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

In one embodiment, an antibody having the Fc modifications described herein (e.g., D285C, L234A, L235A, and/or H435A) has at least a 70% decrease, at least an 80% decrease, at least a 90% decrease, at least a 95% decrease, at least a 98% decrease, at least a 99% decrease, or a 100% decrease in binding to a Fc gamma receptor relative to binding or the identical antibody comprising an unmodified Fc region to the Fc gamma receptor (e.g., as assessed by biolayer interferometry (BLI)).

Without wishing to be bound by any theory, it is believed that Fc region binding interactions with a Fc gamma receptor are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a modified Fc region (e.g., comprising a L234A, L235A, and/or a D265C mutation) has substantially reduced or abolished effector functions. Effector functions can be assayed using a variety of methods known in the art, e.g., by measuring cellular responses (e.g., mast cell degranulation or cytokine release) in response to the antibody of interest. For example, using standard methods in the art, the Fc-modified antibodies can be assayed for their ability to trigger mast cell degranulation in or for their ability to trigger cytokine release, e.g. by human peripheral blood mononuclear cells.

The antibodies of the present disclosure may be further engineered to further modulate antibody half-life by introducing additional Fc mutations, such as those described for example in (Dall'Acqua et al. (2006) J Biol Chem 281: 23514-24), (Zalevsky et al. (2010) Nat Biotechnol 28: 157-9), (Hinton et al. (2004) J Biol Chem 279: 6213-6), (Hinton et al. (2006) J Immunol 176: 346-56). (Shields et al. (2001) J Biol Chem 276: 6591-604), (Petkova et al. (2006) Int Immunol 18: 1759-69), (Datta-Mannan et al. (2007) Drug Metab Dispos 35: 86-94), (Vaccaro et al. (2005) Nat Biotechnol 23: 1283-8), (Yeung et al. (2010) Cancer Res 70: 3269-77) and (Kim et al. (1999) Eur J Immunol 29: 2819-25), and include positions 250, 252, 253, 254, 258, 257, 307, 376, 380, 428, 434 and 435. Exemplary mutations that may be made singularly or in combination are T250Q, M252Y, I253A, S254T, T256E, P257I, T307A, D376V, E380A, M428L, H433K, N434S, N434A, N434H, N434F, H435A and H435R mutations.

Thus, in one embodiment, the Fc region comprises a mutation resulting in a decrease in half life (e.g., relative to an antibody having an unmodified Fc region). An antibody having a short half life may be advantageous in certain instances where the antibody is expected to function as a short-lived therapeutic, e.g., the conditioning step described herein where the antibody is administered followed by HSCs. Ideally, the antibody would be substantially cleared prior to delivery of the HSCs, which also generally express a target antigen (e.g., CD45) but are not the target of the anti-CD45 antibody unlike the endogenous stem cells. In one embodiment, the Fc regions comprise a mutation at position 435 (EU index according to Kabat). In one embodiment, the mutation is an H435A mutation.

In one embodiment, the anti-CD45 antibody described herein has a half-life (e.g., in humans) equal to or less than about 24 hours, equal to or less than about 23 hours, equal to or less than about 22 hours, equal to or less than about 21 hours, equal to or less than about 20 hours, equal to or less than about 19 hours, equal to or less than about 18 hours, equal to or less than about 17 hours, equal to or less than about 16 hours, equal to or less than about 15 hours, equal to or less than about 14 hours, equal to or less than about 13 hours, equal to or less than about 12 hours, or equal to or less than about 11 hours.

In one embodiment, the anti-CD45 antibody described herein has a half-life (e.g., in humans) of about 1-5 hours, about 5-10 hours, about 10-15 hours, about 15-20 hours, or about 20 to 25 hours. In one embodiment, the half-life of the anti-CD45 antibody is about 5-7 hours; about 5-9 hours; about 5-11 hours;

about 5-13 hours; about 5-15 hours; about 5-20 hours; about 5-24 hours; about 7-24 hours; about 9-24 hours; about 11-24 hours; about 12-22 hours; about 10-20 hours; about 8-18 hours; or about 14-24 hours.

In some aspects, the Fc region comprises two or more mutations that confer reduced half-life and reduce an effector function of the antibody. In some embodiments, the Fc region comprises a mutation resulting in a decrease in half-life and a mutation of at least one residue that can make direct contact with an FcγR (e.g., as based on structural and crystallographic analysis). In one embodiment, the Fc region comprises a H435A mutation, a L234A mutation, and a L235A mutation. In one embodiment, the Fc region comprises a H435A mutation and a D265C mutation. In one embodiment, the Fc region comprises a H435A mutation, a L234A mutation, a L235A mutation, and a D265C mutation.

In some embodiments, the antibody or antigen-binding fragment thereof is conjugated to a cytotoxin (e.g., amatoxin) by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys285. In one embodiment, the Fc region of the anti-CD45 antibody (or fragment thereof) comprises an amino acid substitution at amino acid 265 according to the EU index as in Kabat. In one embodiment, the Fc region comprises a D265C mutation. In one embodiment, the Fc region comprises a D265C and H435A mutation. In one embodiment, the Fc region comprises a D265C, a L234A, and a L235A mutation. In one embodiment, the Fc region comprises a D265C, a L234A, a L235A, and a H435A mutation. In one embodiment, the Fc region of the anti-CD45 antibody, or antigen-binding fragment thereof, comprises an amino acid substitution at amino acid 239 according to the EU index as in Kabat. In one embodiment, the Fc region comprises a S239C mutation. In one embodiment, the Fc region comprises a L234A mutation, a L235A mutation, a S239C mutation and a D265A mutation. In another embodiment, the Fc region comprises a S239C and H435A mutation. In another embodiment, the Fc region comprises a L234A mutation, a L235A mutation, and S239C mutation. In yet another embodiment, the Fc region comprises a H435A mutation, a L234A mutation, a L235A mutation, and S239C mutation. In yet another embodiment, the Fc region comprises a H435A mutation, a L234A mutation, a L235A mutation, a S239C mutation and D265A mutation.

Notably, Fc amino acid positions are in reference to the EU numbering index unless otherwise indicated.

The disclosures of each of the foregoing publications are incorporated herein by reference as they pertain to anti-CD45 antibody. Antibodies and antigen-binding fragments that may be used in conjunction with the compositions and methods described herein include the above-described antibodies and antigen-binding fragments thereof, as well as humanized variants of those non-human antibodies and antigen-binding fragments described above and antibodies or antigen-binding fragments that bind the same epitope as those described above, as assessed, for instance, by way of a competitive antigen binding assay.

Methods of engineering antibodies to include any of the Fc modifications herein are well known in the art. These methods include, but are not limited to, preparation by site-directed (or oligonucleotide-mediated) mutagenesis. PCR mutagenesis, and cassette mutagenesis of a prepared DNA molecule encoding the antibody or at least the constant region of the antibody. Site-directed mutagenesis is well known in the art (see, e.g., Carter et al., Nucleic Acids Res., 13:4431-4443 (1985) and Kunkel et al., Proc. Natl. Acad. Sci. USA, 82:488 (1987)). PCR mutagenesis is also suitable for making amino acid sequence variants of the starting polypeptide. See Higuchi, in PCR Protocols, pp. 177-183 (Academic Press, 1990);

and Vallette et al., Nuc. Acids Res. 17:723-733 (1989). Another method for preparing sequence variants, cassette mutagenesis, is based on the technique described by Wels et al., Gene, 34:315-323 (1985).

Methods of Identifying Antibodies

Methods for high throughput screening of antibody, or antibody fragment libraries capable of binding CD45 expressed by hematopoietic stem can be used to identify anti-CD45 antibodies useful for treating cancers, autoimmune diseases, and conditioning a patient (e.g., a human patient) in need of hematopoietic stem cell therapy as described herein. Such methods can be used to identify improved versions of antibodies AbA, AbB, and AbC described herein. Such methods include in vitro display techniques known in the art, such as phage display, bacterial display, yeast display, mammalian cell display, ribosome display, mRNA display, and cDNA display, among others.

The use of phage display to isolate antibodies, or antigen-binding fragments, that bind biologically relevant molecules has been reviewed, for example, in Felici et al., Biotechnol. Annual Rev. 1:149-183, 1995; Katz. Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). Human anti-CD45 antibodies can also be generated, for example, in the HuMAb-Mouse® or XenoMouse™. These techniques, among others, can be used to identify and improve the affinity of antibodies, antibody or fragments, capable of binding CD45 expressed by hematopoietic stem cells in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies capable of binding an antigen (e.g., CD45) expressed by hematopoietic stem cells. For example, using computational modeling techniques, one of skill in the art can screen libraries of antibodies, or antibody fragments, in silico for molecules capable of binding specific epitopes on an antigen expressed by hematopoietic stem cells (e.g., CD45), such as extracellular epitopes of the antigen.

Additional techniques can be used to identify antibodies, or antibody fragments, capable of binding CD45 expressed by hematopoietic stem cells and that are internalized by the cell, for instance, by receptor-mediated endocytosis. For example, the in vitro display techniques described above can be adapted to screen for antibodies, or antibody fragments, that bind CD45 and that are subsequently internalized. Phage display represents one such technique that can be used in conjunction with this screening paradigm. To identify an anti-CD45 antibody, or antibody fragment, that can be internalized by hematopoietic stem cells, one of skill in the art can use the phage display techniques described in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD45 for instance, by first incubating the phage library with blocking agents (such as, for instance, milk protein, bovine serum albumin, and/or IgG so as to remove phage encoding antibodies, or antibody fragments, that exhibit non-specific protein binding and phage that encode antibodies or fragments thereof that bind Fc domains, and then incubating the phage library with a population of cells, e.g., hematopoietic stem cells, which express CD45. The phage library can be incubated with the hematopoietic stem cells for a time sufficient to allow anti-CD45 antibodies, or antibody fragments, to bind the cognate cell-surface antigen and to subsequently be internalized by the hematopoietic stem cells (e.g., from 30 minutes to 6 hours at 4° C., such as 1 hour at 4° C.). Phage containing antibodies, or antibody fragments, that do not exhibit sufficient affinity for the CD45 so as to permit binding to, and internalization by, hematopoietic stem cells can subsequently be removed by washing the cells, for instance, with cold (4° C.) 0.1 M glycine buffer at pH 2.8. Phage bound to antibodies, or antibody fragments, that have been internalized by the hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or antibody fragments, inserted within the phage genome. The encoded antibodies, or antibody fragments, can subsequently be prepared de novo by chemical synthesis (for instance, of antibody fragments, such as scFv fragments) or by recombinant expression (for instance, of full-length antibodies).

In addition, the epitope regions described herein may be used as peptides by which to screen for additional anti-hCD45 antibodies using the screening techniques disclosed herein and known in the art.

Methods of Production

Antibodies may be produced using recombinant methods and compositions, e.g., as described in U.S. Pat. No. 4,816,567. In one embodiment, isolated nucleic acid encoding an anti-CD45 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD45 antibody, a nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Nucleic acids that may be used to express antibodies, or fragments, disclosed herein include those described in SEQ ID Nos: 25 to 30 in Table 3.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Chariton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 38:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060582); TRI cells, as described, e.g., in Mather et al., Annals N.Y. Acad. Sci. 383:44-88 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003). In one embodiment, the host cell is eukaryotic, e.g. a Chinese Hamster Ovary (CHO) cell or lymphoid cell (e.g., Y0, NS0, Sp20 cell).

The internalizing capacity of anti-CD45 antibodies, or antibody fragments, can be assessed, for instance, using radionuclide internalization assays known in the art. For example, anti-CD45 antibodies, or antibody fragments, identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{189}$Yb, $^{186}$Re, $^{64}$Cu, $^{67}$Cu, $^{177}$Lu, $^{77}$As, $^{72}$As, $^{86}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, or antibody fragments, using beads, such as polystyrene beads, containing electrophilic halogen reagents (e.g., Iodination Beads, Thermo Fisher Scientific, Inc., Cambridge, MA). Radiolabeled antibodies, fragments thereof, or ADCs, can be incubated with hematopoietic stem cells for a time sufficient to permit internalization (e.g., from 30 minutes to 6 hours at 4° C., such as 1 hour at 4° C.). The cells can then be washed to remove non-internalized antibodies or fragments thereof. (e.g., using cold (4° C.) 0.1 M glycine buffer at pH 2.8). Internalized antibodies, or antibody fragments, can be identified by detecting the emitted radiation (e.g., γ-radiation) of the resulting hematopoietic stem cells in comparison with the emitted radiation (e.g., γ-radiation) of the recovered wash buffer. The foregoing internalization assays can also be used to characterize ADCs.

Antibody Drug Conjugates (ADCs)

Anti-CD45 antibodies, or antigen-binding fragments thereof, described herein can be conjugated (linked) to a cytotoxin via a linker. In some embodiments, the cytotoxic molecule is conjugated to a cell internalizing antibody, or antigen-binding fragment thereof as disclosed herein such that following the cellular uptake of the antibody, or fragment thereof, the cytotoxin may access its intracellular target and mediate hematopoietic cell death.

Cytotoxins

Various cytotoxins can be conjugated to an anti-CD45 antibody via a inker for use in the therapies described herein. In particular, the anti-CD45 ADCs include an anti-CD45 antibody (or an antigen-binding fragment thereof) conjugated (i.e., covalently attached by a linker) to a cytotoxic moiety (or cytotoxin). In various embodiments, the cytotoxic moiety exhibits reduced or no cytotoxicity when bound in a conjugate, but resumes cytotoxicity after cleavage from the linker. In various embodiments, the cytotoxic moiety maintains cytotoxicity without cleavage from the linker. In some embodiments, the cytotoxic molecule is conjugated to a cell internalizing antibody, or antigen-binding fragment thereof as disclosed herein, such that following the cellular uptake of the antibody, or fragment thereof, the cytotoxin may access its intracellular target and, e.g., mediate T cell death.

ADCs of the present invention therefore may be of the general Formula

Ab-(Z-L-D)$_n$ wherein an antibody or antigen-binding fragment thereof (Ab) is conjugated (covalently linked) to linker (L), through a chemical moiety (Z), to a cytotoxic moiety ("drug," D).

Accordingly, the anti-CD45 antibody or antigen-binding fragment thereof may be conjugated to a number of drug moieties as indicated by integer n, which represents the average number of cytotoxins per antibody, which may range, e.g., from about 1 to about 20. In some embodiments, n is from 1 to 4. In some embodiments, n is 1. The average number of drug moieties per antibody in preparations of ADC from conjugation reactions may be characterized by conventional means such as mass spectroscopy, ELISA assay, and HPLC. The quantitative distribution of ADC in terms of n may also be determined. In some instances, separation, purification, and characterization of homogeneous ADC where n is a certain value from ADC with other drug loadings may be achieved by means such as reverse phase HPLC or electrophoresis.

For some anti-CD45 ADCs, they may be limited by the number of attachment sites on the antibody. For example, where the attachment is a cysteine thiol, an antibody may have only one or several cysteine thiol groups, or may have only one or several sufficiently reactive thiol groups through which a linker may be attached. Generally, antibodies do not contain many free and reactive cysteine thiol groups which may be linked to a drug moiety; primarily, cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, higher drug loading (DAR), e.g. n>5, may cause aggregation, insolubility, toxicity, or loss of cellular permeability of certain antibody-drug conjugates.

In certain embodiments, fewer than the theoretical maximum of drug moieties are conjugated to an antibody during a conjugation reaction. An antibody may contain, for example, lysine residues that do not react with the drug-inker intermediate or linker reagent, as discussed below. Only the most reactive lysine groups may react with an amine-reactive linker reagent. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-inker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments.

Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), and agents capable of disrupting protein biosynthesis (e.g., agents that exhibit rRNA N-glycosidase activity, such as saporin and ricin A-chain), among others known in the art.

In some embodiments, the cytotoxin is a microtubule-binding agent (for instance, maytansine or a maytansinoid), an amatoxin, pseudomonas exotoxin A, deBouganin, diphtheria toxin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, an indolinobenzodiazepine pseudodimer, or a variant thereof, or another cytotoxic compound described herein or known in the art.

In some embodiments, the cytotoxin of the antibody-drug conjugate is an RNA polymerase inhibitor. In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

Additional details regarding cytotoxins that can be used in the anti-CD45 ADCs useful in the compositions and methods of the invention are described below.

Amatoxins

In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

In some embodiments, the cytotoxin of the antibody-drug conjugate is an RNA polymerase inhibitor. In some embodiments, the RNA polymerase inhibitor is an amatoxin or derivative thereof.

In some embodiments, the cytotoxin is an amatoxin or derivative thereof, such as α-amanitin, β-amanitin, γ-amanitin, ε-amanitin, amanin, amaninamide, amanullin, amanullinic acid, and proamanullin. Structures of the various naturally occurring amatoxins are disclosed in, e.g., Zanotti et al., Int. J. Peptide Protein Res. 30, 1987, 450-459.

Amatoxins useful in conjunction with the compositions and methods described herein include compounds according to, but are not limited to, formula (IV), (IV)

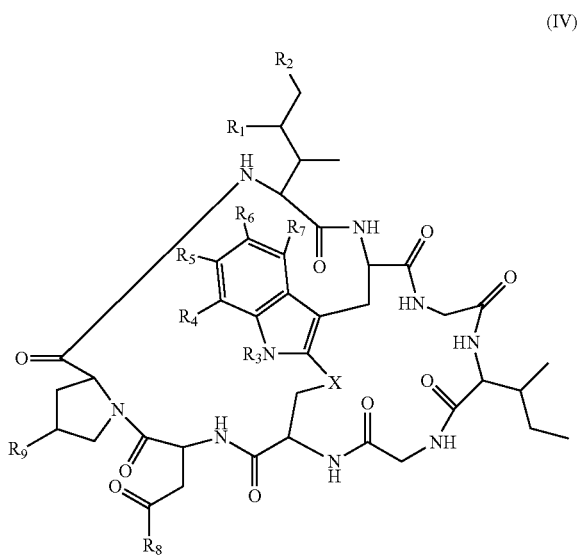

wherein:
R₁ is H, OH, or OR$_A$;
R₂ is H, OH, or OR$_B$;
R$_A$ and R$_B$, when present, together with the oxygen atoms to which they are bound, combine to form an optionally substituted 5-membered heterocycloalkyl group;
R₃ is H or R$_D$;
R₄ is H, OH, OR$_D$, or R$_D$;
R₅ is H, OH, OR$_D$, or R$_D$;
R₆ is H, OH, OR$_D$, or R$_D$;
R₇ is H, OH, OR$_D$, or R$_D$;
R₈ is OH, NH₂, or OR$_D$;
R₉ is H, OH, or OR$_D$;
X is —S—, —S(O)—, or —SO₂—; and
R$_D$ is optionally substituted alkyl (e.g., C₁-C₆ alkyl, optionally substituted heteroalkyl (e.g., C₁-C₆ heteroalkyl), optionally substituted alkenyl (e.g., C₂-C₆ alkenyl), optionally substituted heteroalkenyl (e.g., C₂-C₆ heteroalkenyl), optionally substituted alkynyl (e.g., C₂-C₆ alkynyl), optionally substituted heteroalkynyl (e.g., C₂-C₆ heteroalkynyl), optionally substituted cycloalkyl, optionally substituted heterocycloalkyl, optionally substituted aryl, or optionally substituted heteroaryl.

For instance, in one embodiment, amatoxins useful in conjunction with the compositions and methods described herein include compounds according to formula (IVA)

(IVA)

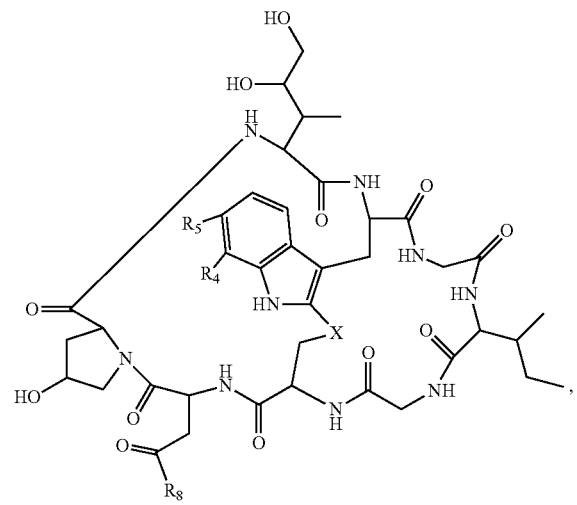

wherein R₄, R₅, X, and R₈ are each as defined above.

For instance, in one embodiment, amatoxins useful in conjunction with the compositions and methods described herein include compounds according to formula (IVB), below:

(IVB)

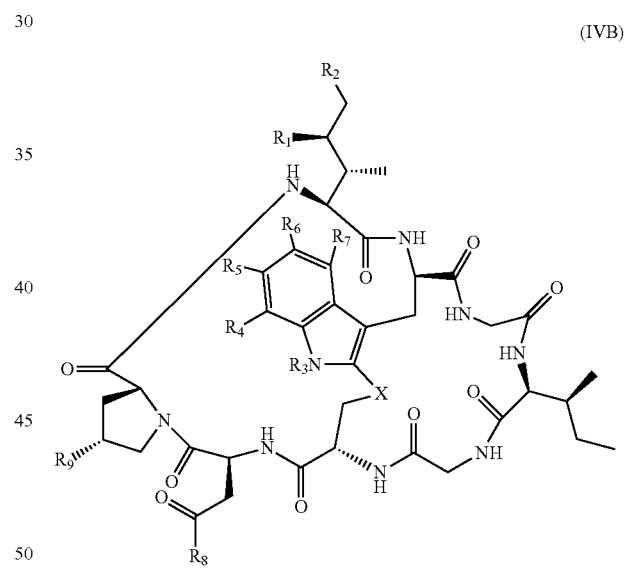

wherein:
R₁ is H, OH, or OR$_A$;
R₂ is H, OH, or OR$_B$;
R$_A$ and R$_B$, when present, together with the oxygen atoms to which they are bound, combine to form an optionally substituted 5-membered heterocycloalkyl group;
R₃ is H or R$_D$;
R₄ is H, OH, OR$_D$, or R$_D$;
R₅ is H, OH, OR$_D$, or R$_D$;
R₆ is H, OH, OR$_D$, or R$_D$;
R₇ is H, OH, OR$_D$, or R$_D$;
R₈ is OH, NH₂, or OR$_D$;
R₉ is H, OH, or OR$_D$;
X is —S—, —S(O)—, or —SO₂—; and
R$_D$ is optionally substituted alkyl (e.g., C₁-C₆ alkyl), optionally substituted heteroalkyl (e.g., C₂-C₆ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

In one embodiment, amatoxins useful in conjunction with the compositions and methods described herein also include compounds according to formula (IVC), below:

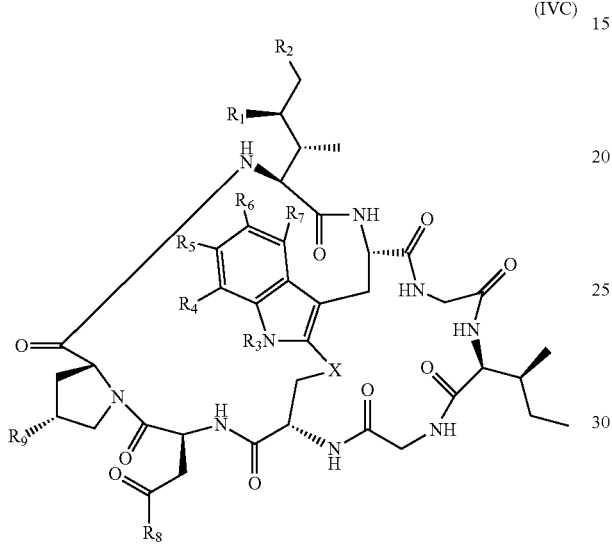

(IVC)

wherein:
$R_1$ is H, OH, or $OR_A$;
$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

Synthetic methods of making amatoxin are described in U.S. Pat. No. 9,676,702, which is incorporated by reference herein.

For instance, the antibodies, and antigen-binding fragments, described herein may be bound to an amatoxin (e.g., of Formula IV, IVA, IVB, or IVC) so as to form a conjugate represented by the formula Ab-Z-L-Am, wherein Ab is the antibody, or antigen-binding fragment thereof, L is a inker, Z is a chemical moiety and Am is an amatoxin. Many positions on amatoxins or derivatives thereof can serve as the position to covalently bond the linking moiety L, and, hence the antibodies or antigen-binding fragments thereof. In some embodiments, the amatoxin-linker conjugate Am-L-Z is represented by formula (I)

(I)

wherein:

$R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl, optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —C(=O)—, a disulfide, a hydrazone, or a combination thereof;

and

Z is a chemical moiety formed from a coupling reaction between a reactive substituent Z' present on L and a reactive substituent present within an antibody, or antigen-binding fragment thereof, that binds a target antigen (e.g., CD45).

In some embodiments, Am contains exactly one $R_C$ substituent.

In some embodiments, L-Z is

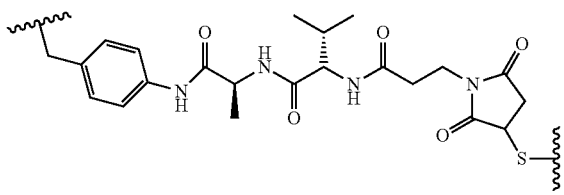

where S is a sulfur atom which represents the reactive substituent present within an antibody, or antigen-binding fragment thereof, that binds a target antigen (e.g., from the —SH group of a cysteine residue).

In some embodiments, the conjugate Am-L-Z-Ab is represented by one of formulas III, IIIA, or IIIB:

(III)

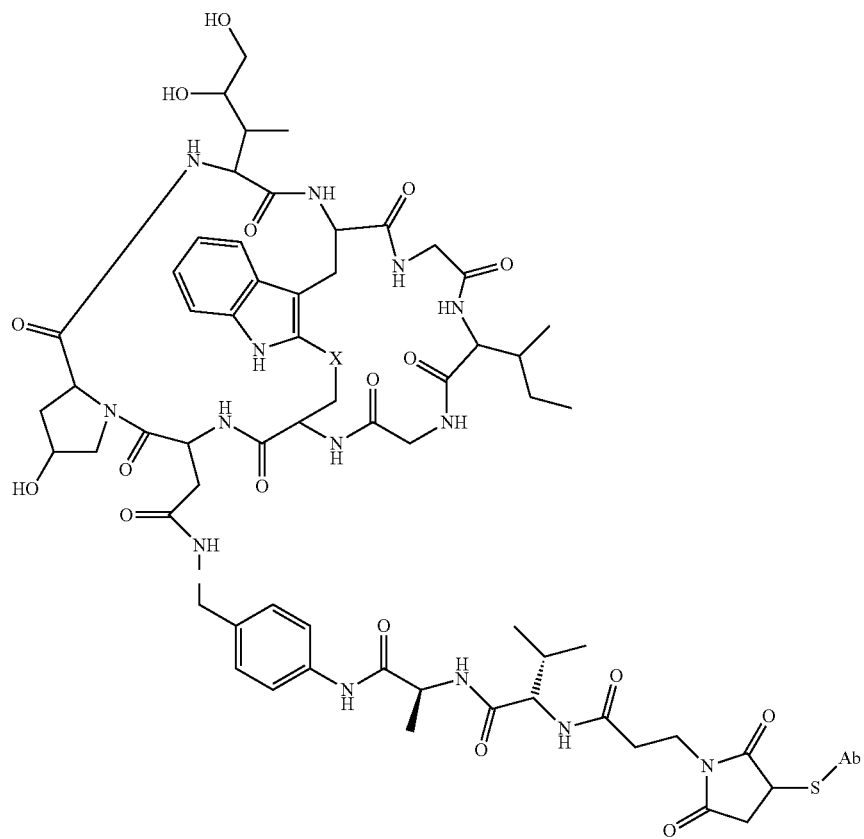

(IIIA)
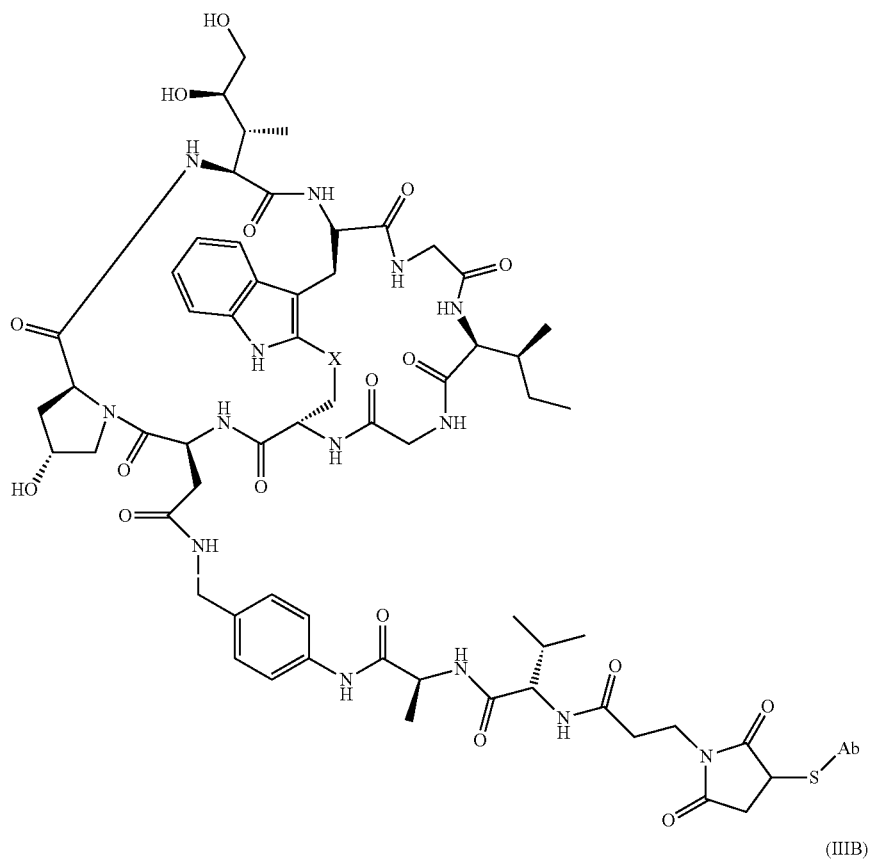
(IIIB)
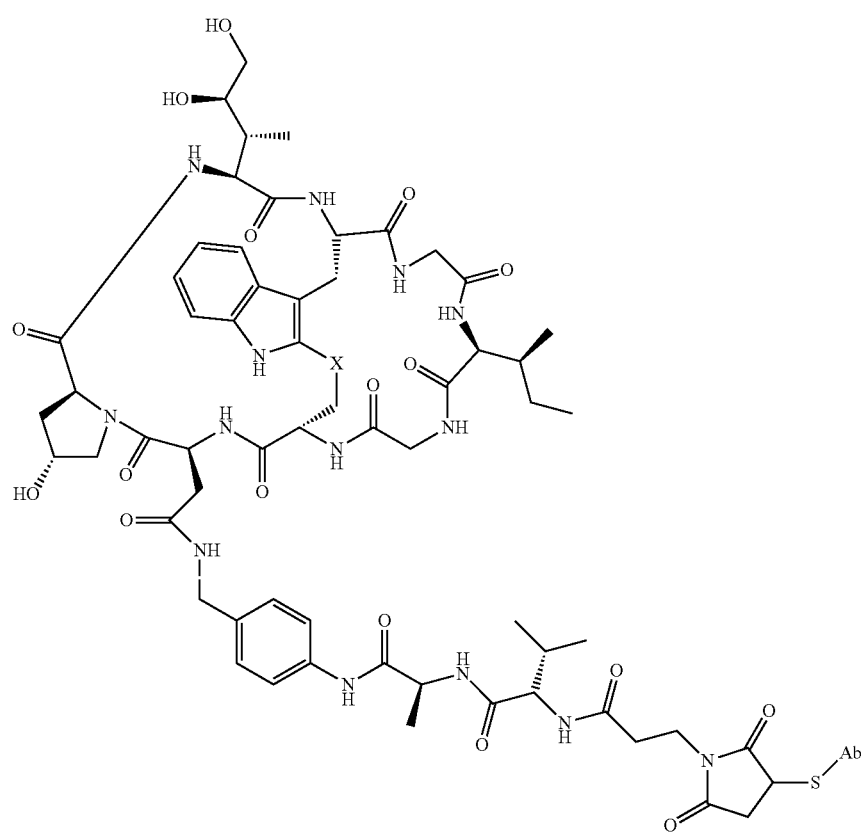

where X is S, SO or SO$_2$, and the Ab is shown to indicate the point of Ab attachment.

In some embodiments, Am-L-Z-Ab is

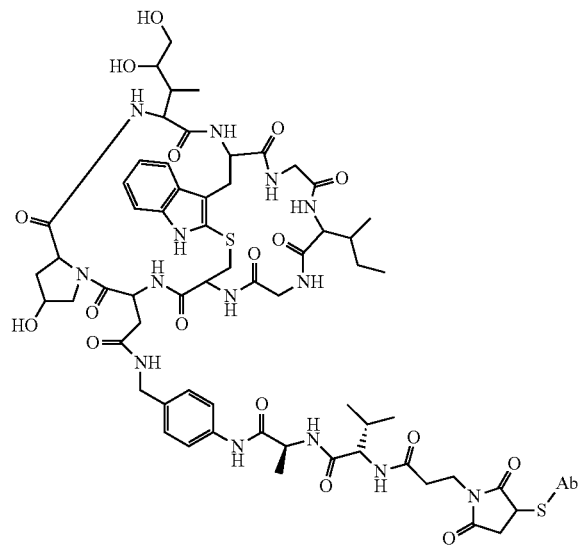

where Ab is shown to indicate the point of Ab attachment.

In some embodiments, Am-L-Z-Ab is

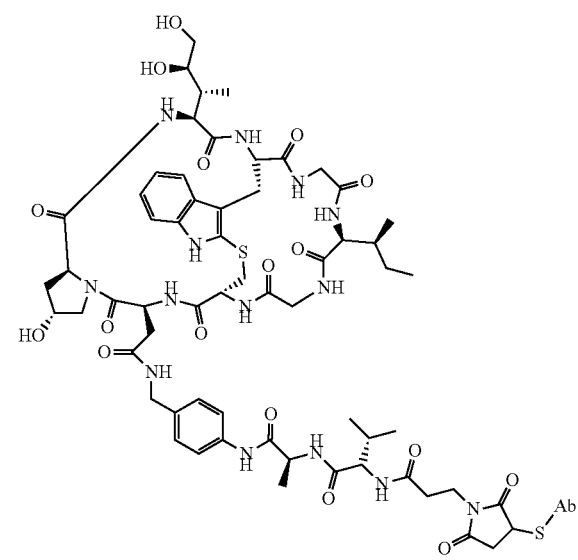

where Ab is shown to indicate the point of Ab attachment.

In some embodiments, Am-L-Z-Ab is

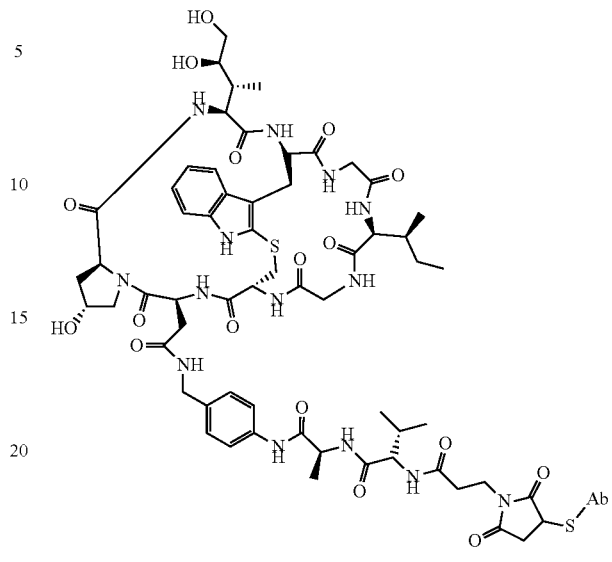

where Ab is shown to indicate the point of Ab attachment.

In some embodiments, the Am-L-Z-Ab precursor Am-L-Z is wherein the maleimide reacts with a thiol group found on a cysteine in the antibody.

In some embodiments, the Am-L-Z-Ab precursor Am-L-Z is

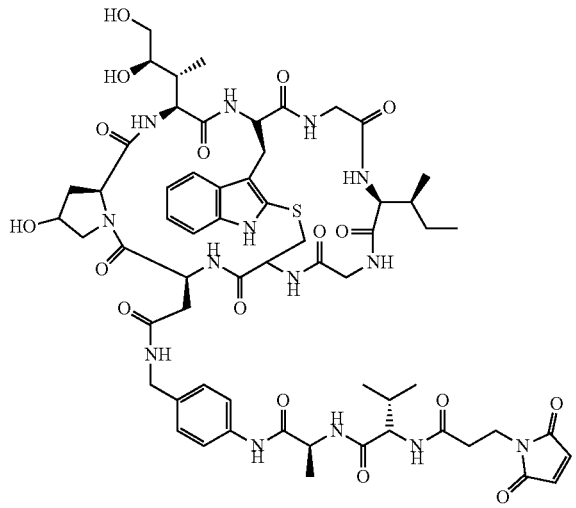

wherein the maleimide reacts with a thiol group found on a cysteine in the antibody.

In some embodiments, Am-L-Z is represented by formula (IA)

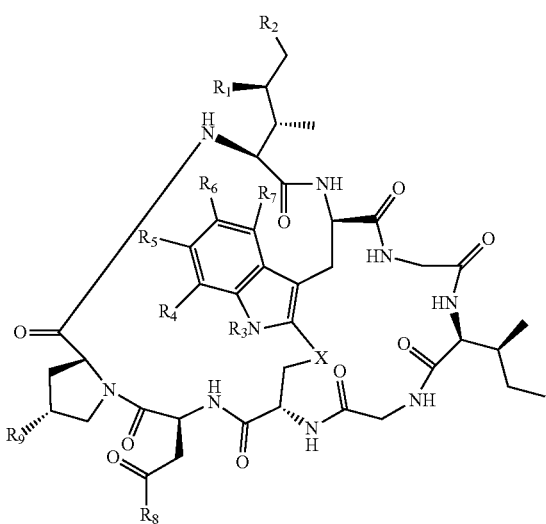

wherein:
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;

$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —C(=O)—, a disulfide, a hydrazone, or a combination thereof;
Z is a chemical moiety formed from a coupling reaction between a reactive substituent Z present on L and a reactive substituent present within an antibody, or antigen-binding fragment thereof, that binds CD45; and
wherein Am contains exactly one $R_C$ substituent.
In some embodiments, L-Z is

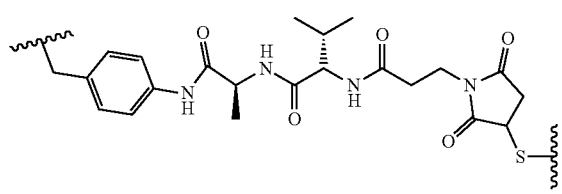

In some embodiments, Am-L-Z is represented by formula (IB)

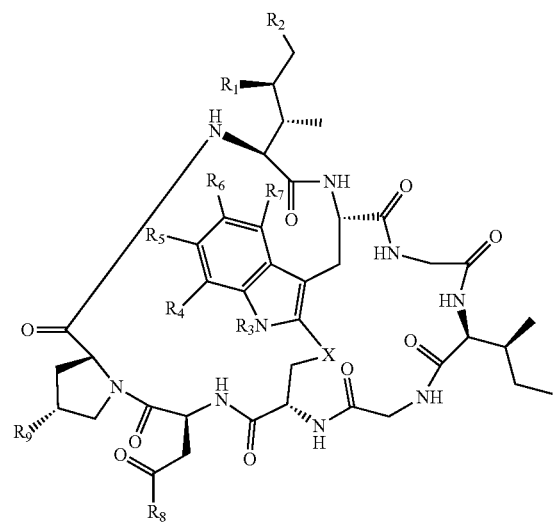

wherein:
R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form an optionally substituted 5-membered heterocycloalkyl group;
R$_3$ is H, R$_C$, or R$_D$;
R$_4$ is H, OH, OR$_C$, OR$_D$, R$_C$, or R$_D$;
R$_5$ is H, OH, OR$_C$, OR$_D$, R$_C$, or R$_D$;
R$_6$ is H, OH, OR$_C$, OR$_D$, R$_C$, or R$_D$;
R$_7$ is H, OH, OR$_C$, OR$_D$, R$_C$, or R$_D$;
R$_8$ is OH, NH$_2$, OR$_C$, OR$_D$, NHR$_C$, or NR$_C$R$_D$;
R$_9$ is H, OH, OR$_C$, or OR$_D$;
X is —S—, —S(O)—, or —SO$_2$—;
R$_C$ is -L-Z;
R$_D$ is optionally substituted alkyl (e.g., C$_1$-C$_6$ alkyl), optionally substituted heteroalkyl (e.g., C$_1$-C$_6$ heteroalkyl), optionally substituted alkenyl (e.g., C$_2$-C$_6$ alkenyl), optionally substituted heteroalkenyl (e.g., C$_2$-C$_6$ heteroalkenyl), optionally substituted alkynyl (e.g., C$_2$-C$_6$ alkynyl), optionally substituted heteroalkynyl (e.g., C$_2$-C$_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., C$_1$-C$_6$ alkylene), optionally substituted heteroalkylene (C$_1$-C$_6$ heteroalkylene), optionally substituted alkenylene (e.g., C$_2$-C$_6$ alkenylene), optionally substituted heteroalkenylene (e.g., C$_2$-C$_6$ heteroalkenylene), optionally substituted alkynylene (e.g., C$_2$-C$_6$ alkynylene), optionally substituted heteroalkynylene (e.g., C$_2$-C$_6$ heteroalkynylene), optionally substituted cycloalkylene, optionally substituted heterocycloalkylene, optionally substituted arylene, optionally substituted heteroarylene, a peptide, a dipeptide, —C(=O)—, a disulfide, a hydrazone, or a combination thereof;
Z is a chemical moiety formed from a coupling reaction between a reactive substituent present on L and a reactive substituent present within an antibody, or antigen-binding fragment thereof, that binds CD45; and
wherein Am contains exactly one R$_C$ substituent.
In some embodiments, L-Z is

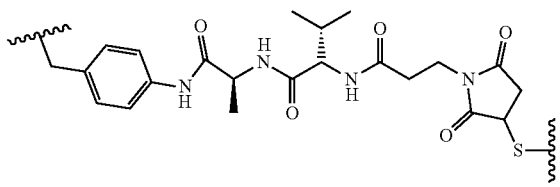

In some embodiments, R$_A$ and R$_B$, when present, together with the oxygen atoms to which they are bound, combine to form a 5-membered heterocycloalkyl group of formula:

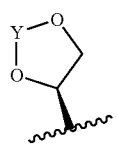

wherein Y is —C(=O)—, —C(=S)—, —C(=NR$_E$)—, or —C(R$_E$R$_{E'}$)—; and
R$_E$ and R$_{E'}$ are each independently optionally substituted C$_1$-C$_6$ alkylene-R$_C$, optionally substituted C$_1$-C$_6$ heteroalkylene-R$_C$, optionally substituted C$_2$-C$_6$ alkenylene-R$_C$, optionally substituted C$_2$-C$_6$ heteroalkenylene-R$_C$, optionally substituted C$_2$-C$_6$ alkynylene-R$_C$, optionally substituted C$_2$-C$_6$ heteroalkynylene-R$_C$, optionally substituted cycloalkylene-R$_C$, optionally substituted heterocycloalkylene-R$_C$, optionally substituted arylene-R$_C$, or optionally substituted heteroarylene-R$_C$.
In some embodiments, Am-L-Z is represented by formula (IA) or formula (IB),
wherein:
R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form:

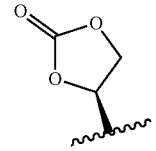 [SMILES: *[C@@H]1COC(=O)O1]

R$_3$ is H or R$_C$;
R$_4$ is H, OH, OR$_C$, OR$_D$, R$_C$, or R$_D$;
R$_5$ is H, OH, OR$_C$, OR$_D$, R$_C$, or R$_D$;
R$_6$ is H, OH, OR$_C$, OR$_D$, R$_C$, or R$_D$;
R$_7$ is H, OH, OR$_C$, OR$_D$, R$_C$, or R$_D$;
R$_8$ is OH, NH$_2$, OR$_C$, or NHR$_C$;
R$_9$ is H or OH;
X is —S—, —S(O)—, or —SO$_2$—; and
wherein R$_C$ and R$_D$ are each as defined above.
In some embodiments, Am-L-Z is represented by formula (IA) or formula (IB),
wherein R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form:

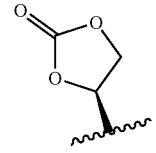 [SMILES: *[C@@H]1COC(=O)O1]

R$_3$ is H or R$_C$;
R$_4$ and R$_5$ are each independently H, OH, OR$_C$, R$_C$, or OR$_D$;
R$_6$ and R$_7$ are each H;
R$_8$ is OH, NH$_2$, OR$_C$, or NHR$_C$;
R$_9$ is H or OH;
X is —S—, —S(O)—, or —SO$_2$—; and
wherein R$_C$ is as defined above.
In some embodiments, Am-L-Z is represented by formula (IA) or formula (IB),
wherein R$_1$ is H, OH, or OR$_A$;
R$_2$ is H, OH, or OR$_B$;
R$_A$ and R$_B$, when present, together with the oxygen atoms to which they are bound, combine to form:

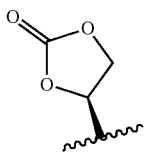 [SMILES: *[C@@H]1COC(=O)O1]

$R_3$, $R_4$, $R_6$, and $R_7$ are each H;
$R_5$ is $OR_C$;
$R_8$ is OH or $NH_2$;
$R_9$ is H or OH;
X is —S—, —S(O)—, or —$SO_2$—; and
wherein $R_C$ is as defined above. Such amatoxin conjugates are described, for example, in US Patent Application Publication No. 2016/0002298, the disclosure of which is incorporated herein by reference in its entirety.

In some embodiments, Am-L-Z is represented by formula (IA) or formula (IB),
wherein $R_1$ and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$;
$R_9$ is H or OH;
X is —S—, —S(O)—, or —$SO_2$—; and
wherein $R_C$ is as defined above. Such amatoxin conjugates are described, for example, in US Patent Application Publication No. 2014/0294865, the disclosure of which is incorporated herein by reference in its entirety.

In some embodiments, Am-L-Z is represented by formula (IA) or formula (IB),
wherein $R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH;
X is —S—, —S(O)—, or —$SO_2$—; and
wherein $R_C$ is as defined above. Such amatoxin conjugates are described, for example, in US Patent Application Publication No. 2015/0218220, the disclosure of which is incorporated herein by reference in its entirety.

In some embodiments, Am-L-Z is represented by formula (IA) or formula (IB),
wherein:
$R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH;
X is —S—, —S(O)—, or —$SO_2$—; and
wherein $R_C$ is as defined above. Such amatoxin conjugates are described, for example, in U.S. Pat. Nos. 9,233,173 and 9,399,681, as well as in US 2016/0089450, the disclosures of each of which are incorporated herein by reference in their entirety.

In some embodiments, Am-L-Z' is

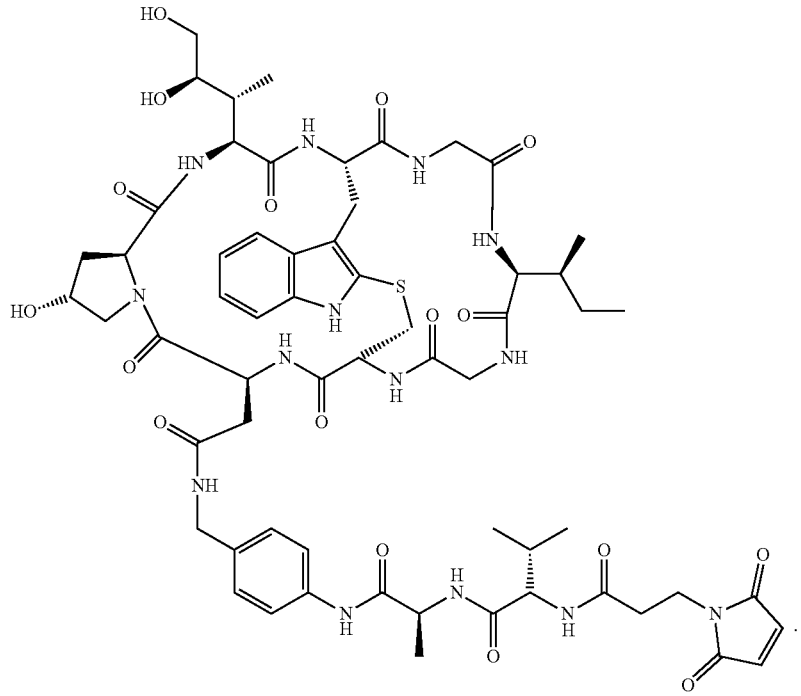

Additional amatoxins that may be used for conjugation to an antibody, or antigen-binding fragment thereof, in accordance with the compositions and methods described herein are described, for example, in WO 2016/142049; WO 2016/071856; WO 2017/149077; WO 2018/115466; and WO 2017/046658, the disclosures of each of which are incorporated herein by reference in their entirety.

In some embodiments, Am-L-Z is represented by formula (II), formula (IIA), or formula (IIB)

(II)

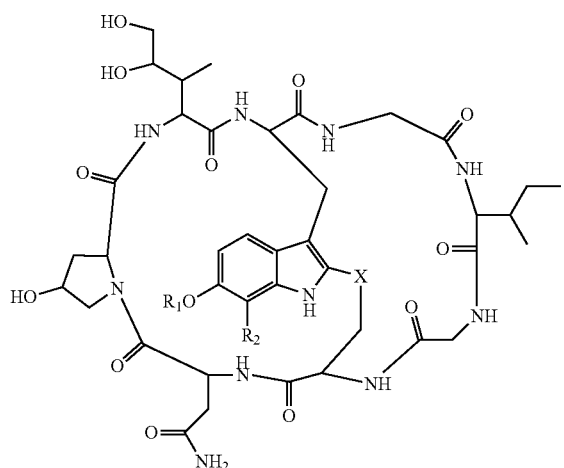

(IIA)

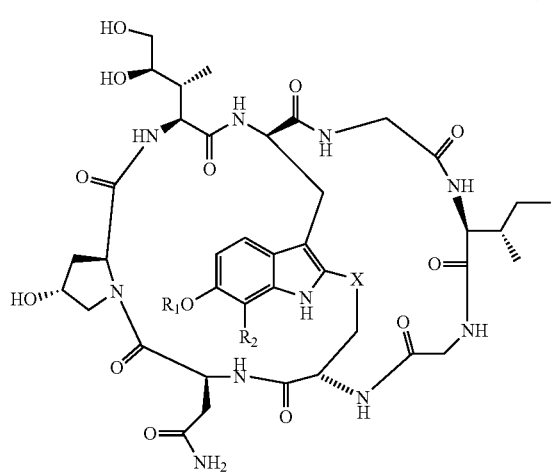

(IIB)

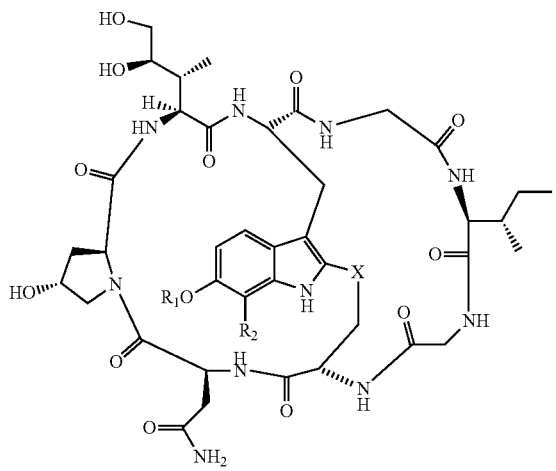

wherein X is S, SO, or SO$_2$; R$_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and R$_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; wherein when R$_1$ is H, R$_2$ is the linker, and when R$_2$ is H, R$_1$ is the linker. In some embodiments, R$_1$ is the linker and R$_2$ is H, and the linker and chemical moiety, together as L-Z, is

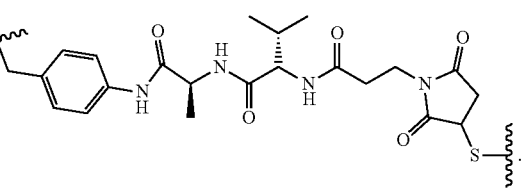

In some embodiments, R$_1$ is the linker and R$_2$ is H, and the linker and chemical moiety, together as L-Z, is

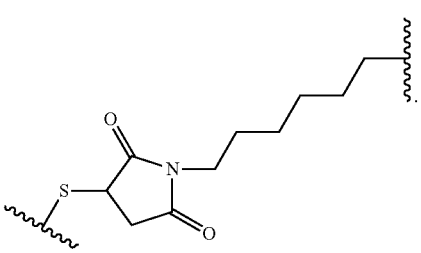 [SMILES: *CCCCCCN1C(=O)CC(S*)C1=O]

In one embodiment, Am-L-Z-Ab is:

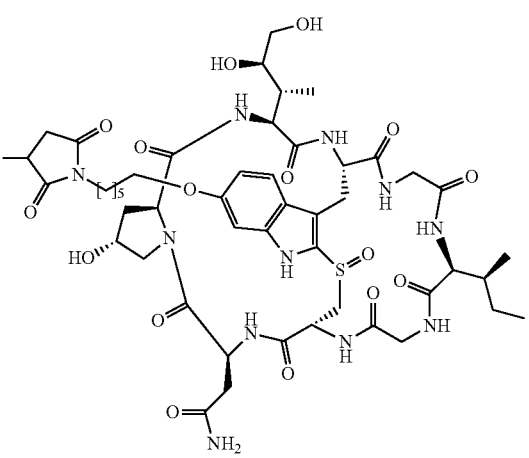

In one embodiment, Am-L-Z-Ab is:

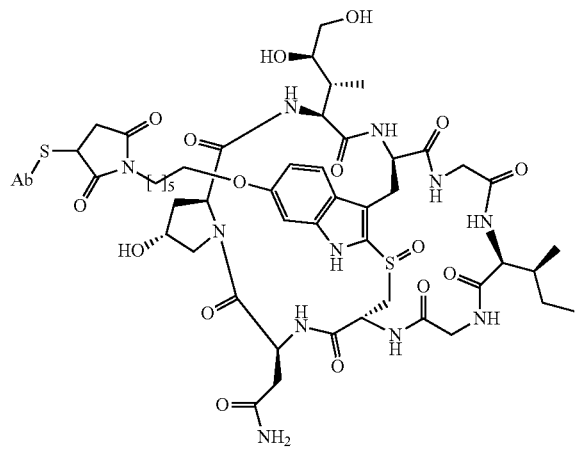

In some embodiments, the Am-L-Z-Ab precursor (i.e., Am-L-Z') is one of:

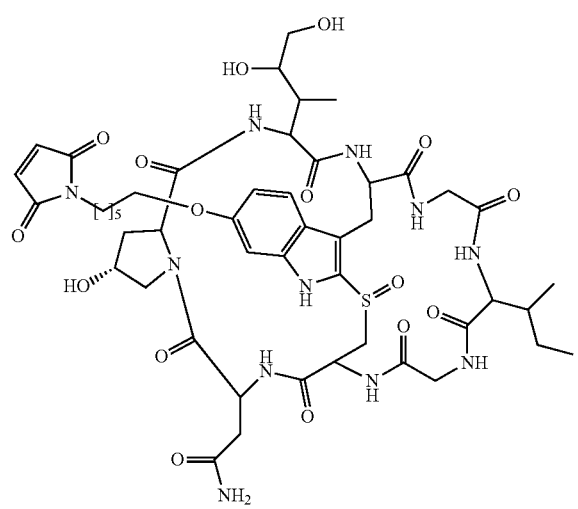

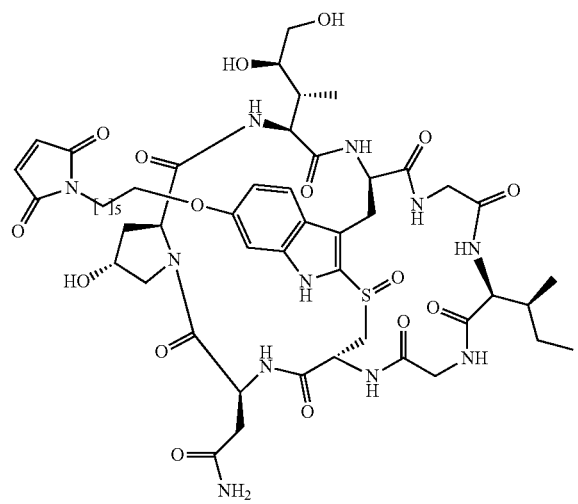

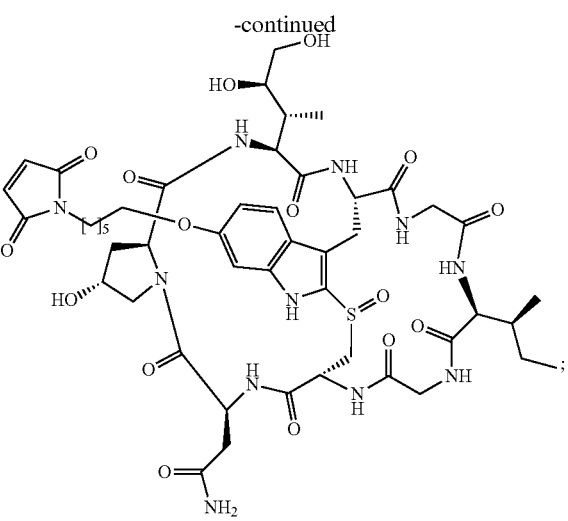

wherein the maleimide reacts with a thiol group found on a cysteine in the antibody.

In some embodiments, the cytotoxin is an α-amanitin. In some embodiments, the α-amanitin is attached to an anti-CD45 antibody via a linker L. In some embodiments, the α-amanitin is a compound of formula IV. The linker L may be attached to the α-amanitin of formula IV at any one of several possible positions (e.g., any of $R^1$-$R^9$) to provide an α-amanitin-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

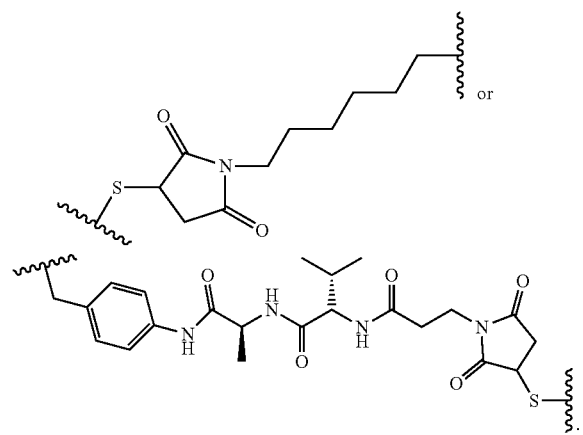

In some embodiments, the cytotoxin is a β-amanitin. In some embodiments, the β-amanitin is attached to an anti- CD45 antibody via a linker L. In some embodiments, the β-amanitin is a compound of formula IV. The linker L may be attached to the β-amanitin of formula IV at any one of several possible positions (e.g., any of $R^1$-$R^9$) to provide an β-amanitin-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is In some embodiments, the cytotoxin is a γ-amanitin. In some embodiments, the γ-amanitin is attached to an anti-CD45 antibody via a linker L. In some embodiments, the γ-amanitin is a compound of formula IV. The linker L may be attached to the γ-amanitin of formula IV at any one of several possible positions (e.g., any of $R^1$-$R^9$) to provide an γ-amanitin-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O) (CH$_2$)$_n$—. In some embodiments, the linker L and the chemical moiety Z, taken together as L-Z, is In some embodiments, the cytotoxin is a ε-amanitin. In some embodiments, the ε-amanitin is attached to an anti-CD45 antibody via a linker L. In some embodiments, the ε-amanitin is a compound of formula IV. The linker L may be attached to the ε-amanitin of formula IV at any one of several possible positions (e.g., any of $R^1$-$R^9$) to provide an ε-amanitin-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O) (CH$_2$)$_n$—. In some embodiments, the linker L and the chemical moiety Z, taken together as L-Z, is In some embodiments, the cytotoxin is an amanin. In some embodiments, the amanin is attached to an anti-CD45 antibody via a linker L. In some embodiments, the amanin is a compound of formula IV. The linker L may be attached to the amanin of formula IV at any one of several possible positions (e.g., any of $R^1$-$R^9$) to provide an amanin-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

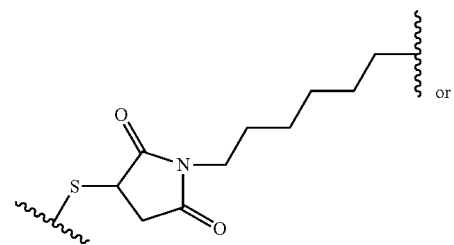

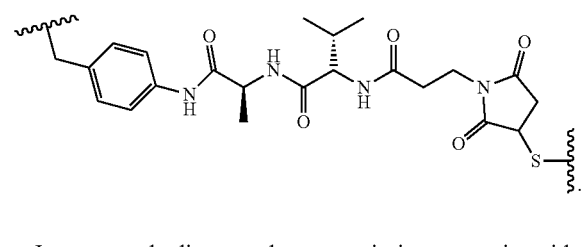

In some embodiments, the cytotoxin is an amaninamide. In some embodiments, the amaninamide is attached to an anti-CD45 antibody via a linker L. In some embodiments, the amaninamide is a compound of formula IV. The linker L may be attached to the amaninamide of formula IV at any one of several possible positions (e.g., any of R$^1$-R$^9$) to provide an amaninamide-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

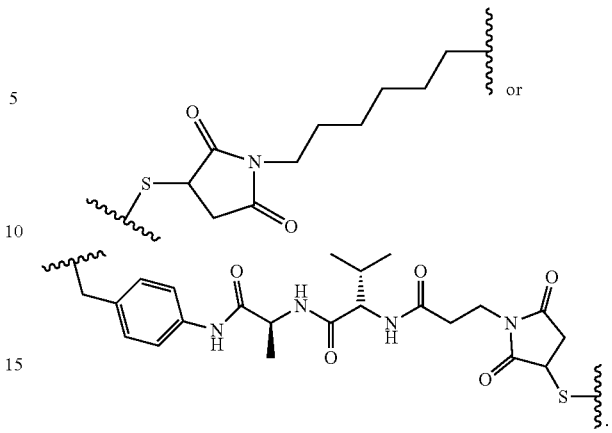

In some embodiments, the cytotoxin is an amanullin. In some embodiments, the amanullin is attached to an anti-CD45 antibody via a linker L. In some embodiments, the amanullin is a compound of formula IV. The linker L may be attached to the amanullin n of formula IV at any one of several possible positions (e.g., any of R$^1$-R$^9$) to provide an amanullin-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

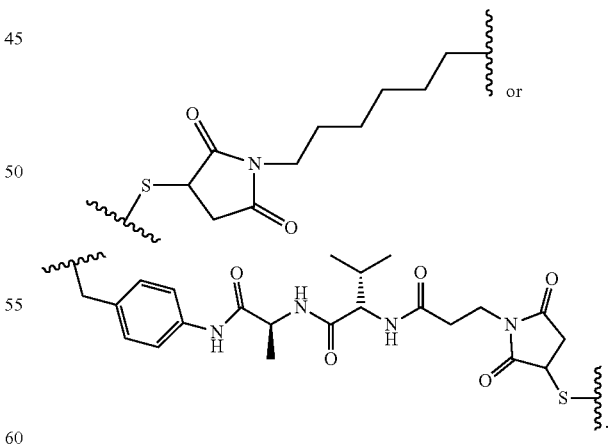

In some embodiments, the cytotoxin is an amanullinic acid. In some embodiments, the amanullinic acid is attached to an anti-CD45 antibody via a linker L. In some embodiments, the amanullinic acid is a compound of formula IV. The linker L may be attached to the amanullinic acid of formula IV at any one of several possible positions (e.g., any of $R^1$-$R^9$) to provide an amanullinic acid-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-8. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

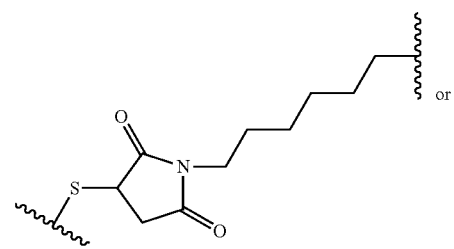

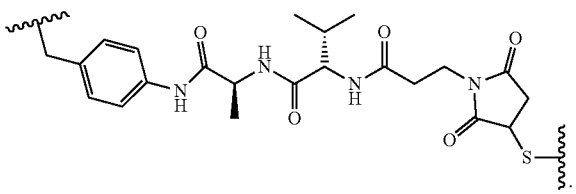

In some embodiments, the cytotoxin is a proamanullin. In some embodiments, the proamanullin is attached to an anti-CD45 antibody via a linker L. In some embodiments, the proamanullin is a compound of formula IV. The linker L may be attached to the proamanullin of formula IV at any one of several possible positions (e.g., any of $R^1$-$R^9$) to provide an proamanullin-linker conjugate of formula I, IA, IB, II, IIA, or IIB. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

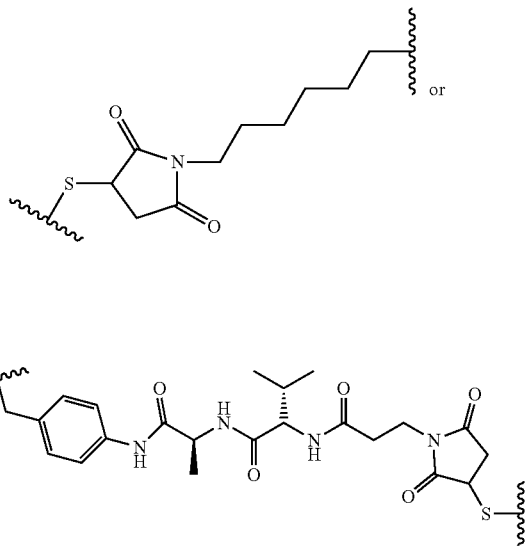

Antibodies, and antigen-binding fragments, for use with the compositions and methods described herein can be conjugated to an amatoxin, such as α-amanitin or a variant thereof, using conjugation techniques known in the art or described herein. For instance, antibodies, and antigen-binding fragments thereof, that recognize and bind a target antigen (an anti-CD45 antibody can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Auristatins

An anti-CD45 antibody or antigen-binding fragment thereof, described herein can be conjugated to a cytotoxin that is an auristatin (U.S. Pat. Nos. 5,635,483; 5,780,588). Auristatins are anti-mitotic agents that interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). (U.S. Pat. Nos. 5,635,483; 5,780,588). The auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE, wherein the wavy line indicates the point of covalent attachment to the linker of an antibody-linker conjugate (-L-Z-Ab or -L-Z', as described herein):

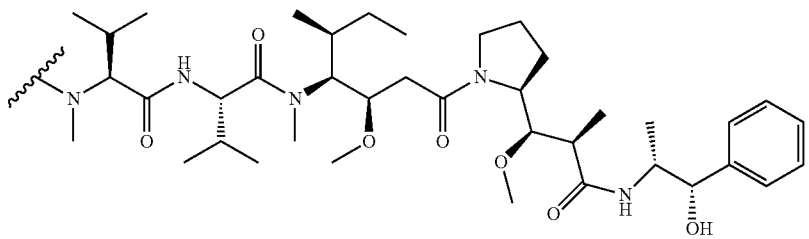 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

Another exemplary auristatin embodiment is MMAF, wherein the wavy line indicates the point of covalent attachment to the linker of an antibody-linker conjugate (-L-Z-Ab or -L-Z', as described herein), as disclosed in US 2005/0238649:

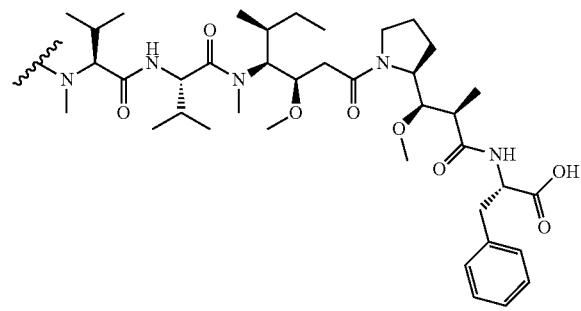 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

Auristatins may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat. Biotechnol. 21(7):778-784.

Maytansinoids

Antibodies and antigen-binding fragments thereof described herein can be conjugated to a cytotoxin that is a microtubule binding agent. In some embodiments, the microtubule binding agent is a maytansine, a maytansinoid or a maytansinoid analog. Maytansinoids are mitototic inhibitors which bind microtubules and act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Examples of suitable maytansinoids include esters of maytansinol, synthetic maytansinol, and maytansinol analogs and derivatives. Included herein are any cytotoxins that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the antibody-drug conjugates (ADCs) of the present disclosure utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula V:

(V)

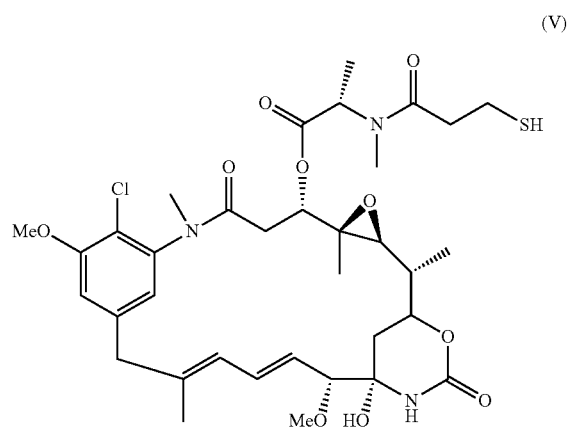 [SMILES: COc1cc2cc(c1Cl)N(C)C(=O)C[C@H](OC(=O)[C@H](C)N(C)C(=O)CCS)[C@]1(C)O[C@H]1[C@H](C)C1C[C@@](O)(NC(=O)O1)[C@H](OC)/C=C/C=C(\C)C2]

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula VI:

(VI)

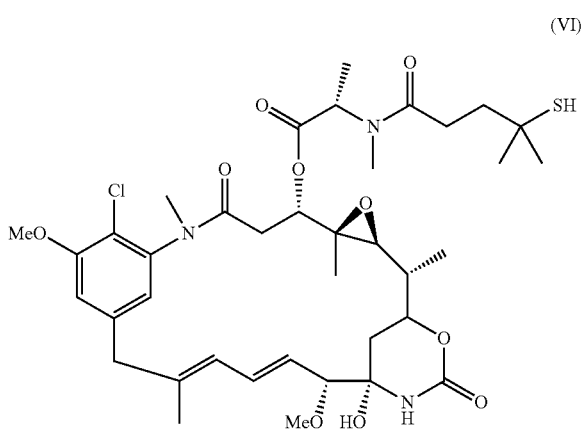 [SMILES: COc1cc2cc(c1Cl)N(C)C(=O)C[C@H](OC(=O)[C@H](C)N(C)C(=O)CCC(C)(C)S)[C@]1(C)O[C@H]1[C@H](C)C1C[C@@](O)(NC(=O)O1)[C@H](OC)/C=C/C=C(\C)C2]

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula VII:

(VII)

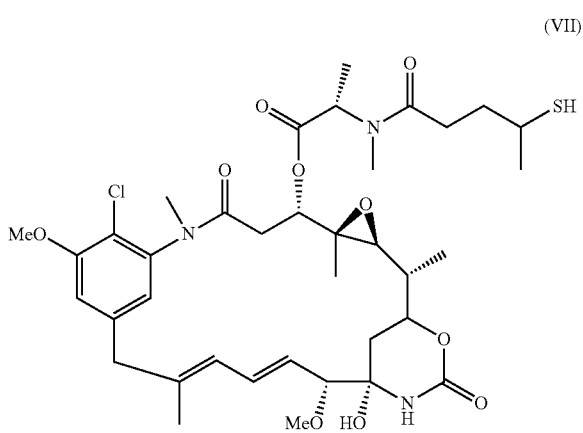 [SMILES: COc1cc2cc(c1Cl)N(C)C(=O)C[C@H](OC(=O)[C@H](C)N(C)C(=O)CCC(C)S)[C@]1(C)O[C@H]1[C@H](C)C1C[C@@](O)(NC(=O)O1)[C@H](OC)/C=C/C=C(\C)C2]

Each of the maytansinoids taught in U.S. Pat. Nos. 5,208,020 and 7,276,497, can also be used in the conjugates of the present disclosure. In this regard, the entire disclosure of U.S. Pat. Nos. 5,208,020 and 7,276,697 is incorporated herein by reference.

Many positions on maytansinoids can serve as the position to covalently bond the linking moiety and, hence the antibodies or antigen-binding fragments thereof (-L-Z-Ab or -L-Z', as described herein). For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to covalently bond the linker moiety, and in some particular embodiments, the C-3 position of maytansinol serves as the position to covalently bond the linking moiety. There are many linking groups known in the art for making antibody-maytansinoid conjugates, including, for example, those disclosed in U.S. Pat. Nos. 5,208,020, 6,441,163, and EP Patent No. 0425235 B1; Chari et al., Cancer Research 52:127-131 (1992); and U.S. 2005/0169933 A1, the disclosures of which are hereby expressly incorporated by reference. Additional linking groups are described and exemplified herein.

The present invention also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020; 5,416,064; 6,333,410; 6,441,163; 6,716,821; and 7,368,565, each of which is incorporated herein in its entirety.

Anthracyclines

In other embodiments, the antibodies and antigen-binding fragments thereof described herein can be conjugated to a cytotoxin that is an anthracycline molecule. Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracycline In Experimental Systems And Human Leukemia" in Anthracycline Antibiotics In Cancer Therapy; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H-Wiemik, in Anthracycline: Current Status And New Developments p 11]. Commonly used anthracyclines include doxorubicin, epirubicin, idarubicin and daunomycin. In some embodiments, the cytotoxin is an anthracycline selected from the group consisting of daunorubicin, doxorubicin, epirubicin, and idarubicin. Representative examples of anthracyclines include, but are not limited to daunorubicin (Cerubidine; Bedford Laboratories), doxorubicin (Adriamycin; Bedford Laboratories; also referred to as doxorubicin hydrochloride, hydroxy-daunorubicin, and Rubex), epirubicin (Ellence; Pfizer), and idarubicin (Idamycin; Pfizer Inc.)

The anthracycline analog, doxorubicin (ADRIAMYCINO) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al., (2007) Cardiovasc. Toxicol. 7:75-79).

One non-limiting example of a suitable anthracycline for use herein is PNU-159682 ("PNU"). PNU exhibits greater than 3000-fold cytotoxicity relative to the parent nemorubicin (Quintieri et al., Clinical Cancer Research 2005, 11, 1608-1617). PNU is represented by structural formula:

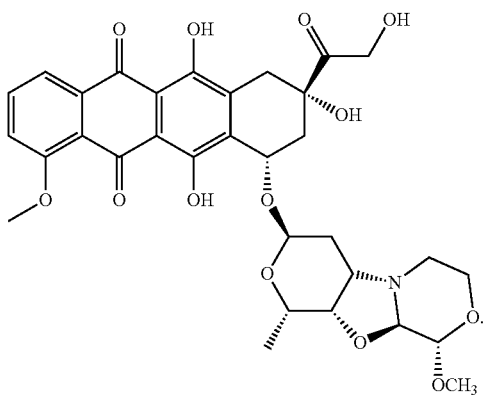

Multiple positions on anthracyclines such as PNU can serve as the position to covalently bond the linking moiety and, hence the anti-CD45 antibodies or antigen-binding fragments thereof as described herein. For example, linkers may be introduced through modifications to the hydroxymethyl ketone side chain.

In some embodiments, the cytotoxin is a PNU derivative represented by structural formula:

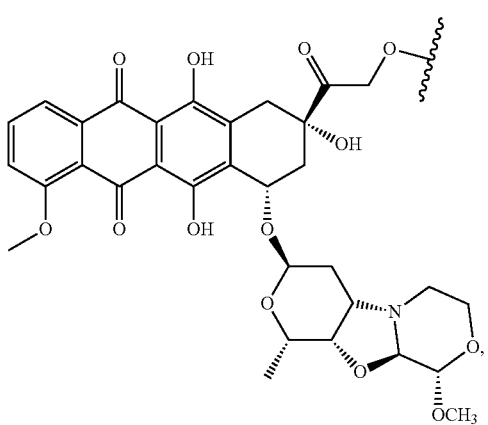

wherein the wavy line indicates the point of covalent attachment to the linker of the ADC as described herein.

In some embodiments, the cytotoxin is a PNU derivative represented by structural formula:

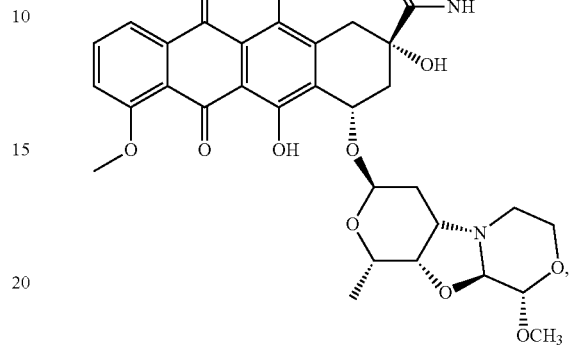

wherein the wavy line indicates the point of covalent attachment to the linker of the ADC as described herein.

Pyrrolobenzodiazepines (PBDs)

In other embodiments, the anti-CD45 antibodies, or antigen-binding fragments thereof, described herein can be conjugated to a cytotoxin that is a pyrrolobenzodiazepine (PBD) or a cytotoxin that comprises a PBD. PBDs are natural products produced by certain actinomycetes and have been shown to be sequence selective DNA alkylating compounds. PBD cytotoxins include, but are not limited to, anthramycin, dimeric PBDs, and those disclosed in, for example, Hartley, J A (2011) The development of pyrrolobenzodiazepines as antitumour agents. Expert Opin Inv Drug, 20(6), 733-744 and Antonow D, Thurston D E (2011) Synthesis of DNA-interactive pyrrolo[2,1-c][1,4]benzodiazepines (PBDs). Chem Rev 111: 2815-2864.

In some embodiments, the cytotoxin is a pyrrolobenzodiazepine dimer represented by the formula:

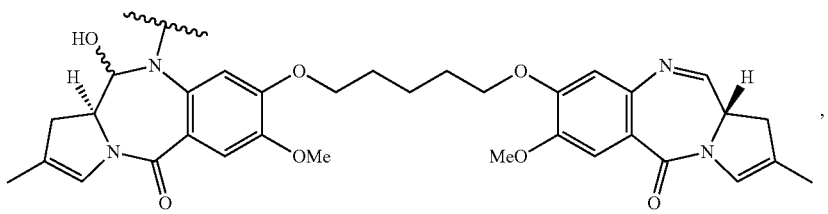

wherein the wavy line indicates the attachment point of the linker.

In some embodiments, the cytotoxin is conjugated to the antibody, or the antigen-binding fragment thereof, by way of a maleimidocaproyl linker.

In some embodiments, the linker comprises one or more of a peptide, oligosaccharide, —(CH$_2$)$_p$—, —(CH$_2$CH$_2$O)$_q$—, —(C=O)(CH$_2$)$_r$—, —(C=O)(CH$_2$CH$_2$O)$_t$—, —(NHCH$_2$CH$_2$)$_u$—, -PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB, wherein each of p, q, r, t, and u are integers from 1-12, selected independently for each occurrence.

In some embodiments, the linker has the structure:

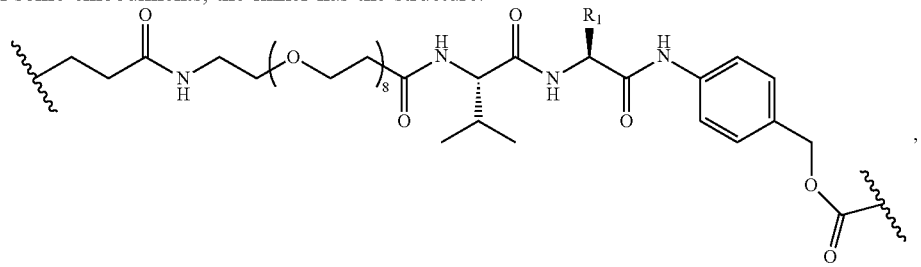

wherein R$_1$ is CH$_3$ (Ala) or (CH$_2$)$_3$NH(CO)NH$_2$ (Cit).

In some embodiments, the linker, prior to conjugation to the antibody and including the reactive substituent Z', taken together as L-Z', has the structure:

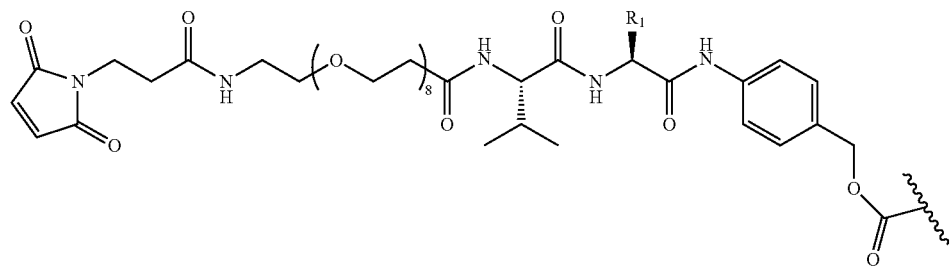

wherein the wavy line indicates the attachment point to the cytotoxin (e.g., a PBD). In certain embodiments, R$_1$ is CH$_3$.

In some embodiments, the cytotoxin-linker conjugate, prior to conjugation to the antibody and including the reactive substituent Z', taken together as Cy-L-Z', has the structure of formula:

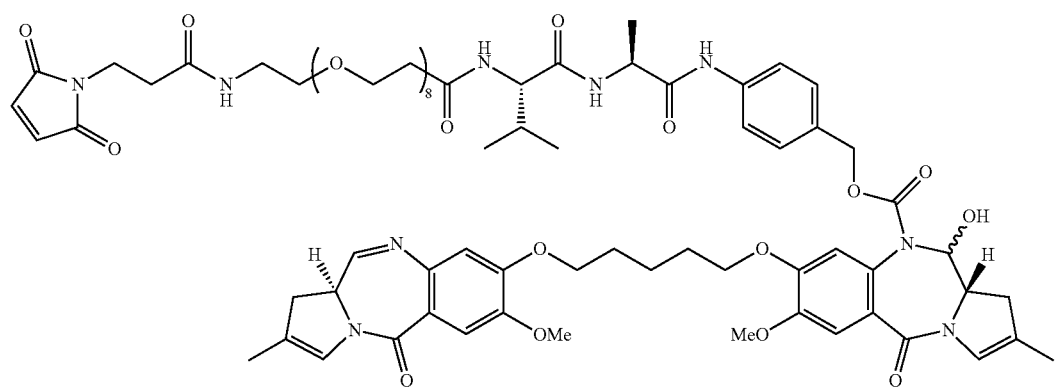

This particular cytotoxin-linker conjugate is known as tesirine (SG3249), and has been described in, for example, Howard et al., ACS Med. Chem. Lett. 2016, 7(11), 983-987, the disclosure of which is incorporated by reference herein in its entirety.

In some embodiments, the cytotoxin is a pyrrolobenzodiazepine dimer represented by the formula:

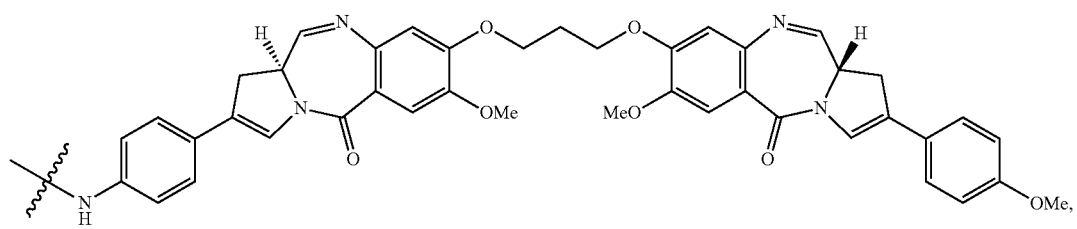 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the attachment point of the linker.

In some embodiments, the cytotoxin-linker conjugate, prior to conjugation to the antibody and including the reactive substituent Z', taken together as Cy-L-Z', has the structure:

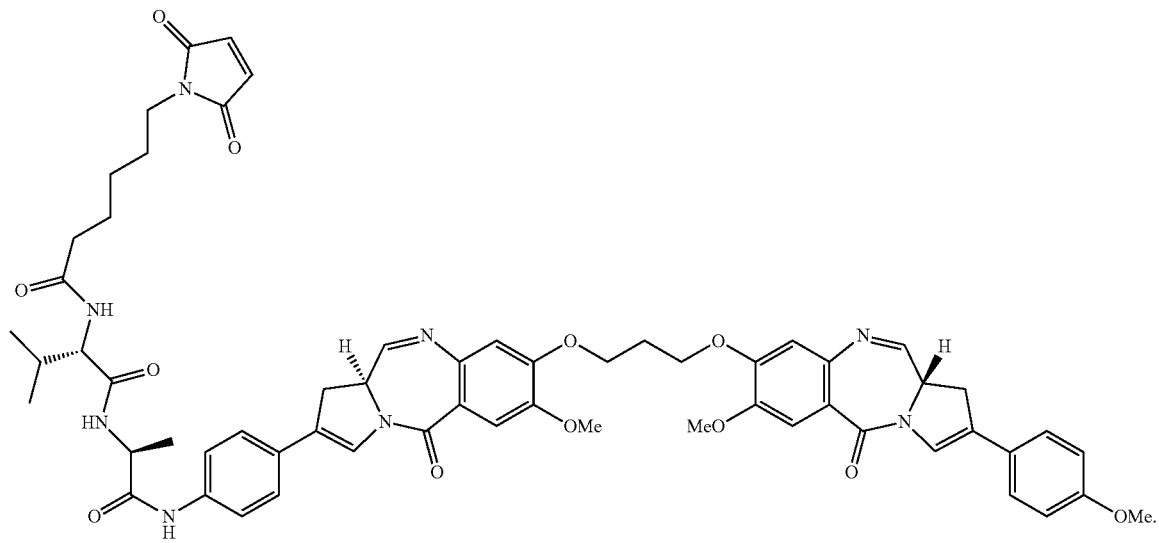 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1]

This particular cytotoxin-linker conjugate is known as talirine, and has been described, for example, in connection with the ADC Vadastuximab talirine (SGN-CD33A), Mantaj et al., Angewandte Chemie International Edition English 2017, 56, 462-488, the disclosure of which is incorporated by reference herein in its entirety.

In some embodiments, the cytotoxin is an indolinobenzodiazepine pseudodimer having the structure of formula:

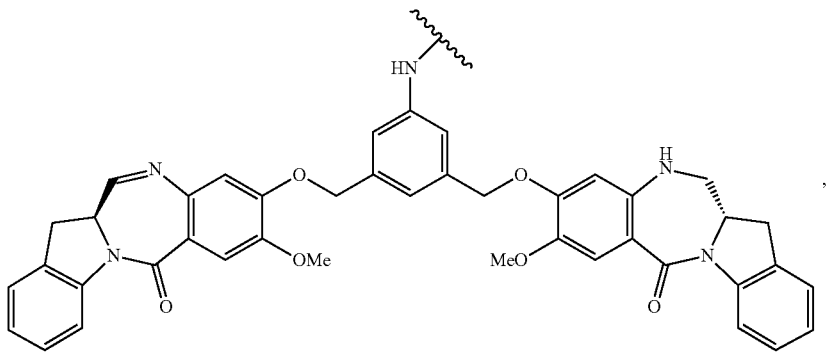 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the attachment point of the linker.

In some embodiments, the cytotoxin-linker conjugate, prior to conjugation to the antibody and including the reactive substituent Z', taken together as Cy-L-Z', has the structure:

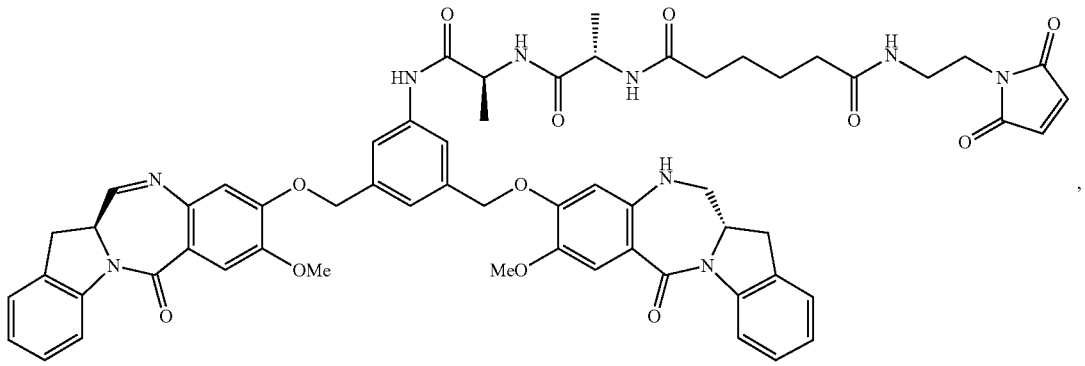 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

which comprises the ADC IMGN632, disclosed in, for example, International Patent Application Publication No. WO2017004026, which is incorporated by reference herein.

Calicheamicin

In other embodiments, the antibodies and antigen-binding fragments thereof described herein can be conjugated to a cytotoxin that is an enediyne antitumor antibiotic (e.g., calicheamicins, ozogamicin). The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

An exemplary calicheamicin is designated $\gamma_1$, which is herein referenced simply as gamma, and has the structural formula:

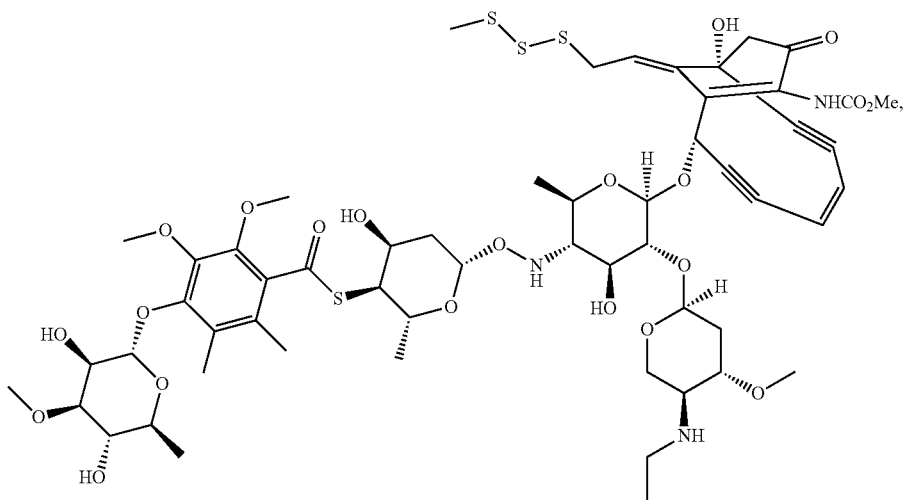

In some embodiments, the calicheamicin is a gamma-calicheamicin derivative or an N-acetyl gamma-calicheamicin derivative. Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents. Calicheamicins contain a methyltrisulfide moiety that can be reacted with appropriate thiols to form disulfides, at the same time introducing a functional group that is useful in attaching a calicheamicin derivative to an anti-CD45 antibody or antigen-binding fragment thereof as described herein, via a linker. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

In one embodiment, the cytotoxin of the ADC as disclosed herein is a calicheamicin disulfide derivative represented by the formula:

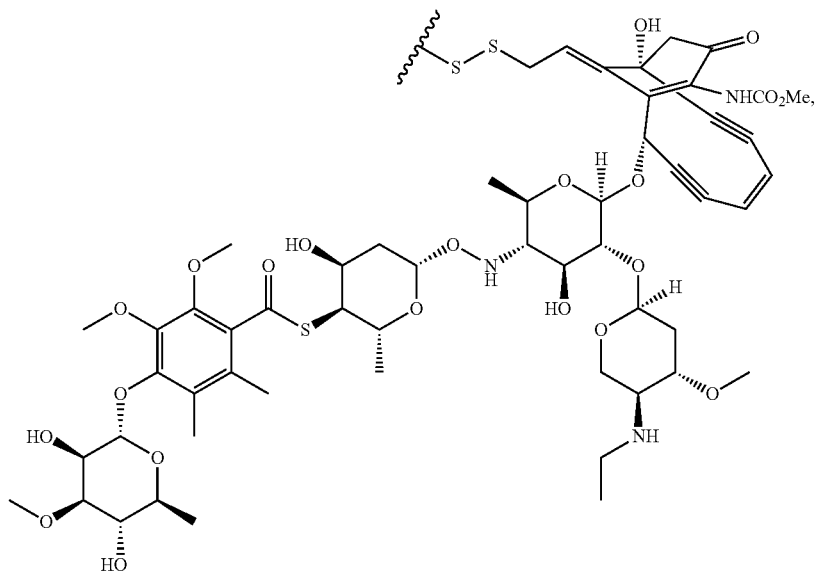

wherein the wavy line indicates the attachment point of the linker.

Additional Cytotoxins

In other embodiments, the antibodies and antigen-binding fragments thereof described herein can be conjugated to a cytotoxin other than or in addition to those cytotoxins disclosed herein above. Additional cytotoxins suitable for use with the compositions and methods described herein include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, antidorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, merbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers

The term "Linker" as used herein means a divalent chemical moiety comprising a covalent bond or a chain of atoms that covalently attaches an anti-CD45 antibody-drug conjugates (ADC) of formula I. Suitable linkers have two reactive termini, one for conjugation to an antibody and the other for conjugation to a cytotoxin. The antibody conjugation reactive terminus of the linker (reactive moiety, Z') is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. When the term "linker" is used in describing the linker in conjugated form, one or both of the reactive termini will be absent (such as reactive moiety Z', having been converted to chemical moiety Z) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

A variety of linkers can be used to conjugate the antibodies, or antibody fragments, described to a cytotoxic molecule. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Suitable cleavable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Suitable cleavable linkers may include, for example, chemical moieties such as a hydrazine, a disulfide, a thioether or a dipeptide.

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker includes a dipeptide selected from Val-Ala and Val-Cit.

Linkers suitable for conjugating the antibodies, or antibody fragments, described herein to a cytotoxic molecule include those capable of releasing a cytotoxin by a 1,6-elimination process. Chemical moieties capable of this elimination process include the p-aminobenzyl (PAB) group, 6-maleimidohexanoic acid, pH-sensitive carbonates, and other reagents as described in Jain et al., Pharm. Res. 32:3526-3540, 2015, the disclosure of which is incorporated herein by reference in its entirety as it pertains to linkers suitable for covalent conjugation.

In some embodiments, the linker includes a "self-immolative" group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837. In some embodiments, a dipeptide is used in combination with a self-immolative linker.

Linkers suitable for use herein further may include one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted. Non-limiting examples of such groups include $(CH_2)_p$, $(CH_2CH_2O)_p$, and —$(C=O)(CH_2)_p$— units, wherein p is an integer from 1-6, independently selected for each occasion.

Suitable linkers may contain groups having solubility enhancing properties. Linkers including the $(CH_2CH_2O)_p$ unit (polyethylene glycol, PEG), for example, can enhance solubility, as can alkyl chains substituted with amino, sulfonic acid, phosphonic acid or phosphoric acid residues. Linkers including such moieties are disclosed in, for example, U.S. Pat. Nos. 8,236,319 and 9,504,756, the disclosure of each of which is incorporated herein by reference in its entirety as it pertains to linkers suitable for covalent conjugation. Further solubility enhancing groups include, for example, acyl and carbamoyl sulfamide groups, having the structure:

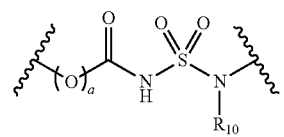

wherein a is 0 or 1; and $R^{10}$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted and/or optionally interrupted by one or more heteroatoms selected from O, S and $NR^{11}R^{12}$, wherein $R^{11}$ and $R^{12}$ are independently selected from the group consisting of hydrogen and $C_1$-$C_4$ alkyl groups; or $R^{10}$ is a cytotoxin, wherein the cytotoxin is optionally connected to N via a spacer moiety. Linkers containing such groups are described, for example, in U.S. Pat. No. 9,636,421 and U.S. Patent Application Publication No. 2017/0298145, the disclosures of which are incorporated herein by reference in their entirety as they pertain to linkers suitable for covalent conjugation to cytotoxins and antibodies or antigen-binding fragments thereof.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, acyl, —C(=O)—, or —$(CH_2CH_2O)_p$— group, wherein p is an integer from 1-6. One of skill in the art will recognize that one or more of the groups listed may be present in the form of a bivalent (diradical) species, e.g., $C_1$-$C_6$ alkylene and the like.

In some embodiments, the linker L comprises the moiety *-$L_1L_2$-**, wherein:
$L_1$ is absent or is —$(CH_2)_mNR^{13}C(=O)$—, —$(CH_2)_mNR^{13}$—, —$(CH_2)_mX_3(CH_2)_m$—,

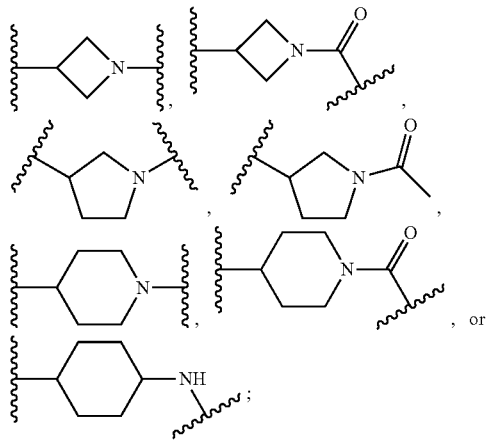

$L_2$ is absent or is —$(CH_2)_m$—, —$NR^{13}(CH_2)_m$—, —$(CH_2)_mNR^{13}C(=O)(CH_2)_m$—, —$X_4$, —$(CH_2)_mNR^{13}C(=O)X_4$, —$(CH_2)_mNR^{13}C(=O)$—, —$((CH_2)_mO)_n(CH_2)_m$—, —$((CH_2)_mO)_n(CH_2)_mX_3(CH_2)_m$—, —$NR^{13}((CH_2)_mO)_nX_3(CH_2)_m$—, —$NR^{13}((CH_2)_mO)_n(CH_2)_mX_3(CH_2)_m$—, —$X_1X_2C(=O)(CH_2)_m$—, —$(CH_2)_m(O(CH_2)_m)_n$—, —$(CH_2)_mNR^{13}(CH_2)_m$—, —$(CH_2)_mNR^{13}C(=O)(CH_2)_mX_3(CH_2)_m$—, —$(CH_2)_mC(=O)NR^{13}(CH_2)_mNR^{13}C(=O)(CH_2)_m$—, —$(CH_2)_mC(=O)$—, —$(CH_2)_mNR^{13}(CH_2)_mC(=O)X_2X_1C(=O)$—, —$(CH_2)_mX_3(CH_2)_mC(=O)X_2X_1C(=O)$—, —$(CH_2)_mC(=O)NR^{13}(CH_2)_m$—, —$(CH_2)_mC(=O)NR^{13}(CH_2)_mX_3(CH_2)_m$—, —$(CH_2)_mX_3(CH_2)_mNR^{13}C(=O)(CH_2)_m$—, —$(CH_2)_mX_3(CH_2)_mC(=O)NR^{13}$, —$(CH_2)_m$—, —$(CH_2)_mO)_n(CH_2)_mNR^{13}C(=O)$—, —$(CH_2)_m$—, —$(CH_2)_mC(=O)NR^{13}(CH_2)_m$ $(O(CH_2)_m)_n$—, —$(CH_2)_m(O(CH_2)_m)_nC(=O)$—, —$(CH_2)_mNR^{13}(CH_2)_mC(=O)$—, —$(CH_2)_mC(=O)$ $NR^{13}(CH_2)_mNR^{13}C(=O)$—, —$(CH_2)_m(O(CH_2)_m)_nX_3$ $(CH_2)_m$—, —$(CH_2)_mX_3((CH_2)_mO)_n(CH_2)_m$—, —$(CH_2)_mX_3(CH_2)_mC(=O)$—, —$(CH_2)_mC(=O)NR^{13}$ $(CH_2)_mO)_n(CH_2)_mX_3(CH_2)_m$—, —$(CH_2)_mX_3(CH_2)_m$ $(O(CH_2)_m)_nNR^{13}C(=O)(CH_2)_m$—, —$(CH_2)_mX_3$ $(CH_2)_m(O(CH_2)_m)_nC(=O)$—, —$(CH_2)_mX_3(CH_2)_m(O$ $(CH_2)_m)_n$—, —$(CH_2)_mC(=O)NR^{13}(CH_2)_mC(=O)$—, —$(CH_2)_mC(=O)NR^{13}(CH_2)_m(O(CH_2)_m)_nC(=O)$—, —$((CH_2)_mO)_n(CH_2)_mNR^{13}C(=O)(CH_2)_m$—, —$(CH_2)_mC(=O)NR^{13}(CH_2)_mC(=O)NR^{13}(CH_2)_m$—, —$(CH_2)_mNR^{13}C(=O)(CH_2)_mNR^{13}C(=O)(CH_2)_m$— $(CH_2)_mX_3(CH_2)_mC(=O)NR^{13}$—, —$(CH_2)_mC(=O)$ $NR^{13}$—, —$(CH_2)_mX_3$—, —$C(R^{13})_2(CH_2)_m$—, —$(CH_2)_mC(R^{13})_2NR^{13}$—, —$(CH_2)_mC(=O)NR^{13}$ $(CH_2)_mNR^{13}$—, —$(CH_2)_mC(=O)NR^{13}(CH_2)_mNR^{13}C$ $(=O)NR^{13}$—, —$(CH_2)_mC(=O)X_2X_1C(=O)$—, —$C(R^{13})_2(CH_2)_mNR^{13}C(=O)(CH_2)_m$—, —$(CH_2)_mC$ $(=O)NR^{13}(CH_2)_mC(R^{13})_2NR^{13}$—, —$C(R^{13})_2$ $(CH_2)_mX_3(CH_2)_m$—, —$(CH_2)_mX_3(CH_2)_m$ $C(R^{13})_2NR^{13}$—, —$C(R^{13})_2(CH_2)_mOC(=O)NR^{13}$ $(CH_2)_m$—, —$(CH_2)_mNR^{13}C(=O)O(CH_2)_m$ $C(R^{13})_2NR^{13}$—, —$(CH_2)_mX_3(CH_2)_mNR^{13}$—, —$(CH_2)_mX_3(CH_2)_m(O(CH_2)_m)_nNR^{13}$—, —$(CH_2)_m$ $NR^{13}$, —$(CH_2)_mC(=O)NR^{13}(CH_2)_m(O(CH_2)_m)_n$ $NR^{13}$—, —$(CH_2)_m(O(CH_2)_m)_nNR^{13}$—, —$(CH_2CH_2O)_n(CH_2)_m$—, —$(CH_2)_m(OCH_2CH_2)_n$—, —$(CH_2)_mO(CH_2)_m$—, —$(CH_2)_mS(=O)_2$—, —$(CH_2)_mC(=O)NR^{13}(CH_2)_mS(=O)_2$—, —$(CH_2)_m$ $X_3(CH_2)_mS(=O)_2$, —$(CH_2)_mX_2X_1C(=O)$—, —$(CH_2)_m(O(CH_2)_m)_nC(=O)X_2X_1C(=O)$—, —$(CH_2)_m(O(CH_2)_m)X_2X_1C(=O)$—, —$(CH_2)_mX_3$ $(CH_2)_mX_2X_1C(=O)$—, —$(CH_2)_mX_3(CH_2)_m$ $(O(CH_2)_m)_nX_2X_1C(=O)$—, —$(CH_2)_mX_3(CH_2)_mC$ $(=O)NR^{13}(CH_2)_mNR^{13}C(=O)$—, —$(CH_2)_m$ $X_3(CH_2)_mC(=O)NR^{13}(CH_2)_mC(=O)$—, —$(CH_2)_mX_3$ $(CH_2)_mC(=O)NR^{13}(CH_2)_m(O(CH_2)_m)_nC(=O)$—, —$(CH_2)_mC(=O)X_2X_1C(=O)NR^{13}(CH_2)_m$—, —$(CH_2)_mX_3(O(CH_2)_m)_nC(=O)$—, —$(CH_2)_mNR^{13}C$ $(=O)((CH_2)_mO)_n(CH_2)_m$—, —$(CH_2)_m(O(CH_2)_m)_nC$ $(=O)NR^{13}(CH_2)_m$—, —$(CH_2)_mNR^{13}C(=O)NR^{13}$ $(CH_2)_m$— or —$(CH_2)_mX_3(CH_2)_mNR^{13}C(=O)$—;
wherein
$X_1$ is

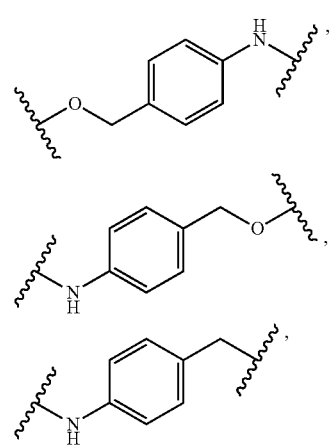

-continued

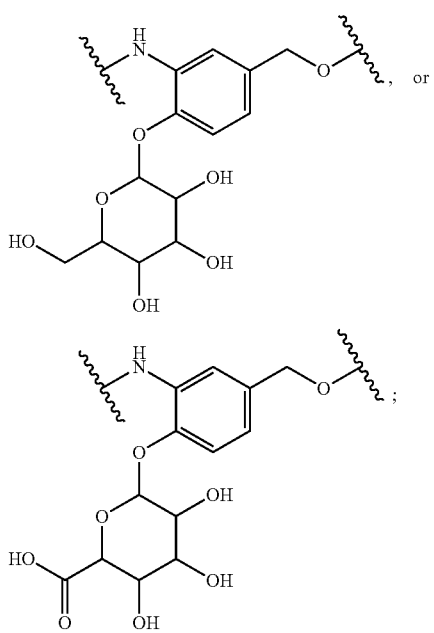

$X_2$ is

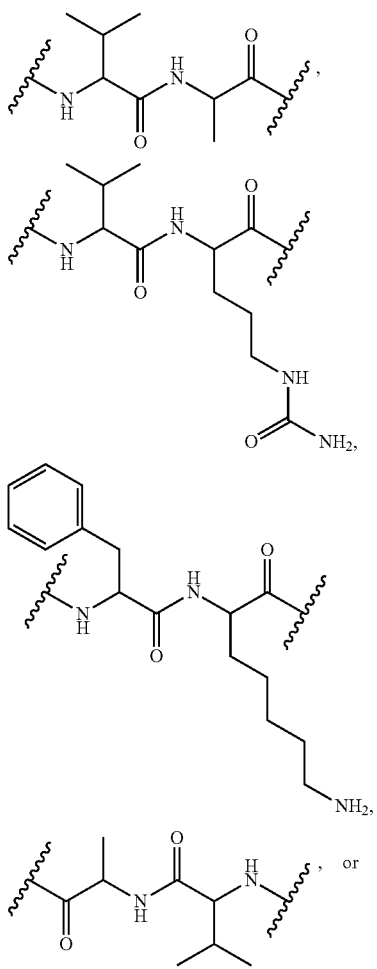

-continued

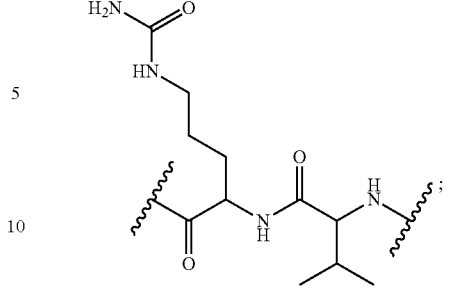

$X_3$ is

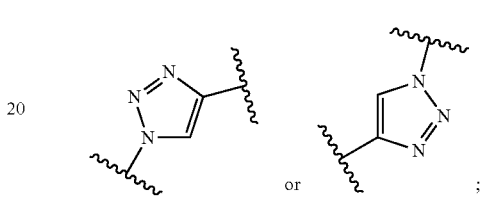

and
$X_4$ is

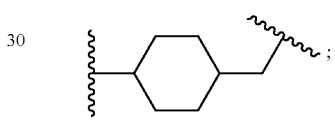

wherein
$R^{13}$ is independently selected for each occasion from H and $C_1$-$C_6$ alkyl;
m is independently selected for each occasion from 1, 2, 3, 4, 5, 6, 7, 8, 9 and 10;
n is independently selected for each occasion from 1, 2, 3, 4, 5, 6, 7, 8, 9, 10, 11, 12, 13 and 14; and
wherein the single asterisk (*) indicates the attachment point to the cytotoxin (e.g., an amatoxin), and the double asterisk (**) indicates the attachment point to the reactive substituent Z' or chemical moiety Z, with the proviso that $L_1$ and $L_2$ are not both absent.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, —(CH$_2$)$_p$—, —(CH$_2$CH$_2$O)$_p$—, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a —(C=O) (CH$_2$)$_p$— unit, wherein p is an integer from 1-6.

In one specific embodiment, the linker comprises the structure:

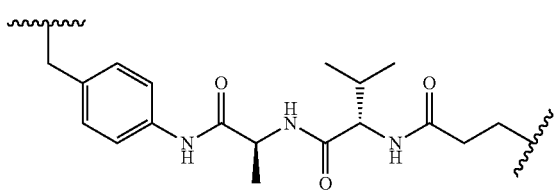 [SMILES: *CCC(=O)N[C@H](C(=O)N[C@@H](C)C(=O)Nc1ccc(C*)cc1)C(C)C]

wherein the wavy lines indicate attachment points to the cytotoxin and the reactive moiety Z'. In another specific embodiment, the linker comprises the structure:

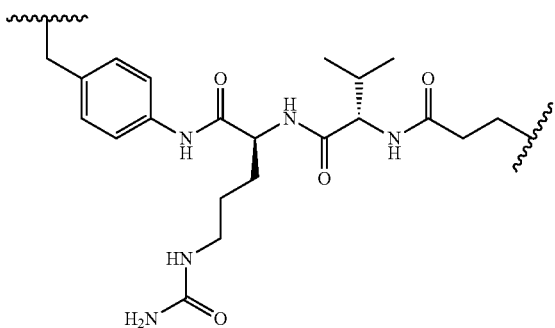 [SMILES: *CCC(=O)N[C@H](C(=O)N[C@@H](CCCNC(N)=O)C(=O)Nc1ccc(C*)cc1)C(C)C]

wherein the wavy lines indicate attachment points to the cytotoxin and the reactive moiety Z'. Such PAB-dipeptide-propionyl linkers are disclosed in, e.g., Patent Application Publication No. WO2017/149077, which is incorporated by reference herein in its entirety. Further, the cytotoxins disclosed in WO2017/149077 are incorporated by reference herein.

In certain embodiments, the linker of the ADC is maleimidocaproyl-Val-Ala-para-aminobenzyl (mc-Val-Ala-PAB).

In certain embodiments, the linker of the ADC is maleimidocaproyl-Val-Cit-para-aminobenzyl (mc-vc-PAB).

In some embodiments, the linker comprises

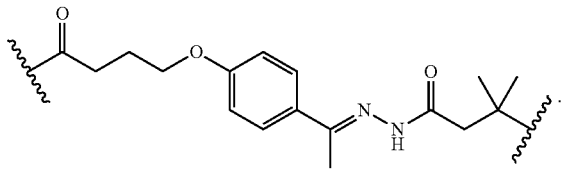 [SMILES: *C(=O)CCCOc1ccc(/C(C)=N/NC(=O)CC(*)(C)C)cc1]

In some embodiments, the linker comprises MCC (4-[N-maleimidomethyl]cyclohexane-1-carboxylate).

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

In certain embodiments, an intermediate, which is the precursor of the linker, is reacted with the drug moiety under appropriate conditions. In certain embodiments, reactive groups are used on the drug and/or the intermediate or linker. The product of the reaction between the drug and the intermediate, or the derivatized drug, is subsequently reacted with the antibody or antigen-binding fragment under appropriate conditions. Alternatively, the linker or intermediate may first be reacted with the antibody or a derivatized antibody, and then reacted with the drug or derivatized drug. Such conjugation reactions will now be described more fully.

A number of different reactions are available for covalent attachment of linkers or drug-linker conjugates to the antibody or antigen-binding fragment thereof. Suitable attachment points on the antibody molecule include the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a compound to an amino (or carboxy) group on an antibody moiety. Additionally, bifunctional agents such as dialdehydes or imidoesters may also be used to link the amino group on a compound to an amino group on an antibody moiety. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure.

Linkers useful in for conjugation to the antibodies or antigen-binding fragments as described herein include, without limitation, linkers containing chemical moieties Z formed by coupling reactions as depicted in Table 1, below. Curved lines designate points of attachment to the antibody or antigen-binding fragment, and the cytotoxic molecule, respectively.

TABLE 1

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition | (structure) |

TABLE 1-continued
Exemplary chemical moieties Z formed by coupling reactions in the formation of antibody-drug conjugates
| Exemplary Coupling Reactions | Chemical Moiety Z Formed by Coupling Reactions |
|---|---|
| [3 + 2] Cycloaddition | 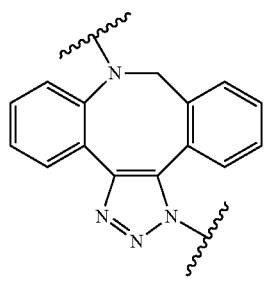 [SMILES: *N1Cc2ccccc2-c2c(nnn2*)-c2ccccc21] |
| [3 + 2] Cycloaddition, Esterification | 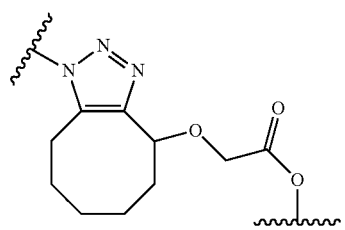 [SMILES: *OC(=O)COC1CCCCCc2c1nnn2*] |
| [3 + 2] Cycloaddition, Esterification | 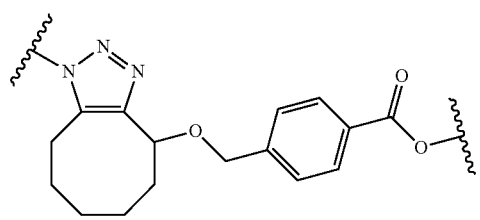 [SMILES: *OC(=O)c1ccc(COC2CCCCCc3c2nnn3*)cc1] |
| [3 + 2] Cycloaddition, Esterification | 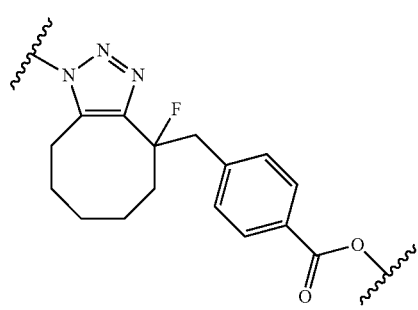 [SMILES: *OC(=O)c1ccc(CC2(F)CCCCCc3c2nnn3*)cc1] |
| [3 + 2] Cycloaddition, Esterification | 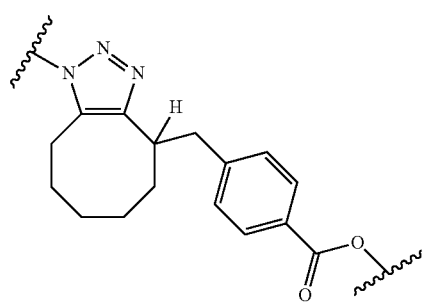 [SMILES: *OC(=O)c1ccc(CC2CCCCCc3c2nnn3*)cc1] |

TABLE 1-continued

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition, Esterification | 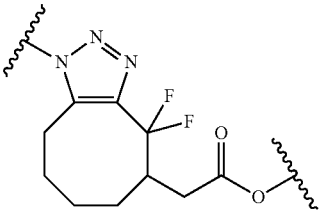 [SMILES: *OC(=O)CC1CCCCc2c(nnn2*)C1(F)F] |
| [3 + 2] Cycloaddition, Esterification | 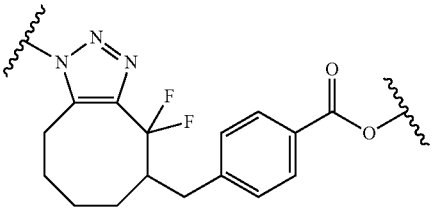 [SMILES: *OC(=O)c1ccc(CC2CCCCc3c(nnn3*)C2(F)F)cc1] |
| [3 + 2] Cycloaddition, Esterification | 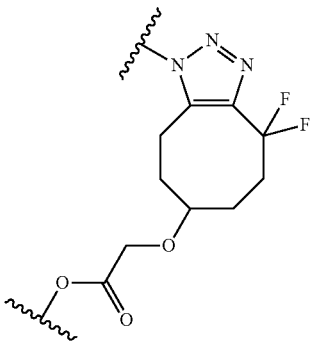 [SMILES: *OC(=O)COC1CCc2c(nnn2*)C(F)(F)CC1] |
| [3 + 2] Cycloaddition, Esterification | 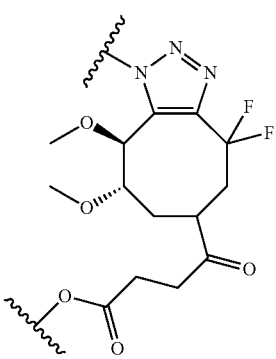 [SMILES: *OC(=O)CCC(=O)C1C[C@H](OC)[C@@H](OC)c2c(nnn2*)C(F)(F)C1] |
| [3 + 2] Cycloaddition, Esterification | 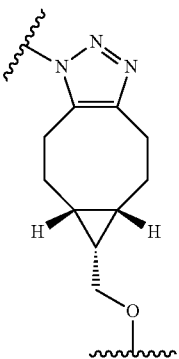 [SMILES: *OC[C@@H]1[C@@H]2CCc3c(nnn3*)CC[C@@H]21] |

TABLE 1-continued
Exemplary chemical moieties Z formed by coupling reactions in the formation of antibody-drug conjugates
| Exemplary Coupling Reactions | Chemical Moiety Z Formed by Coupling Reactions |
|---|---|
| [3 + 2] Cycloaddition, Esterification | 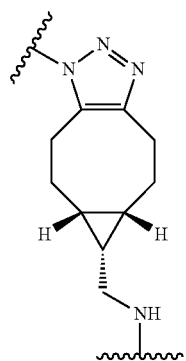 [SMILES: *NC[C@@H]1[C@@H]2CCc3c(nnn3*)CC[C@@H]21] |
| [3 + 2] Cycloaddition, Esterification | 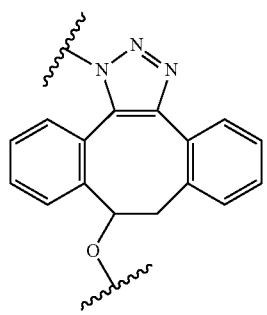 [SMILES: *OC1Cc2ccccc2-c2nnn(*)c2-c2ccccc21] |
| [3 + 2] Cycloaddition, Etherification | 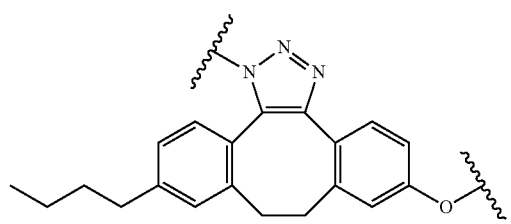 [SMILES: *Oc1ccc2c(c1)CCc1cc(CCCC)ccc1-c1c-2nnn1*] |
| [3 + 2] Cycloaddition | 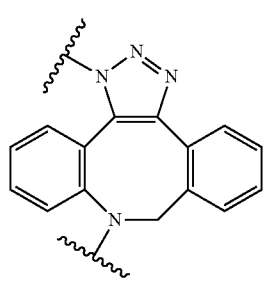 [SMILES: *N1Cc2ccccc2-c2nnn(*)c2-c2ccccc21] |
| Michael addition | 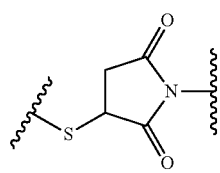 [SMILES: *SC1CC(=O)N(*)C1=O] |

TABLE 1-continued

Exemplary chemical moieties Z formed by coupling reactions in the formation of antibody-drug conjugates

| Exemplary Coupling Reactions | Chemical Moiety Z Formed by Coupling Reactions |
|---|---|
| Michael addition | *(structure: pyrrolidinone with S and O substituents)* |
| Imine condensation, Amidation | *(structure: oxime-ether linked amide)* |
| Imine condensation | *(structure: oxime ether)* |
| Disulfide formation | *(structure: S–S)* |
| Thiol alkylation | *(structure: S–CH2–C(=O)–)* |
| Condensation, Michael addition | *(structure: amidine–CH2CH2–S–maleimide)* |

One of skill in the art will recognize that a reactive substituent Z' attached to the linker and a reactive substituent on the antibody or antigen-binding fragment thereof, are engaged in the covalent coupling reaction to produce the chemical moiety Z, and will recognize the reactive moiety Z'. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z', suitable for reaction with a reactive substituent on the antibody, or antigen-binding fragment thereof, to form the chemical moiety Z.

In some embodiments, Z' is —NR$^{13}$C(=O)CH=CH$_2$, —N$_3$, —SH, —S(=O)$_2$(CH=CH$_2$), —(CH$_2$)$_2$S(=O)$_2$(CH=CH$_2$), —NR$^{13}$S(=O)$_2$(CH=CH$_2$), —NR$^{13}$C(=O)CH$_2$R$^{14}$, —NR$^{13}$C(=O)CH$_2$Br, —NR$^{13}$C(=O)CH$_2$I, —NHC(=O)CH$_2$Br, —NHC(=O)CH$_2$I, —ONH$_2$, —C(O)NHNH$_2$, —CO$_2$H, —NH$_2$, —NH(C=O), —NC(=S),

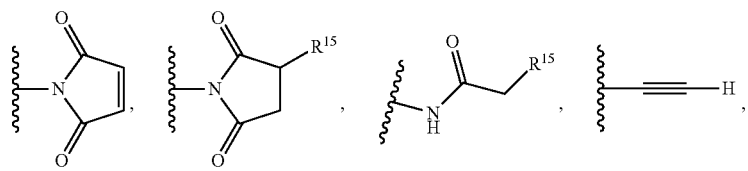

105
-continued
106
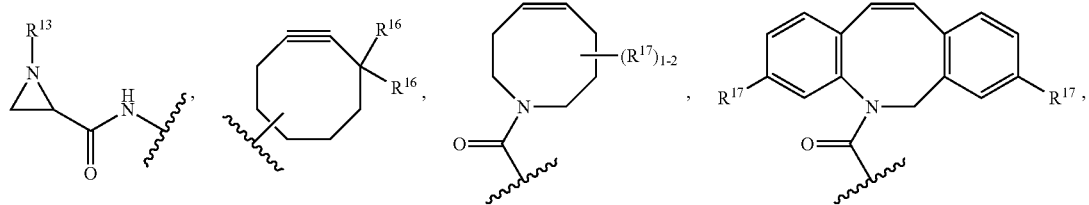
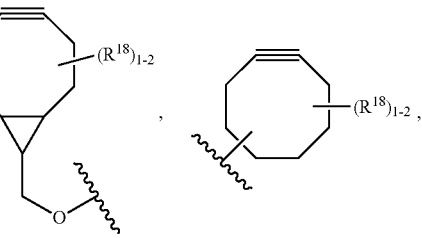
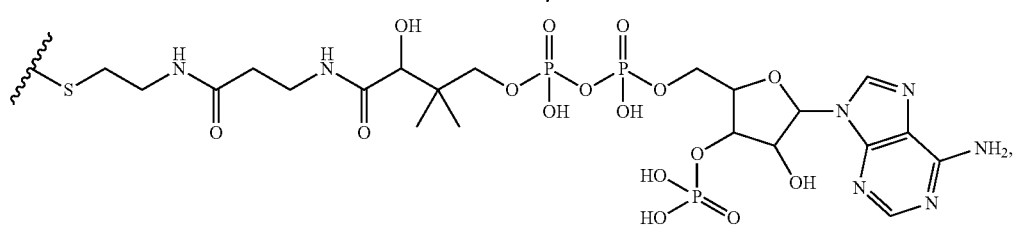
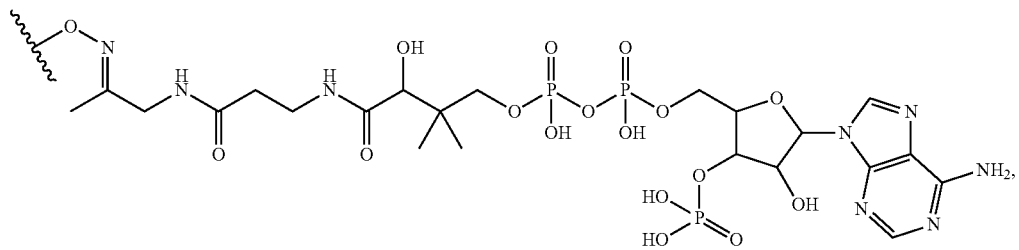
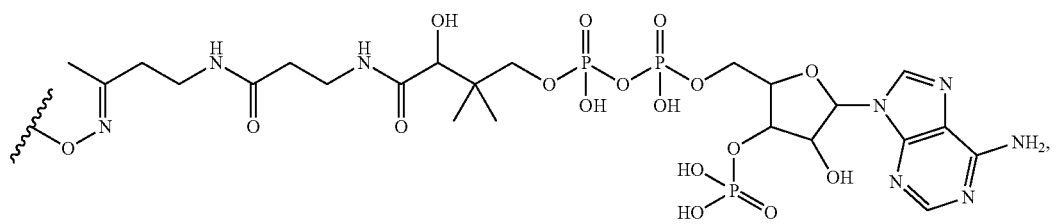
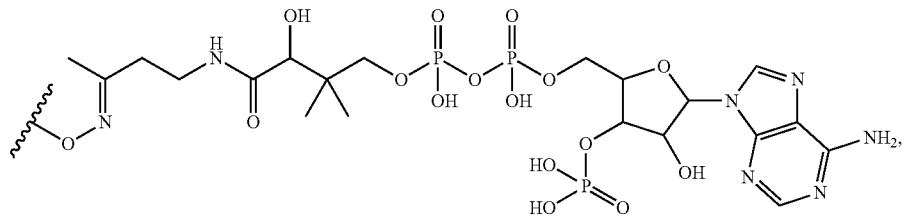
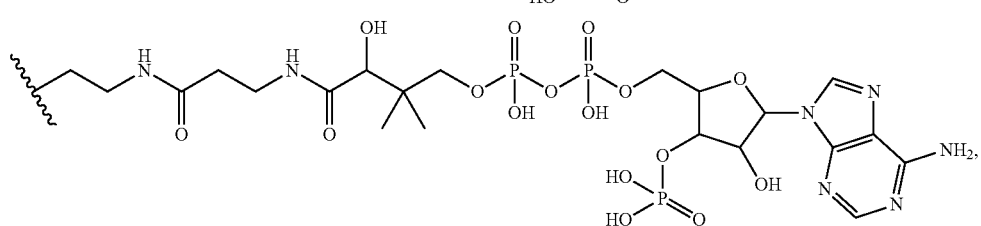

-continued

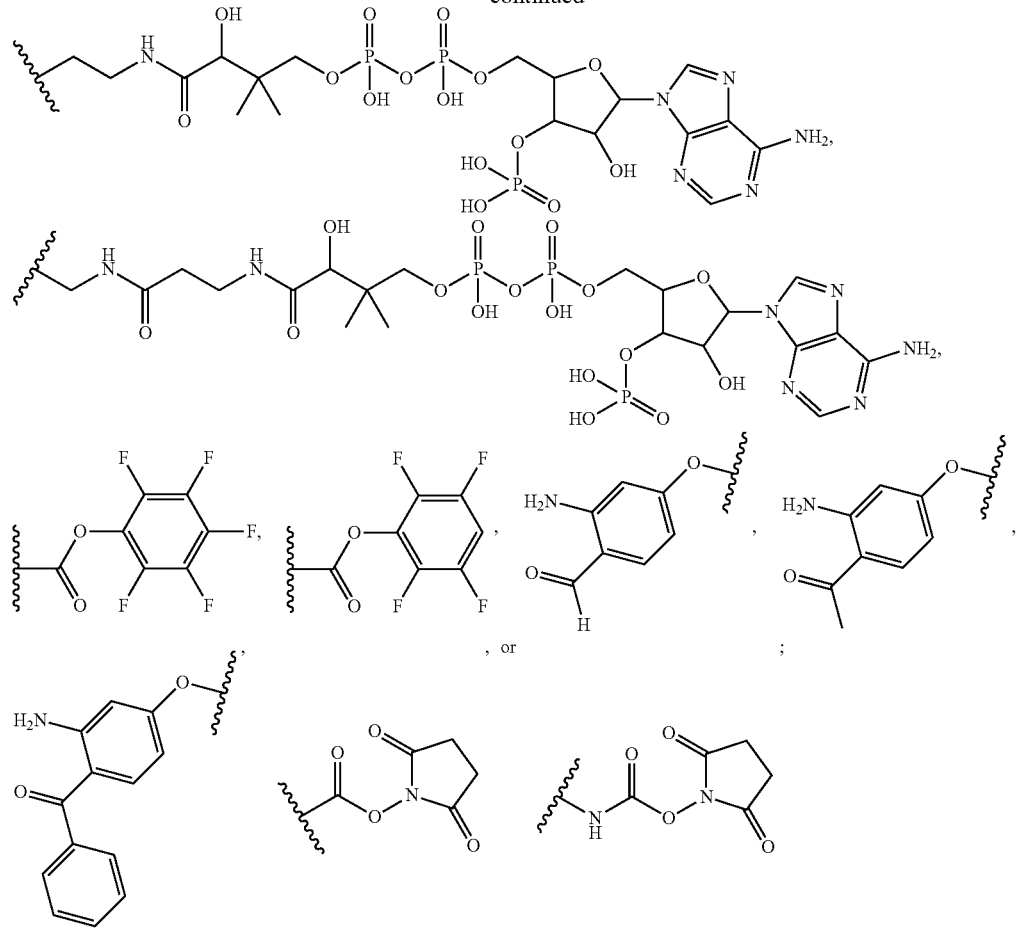

wherein $R^{13}$ is independently selected for each occasion from H and $C_1$-$C_6$ alkyl;

$R^{14}$ is —S(CH$_2$)$_n$CHR$^{15}$NHC(=O)R$^{13}$;

$R^{15}$ is $R^{13}$ or —C(=O)OR$^{13}$;

$R^{16}$ is independently selected for each occasion from H, $C_1$-$C_6$ alkyl, F, Cl, and —OH;

$R^{17}$ is independently selected for each occasion from H, $C_1$-$C_6$ alkyl, F, Cl, —NH$_2$, —OCH$_3$, —OCH$_2$CH$_3$, —N(CH$_3$)$_2$, —CN, —NO$_2$ and —OH; and $R^{18}$ is independently selected for each occasion from H, $C_1$-$C_6$ alkyl, F, benzyloxy substituted with —C(=O)OH, benzyl substituted with —C(=O)OH, $C_1$-$C_4$ alkoxy substituted with —C(=O)OH, and $C_1$-$C_4$ alkyl substituted with —C(=O)OH.

As depicted in Table 31, examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substituents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i) N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z' attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z'. For instance, Z' may be a Michael acceptor (e.g., maleimide), activated ester, electron-deficient carbonyl compound, and aldehyde, among others.

For instance, linkers suitable for the synthesis of ADCs include, without limitation, reactive substituents Z' such as maleimide or haloalkyl groups. These may be attached to the linker by reagents such as succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, in for instance, Liu et al., 18:690-697, 1979, the disclosure of which is incorporated herein by reference as it pertains to linkers for chemical conjugation.

In some embodiments, the reactive substituent Z' attached to linker L is a maleimide, azide, or alkyne. An example of a maleimide-containing linker is the non-cleavable maleimidocaproyl-based linker, which is particularly useful for the conjugation of microtubule-disrupting agents such as auristatins. Such linkers are described by Doronina et al., Bioconjugate Chem. 17:14-24, 2006, the disclosure of which is incorporated herein by reference as it pertains to linkers for chemical conjugation.

In some embodiments, the reactive substituent Z' is —(C═O)— or —NH(C═O)—, such that the linker may be joined to the antibody, or antigen-binding fragment thereof, by an amide or urea moiety, respectively, resulting from reaction of the —(C═O)— or —NH(C═O)— group with an amino group of the antibody or antigen-binding fragment thereof.

In some embodiments, the reactive substituent is an N-maleimidyl group, halogenated N-alkylamido group, sulfonyloxy N-alkylamido group, carbonate group, sulfonyl halide group, thiol group or derivative thereof, alkynyl group comprising an internal carbon-carbon triple bond, (hetero)cycloalkynyl group, bicyclo[6.1.0]non-4-yn-9-yl group, alkenyl group comprising an internal carbon-carbon double bond, cycloalkenyl group, tetrazinyl group, azido group, phosphine group, nitrile oxide group, nitrone group, nitrile imine group, diazo group, ketone group, (O-alkyl) hydroxylamino group, hydrazine group, halogenated N-maleimidyl group, 1,1-bis (sulfonylmethyl)methylcarbonyl group or elimination derivatives thereof, carbonyl halide group, or an allenamide group, each of which may be optionally substituted. In some embodiments, the reactive substituent comprises a cycloalkene group, a cycloalkyne group, or an optionally substituted (hetero)cycloalkynyl group.

Non-limiting examples of amatoxin-linker conjugates containing a reactive substituent Z' suitable for reaction with a reactive residue on the antibody or antigen-binding fragment thereof include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl)piperazin-1-yl)-amatoxin; 7'C-(4-(4-((maleimido)methyl) cyclohexanecarbonyl)piperazin-1-yl)-amatoxin; 7'C-(4-(6-(4-((maleimido)methyl)cyclohexanecarboxamido) hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido) ethyl)piperidin-1-yl)-amatoxin; 7'C-(4-(2-(4-((maleimido) methyl)cyclohexanecarboxamido)ethyl)piperidin-1-yl)-amatoxin; 7'C-(4-(2-(6-(4-((maleimido)methyl) cyclohexanecarboxamido)hexanamido)ethyl)piperidin-1-yl)-amatoxin; 7'C-(4-(2-(3-carboxypropanamido)ethyl) piperidin-1-yl)-amatoxin; 7'C-(4-(2-(2-bromoacetamido) ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl) cyclohexanecarboxamido)hexanamido)ethyl)piperidin-1-yl)-amatoxin; 7'C-(3-((6-(maleimido)hexanamido)methyl) pyrrolidin-1-yl)-amatoxin; 7'C-(3-((6-(6-(maleimido) hexanamido)hexanamido)methyl)pyrrolidin-1-yl)-amatoxin; 7'C-(3-((4-((maleimido)methyl) cyclohexanecarboxamido)methyl)pyrrolidin-1-yl)-amatoxin; 7'C-(3-((6-((4-(maleimido)methyl) cyclohexanecarboxamido)hexanamido)methyl)pyrrolidin-1-yl)-amatoxin; 7'C-(4-(2-(6-(2-(aminooxy)acetamido) hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl) piperazin-1-yl)-amatoxin; 7'C-(4-(6-(2-(aminooxy) acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl) methy)-amatoxin; 7'C-((4-(6-(maleimido)hexanoyl)piperazin-1-yl)methyl)-amatoxin; (R)-7'C-((3-((6-(maleimido) hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido) hexanamido)hexanamido)ethyl)piperidin-1-yl)methyl)-amatoxin; 7'C-((4-(2-(4-((maleimido)methyl) cyclohexanecarboxamido)ethyl)piperidin-1-yl)methyl)-amatoxin; 7'C-((4-(2-(6-(4-((maleimido)methyl) cyclohexanecarboxamido)hexanamido)ethyl)piperidin-1-yl) methyl)-amatoxin; 7'C-((4-(2-(6-(maleimido)hexanamido) ethyl)piperazin-1-yl)methyl)-amatoxin; 7'C-((4-(2-(6-(6-(maleimido)hexanamido)hexanamido)ethyl)piperazin-1-yl) methyl)-amatoxin; 7'C-((4-(2-(4-((maleimido)methyl) cyclohexanecarboxamido)ethyl)piperazin-1-yl)methyl)-amatoxin; 7'C-((4-(2-(6-(4-((maleimido)methyl) cyclohexanecarboxamido)hexanamido)ethyl)piperazin-1-yl)methyl)-amatoxin; 7'C-((3-((6-(6-(maleimido) hexanamido)hexanamido)-S-methyl)pyrrolidin-1-yl)

methyl)-amatoxin; 7'C-((3-((6-(6-(maleimido)hexanamido) hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl) pyrrolidin-1-yl)methyl)-amatoxin; 7'C-((3-((6-(4-((maleimido)methyl)cyclohexanecarboxamido) hexanamido)methyl)pyrrolidin-1-yl)methyl)-amatoxin; 7'C-((4-(2-(3-carboxypropanamido)ethyl)piperazin-1-yl) methyl)-amatoxin; 7'C-((4-(6-(6-(maleimido)hexanamido) hexanoyl)piperazin-1-yl)methyl)-amatoxin; 7'C-((4-(6-(4-((maleimido)methyl)cyclohexanecarboxamido)hexanoyl) piperazin-1-yl)methyl)-amatoxin; 7'C-((4-(2-(maleimido) acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido) butanamido)ethyl)piperidin-1-yl)methyl)-amatoxin; 7'C-((4-(2-(6-(4-((maleimido)methyl)cyclohexanecarboxamido) hexanamido)ethyl)piperidin-1-yl)methyl)-amatoxin; 7'C-((3-((6-(maleimido)hexanamido)methyl)azetidin-1-yl) methyl)-amatoxin; 7'C-((3-(2-(6-(maleimido)hexanamido) ethyl)azetidin-1-yl)methyl)-amatoxin; 7'C-((3-((4-((maleimido)methyl)cyclohexanecarboxamido)methyl) azetidin-1-yl)methyl)-amatoxin; 7'C-((3-(2-(4-((maleimido) methyl)cyclohexanecarboxamido)ethyl)azetidin-1yl) methyl)-amatoxin; 7'C-((3-(2-(6-(4-((maleimido)methyl) cyclohexanecarboxamido)hexanamido)ethyl)azetidin-1-yl) methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido) butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methy) cyclohexanecarboxamido)hexanamido)ethyl)aziridin-1-yl) methyl)-amatoxin; 7'C-((4-(6-(6-(2-(aminooxy)acetamido) hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl) piperazin-1-yl)methyl)-amatoxin; 7'C-((4-(4-(2-(aminooxy) acetamido)butanoyl)piperazin-1-yl)methyl)-amatoxin; 7'C-((4-(2-(6-(2-(aminooxy)acetamido)hexanamido)ethyl) piperidin-1-yl)methyl)-amatoxin; 7'C-((4-(2-(2-(2-(aminooxy)acetamido)acetamido)ethyl)piperidin-1-yl) methyl)-amatoxin; 7'C-((4-(2-(4-(2-(aminooxy)acetamido) butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl) (methyl)amino)methyl)-amatoxin; 7'C-(((4-(6-(2-(aminooxy)acetamido)-N-methylhexanamido)butyl) (methyl)amino)methyl)-amatoxin; 7'C-((3-((6-(4-((maleimido)methyl)cyclohexanecarboxamido) hexanamido)methypyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl) piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl) cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido)ethyl)piperazin-1-yl)-amatoxin; 6'O-(6-(6-(11,12-didehydro-5,6-dihydro-dibenz[b,f]azocin-5-yl)-8-oxohexanamido)hexyl)-amatoxin; 6'O-(6-(hex-5-ynoylamino)hexyl)-amatoxin; 6'O-(6-(2-(aminooxy) acetylamido)hexyl)-amatoxin; 6'O-((6-aminooxy)hexyl)-amatoxin; and 6'O-(6-(2-iodoacetamido)hexyl)-amatoxin.

In some embodiments, the chemical moiety Z is selected from Table 1. In some embodiments, the chemical moiety Z is where S is a sulfur atom which represents the reactive substituent present within an antibody, or antigen-binding fragment thereof, that binds CD45 (e.g., from the —SH group of a cysteine residue).

In some embodiments, the linker-reactive substituent group structure L-Z', prior to conjugation with the antibody or antigen binding fragment thereof, is:

In some embodiments, an amatoxin as disclosed herein is conjugated to a linker-reactive moiety -L-Z' having the following formula:

In some embodiments, an amatoxin as disclosed herein is conjugated to a linker-reactive moiety -L-Z' having the following formula:

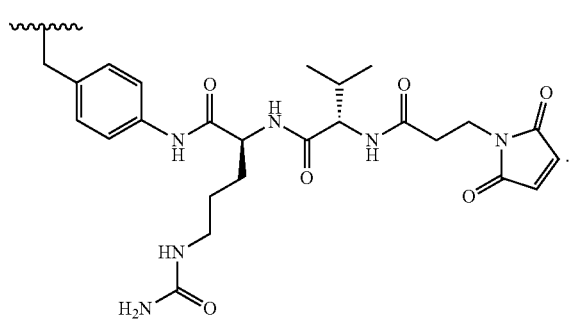 [SMILES: *Cc1ccc(NC(=O)[C@H](CCCNC(N)=O)NC(=O)[C@@H](NC(=O)CCN2C(=O)C=CC2=O)C(C)C)cc1]

The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

Preparation of Antibody-Drug Conjugates

In the ADCs of formula I as disclosed herein, an anti-CD45 antibody, or antigen binding fragment thereof, is conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z', followed by reaction with a reactive substituent of an antibody or antigen binding fragment thereof as described herein above. Additional methods for preparing ADC are described herein.

In another aspect, the anti-CD45 antibody, or antigen binding fragment thereof, has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the anti-CD45 antibody, or antigen binding fragment thereof, can have one or more carbohydrate groups that can be chemically modified to have one or more sulfhydryl groups. The ADC is then formed by conjugation through the sulfhydryl group's sulfur atom as described herein above.

In yet another aspect, the anti-CD45 antibody can have one or more carbohydrate groups that can be oxidized to provide an aldehyde (—CHO) group (see, for e.g., Laguzza, et al., J. Med. Chem. 1989, 32(3), 548-55).

The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO20061034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

ADCs described herein can be administered to a patient (e.g., a human patient suffering from an immune disease or cancer) in a variety of dosage forms. For instance, ADCs described herein can be administered to a patient suffering from an immune disease or cancer in the form of an aqueous solution, such as an aqueous solution containing one or more pharmaceutically acceptable excipients. Suitable pharmaceutically acceptable excipients for use with the compositions and methods described herein include viscosity-modifying agents. The aqueous solution may be sterilized using techniques known in the art.

Pharmaceutical formulations comprising anti-CD45 ADCs as described herein are prepared by mixing such ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Methods of Treatment

CD45 is an important cell surface molecule broadly expressed throughout the hematopoietic and immune systems. Described herein are anti-CD45 antibodies and anti-CD45 ADCs that can be used to treat patients with leukemias and lymphomas, as well as patients with autoimmune diseases such as multiple sclerosis and scleroderma. Furthermore, there is currently a need for compositions and methods for promoting the engraftment of exogenous hematopoietic stem cell grafts such that the multi-potency and hematopoietic functionality of these cells is preserved following transplantation. The compositions disclosed herein further provide a solution to this challenging problem.

Thus, disclosed herein are methods of treating a variety of disorders, such as diseases of a cell type in the hematopoietic lineage, cancers, autoimmune diseases, metabolic disorders, and stem cell disorders, among others. The compositions and methods described herein may (i) directly deplete a population of cells that give rise to a pathology, such as a population of cancer cells (e.g., leukemia cells) and autoimmune cells (e.g., autoreactive T-cells), and/or (ii) deplete a population of endogenous hematopoietic stem cells so as to promote the engraftment of transplanted hematopoietic stem cells by providing a niche to which the transplanted cells may home. The foregoing activities can be achieved by administration of an ADC, antibody, or antigen-binding fragment thereof, capable of binding an antigen expressed by an endogenous disease-causing cell or a hematopoietic stem cell. In the case of direct treatment of a disease, this administration can cause a reduction in the quantity of the cells that give rise to the pathology of interest. In the case of preparing a patient for hematopoietic stem cell transplant therapy, this administration can cause the selective depletion of a population of endogenous hematopoietic stem cells, thereby creating a vacancy in the hematopoietic tissue, such as the bone marrow, that can subsequently be filled by transplanted, exogenous hematopoietic stem cells. The invention is based in part on the discovery that ADCs, antibodies, or antigen-binding fragments thereof, capable of binding CD45 expressed by hematopoietic stem cells can be administered to a patient to effect both of the above activities. ADCs, antibodies, or antigen-binding fragments thereof, that bind an antigen expressed by hematopoietic stem cells (e.g., CD45) can be administered to a patient suffering from a cancer or autoimmune disease to directly deplete a population of cancerous cells or autoimmune cells, and can also be administered to a patient in need of hematopoietic stem cell transplant therapy in order to promote the survival and engraftment potential of transplanted hematopoietic stem cells.

As described herein, hematopoietic stem cell transplant therapy can be administered to a subject in need of treatment so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo, thereby treating the pathology associated with the defect or depletion in the endogenous blood cell population. The compositions and methods described herein can thus be used to treat a non-malignant hemoglobinopathy (e.g., a hemoglobinopathy selected from the group consisting of sickle cell anemia, thalassemia, Fanconi anemia, aplastic anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy).

Additionally or alternatively, the compositions and methods described herein can be used to treat a malignancy or proliferative disorder, such as a hematologic cancer, myeloproliferative disease. In the case of cancer treatment, the compositions and methods described herein may be administered to a patient so as to deplete a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during cancer cell eradication, such as during systemic chemotherapy. Exemplary hematological cancers that can be treated using the compositions and methods described herein include, without limitation, acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated with the compositions and methods described herein include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

The antibodies, or antigen-binding fragments thereof, and conjugates described herein may be used to induce solid organ transplant tolerance. For instance, the compositions and methods described herein may be used to deplete or ablate a population of cells from a target tissue (e.g., to deplete hematopoietic stem cells from the bone marrow stem cell niche). Following such depletion of cells from the target tissues, a population of stem or progenitor cells from an organ donor (e.g., hematopoietic stem cells from the organ donor) may be administered to the transplant recipient, and following the engraftment of such stem or progenitor cells, a temporary or stable mixed chimerism may be achieved, thereby enabling long-term transplant organ tolerance without the need for further immunosuppressive agents. For example, the compositions and methods described herein may be used to induce transplant tolerance in a solid organ transplant recipient (e.g., a kidney transplant, lung transplant, liver transplant, and heart transplant, among others). The compositions and methods described herein are well-suited for use in connection the induction of solid organ transplant tolerance, for instance, because a low percentage temporary or stable donor engraftment is sufficient to induce long-term tolerance of the transplanted organ.

In addition, the compositions and methods described herein can be used to treat cancers directly, such as cancers characterized by cells that are CD45+. For instance, the compositions and methods described herein can be used to treat leukemia, such as in patients that exhibit CD45+ leukemic cells. By depleting CD45+ cancerous cells, such as leukemic cells, the compositions and methods described herein can be used to treat various cancers directly. Exemplary cancers that may be treated in this fashion include hematological cancers, such as acute myeloid leukemia, acute lymphoid leukemia, chronic myeloid leukemia, chronic lymphoid leukemia, multiple myeloma, diffuse large B-cell lymphoma, and non-Hodgkin's lymphoma, In addition, the compositions and methods described herein can be used to treat autoimmune disorders. For instance, an antibody, or antigen-binding fragment thereof, can be administered to a subject, such as a human patient suffering from an autoimmune disorder, so as to kill a CD45+ immune cell. For example, a CD45+ immune cell may be an autoreactive lymphocyte, such as a T-cell that expresses a T-cell receptor that specifically binds, and mounts an immune response against, a self antigen. By depleting self-reactive, CD45+, the compositions and methods described herein can be used to treat autoimmune pathologies, such as those described below. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can reconstitute a population of cells depleted during autoimmune cell eradication.

Autoimmune diseases that can be treated using the compositions and methods described herein include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

In some embodiments, the transplant is allogeneic. In some embodiments, the transplant is autologous.

In some embodiments, the transplant is a bone marrow transplant, a peripheral blood transplant, or a cord blood transplant.

In some embodiments, the transplant includes hematopoietic cells (e.g., hematopoietic stem cells).

In any of the embodiments described herein, the transplant may be any solid organ or skin transplant. In some embodiments, the transplant is selected from the group consisting of kidney transplant, heart transplant, liver transplant, pancreas transplant, lung transplant, intestine transplant and skin transplant.

Routes of Administration and Dosing

Antibodies, antigen-binding fragments thereof, or ADCs described herein can be administered to a patient (e.g., a human patient suffering from cancer, an autoimmune disease, or in need of hematopoietic stem cell transplant therapy) in a variety of dosage forms. For instance, antibodies, antigen-binding fragments thereof, or ADCs described herein can be administered to a patient suffering from cancer, an autoimmune disease, or in need of hematopoietic stem cell transplant therapy in the form of an aqueous solution, such as an aqueous solution containing one or more pharmaceutically acceptable excipients. Pharmaceutically acceptable excipients for use with the compositions and methods described herein include viscosity-modifying agents. The aqueous solution may be sterilized using techniques known in the art.

Pharmaceutical formulations comprising an anti-CD45 antibody, or conjugates thereof (e.g., ADCs as described herein) are prepared by mixing such antibody or ADC with one or more optional pharmaceutically acceptable carriers (Remington's Pharmaceutical Sciences 16th edition. Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The antibodies, antigen-binding fragments, or ADCs described herein may be administered by a variety of routes, such as orally, transdermally, subcutaneously, intranasally, intravenously, intramuscularly, intraocularly, or parenterally. The most suitable route for administration in any given case will depend on the particular antibody, or antigen-binding fragment, administered, the patient, pharmaceutical formulation methods, administration methods (e.g., administration time and administration route), the patient's age, body weight, sex, severity of the diseases being treated, the patient's diet, and the patient's excretion rate.

The effective dose of an antibody, antigen-binding fragment thereof, or ADC described herein can range, for example from about 0.001 to about 100 mg/kg of body weight per single (e.g., bolus) administration, multiple administrations, or continuous administration, or to achieve an optimal serum concentration (e.g., a serum concentration of about 0.0001-about 5000 µg/mL) of the antibody, antigen-binding fragment thereof, or ADC. The dose may be administered one or more times (e.g., 2-10 times) per day, week, or month to a subject (e.g., a human) suffering from cancer, an autoimmune disease, or undergoing conditioning therapy in preparation for receipt of a hematopoietic stem cell transplant.

In one embodiment, the dose of an anti-CD45 antibody, antigen-binding fragment thereof, or ADC (e.g., an anti-CD45 antibody conjugated via a linker to a cytotoxin) administered to the human patient is about 0.1 mg/kg to about 0.3 mg/kg.

In one embodiment, the dose of an anti-CD45 antibody, antigen-binding fragment thereof, or ADC (e.g., an anti-CD45 antibody conjugated via a linker to a cytotoxin) administered to the human patient is about 0.15 mg/kg to about 0.3 mg/kg.

In one embodiment, the dose of an anti-CD45 antibody, antigen-binding fragment thereof, or ADC (e.g., an anti-CD45 antibody conjugated via a linker to a cytotoxin) administered to the human patient is about 0.15 mg/kg to about 0.25 mg/kg.

In one embodiment, the dose of an anti-CD45 antibody, antigen-binding fragment thereof, or ADC (e.g., an anti-CD45 antibody conjugated via a linker to a cytotoxin) administered to the human patient is about 0.2 mg/kg to about 0.3 mg/kg.

In one embodiment, the dose of an anti-CD45 antibody, antigen-binding fragment thereof, or ADC (e.g., an anti-CD45 antibody conjugated via a linker to a cytotoxin) administered to the human patient is about 0.25 mg/kg to about 0.3 mg/kg.

In one embodiment, the dose of an anti-CD45 antibody, antigen-binding fragment thereof, or ADC (e.g., an anti-CD45 antibody conjugated via a linker to a cytotoxin) administered to the human patient is about 0.1 mg/kg.

In one embodiment, the dose of an anti-CD45 antibody, antigen-binding fragment thereof, or ADC (e.g., an anti-CD45 antibody conjugated via a linker to a cytotoxin) administered to the human patient is about 0.2 mg/kg.

In one embodiment, the dose of an anti-CD45 antibody, antigen-binding fragment thereof, or ADC (e.g., an anti-CD45 antibody conjugated via a linker to a cytotoxin) administered to the human patient is about 0.3 mg/kg.

In one embodiment, the dose of an anti-CD45 antibody, antigen-binding fragment thereof, or ADC (e.g., an anti-CD45 antibody conjugated via a linker to a cytotoxin) described herein administered to the human patient is about 0.001 mg/kg to 10 mg/kg, about 0.01 mg/kg to 9.5 mg/kg, about 0.1 mg/kg to 9 mg/kg, about 0.1 mg/kg to 8.5 mg/kg, about 0.1 mg/kg to 8 mg/kg, about 0.1 mg/kg to 7.5 mg/kg, about 0.1 mg/kg to 7 mg/kg, about 0.1 mg/kg to 6.5 mg/kg, about 0.1 mg/kg to 6 mg/kg, about 0.1 mg/kg to 5.5 mg/kg, about 0.1 mg/kg to 5 mg/kg, about 0.1 mg/kg to 4.5 mg/kg, about 0.1 mg/kg to 4 mg/kg, about 0.5 mg/kg to 3.5 mg/kg, about 0.5 mg/kg to 3 mg/kg, about 1 mg/kg to 10 mg/kg, about 1 mg/kg to 9 mg/kg, about 1 mg/kg to 8 mg/kg, about 1 mg/kg to 7 mg/kg, about 1 mg/kg to 6 mg/kg, about 1 mg/kg to 5 mg/kg, about 1 mg/kg to 4 mg/kg, or about 1 mg/kg to 3 mg/kg.

In one embodiment, the anti-CD45 antibody, antigen binding fragment thereof, or ADC described herein that is administered to a human patient for treatment or conditioning has a half life of equal to or less than 24 hours, equal to or less than 22 hours, equal to or less than 20 hours, equal to or less than 18 hours, equal to or less than 16 hours, equal to or less than 14 hours, equal to or less than 13 hours, equal to or less than 12 hours, equal to or less than 11 hours, equal to or less than 10 hours, equal to or less than 9 hours, equal to or less than 8 hours, equal to or less than 7 hours, equal to or less than 6 hours, or equal to or less than 5 hours. In one embodiment, the half life of the anti-CD45 antibody, antigen binding fragment thereof, or ADC is 5 hours to 7 hours; is 5 hours to 9 hours; is 15 hours to 11 hours; is 5 hours to 13 hours; is 5 hours to 15 hours; is 5 hours to 20 hours; is 5 hours to 24 hours; is 7 hours to 24 hours; is 9 hours to 24 hours; is 11 hours to 24 hours; 12 hours to 22 hours; 10 hours to 20 hours; 8 hours to 18 hours; or 14 hours to 24 hours.

In one embodiment, the methods disclosed herein minimize liver toxicity in the patient receiving the anti-CD45 antibody, antigen binding fragment thereof, or ADC for conditioning. For example, in certain embodiments, the methods disclosed herein result in a liver marker level remaining below a known toxic level in the patient for more than 24 hours, 48 hours, 72 hours, or 96 hours. In other embodiments, the methods disclosed herein result in a liver marker level remaining within a reference range in the patient for more than 24 hours, 48 hours, 72 hours, or 96 hours. In certain embodiments, the methods disclosed herein result in a liver marker level rising not more than 1.5-fold above a reference range, not more than 3-fold above a reference range, not more than 5-fold above a reference range, or not more than 10-fold above a reference range for more than 24 hours, 48 hours, 72 hours, or 96 hours. Examples of liver markers that can be used to test for toxicity include alanine aminotransaminase (ALT), lactate dehydrogenase (LDH), and aspartate aminotransaminase (AST). In certain embodiments, administration of an ADC as described herein, i.e., where two doses are administered instead of a single dose, results in a transient increase in a liver marker, e.g., AST, LDH, and/or ALT. In some instances, an elevated level of a liver marker indicating toxicity may be reached, but within a certain time period, e.g., about 12 hours, about 18 hours, about 24 hours, about 36 hours, about 48 hours, about 72 hours, above 3 days, about 3.5 days, about 4 days, about 4.5 days, about 5 days, about 5.5 days, about 6 days, about 6.5 days, about 7 days, about 7.5 days, or less than a week, the liver marker level returns to a normal level not associated with liver toxicity. For example, in a human (average adult male), a normal, non-toxic level of ALT is 7 to 55 units per liter (U/L); and a normal, non-toxic level of AST is 8 to 48 U/L. In certain embodiments, at least one of the patient's blood AST, ALT, or LDH levels does not reach a toxic level between administration of a first dose of the ADC and 14 days after administration of the first dose to the patient. For example, the patient may be administered a first dose and subsequently a second dose, a third dose, a fourth dose, or more doses within, e.g., 5, 10, or 14 days of being administered the first dose, yet at least one of the patient's blood AST, ALT, or LDH levels does not reach a toxic level between administration of a first dose of the ADC and 14 days after administration of the first dose to the patient.

In certain embodiments, at least one of the patient's blood AST, ALT, or LDH levels does not rise above normal levels, does not rise more than 1.5-fold above normal levels, does not rise more than 3-fold above normal levels, does not rise more than 5-fold above normal levels, or does not rise more than 10-fold above normal levels.

In the case of a conditioning procedure prior to hematopoietic stem cell transplantation, the antibody, or antigen-binding fragment thereof can be administered to the patient at a time that optimally promotes engraftment of the exogenous hematopoietic stem cells, for instance, from about 1 hour to about 1 week (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days) or more prior to administration of the exogenous hematopoietic stem cell transplant. Ranges including the numbers recited herein are also included in the contemplated methods.

Using the methods disclosed herein, a physician of skill in the art can administer to a human patient in need of hematopoietic stem cell transplant therapy an ADC, an antibody or an antigen-binding fragment thereof capable of binding CD45 expressed by hematopoietic stem cells. In this fashion, a population of endogenous hematopoietic stem cells can be depleted prior to administration of an exogenous hematopoietic stem cell graft so as to promote engraftment of the hematopoietic stem cell graft. The antibody may be covalently conjugated to a toxin, such as a cytotoxic molecule described herein or known in the art. For instance, an anti-CD45 antibody or antigen-binding fragment thereof can be covalently conjugated to a cytotoxin, such as pseudomonas exotoxin A, deBouganin, diphtheria toxin, an amatoxin, such as γ-amanitin, α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof. This conjugation can be performed using covalent bond-forming techniques described herein or known in the art. The antibody, antigen-binding fragment thereof, or drug-antibody conjugate can subsequently be administered to the patient, for example, by intravenous administration, prior to transplantation of exogenous hematopoietic stem cells (such as autologous, syngeneic, or allogeneic hematopoietic stem cells) to the patient.

The anti-CD45 antibody, antigen-binding fragment thereof, or ADC can be administered in an amount sufficient to reduce the quantity of endogenous hematopoietic stem cells, for example, by about 10%, about 20%, about 30%, about 40%, about 50%, about 60%, about 70%, about 80%, about 90%, about 95%, or more prior to hematopoietic stem cell transplant therapy. The reduction in hematopoietic stem cell count can be monitored using conventional techniques known in the art, such as by FACS analysis of cells expressing characteristic hematopoietic stem cell surface antigens in a blood sample withdrawn from the patient at varying intervals during conditioning therapy. For instance, a physician of skill in the art can withdraw a blood sample from the patient at various time points during conditioning therapy and determine the extent of endogenous hematopoietic stem cell reduction by conducting a FACS analysis to elucidate the relative concentrations of hematopoietic stem cells in the sample using antibodies that bind to hematopoietic stem cell marker antigens. According to some embodiments, when the concentration of hematopoietic stem cells has reached a minimum value in response to conditioning therapy with an anti-CD45 antibody, antigen-binding fragment thereof, or ADC, the physician may conclude the conditioning therapy, and may begin preparing the patient for hematopoietic stem cell transplant therapy.

The anti-CD45 antibody, antigen-binding fragment thereof, or ADC can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, or drug-antibody conjugate can be administered to the patient at a dosage of, for example, from about 0.001 mg/kg to about 100 mg/kg, from about 0.001 mg/kg to about 10 mg/kg, about 0.01 mg/kg to 9.5 mg/kg, about 0.1 mg/kg to 9 mg/kg, about 0.1 mg/kg to 8.5 mg/kg, about 0.1 mg/kg to 8 mg/kg, about 0.1 mg/kg to 7.5 mg/kg, about 0.1 mg/kg to 7 mg/kg, about 0.1 mg/kg to 6.5 mg/kg, about 0.1 mg/kg to 6 mg/kg, about 0.1 mg/kg to 5.5 mg/kg, about 0.1 mg/kg to 5 mg/kg, about 0.1 mg/kg to 4.5 mg/kg, about 0.1 mg/kg to 4 mg/kg, about 0.5 mg/kg to 3.5 mg/kg, about 0.5 mg/kg to 3 mg/kg, about 1 mg/kg to 10 mg/kg, about 1 mg/kg to 9 mg/kg, about 1 mg/kg to 8 mg/kg, about 1 mg/kg to 7 mg/kg, about 1 mg/kg to 6 mg/kg, about 1 mg/kg to 5 mg/kg, about 1 mg/kg to 4 mg/kg, or about 1 mg/kg to 3 mg/kg prior to administration of a hematopoietic stem cell graft to the patient. The anti-CD45 antibody, antigen-binding fragment thereof, or ADC can be administered to the patient at a time that optimally promotes engraftment of the exogenous hematopoietic stem cells, for instance, from about 1 hour to about 1 week (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, or about 7 days) or more prior to administration of the exogenous hematopoietic stem cell transplant.

In one embodiment, the anti-CD45 antibody, antigen-binding fragment thereof, or ADC is administered to a subject in conjunction with an immunosuppressive agent. In one embodiment, the immunosuppressive agent is an agent that depletes T cells. The immunosuppressive agent can be administered to the subject prior to, concurrently with, or after administration of the anti-CD45 antibody, antigen-binding fragment thereof, or ADC. Exemplary immunosuppressive agents include, but are not limited to, an anti-CD4 antibody, an anti-CD8 antibody, total body irradiation, and Cytoxan, and combinations thereof.

In one embodiment, the anti-CD45 antibody, antigen-binding fragment thereof, or ADC is administered to a subject in conjunction with total body irradiation (TBI), e.g., low dose TBI. In an exemplary embodiment, the subject receives TBI at a dose of 3 Gy or less, e.g., 3 Gy TBI or less, 2.5 Gy TBI or less, 2 Gy TBI or less, 1.5 Gy TBI or less, 1 Gy TBI or less, or 0.5 Gy TBI or less.

In one embodiment, the anti-CD45 antibody, antigen-binding fragment thereof, or ADC is administered to a subject in conjunction with Cytoxan.

Following the conclusion of conditioning therapy, the patient may then receive an infusion (e.g., an intravenous infusion) of exogenous hematopoietic stem cells, such as from the same physician that performed the conditioning therapy or from a different physician. The physician may administer the patient an infusion of autologous, syngeneic, or allogeneic hematopoietic stem cells, for instance, at a dosage of from $1\times10^3$ to $1\times10^9$ hematopoietic stem cells/kg. The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes) following administration of the transplant. This analysis may be conducted, for example, from 1 hour to 6 months, or more, following hematopoietic stem cell transplant therapy e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, or more). A finding that the concentration of hematopoietic stem cells or cells of the hematopoietic lineage has increased (e.g., by about 1%, about 2%, about 3%, about 4%, about 5%, about 6%, about 7%, about 8%, about 9%, about 10%, about 20%, about 30%, about 40%, about 50%, about 60%, about 70%, about 80%, about 90%, about 100%, about 200%, about 500%, or more) following the transplant therapy relative to the concentration of the corresponding cell type prior to transplant therapy provides one indication that treatment with the anti-CD45 antibody, or antigen-binding fragment thereof, or ADC has successfully promoted engraftment of the transplanted hematopoietic stem cell graft.

Engraftment of hematopoietic stem cell transplants due to the administration of an anti-CD45 antibody, antigen-binding fragments thereof, or ADCs, can manifest in a variety of empirical measurements. For instance, engraftment of transplanted hematopoietic stem cells can be evaluated by assessing the quantity of competitive repopulating units (CRU) present within the bone marrow of a patient following administration of an anti-CD45 antibody or antigen-binding fragment thereof, and subsequent administration of a hematopoietic stem cell transplant. Additionally, one can observe engraftment of a hematopoietic stem cell transplant by incorporating a reporter gene, such as an enzyme that catalyzes a chemical reaction yielding a fluorescent, chromophoric, or luminescent product, into a vector with which the donor hematopoietic stem cells have been transfected and subsequently monitoring the corresponding signal in a tissue into which the hematopoietic stem cells have homed, such as the bone marrow. One can also observe hematopoietic stem cell engraftment by evaluation of the quantity and survival of hematopoietic stem and progenitor cells, for instance, as determined by fluorescence activated cell sorting (FACS) analysis methods known in the art. Engraftment can also be determined by measuring white blood cell counts in peripheral blood during a post-transplant period, and/or by measuring recovery of marrow cells by donor cells in a bone marrow aspirate sample.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Preparation of Anti-CD45 Monoclonal Antibodies

Human CD45 (specifically the extracellular region of human CD45 RO) was used to immunize rats to obtain anti-human CD45 antibodies. Cell lines expressing human CD45RO, human full length CD45 (RABC), cyno RABC and mouse CD45 RABC were created and binding of each clone was assessed by flow cytometry. 216 antibodies were assessed in duplicate for killing in secondary Fab-saporin experiments on 2 cell lines and human CD34 bone marrow cells at 10, 100 and 1000 pM of primary antibody, in the presence of anti-Rat Fab-saporin (10 nM for cell lines and 20 nM for CD34). Staurosporine was used as 100% death control on each plate. Rat anti-human CD45 mAbs were included for comparison. Cell lines were incubated for 72 h and CD34 cells for 120 hours, after which Cell titer glo was used to assess viability. Subsequently dose titration killing curves were performed on select clones on a REH cell line and human bone marrow CD34 cells.

Octet binding experiments were performed to identify good cross-reactive mAbs. Clones were selected based on the ability of the antibody to bind human CD45RO and CD45RABC as well as non-human primate cyno CD45RABC. Five clones were identified that had cross-reactivity with human and cynomolgus CD45, and of those, only AbA, AbB, and AbC were identified as having good cross-reactivity to human and non-human primate CD45 RABC.

These monoclonal antibodies were cloned, such that the variable regions were cloned into a vector containing a human IgG1. Chimeric antibodies AbA, AbB, and AbC were subsequently expressed as IgG1 antibodies and tested for binding and activity against human CD45 cells. The degree of monovalent binding of AbA, AbB, and AbC to human CD45 RABC, cynomolgus CD45 RABC and Rhesus CD45RABC as evaluated by Octet, is described in Table 2. The binding of AbA, AbB, and AbC was also assessed in the context of 24 h PBMC binding by flow cytometry. In each case, each clone was detected as binding to human and cyno PBMC.

TABLE 2

| Monovalent binding to CD45 RABC Antigens | | | | | |
|---|---|---|---|---|---|
| Antibody | Human KD (M) | Cyno KD (M) | Rhesus KD (M) | Fold cyno to Hu | Fold Rhesus to Hu |
| AbA chimera | 2.34E−09 | 9.33E−09 | 1.23E−08 | 4 | 5 |
| AbB chimera | 2.84E−09 | 1.45E−08 | 1.58E−08 | 5 | 6 |
| AbC chimera | 7.54E−09 | 6.22E−08 | 6.35E−08 | 8 | 8 |

These antibodies were also tested as ADCs to determine if they could internalize into cells expressing CD45. AbA, AbB, and AbC were each able to internalize.

Fc variant versions of AbA, AbB, and AbC were also made. Specifically, human IgG1 chimeras of AbA, AbB, and AbC were made with or without Fc mutations D265C and V205C (for conjugation purposes for ADCs). Further Fc variant antibodies were made with or without H435A or I253A/H310A/H435A to provide for a further half life of the antibody or ADC.

The amino acid sequences of the CDRs and variable regions of AbA, AbB, and AbC are provided in Table 3.

TABLE 3

ANTIBODY SEQUENCE TABLE

| SEQ ID NO: | Description | Amino acid sequence |
|---|---|---|
| 1 | AbA heavy chain (HC) variable region (CDRs underlined) | EVQLVESGGDRVQPGRSLTLSCVTSGFTFNNYWMTWIRQVPG KGLEWVASISSSGGSIYYPDSVKGRFTISRDNAKNTLYLQMN SLRSEDTATYYCARDERWAGAMDAWGQGTSVTVSS |
| 2 | AbA HC CDR1 | FTFNNYWMT |
| 3 | AbA HC CDR2 | SISSSGGSIYYPDSVKG |
| 4 | AbA HC CDR3 | ARDERWAGAMDA |
| 5 | AbA light chain (LC) variable region (CDRs underlined) | DIQMTQSPSSVLSASVGDRVTLSCKASQNINKNLDWYQQKHG EAPKLLIYETNNLQTGIPSRFSGSGSGTDYTLTISSLQPEDV ATYYCYQHNSRFTFGSGTKLEIK |
| 6 | AbA LC CDR1 | KASQNINKNLD |
| 7 | AbA LC CDR2 | ETNNLQT |
| 8 | AbA LC CDR3 | YQHNSRFT |
| 9 | AbB heavy chain (HC) variable region (CDRs underlined) | EVQLVESGGDLVQPGRSLKLSCIASGFTFTNFWMTWIRQVSG KGLEWVASISSSGGSIYYPDSVKDRFTISRDNAKNTLYLQMN SLRSEDTATYYCVKLHYYSGGDAWGQGTSVTVSS |
| 10 | AbB HC CDR1 | FTFTNFWMT |
| 11 | AbB HC CDR2 | SISSSGGSIYYPDSVKD |
| 12 | AbB HC CDR3 | VKLHYYSGGDA |
| 13 | AbB light chain (LC) variable region (CDRs underlined) | DIQMTQSPSFLSASVGDRVTINCKASQNINKYLDWYQQKHGE APKLLIHYTNNLHTGIPSRFSGSGSGTDYTLTISSLQPEDVA TYFCLQHSSRWTFGGGTKLELK |
| 14 | AbB LC CDR1 | KASQNINKYLD |
| 15 | AbB LC CDR2 | YTNNLHT |
| 16 | AbB LC CDR3 | LQHSSRWT |
| 17 | AbC heavy chain (HC) variable region | EVQLVESGGDLVQPGRSLKLSCVASGFTFNNYWMTWIRQVPG KGLEWVASISSSGGSIYYPDSVKDRFTISRDNAKNTLFLQMN SLRSEDTATYYCARLYYYSGGGDAWGQGTSVTVSS |
| 18 | AbC HC CDR1 | FTFNNYWMT |
| 19 | AbC HC CDR2 | SISSSGGSIYYPDSVKD |
| 20 | AbC HC CDR3 | ARLYYYSGGGDA |
|  | AbC light chain (LC) variable region (CDRs underlined) | DIQMTQSPSFLSASVGDRVTIICKASQDINKYLDWYQQKLGE APKLLIYNTNNLHTGIPSRFSGSGSGTDYTLTISSLQPEDVA TYFCLQHISRWTFGGGTKLELK |
| 22 | AbC LC CDR1 | KASQDINKYLD |
| 23 | AbC LC CDR2 | NTNNLHT |
| 24 | AbC LC CDR3 | LQHISRWT |
| 25 | AbA LC variable DNA | GACATCCAGATGACCCAGTCTCCACCTGTGCTGTCTGCATCT GTAGGAGACAGAGTCACCCTTTCATGCAAGGCAAGTCAGAAT ATTAACAAAAATTTAGACTGGTATCAGCAGAAACATGGGAA GCCCCTAAGCTCCTGATCTATGAGACAAATAATTTGCAAACG GGGATCCCATCAAGGTTCAGTGGCAGTGGATCTGGGACAGAT TACACTCTCACCATCAGCAGTCTGCAACCTGAAGATGTGGCA ACTTACTACTGTTACCAGCACAACTCCAGATTCACTTTTGGC TCAGGGACCAAGCTGGAGATCAAA |

TABLE 3-continued

ANTIBODY SEQUENCE TABLE

| SEQ ID NO: | Description | Amino acid sequence |
|---|---|---|
| 26 | AbA HC variable DNA | GAAGTGCAGCTGGTGGAGTCTGGGGGAGACAGGGTACAGCCT GGCAGGTCCCTGACACTCTCCTGTGTAACATCTGGATTCACC TTTAACAACTATTGGATGACCTGGATCCGGCAAGTACCAGGG AAGGGCCTGGAGTGGGTCGCTTCTATTAGTTCCAGTGGCGGT AGCATATATTATCCCGACTCTGTGAAGGGCCGATTCACCATC TCCAGAGACAACGCCAAGAACACCCTGTATCTGCAAATGAAC AGTCTGAGATCCGAGGACACGGCGACCTACTACTGCGCAAGA GACGAAAGATGGGCTGGCGCTATGGACGCCTGGGGGCAAGGG ACCTCCGTCACCGTCTCCTCA |
| 27 | AbB LC variable DNA | GACATCCAGATGACCCAGTCTCCATCCTTCCTGTCTGCATCT GTAGGAGACAGAGTCACCATCAACTGCAAGGCGAGTCAGAAC ATTAATAAATATTTAGATTGGTATCAGCAGAAACATGGGGAG GCCCCTAAGCTCCTGATCCATTACACCAATAATTTGCACACA GGGATACCATCAAGGTTCAGTGGAAGTGGATCTGGGACAGAT TACACTTTGACCATCAGCAGCCTGCAGCCTGAAGATGTTGCA ACATATTTCTGTCTGCAACATTCCAGCAGGTGGACCTTCGGC GGAGGGACCAAGCTTGAGCTGAAA |
| 28 | AbB HC variable DNA | GGGAAGGGCCTGGAGTGGGTCGCTAGCATTAGTTCTAGTGGA GGTAGCATATATTATCCCGACTCTGTGAAGGACCGATTCACC ATCTCCAGAGACAACGCCAAGAACACACTGTATCTGCAAATG AACAGTCTGAGATCCGAGGACACGGCGACATACTACTGCGTT AAGCTTCACTACTATTCCGGAGGGGGTGATGCTTGGGGCCAA GGAACCTCCGTCACCGTCTCCTCA |
| 29 | AbC LC variable DNA | GACATCCAGATGACCCAGTCTCCATCCTTCCTGTCTGCATCT GTAGGAGACAGAGTCACCATCATCTGCAAGGCGAGTCAGGAC ATTAACAAGTATTTAGACTGGTATCAGCAGAAATTGGGGGAA GCCCCTAAGCTCCTGATCTACAATACAAATAATTTGCACACA GGGATACCATCAAGGTTCAGTGGAAGTGGATCTGGGACAGAT TACACTTTGACCATCAGCAGCCTGCAGCCTGAAGATGTCGCA ACATATTTTTGTCTGCAGCACATTAGCAGATGGACCTTCGGC GGAGGGACCAAGCTGGAGCTGAAA |
| 30 | AbC HC variable DNA | GAAGTGCAGCTGGTGGAGTCTGGGGGAGATTTGGTACAGCCT GGCAGGTCCCTGAAACTCTCCTGTGTTGCCTCTGGATTCACC TTTAATAACTATTGGATGACATGGATTCGGCAAGTTCCAGGG AAGGGCCTGGAGTGGGTCGCTTCCATTAGTAGTAGTGGTGGT AGCATATATTATCCCGACTCTGTGAAGGATCGATTCACCATC TCCAGAGACAACGCCAAGAACACACTGTTTCTGCAAATGAAC AGTCTGAGATCTGAGGACACGGCGACATACTACTGCGCGAGA CTGTATTACTATTCTGGTGGTGGCGATGCGTGGGGCCAAGGA ACCTCCGTCACCGTCTCCTCA |

Example 2. Non-Genotoxic Conditioning Using Amatoxin Antibody Drug Conjugates Targeting CD45 Effectively Deplete Human and Non-Human Primate Hematopoietic Stem Cells and Immune Cells Introduction Bone Marrow Transplant (BMT) is a potentially curative treatment for malignant and non-malignant blood disorders. Current regimens for patient preparation, or conditioning, prior to BMT limit the use of this curative procedure due to regimen-related mortality and morbidities, including risks of organ toxicity, infertility and secondary malignancies. To safely condition patients for BMT, antibody drug conjugates (ADCs) targeting CD45 were developed, a target expressed throughout the hematopoietic system to specifically deplete both hematopoietic stem cell (HSCs) and immune cells prior to transplant.

Results

Figure 1B:
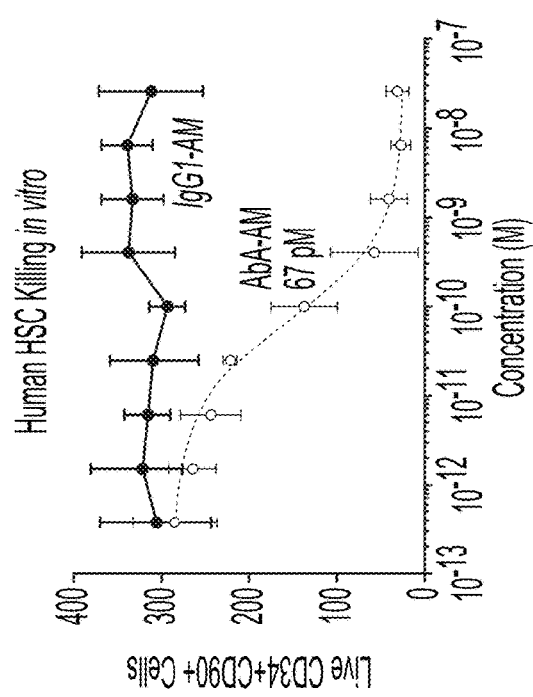
Figure 1C:
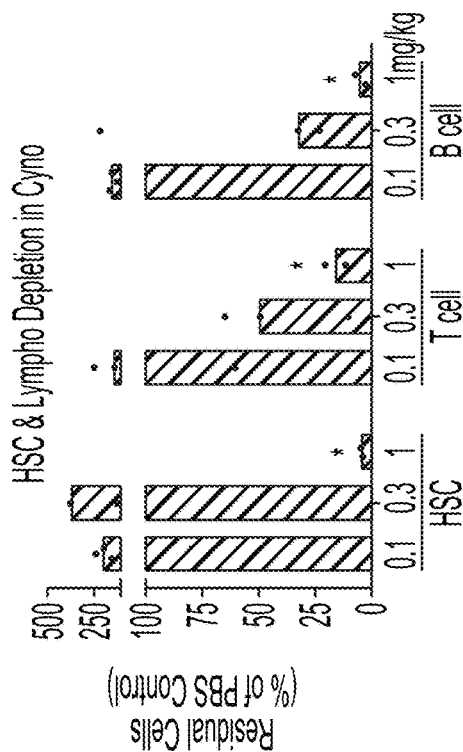
Figure 1D:
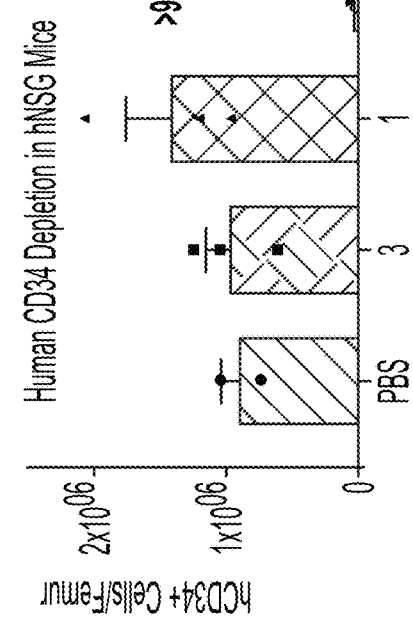
Figure 1E:
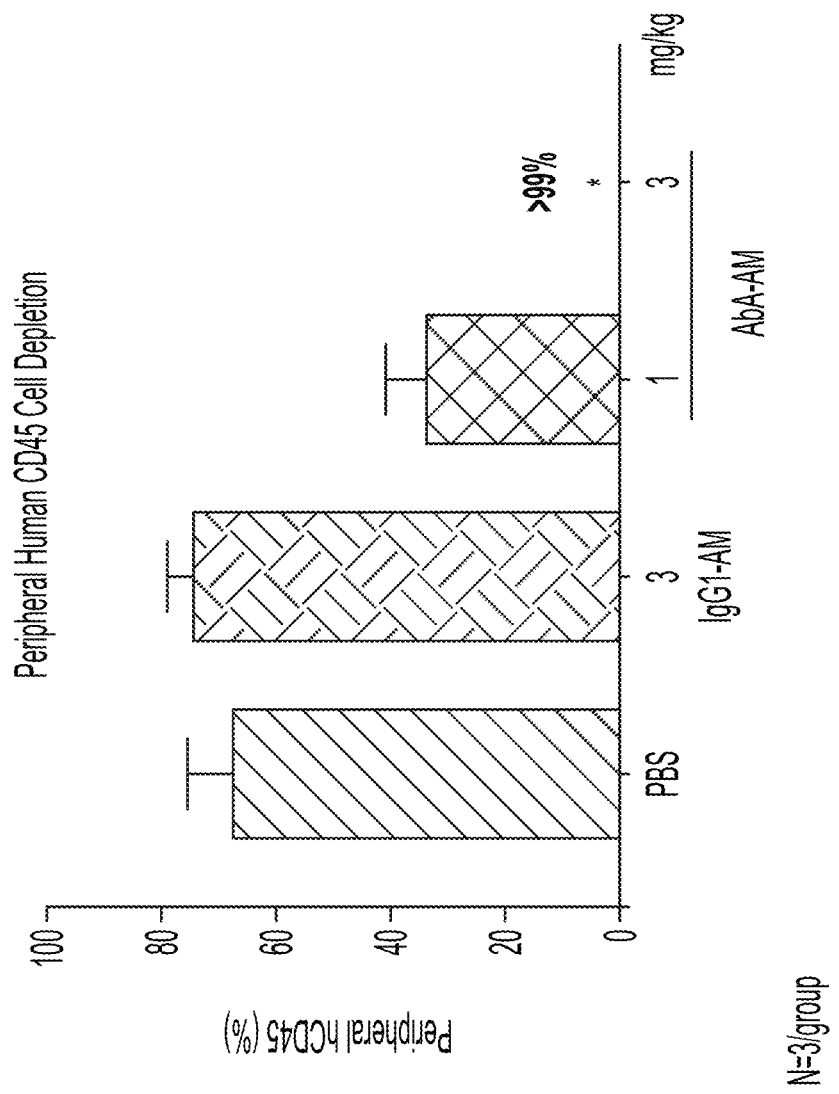

Anti-CD45 ADCs were created by conjugating anti-CD45 antibody AbA (chimeric AbA as IgG1) to amatoxin (AM) payload (an RNA polymerase II inhibitor). A resulting anti-CD45 AM ADC (CD45-AM) exhibited potent in vitro killing of primary human bone marrow CD34+CD90+ HSCs (IC50 67 pM, FIG. 1A) and PBMC immune cells (IC50 55 pM, FIG. 1B). Next, the CD45-AM ADC was studied in vivo in humanized NSG mice. A single dose of 3 mg/kg CD45-AM enabled >95% depletion of human CD34+ cells in the bone marrow (FIG. 1C; 14 days post-dosing) and >95% depletion of human B-, T- and myeloid cells in the periphery and bone marrow (FIG. 1D). A single dose of 3 mg/kg CD45-AM also enabled >99% depletion of peripheral human CD45 cells (FIG. 1E; 14 days post-dosing; N=3/group). Control non-targeting isotype matched-ADCs and anti-CD45 antibody not bearing a toxin had minimal effect on HSC, immune cells, or peripheral human CD45 cells. As CD45 is highly expressed on many leukemia and lymphomas, we also assessed the leukemia-depleting activity of CD45-AM in an ALL model and 3 PDX-AML models. A single dose of 1 mg/kg CD45-AM more than doubled the median survival in all 4 models (p values<0.001) with several mice surviving free-of disease.

As BMT will require fast clearing ADCs to avoid depleting the incoming graft, we engineered a fast-half-life CD45-AM variant with a t½ of 8-15 hours in mice, and 9 hours in cynomolgus monkeys. Dose escalation of the cross-reactive fast half-life CD45-AM in cynomolgus monkeys showed dose-dependent peripheral lymphocyte depletion. A single dose of 1 mg/kg was well tolerated and enabled >95% depletion of HSCs (CD34+CD90+CD45RA− cells) and >80% lymphocyte depletion in the marrow 14 days post-administration (FIG. 1D).

In conclusion, targeting CD45 with an amatoxin ADC resulted in potent in vitro and in vivo human HSC and immune cell depletion. The anti-CD45 amatoxin ADC significantly reduced disease burden in multiple leukemia models. Preliminary assessment of a fast half-life ADC in cynomolgus monkeys showed efficient HSC and immune cell depletion in the marrow. An amatoxin ADC targeted to CD45 may i) be non-genotoxic; ii) avoid bystander toxicity, due to amanitin's poor cell permeability as a free toxin; and iii) kill cycling and non-cycling cells, the latter being necessary for effective HSC and immune cell depletion. Together, these properties may enable safer targeted conditioning and expand the use of BMT in malignant and non-malignant conditions.

Example 3. Anti-CD45 Antibody Drug Conjugates (ADCs) Conditioning Agents has Profound In Vivo Anti-Leukemia Activity in Cell Line and Patient Derived Xenograft Models Allogeneic hematopoietic stem cell transplant (HSCT) is a potentially curative approach in patients with refractory or high risk hematologic malignancies. Prior to transplant, patients are conditioned with high dose chemotherapy or chemotherapy and total body irradiation which are associated with early and late morbidities and substantial risk of mortality. As a result, many eligible patients do not consider transplant and of those transplanted, ⅔ can only tolerate a reduced intensity conditioning which is associated with increased relapse rates. Thus, safer and more effective conditioning agents with improved disease control are urgently needed. To meet this need, we developed a novel antibody drug conjugates (ADCs) using antibody AbB (chimeric AbB in human IgG1) conjugated to amatoxin (AM) targeting CD45 (Rahul 2018) which is expressed on all lympho-hematopoietic cells and nearly all hematologic malignancies except multiple myeloma. The aim of the project was to determine the anti-leukemia potency of anti-CD45-AM, an agent previously shown to deplete primary human HSPCs in vitro and in vivo.

Methods. ADCs were tested in REH-Luc, a CD45 expressing AML cell line tagged with luciferase), and three patient-derived xenografts (PDX) developed from FLT-3+ NPM1+ AML samples (J000106132, J000106565, J000106134) with varying growth kinetics (median survival of vehicle treated groups was 43, 63, 82 days post inoculation) that express both CD117 and CD45 (Jackson Laboratories).

Results. In the REH-Luc model, a single injection of 1 mg/kg CD45-AM on day 5 after AML inoculation resulted in longer survival by a median of 15 days compared to vehicle treated controls or unconjugated anti-CD45 antibody (n=10 mice/group, p<0.0001). With 4-5 mice/group/AML-PDX model, survival was significantly increased in recipients of 0.1 mg/kg CD45-AM as compared to vehicle controls.

Conclusions. In addition to depletion of normal host HSPC, CD45-AM is a potent anti-leukemia agent based on these data in humanized murine models with established AML. Together with prior reports on the potency of CD45-AM a conditioning agent, these non-genotoxic ADCs may be useful in patients with active disease and in recipients of reduced dose conditioning who are at high risk of disease relapse.

Example 4. Single Doses of Antibody Drug Conjugates (ADCs) Targeted to CD45 have Potent In Vivo Anti-Leukemia Activity and Survival Benefit in Patient Derived AML Models Allogeneic bone marrow transplant (BMT) is a potentially curative approach in patients with refractory or high risk hematologic malignancies, such as acute myeloid leukemia (AML) and myelodysplastic syndromes (MDS). Prior to transplant, patients are prepared with non-specific, high dose chemotherapy alone or in combination with total body irradiation, which are associated with early and late morbidities, including organ toxicities, infertility, secondary malignancies, and substantial risk of mortality. As a result, many eligible patients do not consider transplant and of those transplanted, ⅔ can only tolerate reduced intensity conditioning, which is associated with increased relapse rates (Scott et al. Journal of Clinical Oncology 2017, 1154-1161). Thus, safer and more effective conditioning agents with improved disease control are urgently needed. To meet this need, we developed two novel antibody drug conjugates (ADCs) conjugated to amatoxin (AM) targeting CD117 (C-KIT, Pearse 2018), which is expressed on hematopoietic stem and progenitor cells and AML and MDS cells in ~80% of patients (Gao et al. PLOS One. 2015), and CD45 (Palchaudhuri 2018) which is expressed on all lympho-hematopoietic cells and nearly all hematologic malignancies except multiple myeloma. The aim of the project was to design a non-genotoxic agent with the dual benefit of depleting primary human hematopoietic stem progenitor cells (HSPCs) while reducing disease burden in leukemia models.

Method

The anti-CD45 antibody used in the ADC in the following Example is anti-CD45 antibody AbB conjugated (interchain) to amanitin with a drug to antibody ratio (DAR) 4. ADCs were tested in xenograft murine models inoculated with human leukemia cells from immortalized cell lines (REH-Luc, a CD45 expressing ALL cell line tagged with luciferase ($5 \times 10^6$ cells/mouse), and three patient-derived xenografts (PDX) developed from FLT-3+NPM1+ AML samples [AML #1 (J000106132), AML #2 (J000106565), AML #3 (J000106134)] with varying growth kinetics (median survival of vehicle treated groups was 43, 63, 82 days post inoculation) that express CD45 (Jackson Laboratories). All in vivo research was conducted in accordance with the Guide for the Care and Use of Laboratory Animals published by the National Research Council of the National Academies and under the approval of the Institutional Animal Care and Use Committee.

Results

Effective Target Depletion In Vitro

For in vitro killing assays using human PBMCs, human PBMCs were cultured for four days in the presence of the anti-CD45-amatoxin conjugate (antibody AbB-amatoxin; "CD45-AM") or IgG1 isotype conjugated to amatoxin ("Isotype-AM") and cell viability was measured in luminescence (RLU; y-axis) by Celltiter Glo as a function of antibody concentration (x-axis) (FIG. 2A). For in vitro killing assays using Human HSCs (i.e., isolated primary human CD34+ selected Bone Marrow Cells (BMCs), primary human CD34+ bone marrow cells were cultured for 5 days with CD45-AM or Isotype-AM, and live CD34+CD90+ HSC counts (y-axis) were determined by flow cytometry as a function of antibody concentration (x-axis).

Figure 2B:
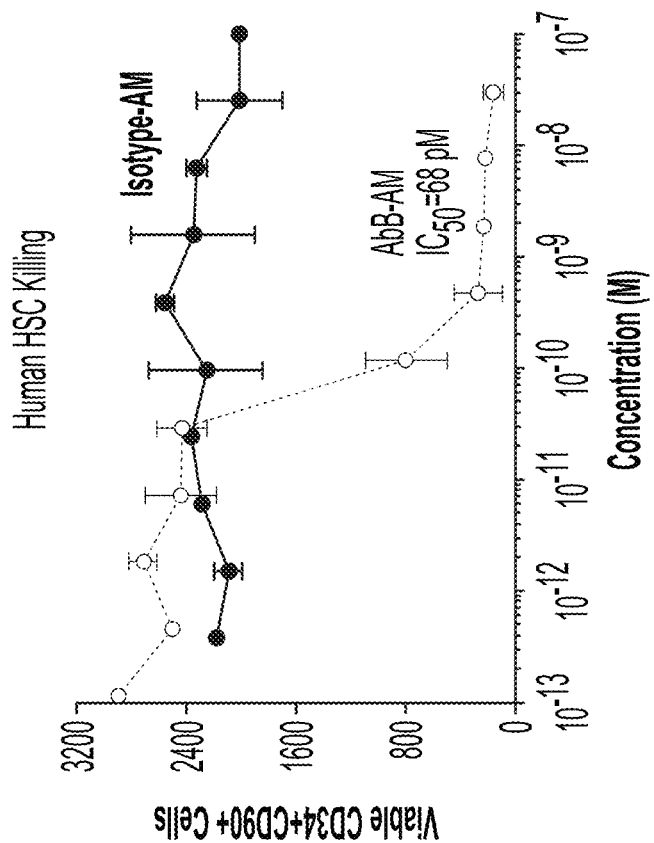
FIGS. 2A and 2B graphically depicts the results of in vitro cell killing assays showing that anti-CD45-AM is highly effective at killing human HSCs in vitro.
Figure 2A:
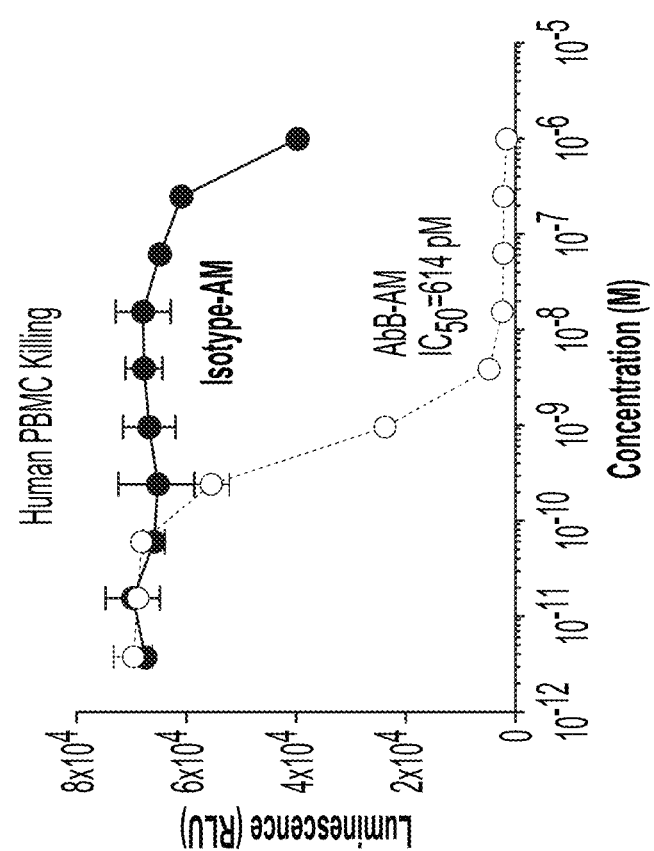

The results in FIGS. 2A and 2B indicate that CD45-ADC is highly effective at killing CD45 expressing cell lines (e.g., PBMCs; 614 pM; FIG. 2A) or primary human CD34+ CD90+ HSCs in vitro (68 pM, FIG. 2B).

Figure 3B:
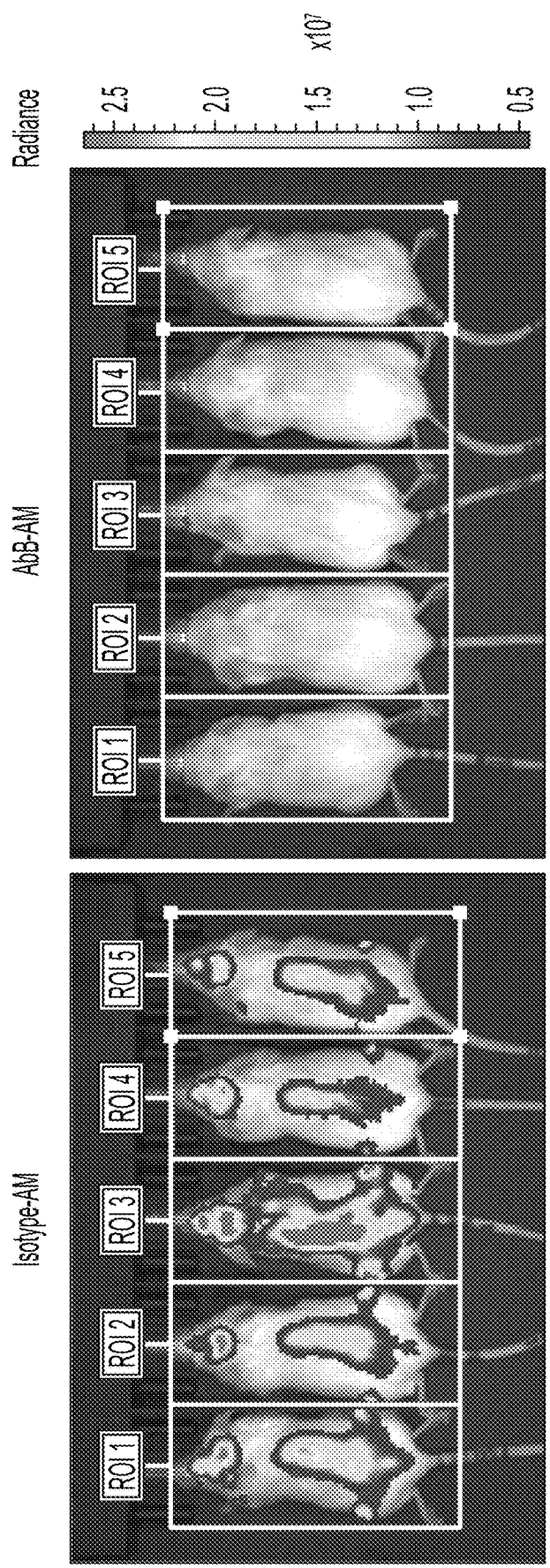

Anti-CD45-AM Doubles Median Survival to 40 Days in REH-Luciferase ALL Xenograft Model The CD45-ADC was tested in xenograft murine models inoculated with human leukemia cells from immortalized cell lines that express CD45 (REH-Luc, a CD45 expressing ALL cell line tagged with luciferase ($5 \times 10^6$ cells/mouse)). As shown in FIG. 3A, a single injection of 1 mg/kg anti-CD45-AM on day 5 after ALL inoculation resulted in longer survival by a median of 15 days compared to vehicle (PBS) treated controls or unconjugated anti-CD45 antibody (n=10 mice/group, p<0.0001). Additionally, representative bioluminescence signal pseudo-colored images were captured using the IVIS imaging system (Perkin Elmer) on day 19 post-implantation of the Anti-CD45-AM and Isotype-AM treatment groups (FIG. 3B). These results indicate that Anti-CD45-AM doubles median survival to 40 days in the REH-Luc Xenograft Model.

Anti-CD45-AM, and Anti-CD117-AM Extends Survival 2 to >4-Fold in Three Patient Derived AML Models Next, CD45-ADCs were tested in three patient-derived xenografts (PDX) developed from FLT-3+NPM1+ AML samples [AML #1 (J000106132), AML #2 (J000106565), AML #3 (J000106134)] with varying growth kinetics (median survival of vehicle treated groups was 43, 63, 82 days post inoculation) that express CD45 (Jackson Laboratories). Characterization of the AML POX models is summarized in Table 4.

TABLE 4

AML PDX model characterization

| PDX Model | AML #1 | AML #2 | AML #3 |
| --- | --- | --- | --- |
| Type | AML recurrent/Relapse | AML M4/5 | AML, M4 |
| Previous treatment | Allogeneic HSCT, Sorafenib, Hydroxyurea, Decitabine | Allogenic HSCT, Induction chemotherapy, consolidation HDACi | No previous treatment reported |
| Karyotype | Normal; FLT3+, | FLT3 ITD+, | 46, XY, |
| Mutation | NPM1+, DNMT3A+, IDH1+ | FLT3+, TKD+, NPM1+ | FLT3+, NPM1+ |

Figure 4A:
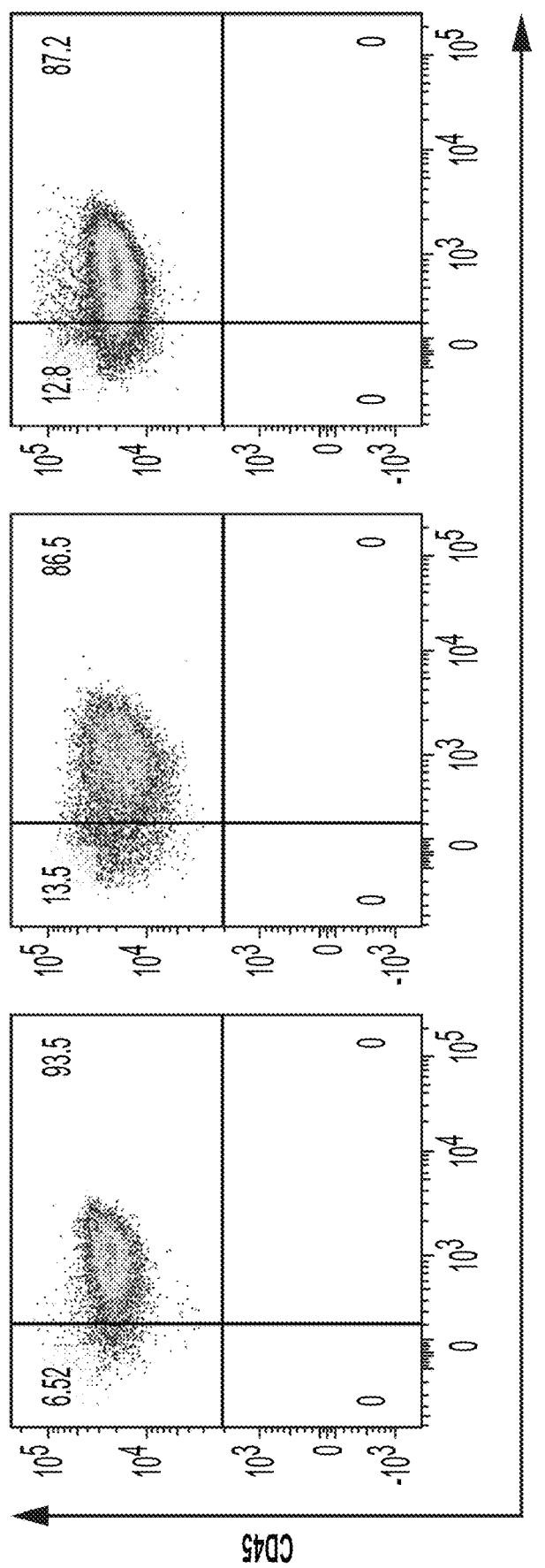
FIGS. 4A-4H graphically depict the results from an in vivo survival study using three AML-patient-derived xenografts developed from FLT-3+NPM1+ AML samples showing that a single dose of anti-CD45 antibody AbB conjugated to amanitin ("Anti-CD45-AM"; 1 mg/kg) effectively depletes human leukemic cells and extends survival in mouse models.
Figures 4B, 4C, 4D:
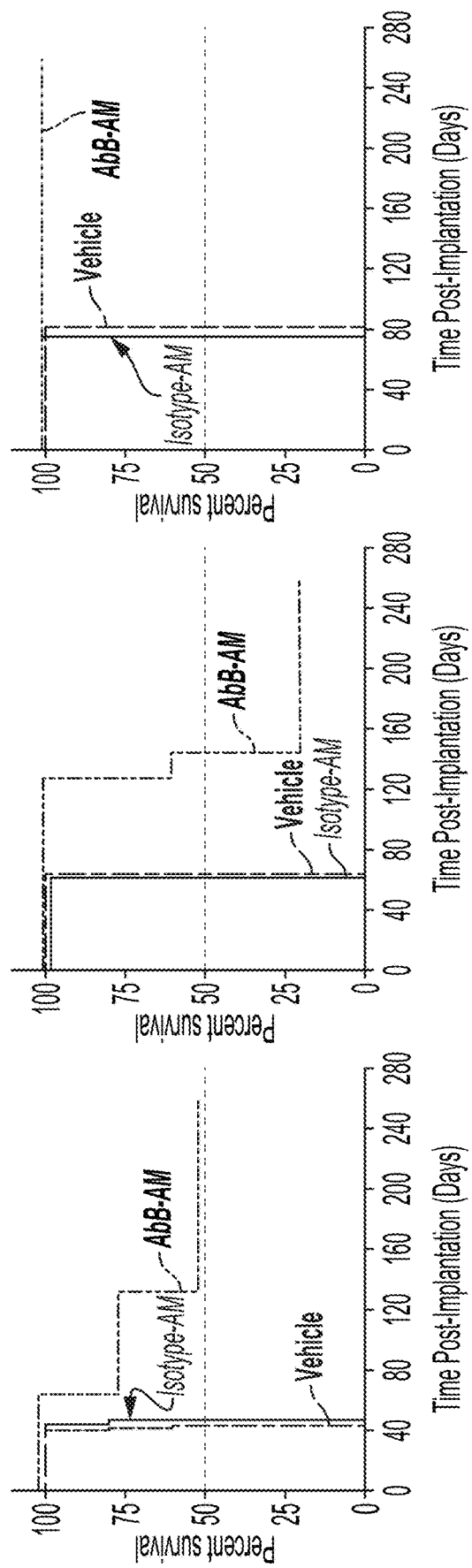
Figures 4E, 4F, 4G:
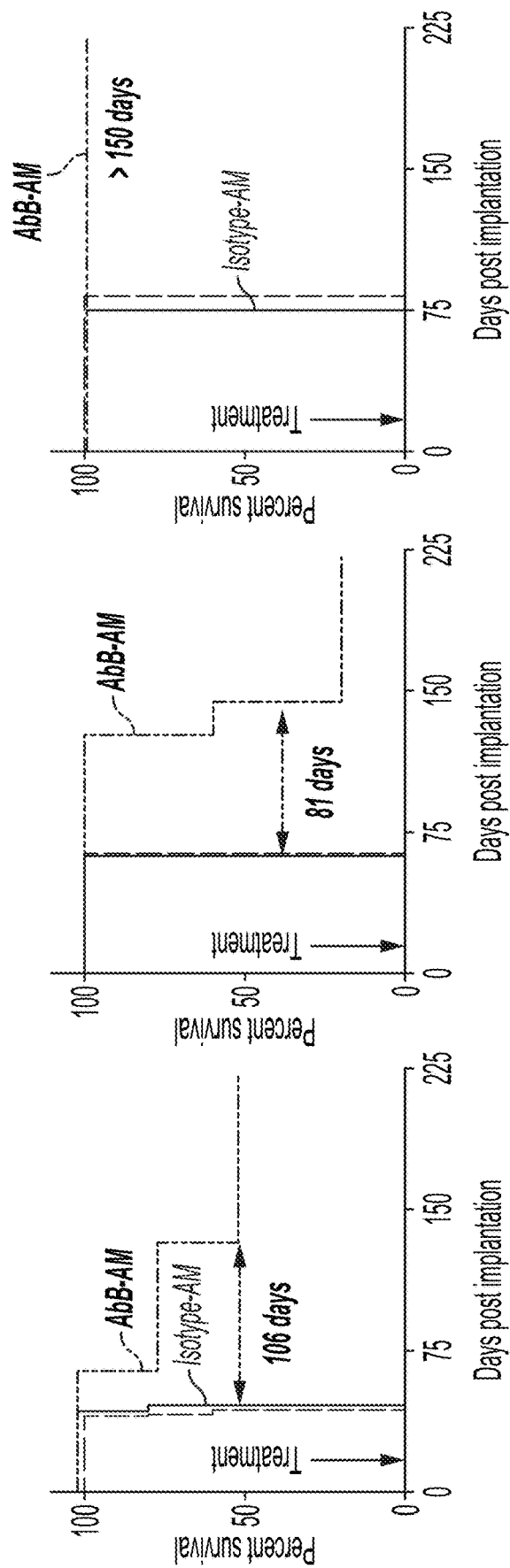
Figure 4H:
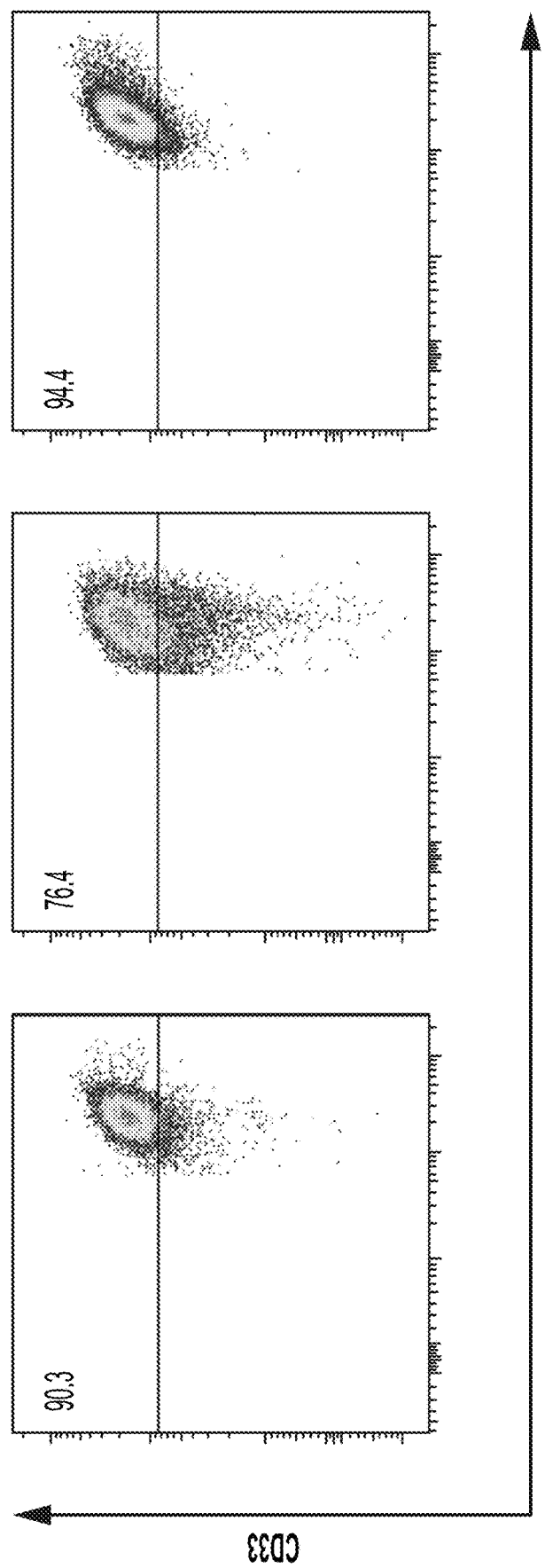

For the three PDX, a single intravenous dose of ADCs (CD45-AM, isotype-AM (ISO-AM), or vehicle PBS) were administered to AML-PDX mice when 2-5% blasts were observed in the blood (i.e., when 2-5% tumor in peripheral blood) with 4-5 mice/group/AML-PDX model. FIG. 4A and FIG. 4H show results from flow cytometry assays to evaluate CD45 cell surface expression on CD33+ splenocytes from diseased mice. As shown in FIGS. 4B-4D, survival was significantly increased in recipients of 1 mg/kg CD45-AM as compared to vehicle or isotype controls (Table 5; FIGS. 4B-4D). FIGS. 4E-4G, which correspond to the same data shown in FIGS. 4B-4D, respectively, but over a shorter period of days post-implantation, illustrate the timing of the administration of the 1 mg/kg CD45-AM (or isotype-AM control or PBS vehicle control and illustrate the difference in the number of days between the anti-CD45-Am survival curve and the control survival curves (i.e., isotype-AM and/or PBS vehicle controls) at 50% survival for each PDX AML model (i.e., POX AML #1 (106 days), POX AML #2 (81 days), and POX AML #3 (>150 days).

TABLE 5

Median survival (days post dose administration) in PDX AML models and statistical analysis (Log-Rank Test) comparing ADCs against either control group

| | Median Survival (Days Post Dose, p-value*) | | |
| --- | --- | --- | --- |
| PDX-AML Model | AML #1 | AML #2 | AML #3 |
| Vehicle (PBS) | 43 | 63 | 82 |
| CD45-AM | 195 (p < 0.01) | 144 (p < 0.01) | >280 |
| Isotype-AM | 46 | 63 | 75 |

These results demonstrate that a single dose administration of anti-CD45-AM is well tolerated and capable of potent killing of human CD34+CD90+ hematopoietic stem cells, AML cell lines, and human PBMCs in vitro. Further, single dose administration of anti-CD45-AM prolongs survival of established leukemia models (cell line and patient derived) and exhibits potent anti-leukemia effects based on these data in humanized murine models with established AML.

Non-genotoxic ADCs may be used to reduce disease burden in patients with active disease and in recipients of reduced dose conditioning who are at high risk of disease relapse.

Example 5. Targeting CD45 with an Amanitin Antibody-Drug Conjugate Effectively Depletes Human HSCs and Immune Cells for Transplant Conditioning Bone Marrow Transplant (BMT) is a potentially curative treatment for malignant and non-malignant blood disorders and has demonstrated impressive outcomes in autoimmune diseases. Prior to BMT, patients are prepared with high-dose chemotherapy alone or with total body irradiation, and both are associated with early and late morbidities, such as organ toxicities, infertility, secondary malignancies and substantial risk of transplant-related mortality. This greatly limits the use of BMT in malignant and non-malignant conditions. To address these issues, we are developing non-genotoxic antibody drug conjugates (ADCs) targeting hematopoietic stem cells (HSCs) and immune cells to safely condition patients for BMT.

An alpha-amanitin ADC targeted to CD45 may be appropriate for conditioning patients for BMT since it may i) be non-genotoxic; ii) avoid bystander toxicity, due to amanitin's poor cell permeability as a free toxin; and iii) kill cycling and non-cycling cells, the latter being necessary for effective HSC and immune cell depletion. Eliminating both immune cells and HSCs with an anti-CD45 ADC has the potential to enable allogeneic transplants in malignant and non-malignant settings. In addition, this strategy may also be effective in enabling immune reset through autologous transplant in patients with autoimmune diseases.

Methods

CD45-ADC. CD45-AM is an antibody-drug conjugate consisting of a chimeric human anti-CD45 antibody conjugated to amatoxin (AM), a RNA polymerase II inhibitor capable of depleting cycling and non-cycling cells. The isotype control ADC is a non-targeted monoclonal human IgG antibody conjugated to amatoxin.

In Vitro Cell Culture. Human peripheral blood mononuclear cells (PBMCs) were cultured in RPMI 1640 with 10% FBS in the presence of ADCs for 4 days and viability assessed by CellTiter Glo. Human HSCs (CD34+ selected BM cells) were cultured in SFEM media containing IL-6, TPO, FLT-3 ligand and SCF. After 5 days of incubating with ADCs, viable HSCs were quantitated by flow cytometry.

In Vivo Studies. Humanized NSG mice (pre-transplanted with human cord blood CD34+ cells) were purchased from the Jackson Laboratories. Mice were given a single i.v. injection of each antibody-drug conjugate. Male cynomolgus monkeys were given single i.v. dosing over 1 hour. All in vivo research was conducted in accordance with the Guide for the Care and Use of Laboratory Animals published by the National Research Council of the National Academies and under the approval of the Institutional Animal Care and Use Committee.

Results

Efficacy in Humanized NSG Mice

Figure 5A:
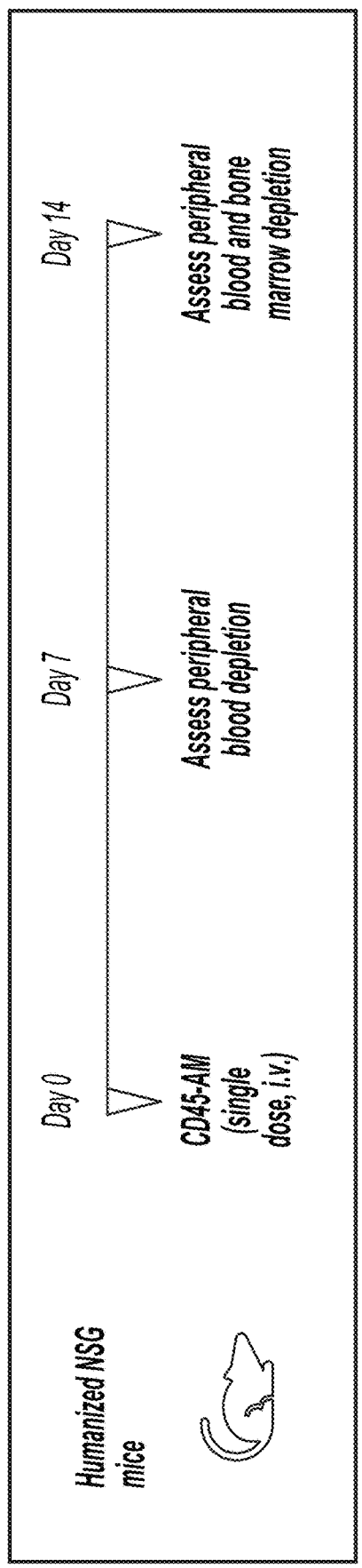
FIGS. 5A-5C graphically depict the results of an in vivo cell depletion assay showing that CD45-AM ADC selectively depletes human HSCs and immune cells in humanized NSG mice.

Anti-CD45 ADCs were created by conjugating anti-CD45 antibody AbB to an amatoxin (AM) payload (an RNA polymerase II inhibitor) (DAR4; interchain conjugation). We explored the CD45-AM ADC in vivo in humanized NSG mice. As shown in the schematic in FIG. 5A, CD45-AM or control antibodies were administered as a single dose on day 0. Peripheral PBMCs were collected on days 7 and 14 and examined by flow cytometry for human CD45 cells. On day 14, the presence or absence of human CD34$^+$ cells in the bone marrow was quantitated.

Figure 5C:
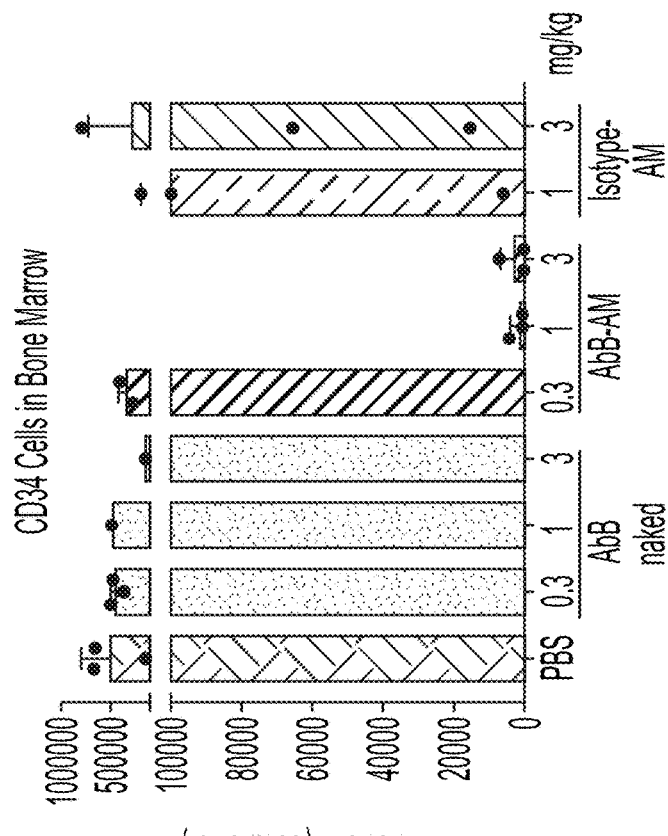
Figure 5B:
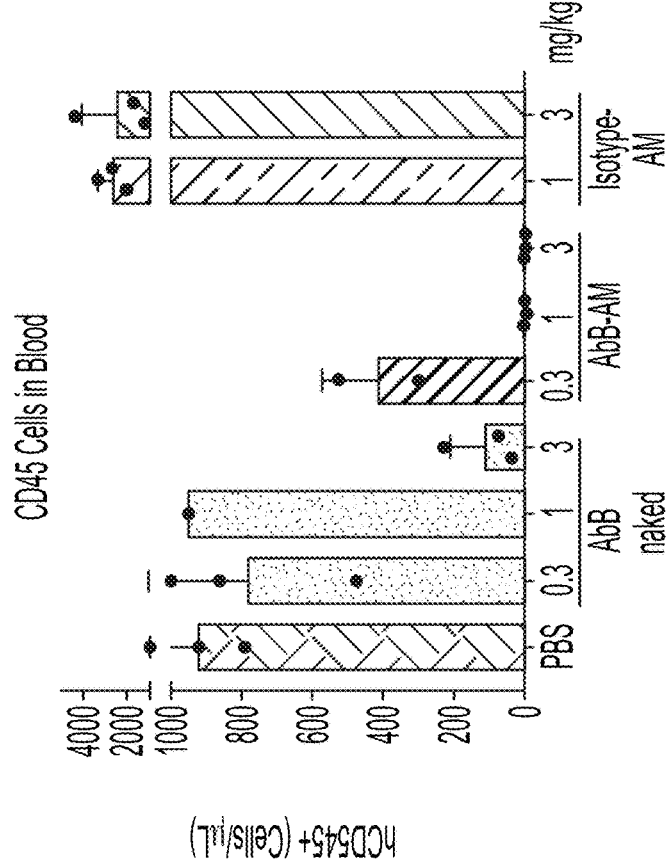

As shown in, FIGS. 5B and 5C, CD45-AM ADC selectively depletes human HSCs and immune cells in humanized NSG mice. FIG. 5B depicts the results of an assay showing the absolute number of human CD45+ cells in peripheral blood 14 days post-injection with anti-CD45-amatoxin ("CD45-AM"), unconjugated anti-CD45 antibody ("CD45-naked"), or control non-targeting isotype matched-ADCs ("isotype-AM"). FIG. 5C depicts the absolute number of human CD34$^+$ cells in the bone marrow of humanized NSG mice 14 days post-administration. Similar results were obtained for CD34$^+$CD90$^+$ (data not shown). These results indicate that CD45-AM ADC selectively depletes human HSCs and Immune cells in humanized NSG mice.

PK and Efficacy in Primates

Figure 6A:
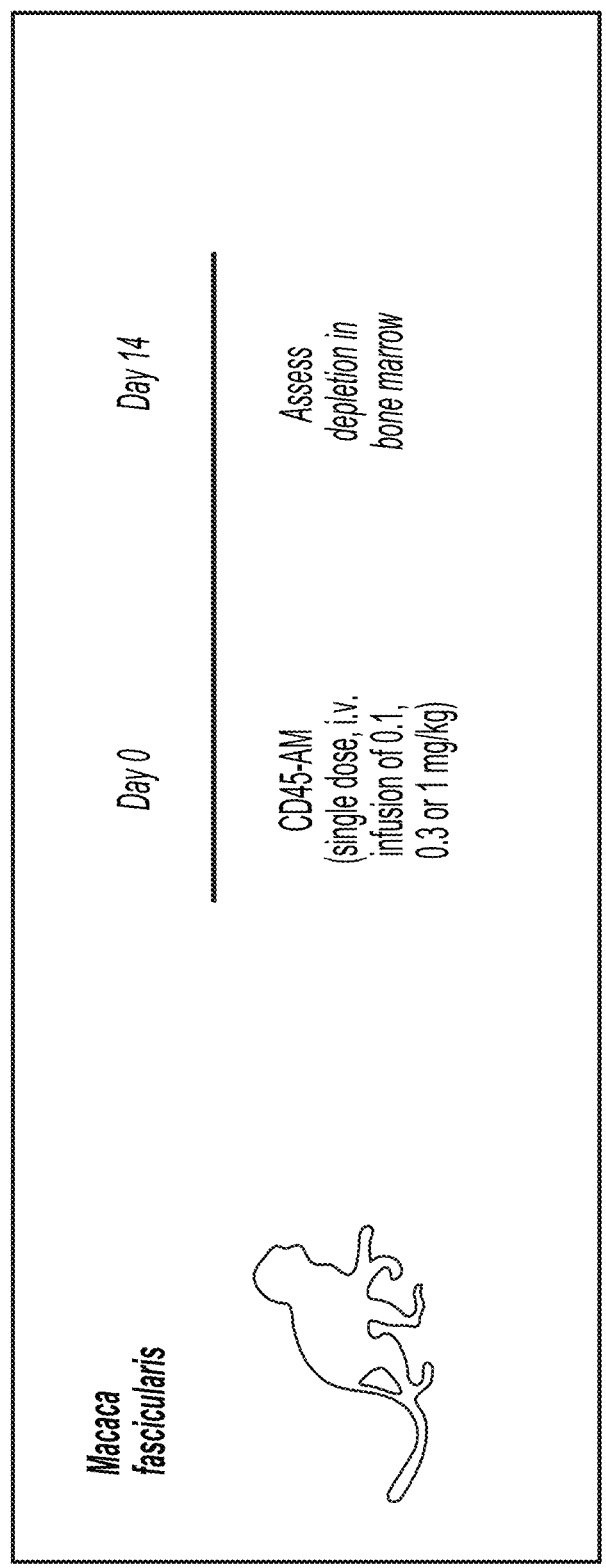
FIGS. 6A-6C show the design and results of an in vivo pharmacokinetic assay showing that CD45-AM ADC has a fast half-life PK profile in cynomolgus monkeys.

As BMT may require fast clearing ADCs to avoid depleting the incoming graft, we engineered a fast-half-life CD45-AM variant (using AbA conjugated to amatoxin (AM) with a drug to antibody ratio (DAR) of 2 and having Fc mutations D265C and H435A (EU index)) with a t % of 8-15 hours in mice, and 9 hours in cynomolgus monkeys. As shown in FIG. 6A, Male cynomolgus monkeys were given single i.v. dosing of the fast-half-life CD45-AM variant at 0.1 mg/kg, 0.3 mg/kg, or 1 mg/kg over 1 hour ((n=3/group except n=2 for 1 mg/kg).

Figure 6B:
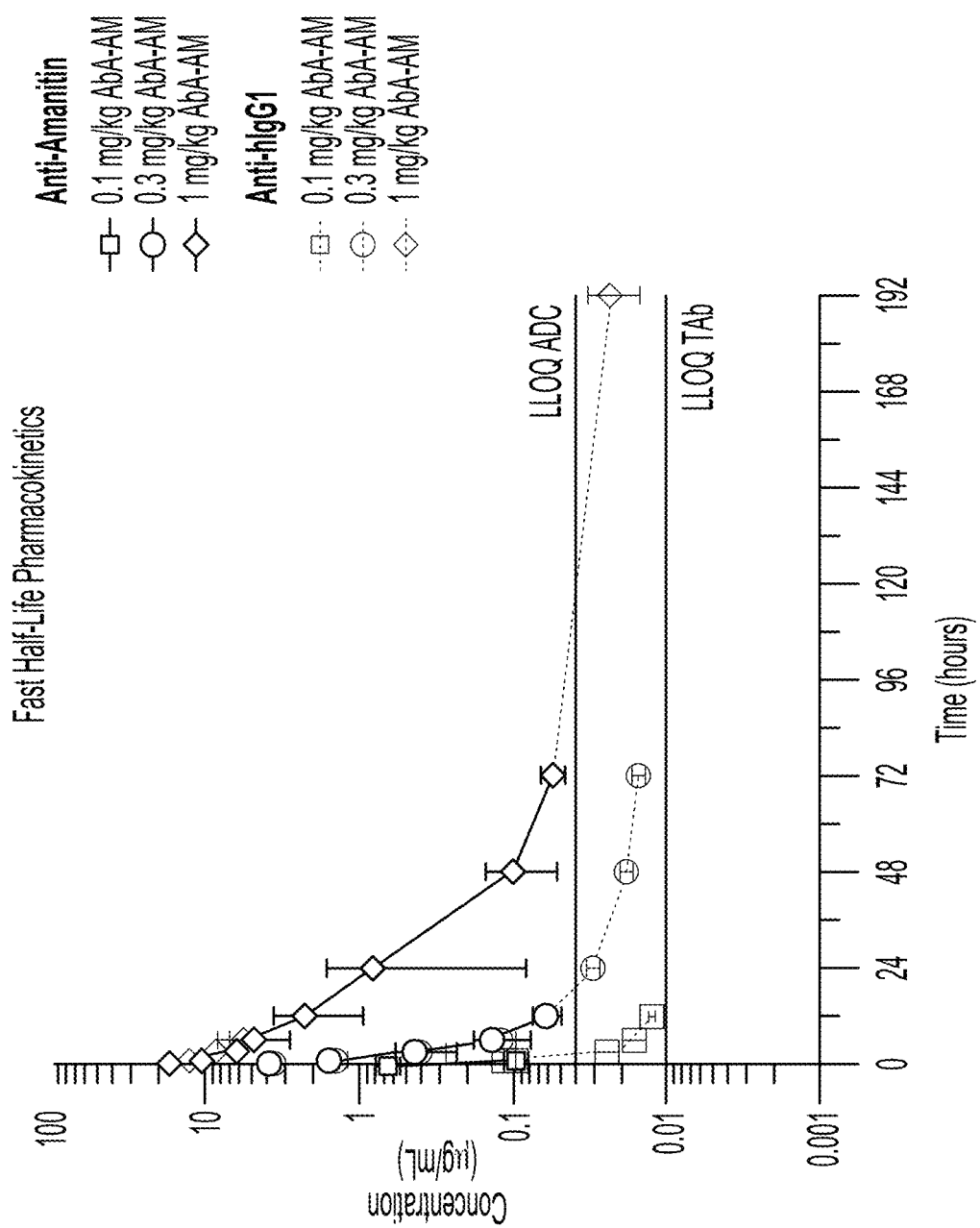

FIG. 6B and Table 6 show the results of an in vivo pharmacokinetic assay showing that the same fast-half-life CD45-AM ADC has a fast half-life PK profile in cynomolgus monkeys. As shown in FIG. 6B, CD45-AM exhibits non-linear PK indicative of target-mediated drug disposition (TMDD) PK with a short half-life suitable for transplant. "TAb" as used in FIG. 6B refers to total antibody using anti-hIgG1 detection, while ADC refers to anti-amanitin detection. These data also indicated that the ADC is stable in vivo as the Tab levels overlap with the ADC levels.

Figure 6C:
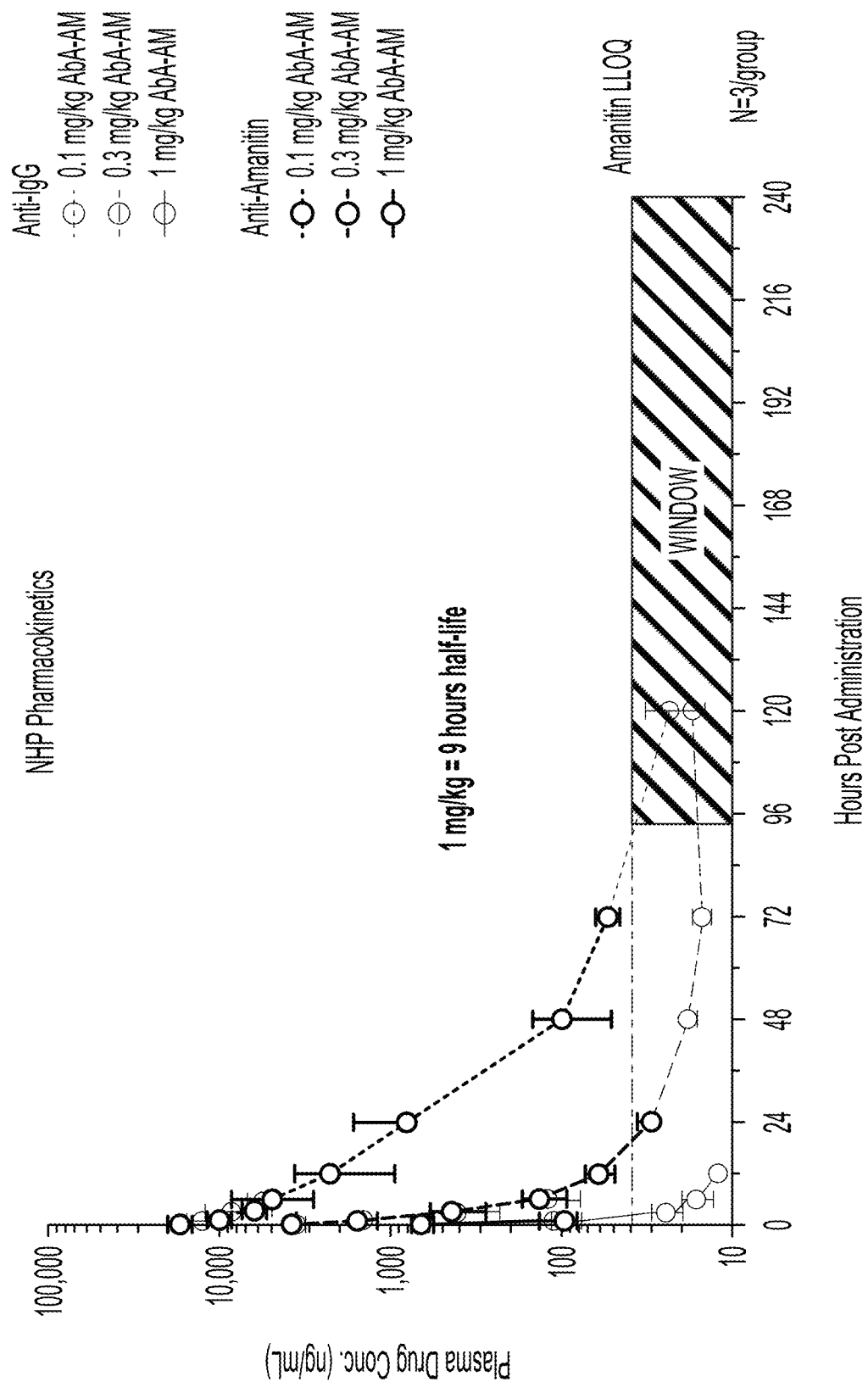

FIG. 6C, which represents the same data in FIG. 6B, but over a longer period of time post administration, further provides a window for graft infusion, which as shown in FIG. 6C, is greater than four-days post-dose administration.

TABLE 6

| ADC Mean NCA PK parameters | | | | | |
|---|---|---|---|---|---|
| Dose (mg/kg) | AUClast (hour*ug/mL) | AUClast/Dose (hour*kg*ug/mL/mg) | Cmax (ug/mL) | Cmax/Dose (kg*ug/mL/mg) | Half-life (hour) |
| 0.1 | 0.292 | 2.92 | 0.647 | 6.47 | N.R. |
| 0.3 | 5.61 | 18.7 | 3.87 | 12.9 | 2.9 |
| 1 | 93.8 | 93.8 | 17.4 | 17.4 | 9.4 |

Figure 7B:
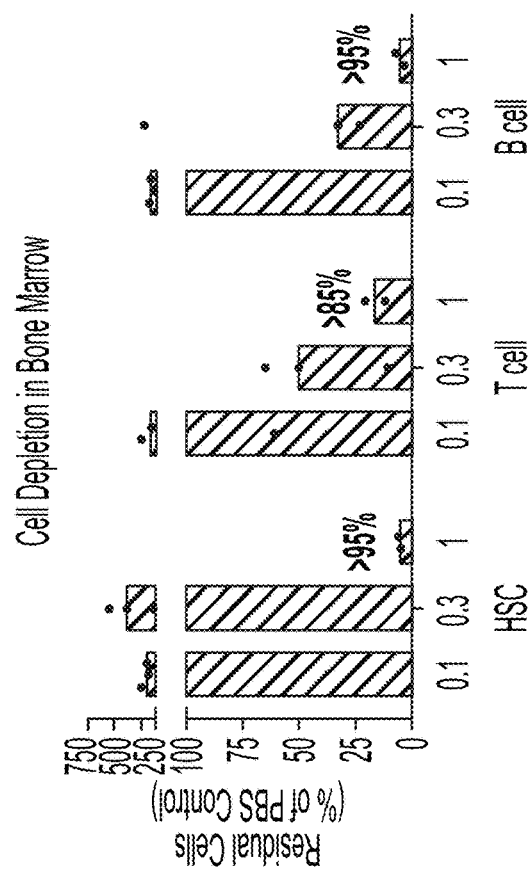
FIGS. 7A, 7B and 7C graphically depict results from in vivo depletion assays showing that anti-CD45 amanitin antibody drug conjugate (CD45-Am) enables in vivo depletion of peripheral lymphocytes (FIG. 7A) and depletion of hematopoietic stem cells (HSCs), T-, and B-cell in the bone marrow of cynomolgus monkeys assessed 14 days post-administration of CD45-AM. The data in FIG. 7C represent the data from the time course described in FIG. 7A, specifically at 1-day post-dose administration.
Figure 7A:
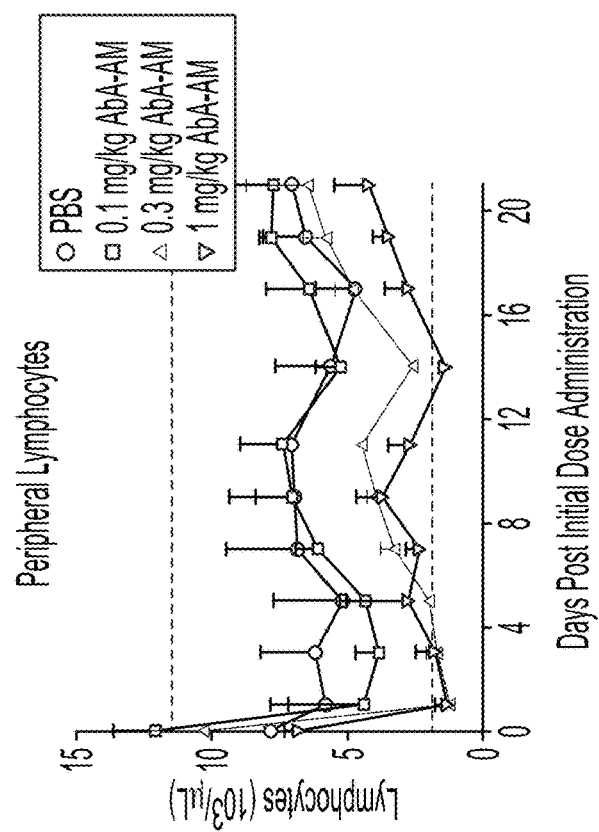
Figure 7C:
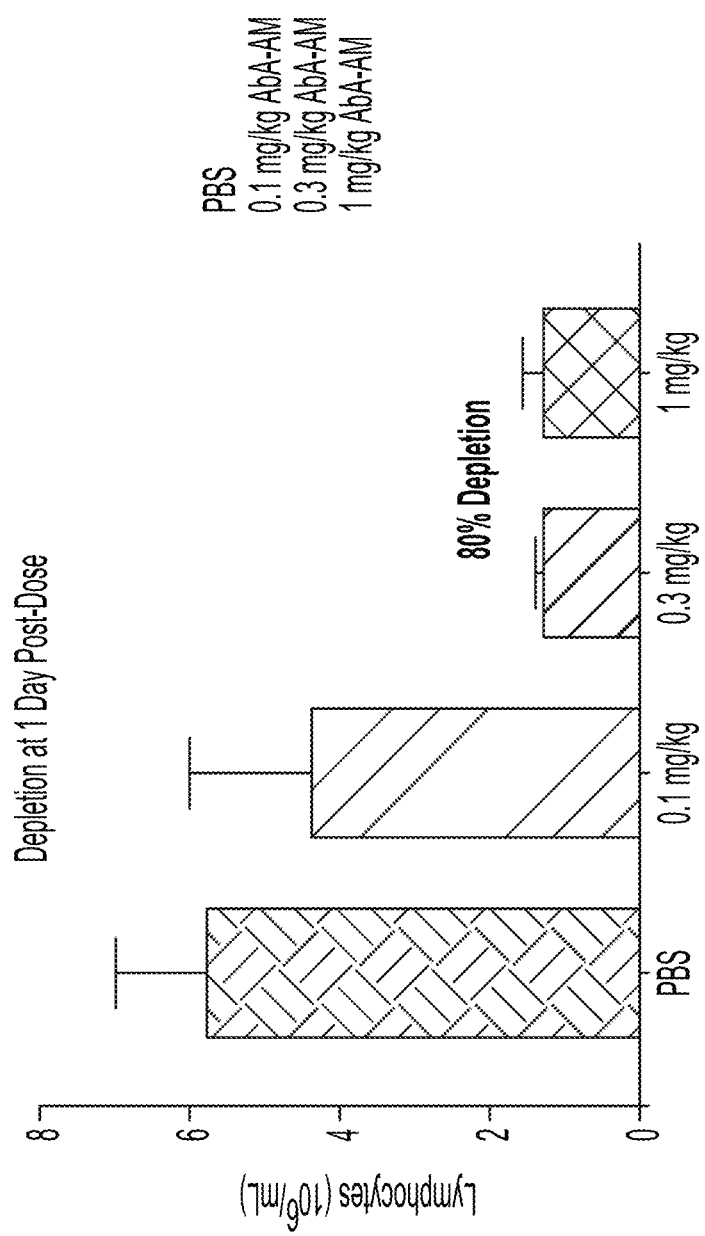

Next, peripheral lymphocyte depletion by the same fast-half-life CD45-AM variant (i.e., AbA conjugated to amanitin with the variant Fc mutations D265C and H435A (EU index)) was assessed by CBC, as shown in FIG. 7A. Further, dose-dependent depletion of bone marrow HSCs (CD34+ CD90+ cells), T cells and B cells was observed 14 days post administration of the same fast-half-life CD45-AM variant (FIG. 7B). The results in FIG. 7C, which represent the data from the time course described in FIG. 7A, specifically at 1-day post-dose administration, show 80% depletion peripheral lymphocytes at the 0.3 mg/kg dose and 1 mg/kg dose. The results in FIGS. 7A to 7C indicate that fast half-life CD45-AM ADC effectively depletes CD45 cells in cynomolgus monkeys. ALT, bilirubin, and platelets remained within normal ranges post CD45-AM dosing.

In conclusion, these studies have demonstrated that a single administration of CD45-AM ADC is well-tolerated and capable of depleting human immune cells and CD34$^+$ cells in the bone marrow of humanized NSG mice. Further, we have demonstrated that a single administration of fast-half-life CD45-AM ADC is well tolerated and capable of depleting immune cells and CD34+ cells in the bone marrow of cynomolgus monkeys. These data also show a decrease in HSCs (CD34+CD90+CD45RA−) and immune cells in bone marrow at day 14. No depletion was observed with the isotype-amanitin conjugate or unconjugated antibody.

Non-genotoxic conditioning with a CD45-ADC may provide an approach for safer conditioning prior to BMT and greatly increase the number of patients eligible for a transplant. In addition to applications in transplant for malignant diseases, this approach may allow for patient preparation for BMT in non-malignant conditions including autoimmune diseases.

Example 6. Analysis of Red Blood Cell Count, Platelet Cell Count, Plasma ALT and Bilirubin in an In Vivo Dose Escalation Study Cohorts of cynomolgus monkeys (3 monkeys per cohort) were administered varying doses of a fast half-life anti-CD45-amanitin ADC (using AbA conjugated to having Fc mutations D265C and H435A (EU index)) at varying doses (i.e., 0.1 mg/kg; 0.3 mg/kg; 1 mg/kg; or a control (PBS)) on day 0. Blood was collected throughout the course of the study. Hematology was evaluated throughout the course of the study. Red blood cell count ($10^6/\mu L$), platelet cell count ($10^3/\mu L$), plasma levels of ALT (alanine aminotransaminase), and plasma levels bilirubin were measured and were graphically represented as a function of days post dose administration as shown in FIGS. 8A through 8D, respectively.

Figure 8A:
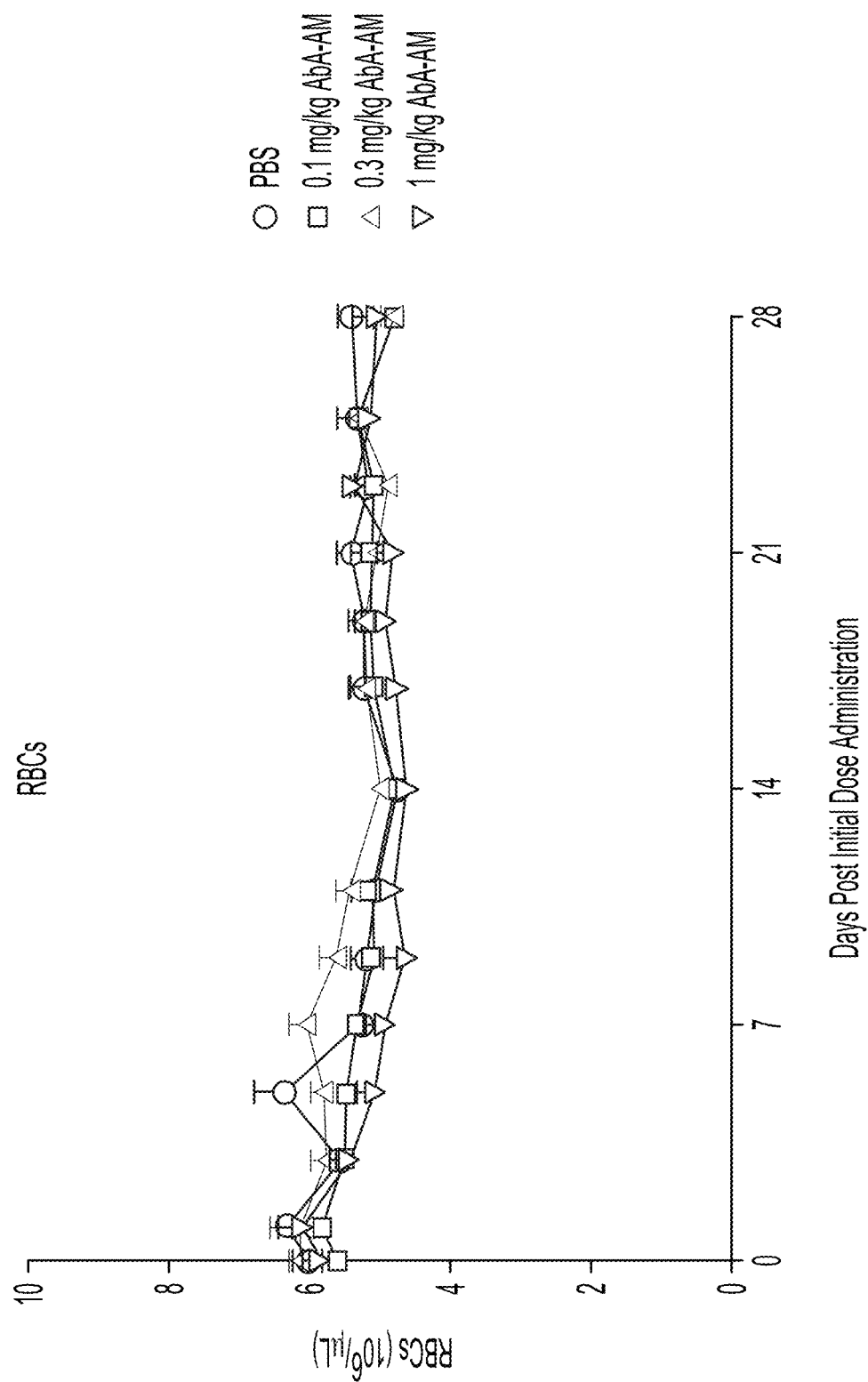
Figure 8B:
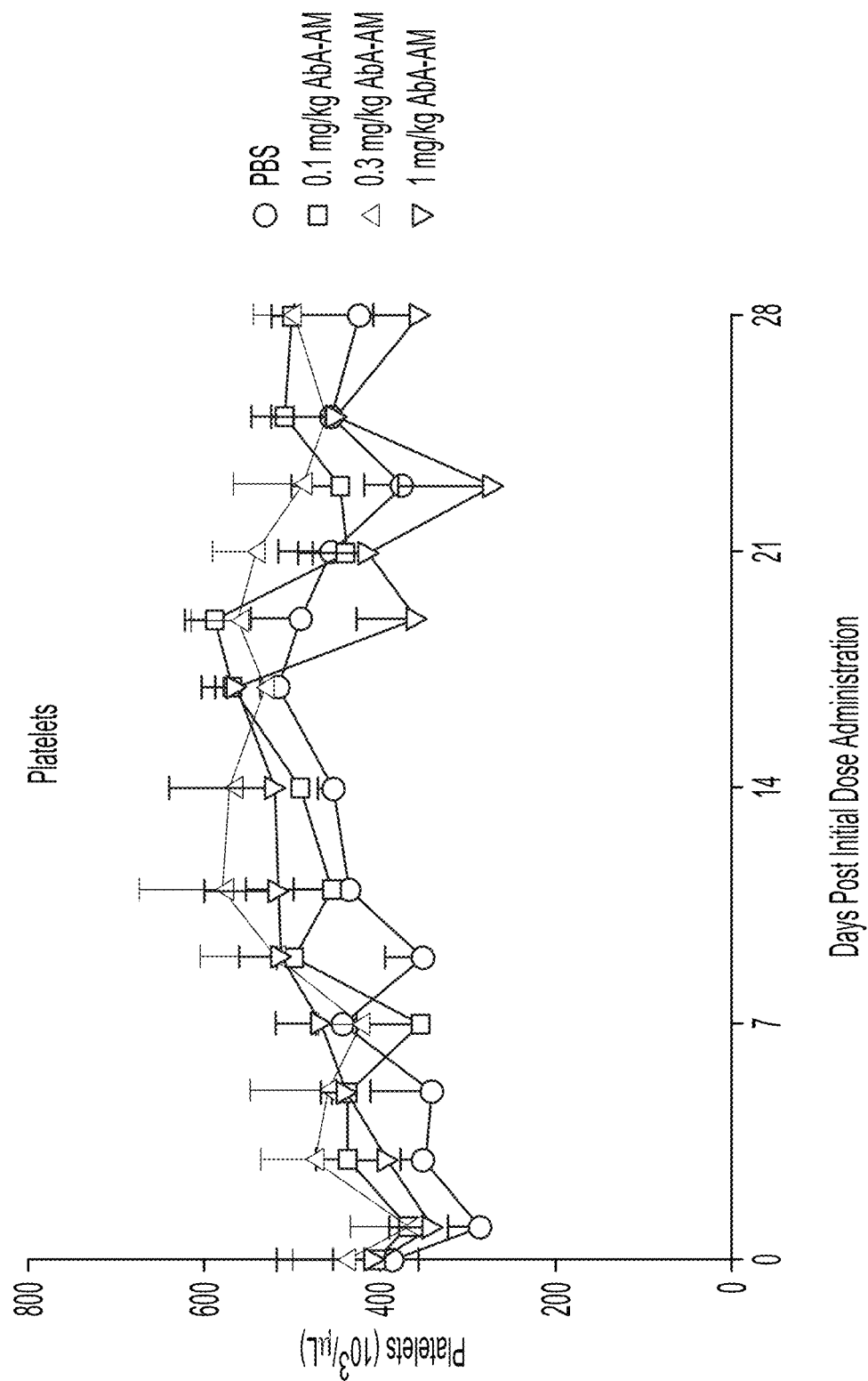

The results in FIGS. 8A and 8B showed that the administration of the fast half-life anti-CD45-amanitin ADC showed no significant changes in the levels of red blood cells or platelets even at the highest doses of the ADC when compared to the PBS control. These data also indicated that the administration of the fast half-life anti-CD45-amanitin ADC did not result in the occurrence of anemia or thrombocytopenia in these non-human primates.

Figure 8C:
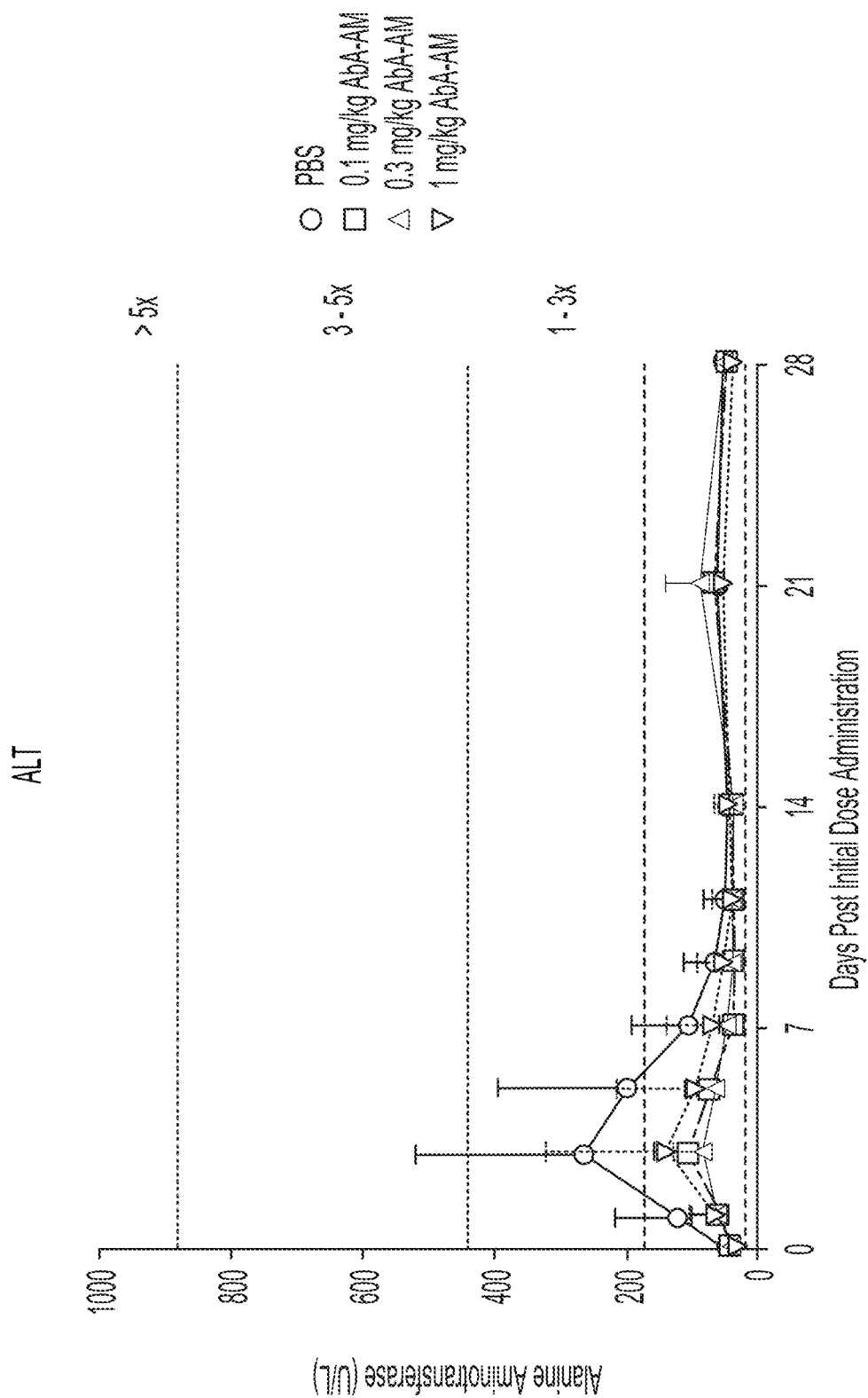

The results in FIGS. 8C and 8D indicated that the administration of the fast half-life anti-CD45-amanitin ADC showed no significant changes in the plasma levels of ALT and bilirubin even at the highest doses of the ADC when compared to the PBS control. In addition, no change above the upper limit normal (ULN) for the following additional parameters, i.e., GGT, albumin, BUN, ALP, creatinine, or glucose, was observed (data not shown). Further, no changes in food consumption or weight change was observed. Taken together, these data indicated that the administration of the fast half-life anti-CD45-amanitin ADC resulted in no liver enzyme elevation or changes in liver function (PT, albumin), indicating that the ADC is safe and well-tolerated in these non-human primates.

Example 7. Epitope Mapping

The epitope bound by AbA was mapped using crosslinking mass spectrometry. The cross-linking experiments allow the direct analysis of non-covalent interaction by High-Mass MALDI mass spectrometry. By mixing a protein sample containing non-covalent interactions with a specially developed cross-linking mixture (Bich, C et al. Anal. Chem., 2010, 82 (1), pp 172-179), it is possible to specifically detect non-covalent complex with high-sensitivity. The covalent binding generated allows the interacting species to survive the sample preparation process and the MALDI ionization. A special High-Mass detection system allows characterization of the interaction in the High-Mass range.

In order to determine the epitope of AbA with high resolution, a protein complex was incubated with deuterated cross-linkers and subjected to multi-enzymatic cleavage. The protein complex was an AbA variant antibody (having the same epitope as AbA) bound to human CD45. After enrichment of the cross-linked peptides, the samples were analyzed by high resolution mass spectrometry (nLC-LTQ-Orbitrap MS) and the data generated were analyzed using XQuest and Stavrox software.

Figure 9A:
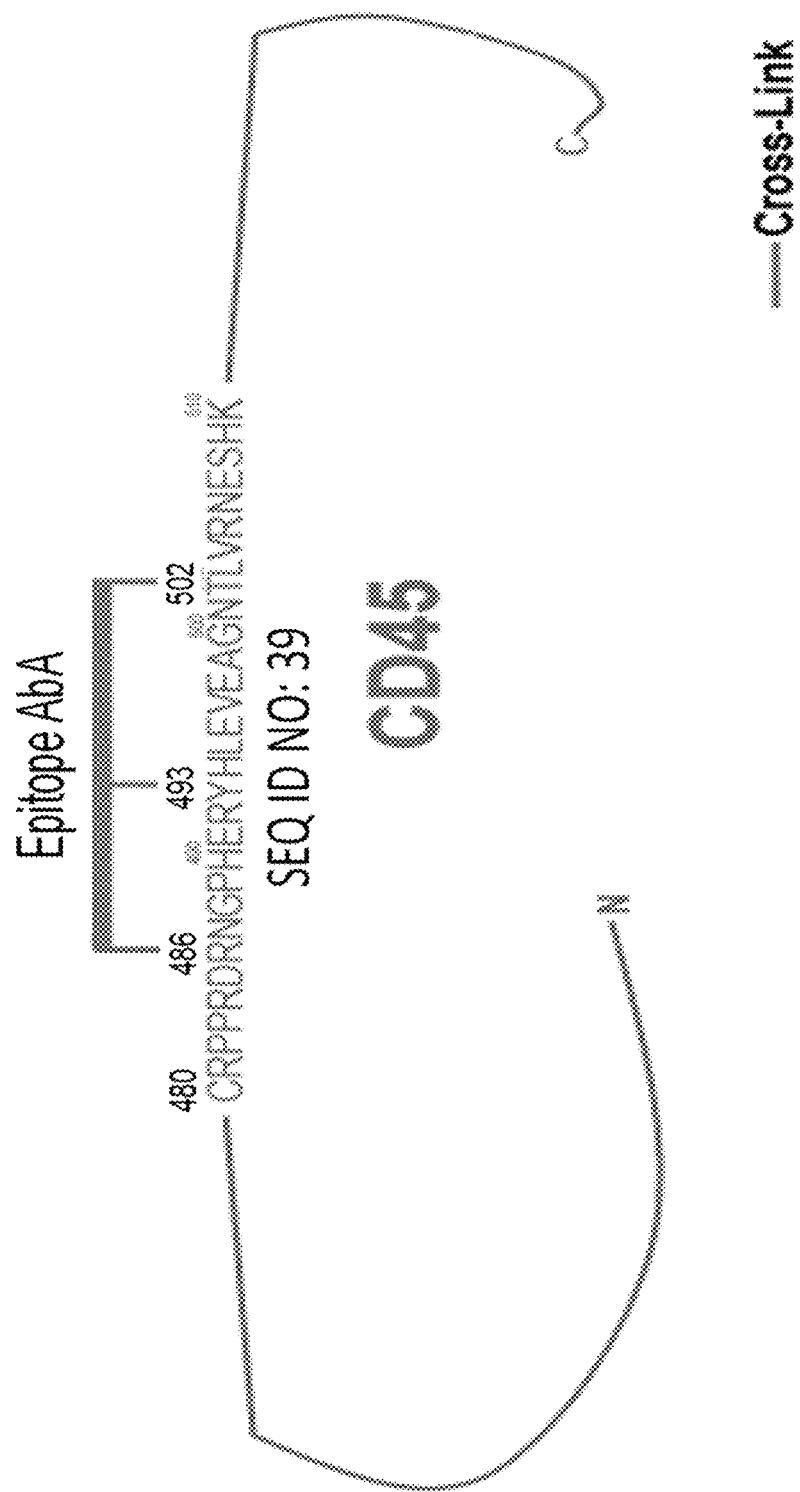
FIGS. 9A and 9B depict the results of an CD45 epitope mapping study with AbA.
Figure 9B:
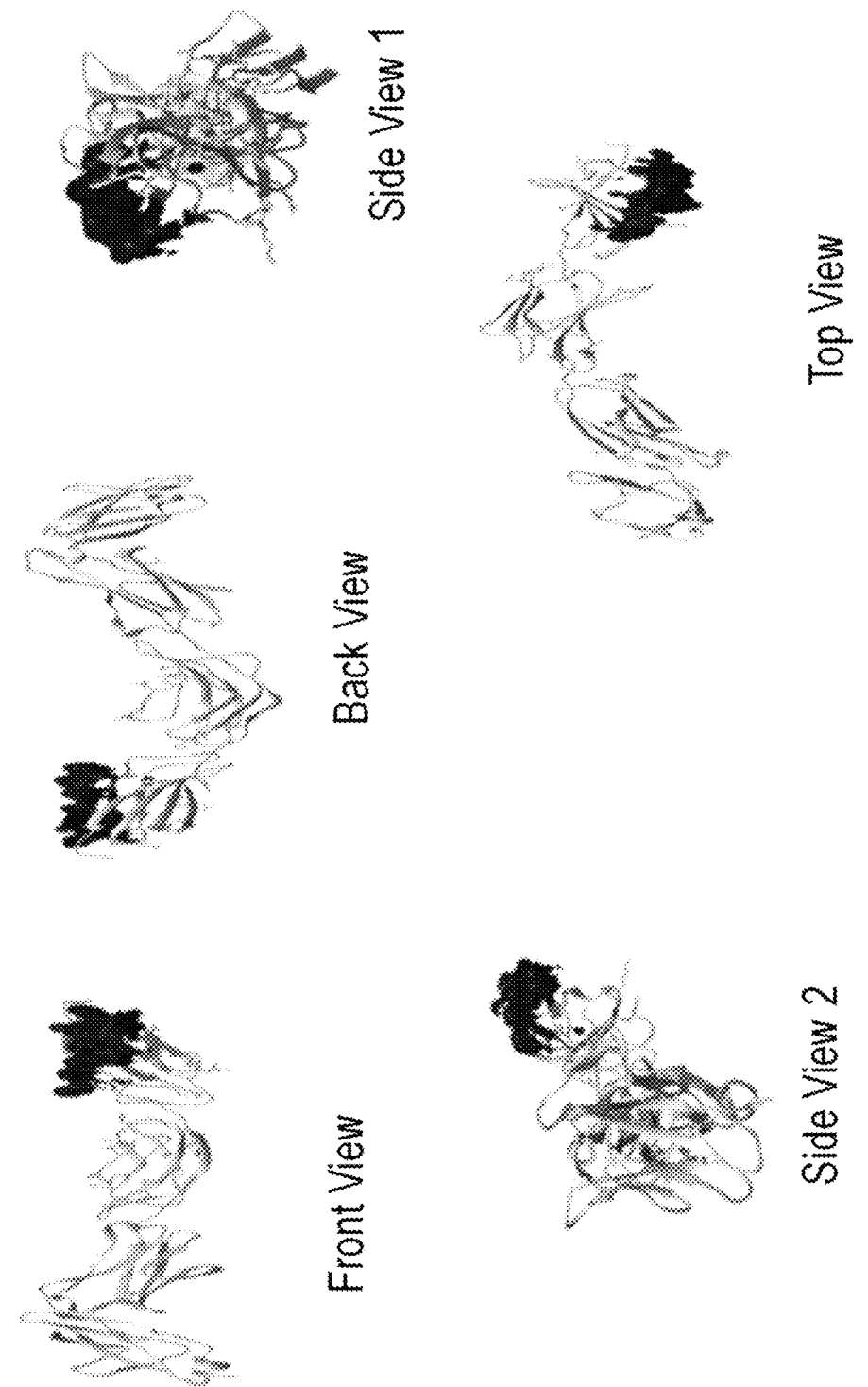

After Trypsin, Chymotrypsin, ASP-N, Elastase and Thermolysin proteolysis of the protein complex CD45/AbA with deuterated d0d12, the nLC-orbitrap MS/MS analysis indicated that the AbA epitope includes residues in the peptide RNGPHERYHLEVEAGNT (SEQ ID NO: 38) and, in particular, interacts with amino acids on human CD45 corresponding to 486R, 493Y, and 502T of SEQ ID NO: 37 (fragment of CD45 isoform corresponding to NP_002829.3). These results are illustrated in FIGS. 9A and 9B. FIG. 9A describes the amino acid fragment containing the epitope of AbA (SEQ ID NO: 39), in particular region RNGPHERYHLEVEAGNT (SEQ ID NO: 38). CD45 includes a mucin-like domain, di-d4 fibronectin-like domain, and transmembrane and phosphatase domains. Based on the present results, AbA interacts with the fibronectin d4 domain of CD45 which is conserved amongst alternatively spliced CD45 isoforms (e.g. RO, RA, RB, RC, RABC etc). As shown in FIG. 10, the di-d4 fibronectin-like domain of human CD45R0 (SEQ ID NO: 40) has 68% identity with that of the corresponding region in cynomolgus CD45 (SEQ ID NO: 41), noting that AbA binds to both cyno and human CD45.

TABLE 7

Sequence Table

| SEQ ID NO: | Description | Amino acid sequence |
|---|---|---|
| 1 | AbA heavy chain (HC) variable region (CDRs underlined) | EVQLVESGGSRVQPGRSLTLSCVTSGFTFNNYWMTWIRQVP GKGLEWVASISSSGGSIYYPDSVKGRFTISRDNAKNTLYLQ MNSLRSEDTATYYCARDERWAGAMDAWGQGTSVTVSS |
| 2 | AbA HC CDR1 | FTFNNYWMT |
| 3 | AbA HC CDR2 | SISSSGGSIYYPDSVKG |
| 4 | AbA HC CDR3 | ARDERWAGAMDA |
| 5 | AbA light chain (LC) variable region (CDRs underlined) | DIQMTQSPPVLSASVGDRVTLSCKASQNINKNLDWYQQKHG EAPKLLIYETNNLQTGIPSRFSGSGSGTDYTLTISSLQPED VATYYCYQHNSRFTFGSGTKLEIK |
| 6 | AbA LC CDR1 | KASQNINKNLD |
| 7 | AbA LC CDR2 | ETNNQLT |
| 8 | AbA LC CDR3 | YQHNSRFT |
| 9 | AbB heavy chain (HC) variable region (CDRs underlined) | EVQLVESGGDLVQPGRSLKLSCIASGFTFTNFWMTWIRQVS GKGLEWVASISSSGGSIYYPDSVKDRFTISRDNAKNTLYLQ MNSLRSEDTATYYCVKLHYYSGGGDAWGQGTSVTVSS |
| 10 | AbB HC CDR1 | FTFTNFWMT |
| 11 | AbB HC CDR2 | SISSSGGSIYYPDSVKD |
| 12 | AbB HC CDR3 | VKLHYYSGGGDA |

TABLE 7-continued

Sequence Table

| SEQ ID NO: | Description | Amino acid sequence |
|---|---|---|
| 13 | AbB light chain (LC) variable region (CDRs underlined) | DIQMTQSPSFLSASVGDRVTINCKASQNINKYLDWYQQKHG EAPKLLIHYTNNLHTGIPSRFSGSGSGTDYTLTISSLQPED VATYFCLQHSSRWTFGGGTKLELK |
| 14 | AbB LC CDR1 | KASQNINKYLD |
| 15 | AbB LC CDR2 | YTNNLHT |
| 16 | AbB LC CDR3 | LQHSSRWT |
| 17 | AbC heavy chain (HC) variable region | EVQLVESGGDLVQPGRSLKLSCVASGFTFNNYWMTWIRQVP GKGLEWVASISSSGGSIYYPDSVKDRFTISRDNAKNTLFLQ MNSLRSEDTATYYCARLYYYSGGGDAWGQGTSVTVSS |
| 18 | AbC HC CDR1 | FTFNNYWMT |
| 19 | AbC HC CDR2 | SISSSGGSIYYPDSVKD |
| 20 | AbC HC CDR3 | ARLYYYSGGGDA |
| 21 | AbC light chain (LC) variable region (CDRs underlined) | DIQMTQSPSFLSASVGDRVTIICKASQDINKYLDWYQQKLG EAPKLLIYNTNNLHTGIPSRFSGSGSGTDYTLTISSLQPED VATYFCLQHISRWTFGGGTKLELK |
| 22 | AbC LC CDR1 | KASQDINKYLD |
| 23 | AbC LC CDR2 | NTNNLHT |
| 24 | AbC LC CDR3 | LQHISRWT |
| 25 | AbA LC variable DNA | GACATCCAGATGACCCAGTCTCCACCTGTGCTGTCTGCATC TGTAGGAGACAGAGTCACCCTTTCATGCAAGGCAAGTCAGA ATATTAACAAAAATTTAGACTGGTATCAGCAGAAACATGGG GAAGCCCCTAAGCTCCTGATCTATGAGACAAATAATTTGCA AACGGGGATCCCATCAAGGTTCAGTGGCAGTGGATCTGGGA CAGATTACACTCTCACCATCAGCAGTCTGCAACCTGAAGAT GTGGCAACTTACTACTGTTACCAGCACAACTCCAGATTCAC TTTTGGCTCAGGGACCAAGCTGGAGATCAAA |
| 26 | AbA HC variable DNA | GAAGTGCAGCTGGTGGAGTCTGGGGGAGACAGGGTACAGCC TGGCAGGTCCCTGACACTCTCCTGTGTAACATCTGGATTCA CCTTTAACAACTATTGGATGACCTGGATCCGGCAAGTACCA GGGAAGGGCCTGGAGTGGGTCGCTTCTATTAGTTCCAGTGG CGGTAGCATATATTATCCCGACTCTGTGAAGGGCCGATTCA CCATCTCCAGAGACAACGCCAAGAACACCCTGTATCTGCAA ATGAACAGTCTGAGATCCGAGGACACGGCGACCTACTACTG CGCAAGAGACGAAAGATGGGCTGGCGCTATGGACGCCTGGG GGCAAGGGACCTCCGTCACCGTCTCCTCA |
| 27 | AbB LC variable DNA | GACATCCAGATGACCCAGTCTCCATCCTTCCTGTCTGCATC TGTAGGAGACAGAGTCACCATCAACTGCAAGGCGAGTCAGA ACATTAATAAATATTTAGATTGGTATCAGCAGAAACATGGG GAGGCCCCTAAGCTCCTGATCCATTACACCAATAATTTGCA CACAGGGATACCATCAAGGTTCAGTGGAAGTGGATCTGGGA CAGATTACACTTTGACCATCAGCAGCCTGCAGCCTGAAGAT GTTGCAACATATTTCTGTCTGCAACATTCCAGCAGGTGGAC CTTCGGCGGAGGGACCAAGCTTGAGCTGAAA |
| 28 | AbB HC variable DNA | GGGAAGGGCCTGGAGTGGGTCGCTAGCATTAGTTCTAGTGG AGGTAGCATATATTATCCCGACTCTGTGAAGGACCGATTCA CCATCTCCAGAGACAACGCCAAGAACACACTGTATCTGCAA ATGAACAGTCTGAGATCCGAGGACACGGCGACATACTACTG CGTTAAGCTTCACTACTATTCCGGAGGGGGTGATGCTTGGG GCCAAGGAACCTCCGTCACCGTCTCCTCA |
| 29 | AbC LC variable DNA | GACATCCAGATGACCCAGTCTCCATCCTTCCTGTCTGCATC TGTAGGAGACAGAGTCACCATCATCTGCAAGGCGAGTCAGG ACATTAACAAGTATTTAGACTGGTATCAGCAGAAATTGGGG GAAGCCCCTAAGCTCCTGATCTACAATACAAATAATTTGCA CACAGGGATACCATCAAGGTTCAGTGGAAGTGGATCTGGGA CAGATTACACTTTGACCATCAGCAGCCTGCAGCCTGAAGAT GTCGCAACATATTTTTGTCTGCAGCACATTAGCAGATGGAC CTTCGGCGGAGGGACCAAGCTGGAGCTGAAA |

TABLE 7-continued

Sequence Table

| SEQ ID NO: | Description | Amino acid sequence |
|---|---|---|
| 30 | AbC HC variable DNA | GAAGTGCAGCTGGTGGAGTCTGGGGGAGATTTGGTACAGCC<br>TGGCAGGTCCCTGAAACTCTCCTGTGTTGCCTCTGGATTCA<br>CCTTTAATAACTATTGGATGACATGGATTCGGCAAGTTCCA<br>GGGAAGGGCCTGGAGTGGGTCGCTTCCATTAGTAGTAGTGG<br>TGGTAGCATATATTATCCCGACTCTGTGAAGGATCGATTCA<br>CCATCTCCAGAGACAACGCCAAGAACACATGTTTCTGCAAA<br>TGAACAGTCTGAGATCTGAGGACACGGCGACATACTACTGC<br>GCGAGACTGTATTACTATTCTGGTGGTGGCGATGCGTGGGG<br>CCAAGGAACCTCCGTCACCGTCTCCTCA |
| 31 | Human CD45RA isoform<br>(Uniprot Accession<br>No: P08575-8) | MTMYLWLKLLAFGFAFLDTEVFVTGQSPTPSPTGLTTAKMP<br>SVPLSSDPLPTHTTAFSPASTFERENDFSETTTSLSPDNTS<br>TQVSPDSLDNASAFNTTDAYLNASETTTLSPSGSAVISTTT<br>IATTPSKPTCDEKYANITVDYLYNKETKLFTAKLNVNENVE<br>CGNNTCTNNEVHNLTECKNASVSISHNSCTAPDKTLILDVP<br>PGVEKFQLHDCTQVEKADTTICLKWKNIETFTCDTQNITYR<br>FQCGNMIFDNKEIKLENLEPEHEYKCDSEILYNNHKFTNAS<br>KIIKTDFGSPGEPQIIFCRSEAAHQGVITWNPPQRSFHNFT<br>LCYIKETEKDCLNLDKNLIKYDLQNLKPYTKYVLSLHAYII<br>AKVQRNGSAAMCHFTTKSAPPSQVWNMTVSMTSDNSMHVKC<br>RPPPRDRNGPHERYHLEVEAGNTLVRNESHKNCDFRVKDLQY<br>STDYTFKAYFHNGDYPGEPFILHHSTSYNSKALIAFLAFLI<br>IVTSIALLVVLYKIYDLHKKRSCNLDEQQELVERDDEKQLM<br>NVEPIHADILLETYKRKIADEGRLFLAEFQSIPRVFSKFPI<br>KEARKPFNQNKNRYVDILPYDYNRVELSEINGDAGSNYINA<br>SYIDGFKEPRKYIAAQGPRDETVDDFWRMIWEQKATVIVMV<br>TRCEEGNRNKCARYWPSMEEGTRAFGDVVVKINQHKRCPDY<br>IIQKLNIVNKKEKATGREVTHIQFTSWPDHGVPEDPHLLLK<br>LRRRVNAFSNFFSGPIVVHCSAGVGRTGTYIGIDAMLEGLE<br>AENKVDVYGYVVKLRRQRCLMVQVEAQYILIHQALVEYNQF<br>GETEVNLSELHPYLHNMKKRDPPSEPSPLEAEFQRLPSYRS<br>WRTQHIGNQEENKSKNRNSNVIPYDYNRVPLKHELEMSKES<br>EHDSDESSDDDSDSEEPSKYINASFIMSYWKPEVMIAAQGP<br>LKETIGDFWQMIFQRKVKVIVMLTELKHGDQEICAQYWGEG<br>KQTYGDIEVDLKDTDKSSTYTLRVFELRHSKRKDSRTVYQY<br>QYTNWSVEQLPAEPKELISMIQVVKQKLPQKNSSEGNKHHK<br>STPLLIHCRDGSQQTGIFCALLNLLESAETEEVVDIFQVVK<br>ALRKARPGMVSTFEQYQFLYDVIASTYPAQNGQVKKNNHQE<br>DKIEFDNEVDKVKQDANCVNPLGAPEKLPEAKEQAEGSEPT<br>SGTEGPEHSVNGPASPALNQGS |
| 32 | Human CD45RO Isoform<br>(NCBI Accession<br>No: NP_563578.2) | MTMYLWLKLLAFGFAFLDTEVFVTGQSPTPSPTDAYLNASE<br>TTTLSPSGSAVISTTTIATTPSKPTCDEKYANITVDYLYNK<br>ETKLFTAKLNVNENVECGNNTCTNNEVHNLTECKNASVSIS<br>HNSCTAPDKTLILDVPPGVEKFQLHDCTQVEKADTTICLKW<br>KNIETFTCDTQNITYRFQCGNMIFDNKEIKLENLEPEHEYK<br>CDSEILYNNHKFTNASKIIKTDFGSPGEPQIIFCRSEAAHQ<br>GVITWNPPQRSFHNFTLCYIEKTEKDCLNLDKNLIKYDLQN<br>LKPYTKYVLSLHAYIIAKVQRNGSAAMCHFTTKSAPPSQVW<br>NMTVSMTSDNSMHVKCRPPRDRNGPHERYHLEVEAGNTLVR<br>NESHKNCDFRVKDLQYSTDYTFKAYFHNGDYPGEPFILHHS<br>TSYNSKALIAFLAFLIIVTSIALLVVLYKIYDLHKKRSCNL<br>DEQQELVERDDEKQLMNVEPIHADILLETYKRKIADEGRLF<br>LAEFQSIPRVFSKFPIKEARKPFNQNKNRYVDILPYDYNRV<br>ELSEINGDAGSNYINASYIDGFKEPRKYIAAQGPRDETVDD<br>FWRMIWEQKATVIVMVTRCEEGNRNKCAEYWPSMEEGTRAF<br>DVVVKINQHKRCPDYIIQKLNIVNKKEKATGREVTHIQFTS<br>WPDHGVPDEPHLLLKLRRRVNAFSNFFSGPIVVHCSAGVGR<br>TGTYIGIDAMLEGLEAENKVDVYGYVVKLRRQRCLMVQVEA<br>QYILIHQALEVEYNQFGETEVNLSELHPYLHNMKKRDPPSE<br>PSPLEAEFQRLPSYRSWRTQHIGNQEENKSKNRNSNVIPYD<br>YNRVPLKHELEMSKESEHDSDESSDDDSDSEEPSKYINASF<br>IMSYWKPEVMIAAQGPKKETIGDFWQMIFQRKVKVIVMLTE<br>LKHGDQEICAQYWGEGKQTYGDIEVDLDKTDKSSTYTLRVF<br>ELRHSKRKDSRTVYQYQYTNWSVEQLPAEPKELISMIQVVK<br>QKLPQKNSSEGNKHHKSTPLLIHCRDGSQQTGIFCALLNLL<br>ESAETEEVVDIFQVVKALRKARPGMVSTFEQYQFLYDVIAS<br>TYPAQNGQVKKNNHQEDKIEFDNEVDKVKQDANCVNPLGAP<br>EKLPEAKEQAEGSEPTSGTEGPEHSVNGPASPALNQGS |
| 33 | Human CD45RB Isoform<br>(NCBI Accession No.<br>XP_006711537.1) | MTMYLWLKLLAFGFAFLDTEVFVTGQSPTPSPTGVSSVQTP<br>HLPTHADSQTPSAGTDQTFSGSAANAKLNPTPGSNAISDAY<br>LNASETTTLSPSGSAVISTTTIATTPSKPTCDEKYANITVD<br>YLYNKETKLFTAKLNVNENVECGNNTCTNNEVHNLTECKNA<br>SVSISHNSCTAPDKTLILDVPPGVEKFQLHDCTQVEKADTT<br>ICLKWKNIETFTCDTQNITYRFQCGNMIFDNKEIKLENLEP |

TABLE 7-continued

Sequence Table

| SEQ ID NO: | Description | Amino acid sequence |
|---|---|---|
| | | EHEYKCDSEILYNNHKFTNASKIIKTDFGSPGEPQIIFCRS
EAAHQGVITWNPPQRSFHNFTLCYIKETEKDCLNLDKNLIK
YDLQNLKPYTKYVLSLHAYIIAKVQRNGSAAMCHFTTKSAP
PSQVWNMTVSMTSDNSMHVKCRPPRDRNGPHERYHLEVEAG
NTLVRNESHKNCDFRVKDLQYSTDYTFKAYFHNGDYPGEPF
ILHHSTSYNSKALIAFLAFLIIVTSIALLVVLYKIYDLHKK
RSCNLDEQQELVERDDEKQLMNVEPIHADILLETYKRKIAD
EGRLFLAEFQSIPRVFSKFPIKEARKPFNQNKNRYVDILPY
DYNRVELSEINGDAGSNYINASYIDGFKEPRKYIAAQGPRD
ETVDDFWRMIWEQKATVIVMVTGRCEEGNRNKCAEYWPSME
EGTRAFGDVVVKINQHKRCPDYIIQKLNIVNKKEKATGREV
THIQFTSWPDHGVPEDPHLLLKLRRRVNAFSNFFSGPIVVH
CSAGVGRTGTYIGIDAMLEGLEAENKVDVYGYVVKLRRQRC
LMVQVEAQYLILHQALVEYNQFGETEVNLSELHPYLHNMKK
RDPPSEPSPLEAEFQRLPSYSRSWRTQHIGNQEENKSKNRN
SNVIPYDYNRVPLKHELEMSKESEHDSDESSDDDSDSEEPS
KY8INASFIMSYWKPEVMIAAQGPLKETIGDFWQMIFQRKV
KVIVMLTELKHGDQEICAQYWGEGKQTYGDIEVDLKDTDKS
STYTLRVFELRHSKRKDSRTVYQYQYTNWSVEQLPAEPKEL
ISMIQVVKQKLPQKNSSEGNKHHKSTPLLIHCRDGSQQTGI
FCALLNLLESAETEEVVDIFQVVKALRKARPGMVSTFEQYQ
FLYDVIASTYPAQNGQVKKNNHQEDKIEFDNEVDKVKQDAN
CVNPLGAPEKLPEAKEQAEGSEPTSGTEGPEHSVNGPASPA
LNQGS |
| 33 | Human CD45RB Isoform (NCBI Accession No. XP_006711537.1) | MTMYLWLKLLAFGFAFLDTEVFVTGQSPTPSPTGVSSVQTP
HLPTHADSQTPSAGTDTQTFSGSAANAKLNPTPGSNAISDA
YLNASETTTLSPSGSAVISTTTIATTPSKPTCDEKYANITV
DYLYNKETKLFTAKLNVENVECGNNTCTNNEVHNLTECKN
ASVSISHNSCTAPDKTLILDVPPGVEKFQLHDCTQVEKADT
TICLKWKNIETFTCDTQNITYRFQCGNMIFDNKEIKLENLE
PEHEYKCDSEILYNNHKFTNASKIIKTDFGSPGEPQIIFCR
SEAAHQGVITWNPPQRSFHNFTLCYIKETEKDCLNLDKNLI
KYDLQNLKPYTKYVLSLHAYIIAKVQRNGSAAMCHFTTKSA
PPSQVWNMTVSMTSDNSMHVKCRPPRDRNGPHERYHLEVEA
GNTLVRNESHKNCDFRVKDLQYSTDYTFKAYFHNGDYPGEP
FILHHSTSYNSKALIAFLAFLIIVTSIALLVVLYKIYDLHK
KRSCNLDEQQELVERDDEKQLMNVEPIHADILLETYKRKIA
DEGRLFLAEFQSIPRVFSKFPIKEARKPFNQNKNRYVDILP
YDYNRVELSEINGDAGSNYINASYIDGFKEPRKYIAAQGPR
DETVDDFWRMIWEQKATVIVMVTRCEEGNRNKCAEYWPSME
EGTRAFGDVVVKINQHKRCPDYIIQKLNIVNKKEKATGREV
THIQFTSWPDHGVPEDPHLLLKLRRRVNAFSNFFSGPIVVH
CSAGVGRTGTYIGIDAMLEGLEAENKVDVYGYVVKLRRQRC
LMVQVEAQYILIHQALVEYNQFGETEVNLSELHPYLHNMKK
RDPPSEPSPLEAEFQRLPSYRSWRTQHIGNQEENKSKNRNS
NVIPYDYNRVPLKHELEMSKESEHDSESSDDDSDSEEPSK
YINASFIMSYWKPEVMIAAQGPLKETIGDFWQMIFQRKVKV
IVMLTELKHGDQEICAQYWGEGKQTYGDIEVDLKDTDKSST
YTLRVFELRHSKRKDSRTVYQYQYTNWSVEQLPAEPKELIS
MIQVVKQKLPQKNSSEGNKHHKSTPLLIHCRDGSQQTGIFC
ALLNLLESAETEEVVDIFQVVKALRKARPGMVSTFEQYQFL
YDVIASTYPAQNGQVKKNNHQEDKIEFDNEVDKVKQDANCV
NPLGAPEKLPEAKEQAEGSEPTSGTEGPEHSVNGPASPALN
QGS |
| 34 | Human CD45RAB Isoform (NCBI Accession No. XP_006711535.1) | MTMYLWLKLLAFGFAFLDTEVFVTGQSPTPSPTGLTTAKMP
SVPLSSDPLPTHTTAFSPASTFERENDFSETTTSLSPDNTS
TQVSPDSLDNASAFNTTGVSSVQTPHLPTHADSQTPSAGTD
TQTFSGSAANAKLNPTPGSNAISDAYLNASETTTLSPSGSA
VISTTTIATTPSKPTCDEKYANITVDYLYNKETKLFTAKLN
VNENVECGNNTCTNNEVHNLTECKASVSISHNSCTAPDKTL
ILDVPPGVEKFQLHDCTQVEKADTTICLKWKNIETFTCDTQ
NITYRFQCGNMIFDNKEIKLENLEPEHEYKCDSEILYNNHK
FTNASKIIKTDFGSPGEPQIIFCRSEAAHQGVITWLPPQRS
FHNFTLCYIKETEKDCLNLDKNLIKYDLQNLKPYTKYVLSL
HAYIIAKVQRNGSAAMCHFTTKSAPPSQVWNMTVSMTSDNS
MHVKCRPPRDRNGPHERYHLEVEAGNTLVRNESHKNCDFRV
KDLQYSTDYTFKAYFHNGDYPGEPRILHHSTSYNSKALIAF
LAFLIIVTSIALLVVLYKIYDLHKKRSCNLDEQQELVERDD
EKQLMNVEPIHADILLETYKRKIADEGRLFLAEFQSIPRVF
SKFPIKEARKPFNQNKNRYVDILPYDYNRVELSEINGDAGS
NYINASYIDGFKEPRKYIAAQGPRDETVDDFWRMIWEQKAT
VIVMVTRCEEGNRNKCAEYWPSMEEGTRAFGDVVVKINQHK
RCPDYIIQKLNIVNKKEKATGREVTHIQFTSWPDHGVPEDP
HLLLKLRRRVNAFSNFFSGPIVVHCSAGVGRTGTYIGIDAM |

TABLE 7-continued

Sequence Table

| SEQ ID NO: | Description | Amino acid sequence |
|---|---|---|
| | | LEGLEAENKVDVYGYVVKLRRQRCLMVQVEAQYILIHQALV EYNQFGETEVNLSELHPYLHNMKKRDPPSEPSPLEAEFQRL PSYSWRTQHIGNQEENKSKNRNSNVIPYDYNRVPLKHELEM SKESEHDSDESSDDDSDSEEPSKYINASFIMSYWKPEVMIA AQGPLKETIGDFWQMIFQRKVKVIVMLTELKHGDQEICAQY WGEGKQTYGDIEVDLKDTDKSSTYTLRVFELRHSKRKDSRT VYQYQYTNWSVEQLPAEPKELISMIQVVKQKLPQKNSSEGN KHHKSTPLLIHCRDGSQQTGIFCALLNLLESAETEEVVDIF QVVKALRKARKPGMVSTFEQYQFLYDVIASTYPAQNGQVKK NNHQEDKIEFDNEVDKVKQDANCVNPLGAPEKLPEAKEQAE GSEPTSGTEGPEHSVNGPASPALNQGS |
| 35 | Human CD45RBC Isoform (NCBI Accession No. XP_006711536.1) | MTMYLWLKLLAFGFAFLDTEVFVTGQSPTPSPTGVSSVQTP HLPTHADSQTPSAGTDTQTFSGSAANAKLNPTPGSNAISDV PGERSTASTFPTDPVSPLTTTLSLAHHSSAALPARTSNTTI TANTSDAYLNASETTTLSPSGSAVISTTTIATTPSKPTCDE KYANITVDYLYNKETKLFTAKLNVNENVECGNNTCTNNEVH NLTECKNASVSISHNSCTAPDKTLILDVPPGVEKFQLHDCT QVEKADTTICLKWKNIETFTCDTQNITYRFQCGNMIFDNKE IKLENLEPEHEYKCDSEILYNNHKFTNASKIIKTDFGSPGE PQIIFCRSEAAHQGVITWNPPQRSFHNFTLCYIKETEKDCL NLDKNLIKYDLQNLKPYTKYVLSLHAYIIAKVQRNGSAAMC HFTTKSAPPSQVWNMTVSMTSDNSMHVKCRPPRDRNGPHER YHLEVEAGNTLVRNESHKNCDFRVKDLQYSTDYTFKAYFHN GDYPGEPFILHHSTSYNSKALIAFLAFLIIVTSIALLVVLY KIYDKHKKRSCNLDEQQELVERDDEKQLMNVEPIHADILLE TYKRKIADEGRLFLAEFQSIPRVFSKFPIKEARKPFNQNKN RYVDILPYDYNRVELSEINGDAGSNYINASYIDGFKEPRKY IAAQGPRDETVDDFWRMIWEQKATVIVMVTRCEEGNRNKCA EYWPSMEEGTRAFGDVVVKINQHKRCPDYIIQKLNIVNKKE KATGREVTHIQFTSWPDHGVPEDPHLLLKLRRRVNAFSNFF SGPIVVHCSAGVGRTFTYIGIDAMLEGLEAENKVDVYGYVV KLRRQRCLMVQVEAQYILIHQALVEYNQFGETEVNLSELHP YLHNMKKRDPPSEPSPLEAEFQRLPSYRSWRTQHIGNQEEN KSKNRNSNVIPYDYNRVPLKHELEMSKESEHDSDESSDDDS DSEEPSKYINASFIMSYWKPEVMIAAQGPLKETIGDFWQMI FQRKVKVIVMLTELKHGDQEICAQYWGEGKQTYGDIEVDLK DTDKSSTYTLRVFELRHSKRKDSRTVYQYQYTNWSVEQLPA EPKELISMIQVVKQKLPQKNSSEGNKHHKSTPLLIHCRDGS QQTGIFCALLNLLESAETEEVVDIFQVVAKLRKARPGMVST FEQYQFLYDVIASTYPAQNGQVKKNNHQEDKIEFDNEVDKV KQDANCVNPLGAPEKLPEAKEQAEGSEPTSGTEGPEHSVNG PASPALNQGS |
| 36 | Human CD45RABC Isoform (NCBI Accession No. NP_002829.3) | MTMYLWLKLLAFGFAFLDTEVFVTGQSPTPSPTGLTTAKMP SVPLSSDPLPTHTTAFSPASTFERENDFSETTTSLSPDNTS TQVSPDSLDNASAFNTTGVSSVQTPHLPTHADSQTPSAGTD TQTFSGSAANAKLNPTPGSNAISDVPGERSTASTFPTDPVS PLTTTLSLAHHSSAALPARTSNTTITANTSDAYLNASETTT LSPGGSAVISTTTIATTPSKPTCDEKYANITVDYLYNKETK LFTAKLNVNENVECGNNTCTNNEVHNLTECKNASVSISHNS CTAPDKTLILDVPPGVEKFQLHDCTQVEKADTTICLKWKNI ETFTCDTQNITYRFQCGNMIFDNKEIKLENLEPEHEYKCDS EILYNNHKFTNASKIIKTDFGSPGEPQIIFCRSEAAHQGVI TWNPPQRSFHNFTLCYIKETEKDCLNLDKNLIKYDLQNLKP YTKYVLSLHAYIIAKVQRNGSAAMCHFTTKSAPPSQVWNMT VSMTSDNSMHVKCRPPRDRNGPHERYHLEVEAGNTLVRNES HKNCDFRVKDLQYSTDYTFKAYFHNGDYPGEPFILHHSTSY NSKALIAFLAFLIIVTSIALLVVLYKIYDLHKKRSCNLDEQ QELVERDDEKQLMNVEPIHADILLETKRKIADEGRLFLAEF QSIPRVFSKFPIKEARKPFNQNKNRYVDILPYDYNRVELSE INGDAGSNYINSYIDGFKEPRKYIAAQGPRDETVDDFWRMI WEQKATVIVMVTRCEEGNRNKCAEYWPSMEEGTRAFGDVVV KINQHKRCPDYIIQKLNIVNKKEKATGREVTHIQFTSWPDH GVPEDPHLLLKLRRRVNAFSNFFSGPIVVHCSAGVGRTGTY IGIDAMLEGLEAENKVDVYGYVVKLRRQRCDLMVQVEAQYI LIHQALVEYNQFGETEVNLSELHPYLHNMKKRDPPSEPSPL EAEFQRLPSYRSWRTQHIGNQEENKSKNRNSNVIPYDYNRV PLKHELEMSKESEHDSDESSDDDSDSEEPSKYINASFIMSY WKPEVMIAAQGPLKETIGDFWQMIFQRKVKVIVMLTELKHG DQEICAQYWGEGKQTYGDIEVDLKDTDKSSTYTLRVFELRH SKRKDSRTVYQYQYTNWSVEQLPAEPKELISMIQVVKQKLP QKNSSEGNKHHKSTPLLIHCRDGSQQTGIFCALLNLLESAE TEEVVDIFQVVAKLRKARPGMVSTFEQYQFLYDVIASTYPA QNGQVKKNNHQEDKIEFDNEVDKVKQDANCVNPLGAPEKLP EAKEQAEGSEPTSGTEGPEHSVNGPASPALNQGS |

TABLE 7-continued

Sequence Table

| SEQ ID NO: | Description | Amino acid sequence |
|---|---|---|
| 37 | Human CD45RABC Antigen (Fragment of Human CD45RABC Isoform) | QSPTPSPTGLTTAKMPSVPLSSDPLPTHTTAFSPASTFERE NDFSETTTSLSPDNTSTQVSPDSLDNASAFNTTGVSSVQTP HLPTHADSQTPSAGTDTQTFSGSAANAKLNPTPGSNAISDV PGERSTASTFPTDPVSPLTTTLSLAHHSSAALPARTSNTTI TANTSDAYLNASETTTLSPSGSAVISTTTIATTPSKPTCDE KYANITVDYLYNKETKLFTAKLNVNENVECGNNTCTNNEVH NLTECKNASVSISHNSCTAPDKTLILDVPPGVEKFQLHDCT QVEKADTTICLKWKNIETFTCDTQNITRFQCGNMIFDNKEI KLENLEPEHEYKCDSEILYNNHKFTNASKIIKTDFGSPGEP QIIFCRSEAAHQGVITWNPPQRSFHNFTLCYIKETEKDCLN LDKNLIKYDLQNLKPYTKYVLSLHAYIIAKVQRNGSAAMCH FTTKSAPPSQVWNMTVSMTSDNSMHVKCRPPRDRNGPHERY HLEVEAGNTLVRNESHKNCDFRVKDLQYSTDYTFKAYFHNG DYPGEPFILHHSTSYNSK |
| 38 | CD45 Fragment | RNGPHERYHLEVEAGNT |
| 39 | CD45 Fragment | CRPPRDRNGPHERYHLEVEAGNTLVRNESHK |

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. An isolated anti-CD45 antibody, or antigen binding portion thereof, comprising:
   (i) a heavy chain comprising a variable region comprising a CDR1 having the amino acid sequence as set forth in SEQ ID NO: 2, a CDR2 having the amino acid sequence as set forth in SEQ ID NO: 3, a CDR3 having the amino acid sequence as set forth in SEQ ID NO: 4, and comprising a light chain comprising a variable region comprising a CDR1 having the amino acid sequence as set forth in SEQ ID NO: 6, a CDR2 having the amino acid sequence as set forth in SEQ ID NO: 7, a CDR3 having the amino acid sequence as set forth in SEQ ID NO: 8;
   (ii) a heavy chain comprising a variable region comprising a CDR1 having the amino acid sequence as set forth in SEQ ID NO: 10, a CDR2 having the amino acid sequence as set forth in SEQ ID NO: 11, a CDR3 having the amino acid sequence as set forth in SEQ ID NO: 12, and comprising a light chain comprising a variable region comprising a CDR1 having the amino acid sequence as set forth in SEQ ID NO: 14, a CDR2 having the amino acid sequence as set forth in SEQ ID NO: 15, a CDR3 having the amino acid sequence as set forth in SEQ ID NO: 16; or (iii) a heavy chain comprising a variable region comprising a CDR1 having the amino acid sequence as set forth in SEQ ID NO: 18, a CDR2 having the amino acid sequence as set forth in SEQ ID NO: 19, a CDR3 having the amino acid sequence as set forth in SEQ ID NO: 20, and comprising a light chain comprising a variable region comprising a CDR1 having the amino acid sequence as set forth in SEQ ID NO: 22, a CDR2 having the amino acid sequence as set forth in SEQ ID NO: 23, a CDR3 having the amino acid sequence as set forth in SEQ ID NO: 24.

2. The anti-CD45 antibody, or antigen binding portion thereof, of claim 1, wherein:
(i) the heavy chain variable region comprises the amino acid sequence as set forth in SEQ ID NO: 1;
(ii) the heavy chain variable region comprises the amino acid sequence as set forth in SEQ ID NO: 9; or
(iii) the heavy chain variable region comprises the amino acid sequence as set forth in SEQ ID NO: 17.

3. The anti-CD45 antibody, or antigen binding portion thereof, of claim 1, wherein:
(i) the light chain variable region comprises the amino acid sequence as set forth in SEQ ID NO: 5;
(ii) the light chain variable region comprises the amino acid sequence as set forth in SEQ ID NO: 13; or
(iii) the light chain variable region comprises the amino acid sequence as set forth in SEQ ID NO: 21.

4. The anti-CD45 antibody, or antigen binding portion thereof, of claim 1, which is (i) a de-immunized antibody, or antigen binding fragment thereof, or (ii) a humanized antibody, or antigen binding fragment thereof, or (iii) a chimeric antibody, or antigen binding fragment thereof.

5. An isolated de-immunized monoclonal anti-CD45 antibody, or antigen binding portion thereof, that specifically binds human CD45 and cyno CD45, wherein the anti-CD45 antibody, or antigen binding portion thereof, of claim 1 is the parent antibody of the de-immunized anti-CD45 antibody, or antigen binding portion thereof.

6. The anti-CD45 antibody of claim 1, which is an intact monoclonal IgG antibody.

7. The anti-CD45 antibody, or antigen binding portion thereof of claim 1, wherein the antibody, or antigen binding portion thereof, is an IgG.

8. A pharmaceutical composition comprising the antibody of claim 1, and a pharmaceutically acceptable carrier.

9. A method of depleting a population of hematopoietic stem cells (HSC) in a human patient, the method comprising administering to the patient an effective amount of the antibody of claim 1.

10. The method of claim 9, further comprising administering to the patient a transplant comprising hematopoietic stem cells.

11. A method comprising administering to a human patient a transplant comprising hematopoietic stem cells, wherein the patient has been previously administered the antibody of claim 1 in an amount sufficient to deplete a population of hematopoietic stem cells or a population of immune cells in the patient.

12. The method of claim 11, wherein the hematopoietic stem cell is a CD45+ cell.

13. The method of claim 9, wherein the patient has a blood disease, a metabolic disorder, cancer, or an autoimmune disease, or severe combined immunodeficiency disease (SCID).

14. A method of treating leukemia in a human patient, said method comprising administering the antibody of claim 1 to the human patient having leukemia.

15. An antibody drug conjugate (ADC) comprising the antibody of claim 1 conjugated to a cytotoxin via a linker.

16. The ADC of claim 15, wherein the cytotoxin is an RNA polymerase inhibitor.

17. The ADC of claim 16, wherein the RNA polymerase inhibitor is an amatoxin.

18. The ADC of claim 17, wherein the amatoxin is represented by formula (IV)

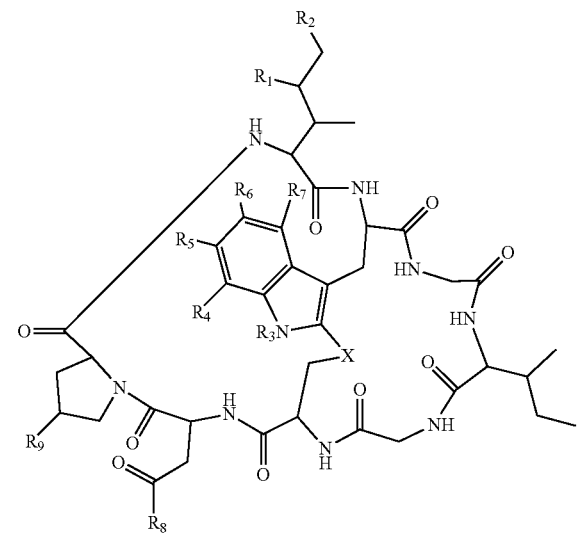

(IV)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a peptide, a dipeptide, —(C=O)—, or a combination thereof; and
Z is a chemical moiety formed from a coupling reaction between a reactive substituent present on L and a reactive substituent present within the antibody or antigen-binding fragment thereof, wherein Am comprises exactly one R$_C$ substituent.

19. The ADC of claim 15, wherein the ADC has a formula of

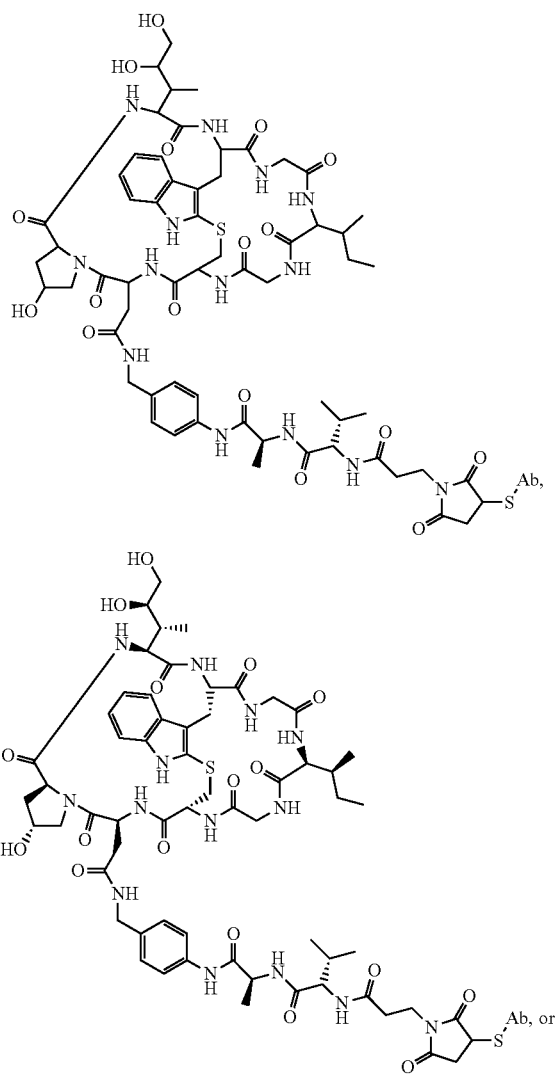

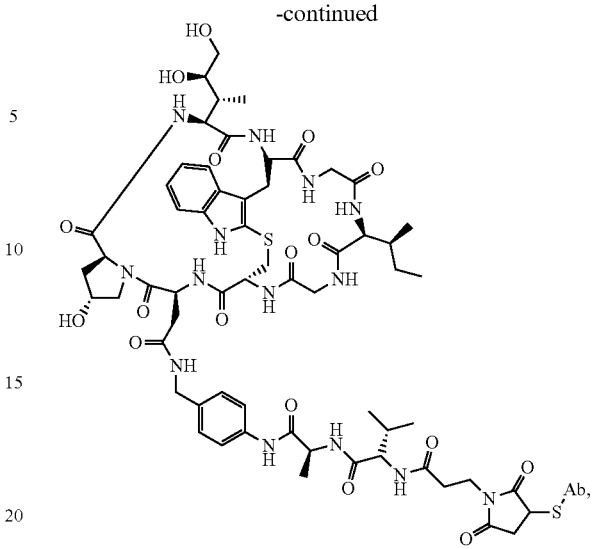

wherein Ab represents the point of attachment of the anti-CD45 antibody.

20. The ADC of claim 15, wherein the cytotoxin is selected from the group consisting of a pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer.

21. The ADC of claim 15, wherein the antibody is conjugated to the cytotoxin by way of a cysteine residue in the Fc domain of the antibody.

22. The ADC of claim 21, wherein the cysteine residue is introduced by way of an amino acid substitution in the Fc domain of the antibody.

23. A pharmaceutical composition comprising the ADC of claim 15, and a pharmaceutically acceptable carrier.

24. A method of depleting a population of hematopoietic stem cells (HSC) in a human patient, the method comprising administering to the patient an effective amount of the ADC of claim 15.

25. A method comprising administering to a human patient a transplant comprising hematopoietic stem cells, wherein the patient has been previously administered the ADC of claim 15 in an amount sufficient to deplete a population of hematopoietic stem cells or a population of immune cells in the patient.

26. A method of treating leukemia in a human patient, said method comprising administering the ADC of claim 15 the human patient having leukemia.

* * * * *